United States Patent
Carlson et al.

(10) Patent No.: US 6,610,511 B1
(45) Date of Patent: Aug. 26, 2003

(54) DROSOPHILA ODORANT RECEPTORS

(75) Inventors: John R. Carlson, North Haven, CT (US); Junhyong Kim, Hamden, CT (US); Peter J. Clyne, San Francisco, CA (US); Coral G. Warr, New Haven, CT (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 09/491,577

(22) Filed: Jan. 25, 2000

Related U.S. Application Data
(60) Provisional application No. 60/117,132, filed on Jan. 25, 1999.

(51) Int. Cl.$^7$ .................. C07H 21/04; C12N 15/12; C12N 15/63; C12N 5/00; C07K 14/00

(52) U.S. Cl. .................. 435/69.1; 435/320.1; 435/325; 536/23.5; 530/358

(58) Field of Search .................. 536/23.5; 435/69.1, 435/320.1, 325; 530/350

(56) References Cited

U.S. PATENT DOCUMENTS

| | | | |
|---|---|---|---|
| 5,772,983 A | 6/1998 | O'Connell et al. | 424/9.2 |
| 5,993,778 A | 11/1999 | Firestein et al. | 424/9.1 |

OTHER PUBLICATIONS

Doerks et al. Protein annotation: detective work for function prediction. Trends in Genetics. Jun. 1998, vol. 14, No. 6, pp. 248–250.*
Mikayama T. Molecular cloning and functional expression of a cDNA encoding glycosylation–inhibiting factor. Proc. Natl. Acad. Sci. USA vol. 90, pp. 10056–10060, 1993.*
Voet et al. Biochemistry. 1990. John Wiley & Sons, Inc.. pp. 126–128 and 228–234.*
Celniker et al. *Drosophila melanogaster* (P1 DS05342 (D92)) DNA Sequence, complete sequence. Accession No. AC 004121. Feb. 4, 1998.*
Ayer et al., (1991) Acj6: a gene affecting olfactory physiology and behavior in Drosophila, Proc. Natl. Acad. Sci. USA, 88, 5467–5471.
Clyne et al., (1999) The odor specificities of a subset of olfactory receptor neurons are governed by Acj6, a POU–domain transcription factor, Neuron, 22, 339–347.
International Search Report, PCT/US00/01823, Sep. 7, 2000 (7 pages).
Written Opinion, PCT/US00/01823, May 4, 2001 (5 pages).
Boeckh et al., Acylated 1,3–aminopropanols as repellents against bloodsucking arthropods, *Pesticide Science* (1996) 48:359–373.
Bogner et al., A potential kairomone stimulates pheromone–responsive receptor neurons in *Utetheisa ornatrix*, *J. Chem. Ecology* (1992) 18:427–439.

Cao et al., Cloning and localization of two multigene receptor families in goldfish olfactory epithelium, *Proc. Natl. Acad. Sci. USA* (1998) 95:11987–11992.
Carlson, Olfaction in Drosophila: from odor to behavior, *Trends Genet.* (1996) 12:175–180.
Carlson, Insulation of signaling pathways: odor discrimination via olfactosomes, *Neuron* (2000) 25:503–504.
Clyne et al., Odorant response of individual sensilla on the Drosophila antennae, *Invert. Neurosci.* (1997) 3:127–135.
Clyne et al., A novel family of divergent seven–transmembrane proteins: candidate odorant receptors in Drosophila, *Neuron* (1999) 22:327–338.
de Bruyne et al., Odor coding in a model olfactory organ: the Drosophila maxillary palp, *J. Neurosci.* (1999) 19:4520–4532.
Dryer & Berghard, Odorant receptors: a plethora of G–protein–coupled receptors, *Trends Pharmacol. Sci.* (1999) 20:413–417.
Gao & Chess, Identification of candidate Drosophila olfactory receptors from genomic DNA sequence, *Genomics* (1999) 60:31–39.
Hekmat–Scafe et al., Olfactory coding in a compound nose: coexpression of odorant–binding proteins in Drosophila, *Ann. NY Acad. Sci.* (1998) 855:311–315.
Grant et al., Different seasonal rearing conditions do not affect pheromone–sensitive receptor neurons of the adult cabbage looper moth, Trichoplusia ni, *Physiol. Entomol.* (1996) 21:59–63.
Hekmat–Scafe et al., Coexpression of two odorant–binding protein homologs in Drosophila: implications for olfactory coding, *J. Neurosci* (1997) 17:1616–1624.
Hekmat–Scafe et al., Genetic and molecular studies of olfaction in Drosophila, *Ciba Found. Symp.* (1996) 200:285–296 (discussion 296–301).
Hefland & Carlson, Isolation and characterization of an olfactory mutant in Drosophila with a chemically specific defect, *Proc. Natl. Acad. Sci. USA* (1989) 86:2908–2912.
Hing & Carlson, Male–male courtship behavior induced by ectopic expression of the Drosophila white gene: role of sensory function and age, *J. Neurobiol.* (1996) 30:454–464.
Karg & Suckling, Applied aspects of insect olfaction, Insect Olfaction (1999) 351–377, Hansson (editor), Springer–Verlag.

(List continued on next page.)

Primary Examiner—Yvonne Eyler
Assistant Examiner—Joseph F. Murphy
(74) *Attorney, Agent, or Firm*—Morgan, Lewis & Bockius, LLP

(57) ABSTRACT

The present invention provides nucleic acids and amino acids for novel olfactory receptors as well as methods for identifying olfactory receptors. More specifically, the present invention provides nucleic acids and amino acids for novel olfactory receptors in Drosophila as well as methods of using the provided nucleic acids and amino acids. In addition, this invention provides methods of identifying ligands which bind to the novel olfactory receptors as well as a variety of methods for using the ligands so identified.

13 Claims, 10 Drawing Sheets

OTHER PUBLICATIONS

Störtkuhl et al., Olfactory adaptation depends on the Trp $Ca^{2+}$ channels in Drosophila, *J. Neurosci.* (1999) 19:4839–4846.

Lilly et al., Evidence that the Drosophila olfactory mutant smellblind defines a novel class of sodium channel mutation, *Genetics* (1994) 136:1087–1096.

McKenna et al., Putative Drosophila pheromone–binding proteins expressed in a subregion of the olfactory system, *J. Biol. Chem.* (1994) 269:16340–16347.

Mombaerts, Seven–transmembrane proteins as odorant and chemosensory receptors, *Science* (1999) 286:707–711.

Riesgo–Escovar et al., The Drosophila antennae: ultrastructure and physiology depends on the lozenge gene, *J. Comp Physiol.* (1997) 180:151–160.

Riesgo–Escovar et al., The maxillary palp of Drosophila: ultrastructure and physiology depends on the lozenge gene, *J. Comp Physiol.* (1997) 180:143–150.

Renou et al., Electrophysiology investigations of pheromone–sensitive sensilla in the hybrids between two moth species, *J. Insect Physiol.* (1996) 42:267–277.

Ryba & Tirindelli, A new multigene family of putative pheromone receptors, *Neuron* (1997) 19:371–379.

Wiltschko, The function of olfactory input in pigeon orientation: does it provide a navigational information or play another role, *J. Exp. Biol.* (1996) 199:113–119.

Vosshall et al., A spatial map of olfactory receptor expression in the Drosophila antennae, *Cell* (1999) 96:725–736.

Yoshikawa et al., Molecular cloning and characterization of the inositol 1,4,5–triphosphate receptor in *Drosophila melongaster*, *J. Biol. Chem.* (1992) 267:16613–16619.

* cited by examiner

TRICHODEA

COELOCONICA

LARGE BASICONICA

SMALL BASICONICA

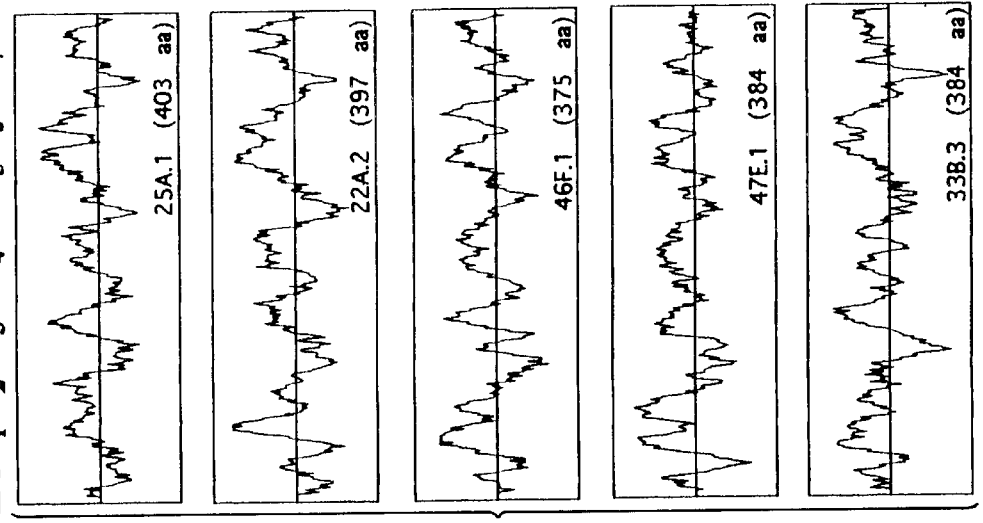
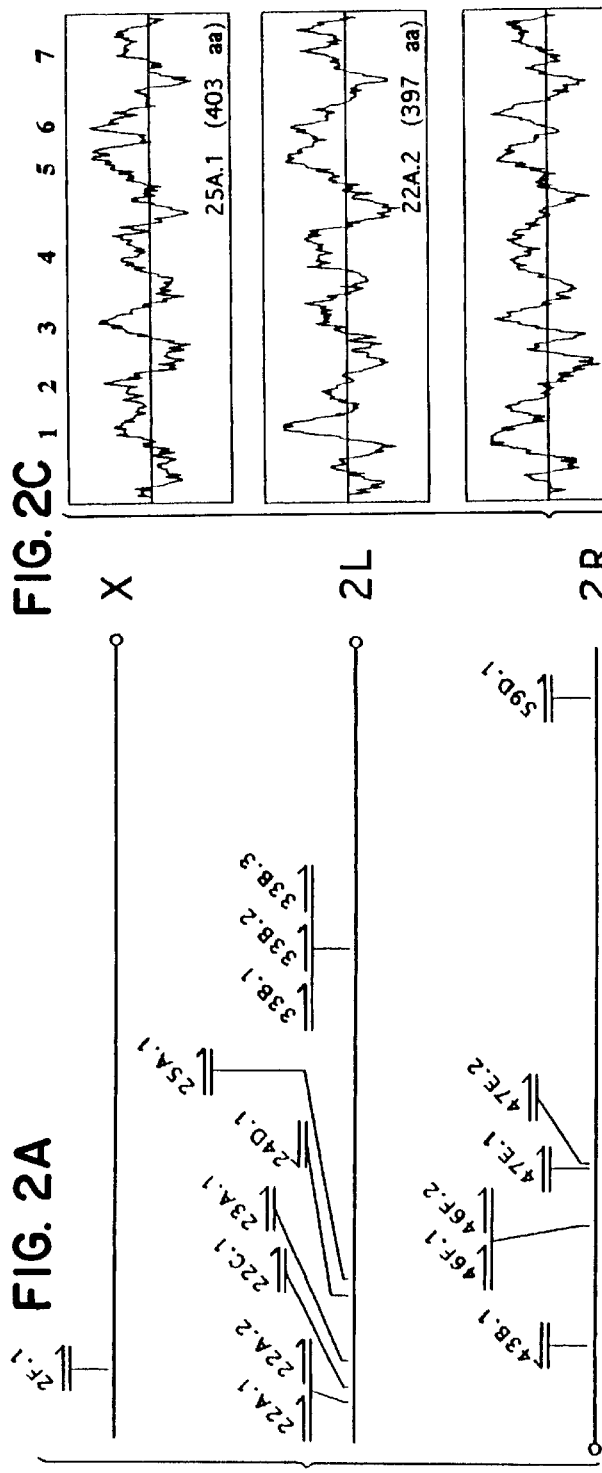
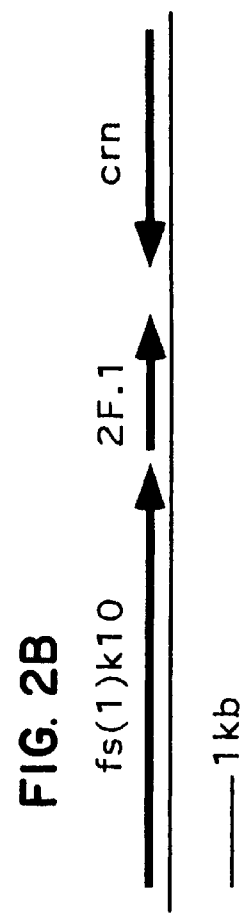

FIG. 3A

```
59D.1   1 ---------MAEVRVDSLEFFKSHWTAWRYLGVAHFRVENWKNLYVFYSIVSNLLVTLCYPVHLGISLFRN---RTITEDILNL  72
23A.1   1 ---------MKLSETLKIDYFRVQLNAWRICGA------LDLSEGRYWSWSMLLCILVYLPTPMLLRGVYS--FEDPVENNFSL  67
33B.1   1 ---------MDSRRKVRSENLYKTYWLYWHLLGV-----EGDYPFRRLVDFTITSFITILFPVHLLIGMYKK---PQIQVFRSL  67
33B.2   1 ---------MDLKPRVIRSEDIYRTYWLYWHLLGL----ESNFFLNRLLDLVITIFVTIWYPIHLILGLFME---RSLGDVCKGL  69
33B.3   1 ---------MVIIDSLSFYRPFWICMRLLVP-TFFKDSSRPVQLYVVLHILVTLWFPLHLLLHLLL----PSTAEFFKNL  68
2F.1    1 ---------MEKQEDFKLNTHSAVYYHWRVWELTGLMRPPGVSSLLYVVSITVNLVVTVLFPLSLLARLLFT---TNMAGLCENL  74
22A.1   1 -MLSKFFPHIKEKPLSERVKSRDAFIYLDRVMWSFGWTEPENKRWILPYKILWLAFVNIVMLILPISISIEYLHRFKTFSAGEFLSSL  87
22A.2   1 -MLSQFFPHIKEKPLSERVKSRDAFVYLDRVMWSFGWTVPENKRWDLHYKLWSTFVTLLIFILLPISVSVEYIQRFKTFSAGEFLSSI  87
47E.1   1 ---------MDSFLQVQKSTIALLGFDLFSENREMWKRPYRAMNVFSIAAIFPFILAAVLHNW---KNVLLLADAM  64
46F.1   1 ---------MSKGVEIFYKGQKAFLNILSLWPQIERRWRIIHQVNYVHVIVFWLVLFDLLLVLHV-----MANLSYMS  64
46F.2   1 ---------MVTEDFYKYQVMFQIL--GVWQLPTWAADHQRRFQSMRFGFILVILFIMLLLF-SFEMLNNISQVR  64
22C.1   1 --MTDSGQPAIADHFYRIPRISGLIVGLWPQRIRGGGGRPWHAHLLFVFAFAMVVGAVGEVSYGCVHLDN---LVVALEAF  77
24D.1   1 ---------MERHYFMVPKFALSLIGFYPEQKR-----TVLVKLWSFFNFFILTYGCYAEAYYGIHYIPI----NIATALDAL  65
43B.1   1 ---------MTIEDIGLVGINVRMRHLAV--LYPTPGSSWRKFAFVLPVTAMNLMQFVYLLRMWGD---LPAFILNM  64
47E.2   1 MNDSGYQSNLSLLRVFLDEFRSVLRQESPGLIPRLAFYYVRAFLSLPLYRWINLFIMCNVMTIFWTMFVALPESK---NVIEMGDDL  84
25A.1   1 --MFGHFKLVYPAPISEPIQSRDSNAYMMETLRNSGLN--LKNDFGIGRKIWRVFSFTYNMVILPVSFPINYVIHLAEFPPELLQSL  84
```

FIG. 3B

```
                2                                                              3
59D.1  73 TTFATCTACSVKCLLYAYNIKDVLEMERLRLLDERVGPEQRSIYGQ------VRVQLRNVLYVFIGIYMPCALFAELSFLFKEE 152
23A.1  68 SLTVTSLSNLMKFCMYVAQLTKMVEVQSLIGQLDARVSGESQSERHRN------MTEHLLRMSKLFQITYAVVFIIAAVPFVFETE 147
33B.1  68 HFTSECLFCSYKFFCFRWKLKEIKTIEGLLQDLDSRVESEEERNYFNQ------NPSRVARMLSKSYLVAAISAIITATVAGLFSTG 148
33B.2  70 PITAACFFASFKFICFRFKLSEIKEIEILFKELDQRALSREECEFFNQ------NTRREANFIWKSFIVAYGLSNISAIASVLFGGG 150
33B.3  69 TMSLTCVACSLKHVAHLYHLPQIVEIESLIEQLDTFIASEQEHRYYRD------HVHCHARRFTRCLYISFGMIYALFLFGVFNQV 148
2F.1   75 TITITDIVANLKFANVYMVRKQLHEIRSILRLMDARARLVGDPEEISA------LRKEVNIAQGTFRTFASIFVFGTTLSCVRVVVR 155
22A.1  88 EIGVNMYGSSFKCAFTLIGFKKRQEAKVLLDQLDKRCLSDKERSTVHR------YVAMGNFFDILYHIFYSTFVVMNFPYFLLE 165
22A.2  88 QIGVNMYGSSFKSYLTMMGYKKRQEAKMSLDELDKRCVCDEERTIVHR------HVALGNFCYIFYHIAYTSFLISNFLSFIMK 165
47E.1  65 VALLITILGLFKFSMILYLRRDFKRLIDKFRLLMSNEAEOGEEYAEILNAANKQDQRMCTLFRTCFLLAWALNSVLPLVRMGLSYWLA 152
46F.1  65 EVVKAIFILATSAGHTTKL-LSIKANNVQMEELFRRLDNEEFRPRGANEELIFAAACERSRKLRDFYGALSFAALSMILIPQFALDWS 151
46F.2  65 EILKVFFMFATEISSCMAKL-LHLKLKSRKLAGLVDAM-LSPEFGVKSE--QEMQMLELDRVAVRMRNSYGIMSLGAASLILIVPCFD 148
22C.1  78 CPGTTKAVCVLKLLWVFFRS---NRRWAELVQRLRAILSLLLSSGTAT-------NAAFTLQPLIMGLYRWIVQLPGQT 146
24D.1  66 CPVASSILSLVKMVAIWWY---QDELRSLIERRFYTLATQLTFLLLCC-----GFCTSTSYSVRHLIDNILRRTHGKDWIYETPFKM- 144
43B.1  65 FFFSAIFNALMRTWLVIIKRRQFEEFLGQLATLFHSILDSTDEWGRGI-LRRAEREARNLAILNLSASFLDIVGALFFEYKFPIGVV 150
47E.2  85 VWISQMALVFTKIFYMHLR---CDEIDELISDFEYYNRELRPHNIDEE------VLGWQRLCYVIESGLYINCFCLVNFFSAAIFLQP 163
25A.1  85 QLCLNTWCFALKFFTLIVYTHRLELANKHFDELDKYCVKPAEKRKVRD------MVATITRLYLTFVVVYLYATSTLLDGLLH 162
```

FIG. 3C

```
59D.1  153  R-----GLMYPAWFPFDWLHST---RNYYIANAYQIVGISFQLLQNYVSDCFPAVVLCLISSHIKMLYNRFEEVGLDPARDAEK----  228
23A.1  148  L-----SLPMPMWFPFDWKNSM---VAYIGALVFQEIGYVFQIMQCFAADSFPPLVLYLISEQCQLLILRISEIGYKTLEENEQ--   225
33B.1  149  R-----NLMYLGWFPYDFQATA---AIYWISFSYQAIGSSLLILENLANDSYPPITFCVVSGHVRLLIMRLSRIGHDVKLSSSENT--  226
33B.2  151  H-----KLLYPAWFPFDLESNR---LIFWLSVTYQIAGVSLAILQNLANDSYPPMTFCVVAGHVRLLAMRLSRIGQGPEETIYLTG--  228
33B.3  149  I-SGNWELLYPAYFPFDLESNR---FLGAVALGYQVFSMLVEGFQGLGNDTYPLTLCLLAGHVHLWSIRMGQLGYFDDETVVNHQ--  230
2F.1   156  P---DRELLYPAWFGVDWMHST---RNYVLINIYQLFGLIVQAIQNCASDSYPPAFLCLLTGHMRALELRVRRIGCRTEKSNKGQTYE 237
22A.1  166  R-----RHAWRMYFPYIDSDEQ---FYISS-IAECFLMTEAIYMDLCTDVCPLISMLMARCHISLLKQRLRNLRSKPGRTEDEYL--  241
22A.2  166  R-----IHAWRMYFPYVDPEKQ---FYISS-IAEVILRGWAVFMDLCTDVCPLISMVIARCHITLLKQRLRNLRSEPGRTEDEYL--  241
47E.1  153  G-HAEPELPFPCLFPWNIHIIR---NYVLSFIWSAFASTGVVLPAVSLDTIFCSFTSNLCAFFKIAQYKVVRFKGGSLKESQATL--  233
46F.1  152  H-----LPLKTYNPLGENTGS---PAYWLLYCYQCLALSVSCITNIGFDSLCSSLFIFLKCQLDILAVRLDKIGRLITTSGGTVE-- 228
46F.2  149  N---FGELPLAMLEVCSIEGWI---CYWSQYLFHSICLLPTCVLNITYDSVAYSLLCFLKVQLOMLVLRLEKLGPVIEPQDNEKI-- 227
22C.1  147  E-----LPFNIILPSFAVQPG---VFPLTYVLLTASGACTVFAFSFVDGFFICSCLYIGGAFRLVQQDIRRIFADLHGVDVFTE}-- 222
24D.1  145  --------MFPDLLLRLP----LYPITYILVHWHGYITVVCFVGADGFFLGFCLYFTVLLLCDDDVCDLLEVENIEKSPSE--    214
43B.1  151  T-FFLPAHPFGLALPGVSMTSS---PVMEVIYLAQLPTPLLLSMMYMPFVSLFAGLAIFGKAMLQILVHRLGQIGGEEQSEEERFQ-- 232
47E.2  164  L-LGEGKLPFHSVYPFQWHRLDLHPYTFWFLYIWQSLTSQHNLMSILMVDMVGISTFLQTALNLKLLCIEIRKLGMEVSDKRFHE--  248
25A.1  163  H-----RVPYNTYYPFINWRVD-RTQMYIQS-FLEYFTVGYAIYVATATDSYPVIYVAALRTHILLLKDRIIYLGDPSNEGSSDPS--  241
```

FIG. 3D

| | | | | |
|---|---|---|---|---|
| 59D.1 | 229 | ----------DLEACITDKHILELFRRIEAFISLPMLIQFTVTALNVCIGLAALVFFVSE---PMARMYFIFYSLAMPLQIFPSCFFGT | 305 |
| 23A.1 | 226 | ----------DLVNCIRDONALYRLLDVTKSLVSYPMMVQFMVIGINIAITLFVLIFYVET---LYDRIYMLCFLLGITVQTYPLCYYGT | 302 |
| 33B.1 | 227 | ----------RKLIEGIQDHRKLMKIIRLRSTLHLSQLGQFLSSGINISITLINILFFAEN---NFAMLYYAVFFAAMLIELFPSCYYGT | 304 |
| 33B.2 | 229 | ----------KQLIESIEDHRKLMKIVELLRSTMNISQLGQFISSGVNISITLVNILFFADN---NFAITYYGVYFLSMVLFLFPCCYYGT | 306 |
| 33B.3 | 231 | ----------RLLDYIEQHKLLVRFHNLVSRTISEVQLVQLGGCGATLCIIVSYMLFFVGD---TISLVYYLVFFGVVCVQLFPSCYFAS | 307 |
| 2F.1 | 238 | AWREEVYQELIECIRDLARVHRLREIIQRVLSVPCMAQFVCSAAVQCTVAMHFLYVADDH-DHTAMIISIVFFSAVTLEVFMICMYFGD | 324 |
| 22A.1 | 242 | ----------EELTECIRDHRLLLDYDALRPVFSGTIFVQFLLIGTVLGLSMINLMFFST---FWTGVATCLFMFDVSMETFPFCYMLCN | 318 |
| 22A.2 | 242 | ----------KELADCVRDHRLLLDYDALRSVFSGTIFVSGTIFVQFLLIGIVLGLSMINIMFFST---LSTGVAVVLFMSCVSMQTFPFCYMLCN | 318 |
| 47E.1 | 234 | ----------NKVFALYQTSLDMCND------LNQCYQPIICAQFFISSLQLCMLGYLFSITFA---QTEGVYYASFIATIIIQAYIYCMCGE | 307 |
| 46F.1 | 229 | ----------QQLKENTRYLHMTIVELSKTVERLLCCKPISVQIFCSVLVLTANFYAIAVLSDE---RLELFKYVTQACMLIQFILQMYAG | 306 |
| 46F.2 | 228 | ----------AMELRECAAYYNRIVRFKDLVELFIKGPGSVQLMCSVLVLVSNLYDMSTMSIANGDAIFMLKTCIYQLVMLWQIFIICYASN | 309 |
| 22C.1 | 223 | EMNAEVRHRLAQVVERHNAIIDFCTDLTRQFTVIVLMHFSAAFVLCSTILDIMLNTS----SLSGLTYICMIIAALTQLFLYCFGGN | 306 |
| 24D.1 | 215 | AEEARIVREMEKLVDRHNEVAELTERLSGVMVEITLAHFVTSSLLIGTSVVDILLFSG-----LGIIVMYYILTMLYVLFTYNRAN | 297 |
| 43B.1 | 233 | ----------RLASCIAYHTQVMRYVWQLNKLVGKANRAFNGAFNAQLMASFSLSISTFETMAAAA-VDPKMAAKFVLLMLVAFIQLSLWCVSGT | 308 |
| 47E.2 | 249 | ----------EFCRVVRFHQHIIKLVGKANRAFNGAFNAQLMASFSLSISTFETMAAAA-VDPKMAAKFVLLMLVAFIQLSLWCVSGT | 326 |
| 25A.1 | 242 | ----------YMFKSLVDCIKAHRTMLNFCDAIQPIISGTIFAQFIICGSILGIIMINMVLFAD----QSTRFGIVIYMAVLLQTFPLCFYCN | 321 |

FIG. 3E

|  |  |  |  |
|---|---|---|---|
| 59D.1 | 306 | DNEYWF-GRLHYAAAFSCNWHTQNRSFKRKMMFVEQSLKKST--AVAGGMMRIHDTFFSTLKGAVSLFTIIRMRK---------- | 379 |
| 23A.1 | 303 | MVQESF-AELHYAVFCSNWVDQSASYRGHMLLAERTKRMQL--LLAGNLVPIHLSTYVACWKGAYSFFTITLMADRDG------- | 377 |
| 33B.1 | 305 | LMTMEF-DKLPYAIFSSNWLKMDKRYNRSLIILMQLTLVPVN--IKAGGIVGIDMSAFFATVRMAVSRYTLALS----------- | 375 |
| 33B.2 | 307 | LISVEM-NQLTYAIYSSNWMSMNRSYSRILLIFMQLTLAEVQ--IKAGGMIGIGMNAFFATVRLAVSFFTLAM------------ | 376 |
| 33B.3 | 308 | EVAEEL-ERLPYAIFSSRMYDQSRDHRFDLLIFTQLTLGNRGWIIKAGGLIELNLNAFFATLKMAYSLFAVVVRAKGI-------- | 384 |
| 2F.1 | 325 | RMRTQS-EALCDAFYDCNWIEQLPKFKRELLFTLARTQRPSL--IYAGNYIALSLETFEQVMRFTYSVFTLLLRAK--------- | 397 |
| 22A.1 | 319 | MIIDDC-QEMSNCLFQSDWTSADRRMKSTLVYFLHNLQQPIT--LTAGGVFPISMQTNLAMVKLAFSVVTIVKQFNLAERFQ--- | 397 |
| 22A.2 | 319 | MIMDDC-QEMADSLFQSDWTSADRRMKSTLVYFLHNLQQPII--LTAGGVFPISMQTNLNMVKLAFTVVTIVKQFNLAEKFQ--- | 397 |
| 47E.1 | 308 | NLKTES-ASFEWAIYDSPWHESLGAGGASTSICRSLLISMR--AHRGFRITGYFFEANILVRTAMSYIIMLRSFS---------- | 380 |
| 46F.1 | 307 | EVTQRS-LDLPHELYKTSWVDWDYRSRRIALLFMQRLHSTLR--IRLNPSLGFDLMLFSSVSSFRVLTFLCTVANFHN------- | 381 |
| 46F.2 | 310 | EVTVQS-SRLCHSIYSSQWTGWNRANRBIVLLMMQRFNSPML-LSTFNPTAFSLEAFGSIVNCSYSYSFALLKRVNS-------- | 384 |
| 22C.1 | 307 | HVSESS-AAVADVLYDMEWYKCDARTRKVILMILRRSQRAKT--IAVPFFTPSLPALQ--ILSTAGGSYIILKTFL--------- | 377 |
| 24D.1 | 298 | HIMEAC-SNLARSTFSSHWYGHSVRVQKMTLMVARAQRVLT--IKIPFFSPSLETLTS-ILRFTGSLIALAKSVI---------- | 369 |
| 43B.1 | 309 | EICLEN-NRVAEAVYYNVPMYEAGTRFRKTLLIFLMQTQHPME-IRVGNVYPMTLAMFQSLLNASYSYSFFTMLRGVTGK------ | 383 |
| 47E.2 | 327 | LVYTQSVEVAQAAFDINDWHTKSPGIQRDISFVILRAQKPLM--YVAEDFLPFTLGTYMLVLKNCYRLLALMQESM--------- | 400 |
| 25A.1 | 322 | AIVDDC-KELAHALFHSAWWVQDKRYQRTVIQFLQKLQQPMT--FTAMNIFNINLATNINVAKFAFTVYAIASGMNLDQKLSIKE | 403 |

A

B

D

A 47E.1

C 25A.1

E 22A.2

B 47E.1

D 25A.1

F ac/sc 22A.2

○ 47E.1
● 25A.1
● 22A.2

22A.2

A  54h

B  60h 47E.1

C  72h

D  93h

OS-E

E  72h

F  93h

SEQUENCE LISTING

<160> NUMBER OF SEQ ID NOS: 112

<210> SEQ ID NO 1
<211> LENGTH: 767
<212> TYPE: DNA
<213> ORGANISM: Drosophila melanogaster
<220> FEATURE:
<221> NAME/KEY: CDS
<222> LOCATION: (1)..(765)
<223> OTHER INFORMATION: DOR 22A.2, coding region of NCBI Accession No. AF127924

<400> SEQUENCE: 1

```
atg tta agc cag ttc ttt ccc cac att aaa gaa aag cca ttg agc gag       48
Met Leu Ser Gln Phe Phe Pro His Ile Lys Glu Lys Pro Leu Ser Glu
 1               5                  10                  15 cgg gtt aag tcc cga gat gcc ttc gtt tac tta gat cgg gtg atg tgg       96
Arg Val Lys Ser Arg Asp Ala Phe Val Tyr Leu Asp Arg Val Met Trp
             20                  25                  30 tcc ttt ggc tgg aca gtg cct gaa aac aaa agg tgg gat cta cat tac      144
Ser Phe Gly Trp Thr Val Pro Glu Asn Lys Arg Trp Asp Leu His Tyr
         35                  40                  45 aaa ctg tgg tca act ttc gtg aca ttg ttg ata ttt atc ctt ctg ccg      192
Lys Leu Trp Ser Thr Phe Val Thr Leu Leu Ile Phe Ile Leu Leu Pro
     50                  55                  60 ata tcg gta agc gtt gag tat att cag cgg ttc aag acc ttc tcg gcg      240
Ile Ser Val Ser Val Glu Tyr Ile Gln Arg Phe Lys Thr Phe Ser Ala
 65                  70                  75                  80
```

```
ggt gag ttt ctt agc tca atc cag att ggc gtt aac atg tac gga agc      288
Gly Glu Phe Leu Ser Ser Ile Gln Ile Gly Val Asn Met Tyr Gly Ser
                85                  90                  95 agc ttt aaa agt tat ttg acc atg atg gga tat aag aag aga cag gag      336
Ser Phe Lys Ser Tyr Leu Thr Met Met Gly Tyr Lys Lys Arg Gln Glu
            100                 105                 110 gct aag atg tca ctg gat gag ctg gac aag aga tgc gtt tgt gat gag      384
Ala Lys Met Ser Leu Asp Glu Leu Asp Lys Arg Cys Val Cys Asp Glu
            115                 120                 125 gag agg acc att gta cat cga cat gtc gcc ctg gga aac ttt tgc tat      432
Glu Arg Thr Ile Val His Arg His Val Ala Leu Gly Asn Phe Cys Tyr
    130                 135                 140 att ttc tat cac att gcg tac act agc ttt ttg att tca aac ttt ttg      480
Ile Phe Tyr His Ile Ala Tyr Thr Ser Phe Leu Ile Ser Asn Phe Leu
145                 150                 155                 160 tca ttt ata atg aag aga atc cat gcc tgg cgc atg tac ttt ccc tac      528
Ser Phe Ile Met Lys Arg Ile His Ala Trp Arg Met Tyr Phe Pro Tyr
                165                 170                 175 gtc gac ccc gaa aag caa ttt tac atc tct agc atc gcc gaa gtc att      576
Val Asp Pro Glu Lys Gln Phe Tyr Ile Ser Ser Ile Ala Glu Val Ile
            180                 185                 190 ctt agg gga tgg gcc gtc ttc atg gat ctc tgc acg gat gtg tgt cct      624
Leu Arg Gly Trp Ala Val Phe Met Asp Leu Cys Thr Asp Val Cys Pro
            195                 200                 205 ttg atc tcc atg gta ata gca cga tgc cac atc acc ctt ctg aaa cag      672
Leu Ile Ser Met Val Ile Ala Arg Cys His Ile Thr Leu Leu Lys Gln
    210                 215                 220 cgc ctg cga aat cta cga tcg gaa cca gga agg acg gaa gat gag tac      720
Arg Leu Arg Asn Leu Arg Ser Glu Pro Gly Arg Thr Glu Asp Glu Tyr
225                 230                 235                 240 ttg aag gag ctc gcc gac tgc gtt cga gat cac cgc ttg ata ttg ga       767
Leu Lys Glu Leu Ala Asp Cys Val Arg Asp His Arg Leu Ile Leu
                245                 250                 255

<210> SEQ ID NO 2
<211> LENGTH: 255
<212> TYPE: PRT
<213> ORGANISM: Drosophila melanogaster

<400> SEQUENCE: 2

Met Leu Ser Gln Phe Phe Pro His Ile Lys Glu Lys Pro Leu Ser Glu
  1               5                  10                  15

Arg Val Lys Ser Arg Asp Ala Phe Val Tyr Leu Asp Arg Val Met Trp
                20                  25                  30

Ser Phe Gly Trp Thr Val Pro Glu Asn Lys Arg Trp Asp Leu His Tyr
            35                  40                  45

Lys Leu Trp Ser Thr Phe Val Thr Leu Leu Ile Phe Ile Leu Leu Pro
        50                  55                  60

Ile Ser Val Ser Val Glu Tyr Ile Gln Arg Phe Lys Thr Phe Ser Ala
 65                  70                  75                  80

Gly Glu Phe Leu Ser Ser Ile Gln Ile Gly Val Asn Met Tyr Gly Ser
                85                  90                  95

Ser Phe Lys Ser Tyr Leu Thr Met Met Gly Tyr Lys Lys Arg Gln Glu
            100                 105                 110

Ala Lys Met Ser Leu Asp Glu Leu Asp Lys Arg Cys Val Cys Asp Glu
        115                 120                 125

Glu Arg Thr Ile Val His Arg His Val Ala Leu Gly Asn Phe Cys Tyr
    130                 135                 140
```

-continued

```
Ile Phe Tyr His Ile Ala Tyr Thr Ser Phe Leu Ile Ser Asn Phe Leu
145                 150                 155                 160

Ser Phe Ile Met Lys Arg Ile His Ala Trp Arg Met Tyr Phe Pro Tyr
            165                 170                 175

Val Asp Pro Glu Lys Gln Phe Tyr Ile Ser Ile Ala Glu Val Ile
            180                 185                 190

Leu Arg Gly Trp Ala Val Phe Met Asp Leu Cys Thr Asp Val Cys Pro
            195                 200                 205

Leu Ile Ser Met Val Ile Ala Arg Cys His Ile Thr Leu Leu Lys Gln
    210                 215                 220

Arg Leu Arg Asn Leu Arg Ser Glu Pro Gly Arg Thr Glu Asp Glu Tyr
225                 230                 235                 240

Leu Lys Glu Leu Ala Asp Cys Val Arg Asp His Arg Leu Ile Leu
                245                 250                 255

<210> SEQ ID NO 3
<211> LENGTH: 1140
<212> TYPE: DNA
<213> ORGANISM: Drosophila melanogaster
<220> FEATURE:
<221> NAME/KEY: CDS
<222> LOCATION: (1)..(1137)
<223> OTHER INFORMATION: DOR 22C.1, a coding segment on BDGP Clone No.
      AC004716

<400> SEQUENCE: 3 atg act gac agc ggg cag cct gcc att gcc gac cac ttt tat cgg att     48
Met Thr Asp Ser Gly Gln Pro Ala Ile Ala Asp His Phe Tyr Arg Ile
1               5                   10                  15 ccc cgc atc tcc ggc ctc att gtc ggc ctc tgg ccg caa agg ata agg     96
Pro Arg Ile Ser Gly Leu Ile Val Gly Leu Trp Pro Gln Arg Ile Arg
                20                  25                  30 ggc ggg ggc ggt cgt cct tgg cac gcc cat ctg ctc ttc gtg ttc gcc    144
Gly Gly Gly Gly Arg Pro Trp His Ala His Leu Leu Phe Val Phe Ala
            35                  40                  45 ttc gcc atg gtg gtg gtg ggt gcg gtg ggc gag gtg tcg tac ggc tgt    192
Phe Ala Met Val Val Val Gly Ala Val Gly Glu Val Ser Tyr Gly Cys
        50                  55                  60 gtc cac ctg gac aac ctg gtg gtg gcg ctg gag gcc ttc tgc ccc gga    240
Val His Leu Asp Asn Leu Val Val Ala Leu Glu Ala Phe Cys Pro Gly
65                  70                  75                  80 acc acc aag gcg gtc tgc gtt ttg aag ctg tgg gtc ttc ttc cgc tcc    288
Thr Thr Lys Ala Val Cys Val Leu Lys Leu Trp Val Phe Phe Arg Ser
                85                  90                  95 aat cgc cgg tgg gcg gag ttg gtc cag cgc ctg cgg gct att ttg ctc    336
Asn Arg Arg Trp Ala Glu Leu Val Gln Arg Leu Arg Ala Ile Leu Leu
            100                 105                 110 agc ctg ttg ttg ctc agc tct ggc acg gcg aca aat gcc gcc ttc acc    384
Ser Leu Leu Leu Leu Ser Ser Gly Thr Ala Thr Asn Ala Ala Phe Thr
        115                 120                 125 ttg caa ccg ctg att atg ggt ctc tac cgc tgg att gtg cag ctg cca    432
Leu Gln Pro Leu Ile Met Gly Leu Tyr Arg Trp Ile Val Gln Leu Pro
    130                 135                 140 ggt caa acc gag ctg ccc ttt aat atc ata ctg ccc tcg ttt gcc gtg    480
Gly Gln Thr Glu Leu Pro Phe Asn Ile Ile Leu Pro Ser Phe Ala Val
145                 150                 155                 160 cag cca gga gtc ttt ccg ctc acc tac gtg ctg ctg acc gct tcc ggt    528
Gln Pro Gly Val Phe Pro Leu Thr Tyr Val Leu Leu Thr Ala Ser Gly
                165                 170                 175
```

```
gcc tgc acc gtt ttc gcc ttc agc ttc gtg gac gga ttc ttc att tgc      576
Ala Cys Thr Val Phe Ala Phe Ser Phe Val Asp Gly Phe Phe Ile Cys
        180                 185                 190 tcg tgc ctc tac atc tgc ggc gct ttc cgg ctg gtg cag cag gac att      624
Ser Cys Leu Tyr Ile Cys Gly Ala Phe Arg Leu Val Gln Gln Asp Ile
    195                 200                 205 cgc agg ata ttt gcc gat ttg cat ggc gtg gat gtg ttc acc gag gag      672
Arg Arg Ile Phe Ala Asp Leu His Gly Val Asp Val Phe Thr Glu Glu
210                 215                 220 atg aac gcg gag gtg cgg cac aga ctg gcc caa gtt gtc gag cgg cac      720
Met Asn Ala Glu Val Arg His Arg Leu Ala Gln Val Val Glu Arg His
225                 230                 235                 240 aat gcg att atc gat ttc tgc acg gac cta aca cgc cag ttc acc gtt      768
Asn Ala Ile Ile Asp Phe Cys Thr Asp Leu Thr Arg Gln Phe Thr Val
                245                 250                 255 atc gtt tta atg cat ttc ctg tcc gcc gcc ttc gtc ctc tgc tcg acc      816
Ile Val Leu Met His Phe Leu Ser Ala Ala Phe Val Leu Cys Ser Thr
            260                 265                 270 atc ctg gac atc atg ttg aac acg tcg tcg ttg agc ggc tta acc tac      864
Ile Leu Asp Ile Met Leu Asn Thr Ser Ser Leu Ser Gly Leu Thr Tyr
        275                 280                 285 atc tgc tat atc atc gcg gcc cta acg cag cta ttc ctc tac tgc ttc      912
Ile Cys Tyr Ile Ile Ala Ala Leu Thr Gln Leu Phe Leu Tyr Cys Phe
    290                 295                 300 gga ggc aat cac gtc agc gag agt agt gcg gct gtg gcg gac gtg ctg      960
Gly Gly Asn His Val Ser Glu Ser Ser Ala Ala Val Ala Asp Val Leu
305                 310                 315                 320 tac gac atg gag tgg tac aaa tgc gat gcg agg act agg aaa gtg att     1008
Tyr Asp Met Glu Trp Tyr Lys Cys Asp Ala Arg Thr Arg Lys Val Ile
                325                 330                 335 tta atg ata ttg cgc cgt tcg cag cgg gca aaa aca att gcg gtg ccg     1056
Leu Met Ile Leu Arg Arg Ser Gln Arg Ala Lys Thr Ile Ala Val Pro
            340                 345                 350 ttt ttt acg ccc tca ctg cca gca ctc cga tct ata ctc agc aca gcc     1104
Phe Phe Thr Pro Ser Leu Pro Ala Leu Arg Ser Ile Leu Ser Thr Ala
        355                 360                 365 ggc tca tat atc acg ctg cta aag acg ttc ctg taa                     1140
Gly Ser Tyr Ile Thr Leu Leu Lys Thr Phe Leu
    370                 375
```

<210> SEQ ID NO 4
<211> LENGTH: 379
<212> TYPE: PRT
<213> ORGANISM: Drosophila melanogaster

<400> SEQUENCE: 4

```
Met Thr Asp Ser Gly Gln Pro Ala Ile Ala Asp His Phe Tyr Arg Ile
 1               5                  10                  15

Pro Arg Ile Ser Gly Leu Ile Val Gly Leu Trp Pro Gln Arg Ile Arg
                20                  25                  30

Gly Gly Gly Gly Arg Pro Trp His Ala His Leu Leu Phe Val Phe Ala
            35                  40                  45

Phe Ala Met Val Val Gly Ala Val Gly Glu Val Ser Tyr Gly Cys
        50                  55                  60

Val His Leu Asp Asn Leu Val Ala Leu Glu Ala Phe Cys Pro Gly
 65                  70                  75                  80

Thr Thr Lys Ala Val Cys Val Leu Lys Leu Trp Val Phe Phe Arg Ser
                85                  90                  95

Asn Arg Arg Trp Ala Glu Leu Val Gln Arg Leu Arg Ala Ile Leu Leu
```

```
                100                    105                    110
Ser Leu Leu Leu Leu Ser Ser Gly Thr Ala Thr Asn Ala Ala Phe Thr
        115                    120                125

Leu Gln Pro Leu Ile Met Gly Leu Tyr Arg Trp Ile Val Gln Leu Pro
    130                    135                140

Gly Gln Thr Glu Leu Pro Phe Asn Ile Ile Leu Pro Ser Phe Ala Val
145                    150                    155                160

Gln Pro Gly Val Phe Pro Leu Thr Tyr Val Leu Thr Ala Ser Gly
                165                    170                    175

Ala Cys Thr Val Phe Ala Phe Ser Phe Val Asp Gly Phe Phe Ile Cys
                180                    185                    190

Ser Cys Leu Tyr Ile Cys Gly Ala Phe Arg Leu Val Gln Gln Asp Ile
        195                    200                    205

Arg Arg Ile Phe Ala Asp Leu His Gly Val Asp Val Phe Thr Glu Glu
        210                    215                    220

Met Asn Ala Glu Val Arg His Arg Leu Ala Gln Val Val Glu Arg His
225                    230                    235                240

Asn Ala Ile Ile Asp Phe Cys Thr Asp Leu Thr Arg Gln Phe Thr Val
                245                    250                    255

Ile Val Leu Met His Phe Leu Ser Ala Ala Phe Val Leu Cys Ser Thr
                260                    265                    270

Ile Leu Asp Ile Met Leu Asn Thr Ser Ser Leu Ser Gly Leu Thr Tyr
            275                    280                    285

Ile Cys Tyr Ile Ile Ala Ala Leu Thr Gln Leu Phe Leu Tyr Cys Phe
        290                    295                    300

Gly Gly Asn His Val Ser Glu Ser Ser Ala Ala Val Ala Asp Val Leu
305                    310                    315                320

Tyr Asp Met Glu Trp Tyr Lys Cys Asp Ala Arg Thr Arg Lys Val Ile
                325                    330                    335

Leu Met Ile Leu Arg Arg Ser Gln Arg Ala Lys Thr Ile Ala Val Pro
                340                    345                    350

Phe Phe Thr Pro Ser Leu Pro Ala Leu Arg Ser Ile Leu Ser Thr Ala
            355                    360                    365

Gly Ser Tyr Ile Thr Leu Leu Lys Thr Phe Leu
        370                    375

<210> SEQ ID NO 5
<211> LENGTH: 1140
<212> TYPE: DNA
<213> ORGANISM: Drosophila melanogaster
<220> FEATURE:
<221> NAME/KEY: CDS
<222> LOCATION: (1)..(1137)
<223> OTHER INFORMATION: DOR23A.1, coding region of AF127925

<400> SEQUENCE: 5 atg aag ctc agc gaa acc cta aaa atc gac tat ttt cga gtc cag ttg      48
Met Lys Leu Ser Glu Thr Leu Lys Ile Asp Tyr Phe Arg Val Gln Leu
  1               5                  10                  15 aat gcc tgg cga att tgt ggt gcc ttg gat ctc agc gag ggt agg tac      96
Asn Ala Trp Arg Ile Cys Gly Ala Leu Asp Leu Ser Glu Gly Arg Tyr
             20                  25                  30 tgg agt tgg tcg atg cta ttg tgc atc ttg gtg tac ctg ccg aca ccc     144
Trp Ser Trp Ser Met Leu Leu Cys Ile Leu Val Tyr Leu Pro Thr Pro
         35                  40                  45 atg cta ctg aga gga gta tac agt ttc gaa gat ccg gtg gaa aat aat     192
Met Leu Leu Arg Gly Val Tyr Ser Phe Glu Asp Pro Val Glu Asn Asn
     50                  55                  60
```

| | | | | | | | | | | | | | | | | |
|---|---|---|---|---|---|---|---|---|---|---|---|---|---|---|---|---|
| | 50 | | | | 55 | | | | | 60 | | | | | | |
| ttc | agc | ttg | agc | ctg | acg | gtc | act | tcg | ctg | tcc | aat | ctc | atg | aag | ttc | 240 |
| Phe | Ser | Leu | Ser | Leu | Thr | Val | Thr | Ser | Leu | Ser | Asn | Leu | Met | Lys | Phe | |
| 65 | | | | | 70 | | | | | 75 | | | | | 80 | |
| tgc | atg | tac | gtg | gcc | caa | cta | aca | aag | atg | gtc | gag | gtc | cag | agt | ctt | 288 |
| Cys | Met | Tyr | Val | Ala | Gln | Leu | Thr | Lys | Met | Val | Glu | Val | Gln | Ser | Leu | |
| | | | | 85 | | | | | 90 | | | | | 95 | | |
| att | ggt | cag | ctg | gat | gcc | cgg | gtt | tct | ggc | gag | agc | cag | tct | gag | cgt | 336 |
| Ile | Gly | Gln | Leu | Asp | Ala | Arg | Val | Ser | Gly | Glu | Ser | Gln | Ser | Glu | Arg | |
| | | | 100 | | | | | 105 | | | | | 110 | | | |
| cat | aga | aat | atg | acc | gag | cac | ctg | cta | agg | atg | tcc | aag | ctg | ttc | cag | 384 |
| His | Arg | Asn | Met | Thr | Glu | His | Leu | Leu | Arg | Met | Ser | Lys | Leu | Phe | Gln | |
| | | 115 | | | | | 120 | | | | | 125 | | | | |
| atc | acc | tac | gct | gta | gtc | ttc | atc | att | gct | gca | gtt | ccc | ttc | gtt | ttc | 432 |
| Ile | Thr | Tyr | Ala | Val | Val | Phe | Ile | Ile | Ala | Ala | Val | Pro | Phe | Val | Phe | |
| | 130 | | | | | 135 | | | | | 140 | | | | | |
| gaa | act | gag | cta | agc | tta | ccc | atg | ccc | atg | tgg | ttt | ccc | ttc | gac | tgg | 480 |
| Glu | Thr | Glu | Leu | Ser | Leu | Pro | Met | Pro | Met | Trp | Phe | Pro | Phe | Asp | Trp | |
| 145 | | | | | 150 | | | | | 155 | | | | | 160 | |
| aag | aac | tcg | atg | gtg | gcc | tac | atc | gga | gct | ctg | gtt | ttc | cag | gag | att | 528 |
| Lys | Asn | Ser | Met | Val | Ala | Tyr | Ile | Gly | Ala | Leu | Val | Phe | Gln | Glu | Ile | |
| | | | | 165 | | | | | 170 | | | | | 175 | | |
| ggc | tat | gtc | ttt | caa | att | atg | caa | tgc | ttt | gca | gct | gac | tcg | ttt | ccc | 576 |
| Gly | Tyr | Val | Phe | Gln | Ile | Met | Gln | Cys | Phe | Ala | Ala | Asp | Ser | Phe | Pro | |
| | | | 180 | | | | | 185 | | | | | 190 | | | |
| ccg | ctc | gta | ctg | tac | ctg | atc | tcc | gag | caa | tgt | caa | ttg | ctg | atc | ctg | 624 |
| Pro | Leu | Val | Leu | Tyr | Leu | Ile | Ser | Glu | Gln | Cys | Gln | Leu | Leu | Ile | Leu | |
| | | 195 | | | | | 200 | | | | | 205 | | | | |
| aga | atc | tct | gaa | atc | gga | tat | ggt | tac | aag | act | ctg | gag | gag | aac | gaa | 672 |
| Arg | Ile | Ser | Glu | Ile | Gly | Tyr | Gly | Tyr | Lys | Thr | Leu | Glu | Glu | Asn | Glu | |
| | 210 | | | | | 215 | | | | | 220 | | | | | |
| cag | gat | ctg | gtc | aac | tgc | atc | agg | gat | caa | aac | gcg | ctg | tat | aga | tta | 720 |
| Gln | Asp | Leu | Val | Asn | Cys | Ile | Arg | Asp | Gln | Asn | Ala | Leu | Tyr | Arg | Leu | |
| 225 | | | | | 230 | | | | | 235 | | | | | 240 | |
| ctc | gat | gtg | acc | aag | agt | ctc | gtt | tcg | tat | ccc | atg | atg | gtg | cag | ttt | 768 |
| Leu | Asp | Val | Thr | Lys | Ser | Leu | Val | Ser | Tyr | Pro | Met | Met | Val | Gln | Phe | |
| | | | | 245 | | | | | 250 | | | | | 255 | | |
| atg | gtt | att | ggc | atc | aac | atc | gcc | atc | acc | cta | ttt | gtc | ctg | ata | ttt | 816 |
| Met | Val | Ile | Gly | Ile | Asn | Ile | Ala | Ile | Thr | Leu | Phe | Val | Leu | Ile | Phe | |
| | | | 260 | | | | | 265 | | | | | 270 | | | |
| tac | gtg | gag | acc | ttg | tac | gat | cgc | atc | tat | tat | ctt | tgc | ttt | ctc | ttg | 864 |
| Tyr | Val | Glu | Thr | Leu | Tyr | Asp | Arg | Ile | Tyr | Tyr | Leu | Cys | Phe | Leu | Leu | |
| | | 275 | | | | | 280 | | | | | 285 | | | | |
| ggc | atc | acc | gtg | cag | aca | tat | cca | ttg | tgc | tac | tat | gga | acc | atg | gtg | 912 |
| Gly | Ile | Thr | Val | Gln | Thr | Tyr | Pro | Leu | Cys | Tyr | Tyr | Gly | Thr | Met | Val | |
| | 290 | | | | | 295 | | | | | 300 | | | | | |
| cag | gag | agt | ttt | gct | gag | ctt | cac | tat | gcg | gta | ttc | tgc | agc | aac | tgg | 960 |
| Gln | Glu | Ser | Phe | Ala | Glu | Leu | His | Tyr | Ala | Val | Phe | Cys | Ser | Asn | Trp | |
| 305 | | | | | 310 | | | | | 315 | | | | | 320 | |
| gtg | gat | caa | agt | gcc | agc | tat | cgt | ggg | cac | atg | ctc | atc | ctg | gcg | gag | 1008 |
| Val | Asp | Gln | Ser | Ala | Ser | Tyr | Arg | Gly | His | Met | Leu | Ile | Leu | Ala | Glu | |
| | | | | 325 | | | | | 330 | | | | | 335 | | |
| cgc | act | aag | cgg | atg | cag | ctt | ctc | ctc | gcc | ggc | aac | ctg | gtg | ccc | atc | 1056 |
| Arg | Thr | Lys | Arg | Met | Gln | Leu | Leu | Leu | Ala | Gly | Asn | Leu | Val | Pro | Ile | |
| | | | 340 | | | | | 345 | | | | | 350 | | | |
| cac | ctg | agc | acc | tac | gtg | gcc | tgt | tgg | aag | gga | gcc | tac | tcc | ttc | ttc | 1104 |
| His | Leu | Ser | Thr | Tyr | Val | Ala | Cys | Trp | Lys | Gly | Ala | Tyr | Ser | Phe | Phe | |
| | | 355 | | | | | 360 | | | | | 365 | | | | |
| acc | ctg | atg | gcc | gat | cga | gat | ggc | ctg | ggt | tct | tag | | | | | 1140 |

-continued

```
Thr Leu Met Ala Asp Arg Asp Gly Leu Gly Ser
    370                 375
```

<210> SEQ ID NO 6
<211> LENGTH: 379
<212> TYPE: PRT
<213> ORGANISM: Drosophila melanogaster

<400> SEQUENCE: 6

```
Met Lys Leu Ser Glu Thr Leu Lys Ile Asp Tyr Phe Arg Val Gln Leu
 1               5                  10                  15

Asn Ala Trp Arg Ile Cys Gly Ala Leu Asp Leu Ser Glu Gly Arg Tyr
             20                  25                  30

Trp Ser Trp Ser Met Leu Leu Cys Ile Leu Val Tyr Leu Pro Thr Pro
         35                  40                  45

Met Leu Leu Arg Gly Val Tyr Ser Phe Glu Asp Pro Val Glu Asn Asn
     50                  55                  60

Phe Ser Leu Ser Leu Thr Val Thr Ser Leu Ser Asn Leu Met Lys Phe
 65                  70                  75                  80

Cys Met Tyr Val Ala Gln Leu Thr Lys Met Val Glu Val Gln Ser Leu
                 85                  90                  95

Ile Gly Gln Leu Asp Ala Arg Val Ser Gly Glu Ser Gln Ser Glu Arg
            100                 105                 110

His Arg Asn Met Thr Glu His Leu Leu Arg Met Ser Lys Leu Phe Gln
        115                 120                 125

Ile Thr Tyr Ala Val Val Phe Ile Ile Ala Ala Val Pro Phe Val Phe
    130                 135                 140

Glu Thr Glu Leu Ser Leu Pro Met Pro Met Trp Phe Pro Phe Asp Trp
145                 150                 155                 160

Lys Asn Ser Met Val Ala Tyr Ile Gly Ala Leu Val Phe Gln Glu Ile
                165                 170                 175

Gly Tyr Val Phe Gln Ile Met Gln Cys Phe Ala Ala Asp Ser Phe Pro
            180                 185                 190

Pro Leu Val Leu Tyr Leu Ile Ser Glu Gln Cys Gln Leu Leu Ile Leu
        195                 200                 205

Arg Ile Ser Glu Ile Gly Tyr Gly Tyr Lys Thr Leu Glu Glu Asn Glu
    210                 215                 220

Gln Asp Leu Val Asn Cys Ile Arg Asp Gln Asn Ala Leu Tyr Arg Leu
225                 230                 235                 240

Leu Asp Val Thr Lys Ser Leu Val Ser Tyr Pro Met Met Val Gln Phe
                245                 250                 255

Met Val Ile Gly Ile Asn Ile Ala Ile Thr Leu Phe Val Leu Ile Phe
            260                 265                 270

Tyr Val Glu Thr Leu Tyr Asp Arg Ile Tyr Tyr Leu Cys Phe Leu Leu
        275                 280                 285

Gly Ile Thr Val Gln Thr Tyr Pro Leu Cys Tyr Tyr Gly Thr Met Val
    290                 295                 300

Gln Glu Ser Phe Ala Glu Leu His Tyr Ala Val Phe Cys Ser Asn Trp
305                 310                 315                 320

Val Asp Gln Ser Ala Ser Tyr Arg Gly His Met Leu Ile Leu Ala Glu
                325                 330                 335

Arg Thr Lys Arg Met Gln Leu Leu Leu Ala Gly Asn Leu Val Pro Ile
            340                 345                 350

His Leu Ser Thr Tyr Val Ala Cys Trp Lys Gly Ala Tyr Ser Phe Phe
        355                 360                 365
```

```
Thr Leu Met Ala Asp Arg Asp Gly Leu Gly Ser
        370                 375

<210> SEQ ID NO 7
<211> LENGTH: 1143
<212> TYPE: DNA
<213> ORGANISM: Drosophila melanogaster
<220> FEATURE:
<221> NAME/KEY: CDS
<222> LOCATION: (1)..(1140)
<223> OTHER INFORMATION: DOR 24D.1, a coding region on BDGP Clone No.
      AC004371

<400> SEQUENCE: 7 atg tta cct cga ttc ctg acc gcc tcc tat cca atg gag cgc cat tat      48
Met Leu Pro Arg Phe Leu Thr Ala Ser Tyr Pro Met Glu Arg His Tyr
 1               5                  10                  15 ttc atg gtg cca aag ttt gca tta tcg ctg att ggt ttt tat ccc gaa      96
Phe Met Val Pro Lys Phe Ala Leu Ser Leu Ile Gly Phe Tyr Pro Glu
             20                  25                  30 cag aag cga acg gtt ttg gtg aaa ctt tgg agt ttc ttc aac ttt ttc     144
Gln Lys Arg Thr Val Leu Val Lys Leu Trp Ser Phe Phe Asn Phe Phe
         35                  40                  45 atc ctc acc tac ggc tgt tat gca gag gct tac tat ggc ata cac tat     192
Ile Leu Thr Tyr Gly Cys Tyr Ala Glu Ala Tyr Tyr Gly Ile His Tyr
     50                  55                  60 ata ccg att aac ata gcc act gca ttg gat gcc ctt tgt cct gtg gcc     240
Ile Pro Ile Asn Ile Ala Thr Ala Leu Asp Ala Leu Cys Pro Val Ala
 65                  70                  75                  80 tcc agc att ttg tcg ctg gtg aaa atg gtc gcc att tgg tgg tat caa     288
Ser Ser Ile Leu Ser Leu Val Lys Met Val Ala Ile Trp Trp Tyr Gln
                 85                  90                  95 gat gaa tta agg agt ttg ata gag cgg agg ttc tat aca ctg gca acg     336
Asp Glu Leu Arg Ser Leu Ile Glu Arg Arg Phe Tyr Thr Leu Ala Thr
            100                 105                 110 caa cta aca ttc ctg cta cta tgc tgt gga ttt tgc acc agt act tcc     384
Gln Leu Thr Phe Leu Leu Leu Cys Cys Gly Phe Cys Thr Ser Thr Ser
        115                 120                 125 tat tcc gtc aga cat ttg att gat aat atc ctg aga cgc acc cat ggc     432
Tyr Ser Val Arg His Leu Ile Asp Asn Ile Leu Arg Arg Thr His Gly
    130                 135                 140 aag gac tgg atc tac gag act ccg ttc aag atg atg ttc ccc gat ctt     480
Lys Asp Trp Ile Tyr Glu Thr Pro Phe Lys Met Met Phe Pro Asp Leu
145                 150                 155                 160 ctc ctg cgt ttg cca ctc tat ccc atc acc tat ata ctc gtg cat tgg     528
Leu Leu Arg Leu Pro Leu Tyr Pro Ile Thr Tyr Ile Leu Val His Trp
                165                 170                 175 cat ggc tac att act gtg gtt tgt ttt gtc ggc gcg gat ggt ttc ttc     576
His Gly Tyr Ile Thr Val Val Cys Phe Val Gly Ala Asp Gly Phe Phe
            180                 185                 190 ctg ggg ttc tgt ttg tac ttc act gtt ttg ctc tgt ctg cag gac         624
Leu Gly Phe Cys Leu Tyr Phe Thr Val Leu Leu Cys Leu Gln Asp
        195                 200                 205 gat gtt tgt gat tta cta gag gtt gaa aac atc gag aag agt ccc tcc     672
Asp Val Cys Asp Leu Leu Glu Val Glu Asn Ile Glu Lys Ser Pro Ser
    210                 215                 220 gaa gcg gag gaa gct cgc ata gtt cgg gaa atg gaa aaa ctg gtg gac     720
Glu Ala Glu Glu Ala Arg Ile Val Arg Glu Met Glu Lys Leu Val Asp
225                 230                 235                 240 cgg cat aac gag gtg gcc gag ctg aca gaa aga ttg tcg ggt gtt atg     768
Arg His Asn Glu Val Ala Glu Leu Thr Glu Arg Leu Ser Gly Val Met
```

```
                245                 250                 255
gtg gaa ata aca ctg gcc cac ttt gtt act tcg agt ttg ata atc gga    816
Val Glu Ile Thr Leu Ala His Phe Val Thr Ser Ser Leu Ile Ile Gly
        260                 265                 270 acc agc gtg gtg gat att tta tta ttt tcc ggc ctg gga atc att gtg    864
Thr Ser Val Val Asp Ile Leu Leu Phe Ser Gly Leu Gly Ile Ile Val
            275                 280                 285 tat gtg gtc tac act tgt gcc gta ggt gtg gaa ata ttt cta tac tgt    912
Tyr Val Val Tyr Thr Cys Ala Val Gly Val Glu Ile Phe Leu Tyr Cys
    290                 295                 300 tta gga gga tct cat att atg gaa gcg tgt tcc aat cta gcg cgc tcc    960
Leu Gly Gly Ser His Ile Met Glu Ala Cys Ser Asn Leu Ala Arg Ser
305                 310                 315                 320 aca ttt tcc agc cac tgg tat ggc cac agt gtt cgg gtc caa aag atg   1008
Thr Phe Ser Ser His Trp Tyr Gly His Ser Val Arg Val Gln Lys Met
                325                 330                 335 acc ctt ttg atg gta gct cgt gct caa cga gtt ctc aca att aaa att   1056
Thr Leu Leu Met Val Ala Arg Ala Gln Arg Val Leu Thr Ile Lys Ile
            340                 345                 350 cct ttc ttt tcc cca tca tta gag act cta act tcg att ttg cgc ttc   1104
Pro Phe Phe Ser Pro Ser Leu Glu Thr Leu Thr Ser Ile Leu Arg Phe
    355                 360                 365 act gga tct ctg att gcc ctg gca aag tcg gtt ata taa               1143
Thr Gly Ser Leu Ile Ala Leu Ala Lys Ser Val Ile
370                 375                 380

<210> SEQ ID NO 8
<211> LENGTH: 380
<212> TYPE: PRT
<213> ORGANISM: Drosophila melanogaster

<400> SEQUENCE: 8

Met Leu Pro Arg Phe Leu Thr Ala Ser Tyr Pro Met Glu Arg His Tyr
  1               5                  10                  15

Phe Met Val Pro Lys Phe Ala Leu Ser Leu Ile Gly Phe Tyr Pro Glu
                 20                  25                  30

Gln Lys Arg Thr Val Leu Val Lys Leu Trp Ser Phe Phe Asn Phe Phe
             35                  40                  45

Ile Leu Thr Tyr Gly Cys Tyr Ala Glu Ala Tyr Gly Ile His Tyr
         50                  55                  60

Ile Pro Ile Asn Ile Ala Thr Ala Leu Asp Ala Leu Cys Pro Val Ala
 65                  70                  75                  80

Ser Ser Ile Leu Ser Leu Val Lys Met Val Ala Ile Trp Trp Tyr Gln
                 85                  90                  95

Asp Glu Leu Arg Ser Leu Ile Glu Arg Arg Phe Tyr Thr Leu Ala Thr
            100                 105                 110

Gln Leu Thr Phe Leu Leu Cys Cys Gly Phe Cys Thr Ser Thr Ser
        115                 120                 125

Tyr Ser Val Arg His Leu Ile Asp Asn Ile Leu Arg Arg Thr His Gly
    130                 135                 140

Lys Asp Trp Ile Tyr Glu Thr Pro Phe Lys Met Met Phe Pro Asp Leu
145                 150                 155                 160

Leu Leu Arg Leu Pro Leu Tyr Pro Ile Thr Tyr Ile Leu Val His Trp
                165                 170                 175

His Gly Tyr Ile Thr Val Val Cys Phe Val Gly Ala Asp Gly Phe Phe
            180                 185                 190

Leu Gly Phe Cys Leu Tyr Phe Thr Val Leu Leu Leu Cys Leu Gln Asp
```

```
                195                 200                 205
Asp Val Cys Asp Leu Leu Glu Val Glu Asn Ile Glu Lys Ser Pro Ser
        210                 215                 220

Glu Ala Glu Ala Arg Ile Val Arg Glu Met Glu Lys Leu Val Asp
225                 230                 235                 240

Arg His Asn Glu Val Ala Glu Leu Thr Glu Arg Leu Ser Gly Val Met
                245                 250                 255

Val Glu Ile Thr Leu Ala His Phe Val Thr Ser Ser Leu Ile Ile Gly
            260                 265                 270

Thr Ser Val Val Asp Ile Leu Leu Phe Ser Gly Leu Gly Ile Ile Val
        275                 280                 285

Tyr Val Val Tyr Thr Cys Ala Val Gly Val Glu Ile Phe Leu Tyr Cys
        290                 295                 300

Leu Gly Gly Ser His Ile Met Glu Ala Cys Ser Asn Leu Ala Arg Ser
305                 310                 315                 320

Thr Phe Ser Ser His Trp Tyr Gly His Ser Val Arg Val Gln Lys Met
                325                 330                 335

Thr Leu Leu Met Val Ala Arg Ala Gln Arg Val Leu Thr Ile Lys Ile
            340                 345                 350

Pro Phe Phe Ser Pro Ser Leu Glu Thr Leu Thr Ser Ile Leu Arg Phe
        355                 360                 365

Thr Gly Ser Leu Ile Ala Leu Ala Lys Ser Val Ile
    370                 375                 380

<210> SEQ ID NO 9
<211> LENGTH: 1212
<212> TYPE: DNA
<213> ORGANISM: Drosophila melanogaster
<220> FEATURE:
<221> NAME/KEY: CDS
<222> LOCATION: (1)..(1209)

<400> SEQUENCE: 9 atg ttc gga cac ttt aag ctc gtc tat ccg gct cct ata tcg gag ccc      48
Met Phe Gly His Phe Lys Leu Val Tyr Pro Ala Pro Ile Ser Glu Pro
 1               5                  10                  15 ata cag tct agg gat tcg aat gca tac atg atg gag acg ctg cga aat     96
Ile Gln Ser Arg Asp Ser Asn Ala Tyr Met Met Glu Thr Leu Arg Asn
            20                  25                  30 tcg ggc ttg aat ttg aag aac gat ttc ggt ata ggc cgc aag att tgg    144
Ser Gly Leu Asn Leu Lys Asn Asp Phe Gly Ile Gly Arg Lys Ile Trp
        35                  40                  45 agg gtg ttt tcg ttc acc tac aat atg gtg ata ctt ccc gta agt ttc    192
Arg Val Phe Ser Phe Thr Tyr Asn Met Val Ile Leu Pro Val Ser Phe
    50                  55                  60 cca atc aac tat gtg ata cat ctg gcg gag ttc ccg ccg gag ctg ctg    240
Pro Ile Asn Tyr Val Ile His Leu Ala Glu Phe Pro Pro Glu Leu Leu
65                  70                  75                  80 ctg caa tcc ctg caa ctg tgc ctc aac act tgg tgc ttc gct ctg aag    288
Leu Gln Ser Leu Gln Leu Cys Leu Asn Thr Trp Cys Phe Ala Leu Lys
                85                  90                  95 ttc ttc act ctg atc gtc tat acg cac cgc ttg gag ctg gcc aac aag    336
Phe Phe Thr Leu Ile Val Tyr Thr His Arg Leu Glu Leu Ala Asn Lys
            100                 105                 110 cac ttt gac gaa ttg gat aag tac tgc gtg aag ccg gcg gag aag cgc    384
His Phe Asp Glu Leu Asp Lys Tyr Cys Val Lys Pro Ala Glu Lys Arg
        115                 120                 125 aag gtt cgc gac atg gtg gcc act att aca aga ctg tac ctg acc ttc    432
```

```
                                                                            -continued Lys Val Arg Asp Met Val Ala Thr Ile Thr Arg Leu Tyr Leu Thr Phe
    130                 135                 140
gtc gtg gtc tac gtc ctc tac gcc acc tcc acg cta ctg gac gga cta       480
Val Val Val Tyr Val Leu Tyr Ala Thr Ser Thr Leu Leu Asp Gly Leu
145                 150                 155                 160
ctg cac cac cgt gtt ccc tac aat acg tac tat ccg ttc ata aac tgg       528
Leu His His Arg Val Pro Tyr Asn Thr Tyr Tyr Pro Phe Ile Asn Trp
                165                 170                 175
cga gtc gat cgg acc cag atg tac atc cag agt ttt ctg gag tac ttc       576
Arg Val Asp Arg Thr Gln Met Tyr Ile Gln Ser Phe Leu Glu Tyr Phe
            180                 185                 190
acc gtg ggt tat gcc ata tat gtg gcc acc gcc acc gat tcc tac cct       624
Thr Val Gly Tyr Ala Ile Tyr Val Ala Thr Ala Thr Asp Ser Tyr Pro
        195                 200                 205
gtg att tac gtg gca gcc ctg cga act cat att ctc ttg ctc aag gac       672
Val Ile Tyr Val Ala Ala Leu Arg Thr His Ile Leu Leu Leu Lys Asp
    210                 215                 220
cgt atc att tac ttg ggc gat ccc agc aac gag ggt agc agc gac ccg       720
Arg Ile Ile Tyr Leu Gly Asp Pro Ser Asn Glu Gly Ser Ser Asp Pro
225                 230                 235                 240
agc tac atg ttt aaa tcg ttg gtg gat tgt atc aag gca cac aga acc       768
Ser Tyr Met Phe Lys Ser Leu Val Asp Cys Ile Lys Ala His Arg Thr
                245                 250                 255
atg cta aat ttt tgt gat gcc att caa cca atc atc tct ggc acg ata       816
Met Leu Asn Phe Cys Asp Ala Ile Gln Pro Ile Ile Ser Gly Thr Ile
            260                 265                 270
ttt gcc caa ttc atc ata tgc gga tcg atc ctg ggc ata att atg atc       864
Phe Ala Gln Phe Ile Ile Cys Gly Ser Ile Leu Gly Ile Ile Met Ile
        275                 280                 285
aac atg gta ttg ttc gct gat caa tcg acc cga ttc ggc ata gtc atc       912
Asn Met Val Leu Phe Ala Asp Gln Ser Thr Arg Phe Gly Ile Val Ile
    290                 295                 300
tac gtt atg gcc gtc ctt ctg cag act ttt ccg ctt tgc ttc tac tgc       960
Tyr Val Met Ala Val Leu Leu Gln Thr Phe Pro Leu Cys Phe Tyr Cys
305                 310                 315                 320
aac gcc atc gtg gac gac tgc aaa gaa ctg gcc cac gca ctt ttc cat      1008
Asn Ala Ile Val Asp Asp Cys Lys Glu Leu Ala His Ala Leu Phe His
                325                 330                 335
tcc gcc tgg tgg gtg cag gac aag cga tac cag cgg act gtc atc cag      1056
Ser Ala Trp Trp Val Gln Asp Lys Arg Tyr Gln Arg Thr Val Ile Gln
            340                 345                 350
ttc ctg cag aaa ctg cag cag ccc atg acc ttc acc gcc atg aac ata      1104
Phe Leu Gln Lys Leu Gln Gln Pro Met Thr Phe Thr Ala Met Asn Ile
        355                 360                 365
ttt aac att aat ttg gcc act aac atc aat gta gcc aag ttc gcc ttc      1152
Phe Asn Ile Asn Leu Ala Thr Asn Ile Asn Val Ala Lys Phe Ala Phe
    370                 375                 380
acc gtg tac gcc atc gcg agc ggt atg aac ctg gac caa aag tta agc      1200
Thr Val Tyr Ala Ile Ala Ser Gly Met Asn Leu Asp Gln Lys Leu Ser
385                 390                 395                 400
att aag gaa tag                                                      1212
Ile Lys Glu <210> SEQ ID NO 10
<211> LENGTH: 403
<212> TYPE: PRT
<213> ORGANISM: Drosophila melanogaster

<400> SEQUENCE: 10

Met Phe Gly His Phe Lys Leu Val Tyr Pro Ala Pro Ile Ser Glu Pro
```

```
                1               5              10              15
            Ile Gln Ser Arg Asp Ser Asn Ala Tyr Met Met Glu Thr Leu Arg Asn
                         20                  25                  30

Ser Gly Leu Asn Leu Lys Asn Asp Phe Gly Ile Gly Arg Lys Ile Trp
                     35                  40                  45

Arg Val Phe Ser Phe Thr Tyr Asn Met Val Ile Leu Pro Val Ser Phe
                 50                  55                  60

Pro Ile Asn Tyr Val Ile His Leu Ala Glu Phe Pro Pro Glu Leu Leu
            65                  70                  75                  80

Leu Gln Ser Leu Gln Leu Cys Leu Asn Thr Trp Cys Phe Ala Leu Lys
                             85                  90                  95

Phe Phe Thr Leu Ile Val Tyr Thr His Arg Leu Glu Leu Ala Asn Lys
                        100                 105                 110

His Phe Asp Glu Leu Asp Lys Tyr Cys Val Lys Pro Ala Glu Lys Arg
                        115                 120                 125

Lys Val Arg Asp Met Val Ala Thr Ile Thr Arg Leu Tyr Leu Thr Phe
                        130                 135                 140

Val Val Val Tyr Val Leu Tyr Ala Thr Ser Thr Leu Leu Asp Gly Leu
            145                 150                 155                 160

Leu His His Arg Val Pro Tyr Asn Thr Tyr Tyr Pro Phe Ile Asn Trp
                            165                 170                 175

Arg Val Asp Arg Thr Gln Met Tyr Ile Gln Ser Phe Leu Glu Tyr Phe
                        180                 185                 190

Thr Val Gly Tyr Ala Ile Tyr Val Ala Thr Ala Thr Asp Ser Tyr Pro
                        195                 200                 205

Val Ile Tyr Val Ala Ala Leu Arg Thr His Ile Leu Leu Leu Lys Asp
                    210                 215                 220

Arg Ile Ile Tyr Leu Gly Asp Pro Ser Asn Glu Gly Ser Ser Asp Pro
            225                 230                 235                 240

Ser Tyr Met Phe Lys Ser Leu Val Asp Cys Ile Lys Ala His Arg Thr
                            245                 250                 255

Met Leu Asn Phe Cys Asp Ala Ile Gln Pro Ile Ile Ser Gly Thr Ile
                        260                 265                 270

Phe Ala Gln Phe Ile Ile Cys Gly Ser Ile Leu Gly Ile Ile Met Ile
                        275                 280                 285

Asn Met Val Leu Phe Ala Asp Gln Ser Thr Arg Phe Gly Ile Val Ile
            290                 295                 300

Tyr Val Met Ala Val Leu Leu Gln Thr Phe Pro Leu Cys Phe Tyr Cys
            305                 310                 315                 320

Asn Ala Ile Val Asp Asp Cys Lys Glu Leu Ala His Ala Leu Phe His
                        325                 330                 335

Ser Ala Trp Trp Val Gln Asp Lys Arg Tyr Gln Arg Thr Val Ile Gln
                        340                 345                 350

Phe Leu Gln Lys Leu Gln Gln Pro Met Thr Phe Thr Ala Met Asn Ile
                        355                 360                 365

Phe Asn Ile Asn Leu Ala Thr Asn Ile Asn Val Ala Lys Phe Ala Phe
                        370                 375                 380

Thr Val Tyr Ala Ile Ala Ser Gly Met Asn Leu Asp Gln Lys Leu Ser
            385                 390                 395                 400

Ile Lys Glu

<210> SEQ ID NO 11
<211> LENGTH: 1137
```

-continued

```
<212> TYPE: DNA
<213> ORGANISM: Drosophila melanogaster
<220> FEATURE:
<221> NAME/KEY: CDS
<222> LOCATION: (1)..(1134)
<223> OTHER INFORMATION: DOR 33B.1, a coding region on BDGP Clone No.
      AC006240

<400> SEQUENCE: 11
```

| | | | | | | | | | | | | | | | | |
|---|---|---|---|---|---|---|---|---|---|---|---|---|---|---|---|---|
| atg | gat | tca | aga | agg | aaa | gtc | cga | agt | gaa | aat | ctt | tac | aaa | acc | tat | 48 |
| Met | Asp | Ser | Arg | Arg | Lys | Val | Arg | Ser | Glu | Asn | Leu | Tyr | Lys | Thr | Tyr | |
| 1 | | | | 5 | | | | | 10 | | | | | 15 | | |
| tgg | ctt | tac | tgg | cga | ctt | ctg | gga | gtc | gag | ggc | gat | tat | cct | ttt | cga | 96 |
| Trp | Leu | Tyr | Trp | Arg | Leu | Leu | Gly | Val | Glu | Gly | Asp | Tyr | Pro | Phe | Arg | |
| | | | 20 | | | | | 25 | | | | | 30 | | | |
| cgg | cta | gtg | gat | ttt | aca | atc | acg | tct | ttc | att | acg | att | tta | ttt | ccc | 144 |
| Arg | Leu | Val | Asp | Phe | Thr | Ile | Thr | Ser | Phe | Ile | Thr | Ile | Leu | Phe | Pro | |
| | | 35 | | | | | 40 | | | | | 45 | | | | |
| gtg | cat | ctt | ata | ctg | gga | atg | tat | aaa | aag | ccc | cag | att | caa | gtc | ttc | 192 |
| Val | His | Leu | Ile | Leu | Gly | Met | Tyr | Lys | Lys | Pro | Gln | Ile | Gln | Val | Phe | |
| | 50 | | | | | 55 | | | | | 60 | | | | | |
| agg | agt | ctg | cat | ttc | aca | tcg | gaa | tgc | ctt | ttc | tgc | agc | tat | aag | ttt | 240 |
| Arg | Ser | Leu | His | Phe | Thr | Ser | Glu | Cys | Leu | Phe | Cys | Ser | Tyr | Lys | Phe | |
| 65 | | | | | 70 | | | | | 75 | | | | | 80 | |
| ttc | tgt | ttt | cgt | tgg | aaa | ctt | aaa | gaa | ata | aag | acc | atc | gaa | gga | ttg | 288 |
| Phe | Cys | Phe | Arg | Trp | Lys | Leu | Lys | Glu | Ile | Lys | Thr | Ile | Glu | Gly | Leu | |
| | | | | 85 | | | | | 90 | | | | | 95 | | |
| ctc | cag | gat | ctc | gat | agt | cga | gtt | gaa | agt | gaa | gaa | gaa | cgc | aac | tac | 336 |
| Leu | Gln | Asp | Leu | Asp | Ser | Arg | Val | Glu | Ser | Glu | Glu | Glu | Arg | Asn | Tyr | |
| | | | 100 | | | | | 105 | | | | | 110 | | | |
| ttt | aat | caa | aat | cca | agt | cgt | gtg | gct | cga | atg | ctt | tcg | aaa | agt | tac | 384 |
| Phe | Asn | Gln | Asn | Pro | Ser | Arg | Val | Ala | Arg | Met | Leu | Ser | Lys | Ser | Tyr | |
| | | 115 | | | | | 120 | | | | | 125 | | | | |
| ttg | gta | gct | gct | ata | tcg | gcc | ata | atc | act | gca | act | gta | gct | ggt | tta | 432 |
| Leu | Val | Ala | Ala | Ile | Ser | Ala | Ile | Ile | Thr | Ala | Thr | Val | Ala | Gly | Leu | |
| | 130 | | | | | 135 | | | | | 140 | | | | | |
| ttt | agt | act | ggt | cga | aat | tta | atg | tat | ctg | ggt | tgg | ttt | ccc | tac | gat | 480 |
| Phe | Ser | Thr | Gly | Arg | Asn | Leu | Met | Tyr | Leu | Gly | Trp | Phe | Pro | Tyr | Asp | |
| 145 | | | | | 150 | | | | | 155 | | | | | 160 | |
| ttt | caa | gca | acc | gcc | gca | atc | tat | tgg | att | agt | ttt | tcc | tat | cag | gcg | 528 |
| Phe | Gln | Ala | Thr | Ala | Ala | Ile | Tyr | Trp | Ile | Ser | Phe | Ser | Tyr | Gln | Ala | |
| | | | | 165 | | | | | 170 | | | | | 175 | | |
| att | ggc | tct | agt | ctg | ttg | att | ctg | gaa | aat | ctg | gcc | aac | gat | tca | tat | 576 |
| Ile | Gly | Ser | Ser | Leu | Leu | Ile | Leu | Glu | Asn | Leu | Ala | Asn | Asp | Ser | Tyr | |
| | | | 180 | | | | | 185 | | | | | 190 | | | |
| ccg | ccg | att | aca | ttt | tgt | gtg | gtc | tct | gga | cat | gtg | aga | cta | ttg | ata | 624 |
| Pro | Pro | Ile | Thr | Phe | Cys | Val | Val | Ser | Gly | His | Val | Arg | Leu | Leu | Ile | |
| | | 195 | | | | | 200 | | | | | 205 | | | | |
| atg | cgt | tta | agt | cga | att | ggt | cac | gat | gta | aaa | tta | tca | agt | tcg | gaa | 672 |
| Met | Arg | Leu | Ser | Arg | Ile | Gly | His | Asp | Val | Lys | Leu | Ser | Ser | Ser | Glu | |
| | 210 | | | | | 215 | | | | | 220 | | | | | |
| aat | acc | aga | aaa | ctc | atc | gaa | ggt | atc | cag | gat | cac | agg | aaa | cta | atg | 720 |
| Asn | Thr | Arg | Lys | Leu | Ile | Glu | Gly | Ile | Gln | Asp | His | Arg | Lys | Leu | Met | |
| 225 | | | | | 230 | | | | | 235 | | | | | 240 | |
| aag | ata | ata | cgc | cta | ctt | cgc | agc | act | tta | cat | ctt | agc | caa | ctg | ggc | 768 |
| Lys | Ile | Ile | Arg | Leu | Leu | Arg | Ser | Thr | Leu | His | Leu | Ser | Gln | Leu | Gly | |
| | | | | 245 | | | | | 250 | | | | | 255 | | |
| cag | ttc | ctt | tct | agt | gga | atc | aac | att | tcc | ata | aca | ctc | atc | aac | atc | 816 |
| Gln | Phe | Leu | Ser | Ser | Gly | Ile | Asn | Ile | Ser | Ile | Thr | Leu | Ile | Asn | Ile | |
| | | | | 260 | | | | | 265 | | | | | 270 | | |
| ctg | ttc | ttt | gcg | gaa | aac | aac | ttt | gca | atg | ctt | tat | tat | gcg | gtg | ttc | 864 |

```
Leu Phe Phe Ala Glu Asn Asn Phe Ala Met Leu Tyr Tyr Ala Val Phe
        275                 280                 285
ttt gct gca atg tta ata gaa cta ttt cca agt tgt tac tat gga att      912
Phe Ala Ala Met Leu Ile Glu Leu Phe Pro Ser Cys Tyr Tyr Gly Ile
290                 295                 300
ctg atg aca atg gag ttt gat aag cta cca tat gcc atc ttc tcc agc      960
Leu Met Thr Met Glu Phe Asp Lys Leu Pro Tyr Ala Ile Phe Ser Ser
305                 310                 315                 320
aac tgg ctt aaa atg gat aaa aga tac aat cga tcc ttg ata att ctg     1008
Asn Trp Leu Lys Met Asp Lys Arg Tyr Asn Arg Ser Leu Ile Ile Leu
            325                 330                 335
atg caa cta aca ctg gtt cca gtg aat ata aaa gca ggt ggt att gtt     1056
Met Gln Leu Thr Leu Val Pro Val Asn Ile Lys Ala Gly Gly Ile Val
            340                 345                 350
ggc atc gat atg agt gca ttt ttt gcc aca gtt cgg atg gca tat tcc     1104
Gly Ile Asp Met Ser Ala Phe Phe Ala Thr Val Arg Met Ala Tyr Ser
            355                 360                 365
ttt tac act tta gcc ttg tca ttt cga gta tag                          1137
Phe Tyr Thr Leu Ala Leu Ser Phe Arg Val
            370                 375

<210> SEQ ID NO 12
<211> LENGTH: 378
<212> TYPE: PRT
<213> ORGANISM: Drosophila melanogaster

<400> SEQUENCE: 12

Met Asp Ser Arg Arg Lys Val Arg Ser Glu Asn Leu Tyr Lys Thr Tyr
1               5                   10                  15

Trp Leu Tyr Trp Arg Leu Leu Gly Val Glu Gly Asp Tyr Pro Phe Arg
            20                  25                  30

Arg Leu Val Asp Phe Thr Ile Thr Ser Phe Ile Thr Ile Leu Phe Pro
        35                  40                  45

Val His Leu Ile Leu Gly Met Tyr Lys Lys Pro Gln Ile Gln Val Phe
    50                  55                  60

Arg Ser Leu His Phe Thr Ser Glu Cys Leu Phe Cys Ser Tyr Lys Phe
65                  70                  75                  80

Phe Cys Phe Arg Trp Lys Leu Lys Glu Ile Lys Thr Ile Glu Gly Leu
                85                  90                  95

Leu Gln Asp Leu Asp Ser Arg Val Glu Ser Glu Glu Arg Asn Tyr
            100                 105                 110

Phe Asn Gln Asn Pro Ser Arg Val Ala Arg Met Leu Ser Lys Ser Tyr
        115                 120                 125

Leu Val Ala Ala Ile Ser Ala Ile Ile Thr Ala Thr Val Ala Gly Leu
    130                 135                 140

Phe Ser Thr Gly Arg Asn Leu Met Tyr Leu Gly Trp Phe Pro Tyr Asp
145                 150                 155                 160

Phe Gln Ala Thr Ala Ala Ile Tyr Trp Ile Ser Phe Ser Tyr Gln Ala
                165                 170                 175

Ile Gly Ser Ser Leu Leu Ile Leu Glu Asn Leu Ala Asn Asp Ser Tyr
            180                 185                 190

Pro Pro Ile Thr Phe Cys Val Val Ser Gly His Val Arg Leu Leu Ile
        195                 200                 205

Met Arg Leu Ser Arg Ile Gly His Asp Val Lys Leu Ser Ser Ser Glu
    210                 215                 220

Asn Thr Arg Lys Leu Ile Glu Gly Ile Gln Asp His Arg Lys Leu Met
225                 230                 235                 240
```

```
Lys Ile Ile Arg Leu Leu Arg Ser Thr Leu His Leu Ser Gln Leu Gly
            245                 250                 255

Gln Phe Leu Ser Ser Gly Ile Asn Ile Ser Ile Thr Leu Ile Asn Ile
        260                 265                 270

Leu Phe Phe Ala Glu Asn Asn Phe Ala Met Leu Tyr Tyr Ala Val Phe
        275                 280                 285

Phe Ala Ala Met Leu Ile Glu Leu Phe Pro Ser Cys Tyr Tyr Gly Ile
        290                 295                 300

Leu Met Thr Met Glu Phe Asp Lys Leu Pro Tyr Ala Ile Phe Ser Ser
305                 310                 315                 320

Asn Trp Leu Lys Met Asp Lys Arg Tyr Asn Arg Ser Leu Ile Ile Leu
                325                 330                 335

Met Gln Leu Thr Leu Val Pro Val Asn Ile Lys Ala Gly Gly Ile Val
            340                 345                 350

Gly Ile Asp Met Ser Ala Phe Phe Ala Thr Val Arg Met Ala Tyr Ser
        355                 360                 365

Phe Tyr Thr Leu Ala Leu Ser Phe Arg Val
        370                 375
```

<210> SEQ ID NO 13
<211> LENGTH: 1140
<212> TYPE: DNA
<213> ORGANISM: Drosophila melanogaster
<220> FEATURE:
<221> NAME/KEY: CDS
<222> LOCATION: (1)..(1137)
<223> OTHER INFORMATION: DOR 33B.2, a coding region on BDGP Clone No. AC006240

<400> SEQUENCE: 13

```
atg gac tta aaa ccg cga gtc att cga agt gaa gat atc tac aga acc        48
Met Asp Leu Lys Pro Arg Val Ile Arg Ser Glu Asp Ile Tyr Arg Thr
 1               5                  10                  15 tat tgg tta tat tgg cat ctt ttg ggc ctg gaa agc aat ttc ttt ctg        96
Tyr Trp Leu Tyr Trp His Leu Leu Gly Leu Glu Ser Asn Phe Phe Leu
             20                  25                  30 aat cgc ttg ttg gat ttg gtg att aca att ttc gta acc att tgg tat       144
Asn Arg Leu Leu Asp Leu Val Ile Thr Ile Phe Val Thr Ile Trp Tyr
         35                  40                  45 cca att cac ctg att ctg gga ctg ttt atg gaa aga tct ttg ggg gat       192
Pro Ile His Leu Ile Leu Gly Leu Phe Met Glu Arg Ser Leu Gly Asp
     50                  55                  60 gtc tgc aag ggt cta cca att acg gca gca tgc ttt ttc gcc agc ttt       240
Val Cys Lys Gly Leu Pro Ile Thr Ala Ala Cys Phe Phe Ala Ser Phe
 65                  70                  75                  80 aaa ttt att tgt ttt cgc ttc aag cta tct gaa att aaa gaa atc gaa       288
Lys Phe Ile Cys Phe Arg Phe Lys Leu Ser Glu Ile Lys Glu Ile Glu
                 85                  90                  95 ata tta ttt aaa gag ctg gat cag cga gct tta agt cga gag gaa tgc       336
Ile Leu Phe Lys Glu Leu Asp Gln Arg Ala Leu Ser Arg Glu Glu Cys
            100                 105                 110 gag ttt ttc aat caa aat acg aga cgt gag gcg aat ttc att tgg aaa       384
Glu Phe Phe Asn Gln Asn Thr Arg Arg Glu Ala Asn Phe Ile Trp Lys
        115                 120                 125 agt ttc att gtg gcc tat gga ctg tcg aat atc tcg gct att gca tca       432
Ser Phe Ile Val Ala Tyr Gly Leu Ser Asn Ile Ser Ala Ile Ala Ser
    130                 135                 140 gtt ctt ttc ggc ggt gga cat aag cta tta tat ccc gcc tgg ttt cca       480
Val Leu Phe Gly Gly Gly His Lys Leu Leu Tyr Pro Ala Trp Phe Pro
```

-continued

| | | | | | | | | | | | | | | | | |
|---|---|---|---|---|---|---|---|---|---|---|---|---|---|---|---|---|
| | 145 | | | | 150 | | | | | 155 | | | | | 160 | |
| tac | gat | gtg | cag | gcc | acg | gaa | cta | ata | ttt | tgg | cta | agt | gta | aca | tac | 528 |
| Tyr | Asp | Val | Gln | Ala | Thr | Glu | Leu | Ile | Phe | Trp | Leu | Ser | Val | Thr | Tyr | |
| | | | | 165 | | | | | 170 | | | | | 175 | | |
| caa | att | gcc | gga | gta | agt | ttg | gcc | ata | ctt | cag | aat | ttg | gcc | aat | gat | 576 |
| Gln | Ile | Ala | Gly | Val | Ser | Leu | Ala | Ile | Leu | Gln | Asn | Leu | Ala | Asn | Asp | |
| | | | 180 | | | | | 185 | | | | | 190 | | | |
| tcc | tat | cca | ccg | atg | aca | ttt | tgc | gtg | gtt | gcc | ggt | cat | gta | aga | ctt | 624 |
| Ser | Tyr | Pro | Pro | Met | Thr | Phe | Cys | Val | Val | Ala | Gly | His | Val | Arg | Leu | |
| | | 195 | | | | | 200 | | | | | 205 | | | | |
| ttg | gcg | atg | cgc | ttg | agt | aga | att | ggc | caa | ggt | cca | gag | gaa | aca | ata | 672 |
| Leu | Ala | Met | Arg | Leu | Ser | Arg | Ile | Gly | Gln | Gly | Pro | Glu | Glu | Thr | Ile | |
| | 210 | | | | | 215 | | | | | 220 | | | | | |
| tac | tta | acc | gga | aag | caa | tta | atc | gaa | agc | atc | gag | gat | cac | cga | aaa | 720 |
| Tyr | Leu | Thr | Gly | Lys | Gln | Leu | Ile | Glu | Ser | Ile | Glu | Asp | His | Arg | Lys | |
| 225 | | | | | 230 | | | | | 235 | | | | | 240 | |
| cta | atg | aaa | ata | gtg | gaa | tta | ctg | cgc | agc | acc | atg | aat | att | tcg | cag | 768 |
| Leu | Met | Lys | Ile | Val | Glu | Leu | Leu | Arg | Ser | Thr | Met | Asn | Ile | Ser | Gln | |
| | | | | 245 | | | | | 250 | | | | | 255 | | |
| ctc | ggc | cag | ttt | att | tca | agt | ggt | gtt | aat | att | tcc | ata | aca | cta | gtc | 816 |
| Leu | Gly | Gln | Phe | Ile | Ser | Ser | Gly | Val | Asn | Ile | Ser | Ile | Thr | Leu | Val | |
| | | | 260 | | | | | 265 | | | | | 270 | | | |
| aac | att | ctc | ttc | ttt | gcg | gat | aat | aat | ttc | gct | ata | acc | tac | tac | gga | 864 |
| Asn | Ile | Leu | Phe | Phe | Ala | Asp | Asn | Asn | Phe | Ala | Ile | Thr | Tyr | Tyr | Gly | |
| | | 275 | | | | | 280 | | | | | 285 | | | | |
| gtg | tac | ttc | cta | tcg | atg | gtg | ttg | gaa | tta | ttc | ccg | tgc | tgc | tat | tac | 912 |
| Val | Tyr | Phe | Leu | Ser | Met | Val | Leu | Glu | Leu | Phe | Pro | Cys | Cys | Tyr | Tyr | |
| | 290 | | | | | 295 | | | | | 300 | | | | | |
| ggc | acc | ctg | ata | tcc | gtg | gag | atg | aac | cag | ctg | acc | tat | gcg | att | tac | 960 |
| Gly | Thr | Leu | Ile | Ser | Val | Glu | Met | Asn | Gln | Leu | Thr | Tyr | Ala | Ile | Tyr | |
| 305 | | | | | 310 | | | | | 315 | | | | | 320 | |
| tca | agt | aac | tgg | atg | agt | atg | aat | cgg | agc | tac | agc | cgc | atc | cta | ctg | 1008 |
| Ser | Ser | Asn | Trp | Met | Ser | Met | Asn | Arg | Ser | Tyr | Ser | Arg | Ile | Leu | Leu | |
| | | | | 325 | | | | | 330 | | | | | 335 | | |
| atc | ttc | atg | caa | ctc | acc | ctg | gcg | gaa | gtg | cag | atc | aag | gcc | ggt | ggg | 1056 |
| Ile | Phe | Met | Gln | Leu | Thr | Leu | Ala | Glu | Val | Gln | Ile | Lys | Ala | Gly | Gly | |
| | | | 340 | | | | | 345 | | | | | 350 | | | |
| atg | att | ggc | atc | gga | atg | aac | gcc | ttc | ttt | gcc | acc | gtg | cga | ttg | gcc | 1104 |
| Met | Ile | Gly | Ile | Gly | Met | Asn | Ala | Phe | Phe | Ala | Thr | Val | Arg | Leu | Ala | |
| | | 355 | | | | | 360 | | | | | 365 | | | | |
| tac | tcc | ttc | ttc | act | ttg | gcc | atg | tcg | ctg | cgt | taa | | | | | 1140 |
| Tyr | Ser | Phe | Phe | Thr | Leu | Ala | Met | Ser | Leu | Arg | | | | | | |
| | 370 | | | | | 375 | | | | | | | | | | |

<210> SEQ ID NO 14
<211> LENGTH: 379
<212> TYPE: PRT
<213> ORGANISM: Drosophila melanogaster

<400> SEQUENCE: 14

Met Asp Leu Lys Pro Arg Val Ile Arg Ser Glu Asp Ile Tyr Arg Thr
 1               5                  10                  15

Tyr Trp Leu Tyr Trp His Leu Leu Gly Leu Glu Ser Asn Phe Phe Leu
            20                  25                  30

Asn Arg Leu Leu Asp Leu Val Ile Thr Ile Phe Val Thr Ile Trp Tyr
         35                  40                  45

Pro Ile His Leu Ile Leu Gly Leu Phe Met Glu Arg Ser Leu Gly Asp
     50                  55                  60

Val Cys Lys Gly Leu Pro Ile Thr Ala Ala Cys Phe Phe Ala Ser Phe

```
                65                  70                  75                  80
Lys Phe Ile Cys Phe Arg Phe Lys Leu Ser Glu Ile Lys Glu Ile Glu
                    85                  90                  95

Ile Leu Phe Lys Glu Leu Asp Gln Arg Ala Leu Ser Arg Glu Glu Cys
                100                 105                 110

Glu Phe Phe Asn Gln Asn Thr Arg Arg Glu Ala Asn Phe Ile Trp Lys
                115                 120                 125

Ser Phe Ile Val Ala Tyr Gly Leu Ser Asn Ile Ser Ala Ile Ala Ser
            130                 135                 140

Val Leu Phe Gly Gly Gly His Lys Leu Leu Tyr Pro Ala Trp Phe Pro
145                 150                 155                 160

Tyr Asp Val Gln Ala Thr Glu Leu Ile Phe Trp Leu Ser Val Thr Tyr
                165                 170                 175

Gln Ile Ala Gly Val Ser Leu Ala Ile Leu Gln Asn Leu Ala Asn Asp
            180                 185                 190

Ser Tyr Pro Pro Met Thr Phe Cys Val Val Ala Gly His Val Arg Leu
        195                 200                 205

Leu Ala Met Arg Leu Ser Arg Ile Gly Gln Gly Pro Glu Glu Thr Ile
    210                 215                 220

Tyr Leu Thr Gly Lys Gln Leu Ile Glu Ser Ile Glu Asp His Arg Lys
225                 230                 235                 240

Leu Met Lys Ile Val Glu Leu Leu Arg Ser Thr Met Asn Ile Ser Gln
                245                 250                 255

Leu Gly Gln Phe Ile Ser Ser Gly Val Asn Ile Ser Ile Thr Leu Val
            260                 265                 270

Asn Ile Leu Phe Ala Asp Asn Phe Ala Ile Thr Tyr Tyr Gly
        275                 280                 285

Val Tyr Phe Leu Ser Met Val Leu Glu Leu Phe Pro Cys Cys Tyr Tyr
    290                 295                 300

Gly Thr Leu Ile Ser Val Glu Met Asn Gln Leu Thr Tyr Ala Ile Tyr
305                 310                 315                 320

Ser Ser Asn Trp Met Ser Met Asn Arg Ser Tyr Ser Arg Ile Leu Leu
                325                 330                 335

Ile Phe Met Gln Leu Thr Leu Ala Glu Val Gln Ile Lys Ala Gly Gly
            340                 345                 350

Met Ile Gly Ile Gly Met Asn Ala Phe Phe Ala Thr Val Arg Leu Ala
        355                 360                 365

Tyr Ser Phe Phe Thr Leu Ala Met Ser Leu Arg
    370                 375
```

<210> SEQ ID NO 15
<211> LENGTH: 1155
<212> TYPE: DNA
<213> ORGANISM: Drosophila melanogaster
<220> FEATURE:
<221> NAME/KEY: CDS
<222> LOCATION: (1)..(1152)
<223> OTHER INFORMATION: DOR 33B3.3, a coding region on BDGP Clone No. AC006240

<400> SEQUENCE: 15

```
atg gtc att atc gac agt ctt agt ttt tat cgt cca ttc tgg atc tgc      48
Met Val Ile Ile Asp Ser Leu Ser Phe Tyr Arg Pro Phe Trp Ile Cys
 1               5                  10                  15 atg cga ttg ctg gta ccg act ttc ttc aag gat tcc tca cgt cct gtc      96
Met Arg Leu Leu Val Pro Thr Phe Phe Lys Asp Ser Ser Arg Pro Val
                20                  25                  30
```

```
cag ctg tac gtg gtg ttg ctg cac atc ctg gtc acc ttg tgg ttt cca      144
Gln Leu Tyr Val Val Leu Leu His Ile Leu Val Thr Leu Trp Phe Pro
         35                  40                  45 ctg cat ctg ctg ctg cat ctt ctg cta ctt cca tct acc gct gag ttc      192
Leu His Leu Leu Leu His Leu Leu Leu Pro Ser Thr Ala Glu Phe
 50                  55                  60 ttt aag aac ctg acc atg tct ctg act tgt gtg gcc tgc agt ctg aag      240
Phe Lys Asn Leu Thr Met Ser Leu Thr Cys Val Ala Cys Ser Leu Lys
 65                  70                  75                  80 cat gtg gcc cac ttg tat cac ttg ccg cag att gtg gaa atc gaa tca      288
His Val Ala His Leu Tyr His Leu Pro Gln Ile Val Glu Ile Glu Ser
                 85                  90                  95 ctg atc gag caa tta gac aca ttt att gcc agc gaa cag gag cat cgt      336
Leu Ile Glu Gln Leu Asp Thr Phe Ile Ala Ser Glu Gln Glu His Arg
            100                 105                 110 tac tat cgg gat cac gta cat tgc cat gct agg cgc ttt aca aga tgt      384
Tyr Tyr Arg Asp His Val His Cys His Ala Arg Arg Phe Thr Arg Cys
                115                 120                 125 ctc tat att agc ttt ggc atg atc tat gcg ctt ttc ctg ttc ggc gtc      432
Leu Tyr Ile Ser Phe Gly Met Ile Tyr Ala Leu Phe Leu Phe Gly Val
    130                 135                 140 ttc gtt cag gtt att agc gga aat tgg gaa ctt ctc tat cca gcc tat      480
Phe Val Gln Val Ile Ser Gly Asn Trp Glu Leu Leu Tyr Pro Ala Tyr
145                 150                 155                 160 ttc cca ttc gac ttg gag agc aat cgc ttt ctc ggc gca gta gcc ttg      528
Phe Pro Phe Asp Leu Glu Ser Asn Arg Phe Leu Gly Ala Val Ala Leu
                165                 170                 175 ggc tat cag gta ttc agc atg tta gtt gaa ggc ttc cag ggg ctg ggc      576
Gly Tyr Gln Val Phe Ser Met Leu Val Glu Gly Phe Gln Gly Leu Gly
            180                 185                 190 aac gat acc tat acc cca ctg acc cta tgc ctt ctg gcc gga cat gtc      624
Asn Asp Thr Tyr Thr Pro Leu Thr Leu Cys Leu Leu Ala Gly His Val
        195                 200                 205 cat ttg tgg tcc ata cga atg ggt caa ctg gga tac ttc gat gac gag      672
His Leu Trp Ser Ile Arg Met Gly Gln Leu Gly Tyr Phe Asp Asp Glu
    210                 215                 220 acg gtg gtg aat cat cag cgt ttg ctg gat tac att gag cag cat aaa      720
Thr Val Val Asn His Gln Arg Leu Leu Asp Tyr Ile Glu Gln His Lys
225                 230                 235                 240 ctc ttg gtg cga ttc cac aac ctg gtg agc cgg acc atc agc gaa gtg      768
Leu Leu Val Arg Phe His Asn Leu Val Ser Arg Thr Ile Ser Glu Val
                245                 250                 255 caa ctg gtg cag ctg ggc gga tgt gga gcc act ctg tgc atc att gtc      816
Gln Leu Val Gln Leu Gly Gly Cys Gly Ala Thr Leu Cys Ile Ile Val
            260                 265                 270 tcc tac atg ctc ttc ttt gtg ggc gac aca atc tcg ctg gtc tac tac      864
Ser Tyr Met Leu Phe Phe Val Gly Asp Thr Ile Ser Leu Val Tyr Tyr
        275                 280                 285 ttg gtg ttc ttt gga gtg gtc tgc gtg cag ctc ttt ccc agc tgc tat      912
Leu Val Phe Phe Gly Val Val Cys Val Gln Leu Phe Pro Ser Cys Tyr
    290                 295                 300 ttt gcc agc gaa gta gcc gag gag ttg gaa cgg ctg cca tat gcg atc      960
Phe Ala Ser Glu Val Ala Glu Glu Leu Glu Arg Leu Pro Tyr Ala Ile
305                 310                 315                 320 ttc tcc agc aga tgg tac gat caa tcg cgg gat cat cga ttc gat ttg     1008
Phe Ser Ser Arg Trp Tyr Asp Gln Ser Arg Asp His Arg Phe Asp Leu
                325                 330                 335 ctc atc ttt aca caa tta aca ctg gga aac cgg ggg tgg atc atc aag     1056
Leu Ile Phe Thr Gln Leu Thr Leu Gly Asn Arg Gly Trp Ile Ile Lys
```

```
                    340             345             350
gca gga ggt ctt atc gag ctg aat ttg aat gcc ttt ttc gcc acc ctg    1104
Ala Gly Gly Leu Ile Glu Leu Asn Leu Asn Ala Phe Phe Ala Thr Leu
            355                 360                 365 aag atg gcc tat tcc ctt ttt gca gtt gtg gtg cgg gca aag ggt ata    1152
Lys Met Ala Tyr Ser Leu Phe Ala Val Val Val Arg Ala Lys Gly Ile
    370                 375                 380 tag                                                                 1155
```

<210> SEQ ID NO 16
<211> LENGTH: 384
<212> TYPE: PRT
<213> ORGANISM: Drosophila melanogaster

<400> SEQUENCE: 16

```
Met Val Ile Ile Asp Ser Leu Ser Phe Tyr Arg Pro Phe Trp Ile Cys
 1               5                  10                  15

Met Arg Leu Leu Val Pro Thr Phe Phe Lys Asp Ser Ser Arg Pro Val
                20                  25                  30

Gln Leu Tyr Val Val Leu Leu His Ile Leu Val Thr Leu Trp Phe Pro
            35                  40                  45

Leu His Leu Leu Leu His Leu Leu Leu Pro Ser Thr Ala Glu Phe
        50                  55                  60

Phe Lys Asn Leu Thr Met Ser Leu Thr Cys Val Ala Cys Ser Leu Lys
 65                  70                  75                  80

His Val Ala His Leu Tyr His Leu Pro Gln Ile Val Glu Ile Glu Ser
                85                  90                  95

Leu Ile Glu Gln Leu Asp Thr Phe Ile Ala Ser Glu Gln Glu His Arg
            100                 105                 110

Tyr Tyr Arg Asp His Val His Cys His Ala Arg Arg Phe Thr Arg Cys
        115                 120                 125

Leu Tyr Ile Ser Phe Gly Met Ile Tyr Ala Leu Phe Leu Phe Gly Val
    130                 135                 140

Phe Val Gln Val Ile Ser Gly Asn Trp Glu Leu Tyr Pro Ala Tyr
145                 150                 155                 160

Phe Pro Phe Asp Leu Glu Ser Asn Arg Phe Leu Gly Ala Val Ala Leu
                165                 170                 175

Gly Tyr Gln Val Phe Ser Met Leu Val Glu Gly Phe Gln Gly Leu Gly
            180                 185                 190

Asn Asp Thr Tyr Thr Pro Leu Thr Leu Cys Leu Leu Ala Gly His Val
        195                 200                 205

His Leu Trp Ser Ile Arg Met Gly Gln Leu Gly Tyr Phe Asp Asp Glu
    210                 215                 220

Thr Val Asn His Gln Arg Leu Leu Asp Tyr Ile Glu Gln His Lys
225                 230                 235                 240

Leu Leu Val Arg Phe His Asn Leu Val Ser Arg Thr Ile Ser Glu Val
                245                 250                 255

Gln Leu Val Gln Leu Gly Gly Cys Gly Ala Thr Leu Cys Ile Ile Val
            260                 265                 270

Ser Tyr Met Leu Phe Phe Val Gly Asp Thr Ile Ser Leu Val Tyr Tyr
        275                 280                 285

Leu Val Phe Phe Gly Val Val Cys Val Gln Leu Phe Pro Ser Cys Tyr
    290                 295                 300

Phe Ala Ser Glu Val Ala Glu Glu Leu Glu Arg Leu Pro Tyr Ala Ile
305                 310                 315                 320
```

```
Phe Ser Ser Arg Trp Tyr Asp Gln Ser Arg Asp His Arg Phe Asp Leu
            325                 330                 335

Leu Ile Phe Thr Gln Leu Thr Leu Gly Asn Arg Gly Trp Ile Ile Lys
        340                 345                 350

Ala Gly Gly Leu Ile Glu Leu Asn Leu Asn Ala Phe Phe Ala Thr Leu
            355                 360                 365

Lys Met Ala Tyr Ser Leu Phe Ala Val Val Arg Ala Lys Gly Ile
        370                 375                 380

<210> SEQ ID NO 17
<211> LENGTH: 1152
<212> TYPE: DNA
<213> ORGANISM: Drosophila melanogaster
<220> FEATURE:
<221> NAME/KEY: CDS
<222> LOCATION: (1)..(1149)
<223> OTHER INFORMATION: DOR 43B.1, coding region of AF127926

<400> SEQUENCE: 17 atg aca atc gag gat atc ggc ctg gtg ggc atc aac gtg cgg atg tgg      48
Met Thr Ile Glu Asp Ile Gly Leu Val Gly Ile Asn Val Arg Met Trp
 1               5                  10                  15 cga cac ttg gcc gtg ctg tac ccc act ccg ggc tcc agc tgg cgc aag      96
Arg His Leu Ala Val Leu Tyr Pro Thr Pro Gly Ser Ser Trp Arg Lys
                20                  25                  30 ttc gcc ttc gtg ctg ccg gtg act gcg atg aat ctg atg cag ttc gtc     144
Phe Ala Phe Val Leu Pro Val Thr Ala Met Asn Leu Met Gln Phe Val
            35                  40                  45 tac ctg ctg cgg atg tgg ggc gac ctg ccc gcc ttc att ctg aac atg     192
Tyr Leu Leu Arg Met Trp Gly Asp Leu Pro Ala Phe Ile Leu Asn Met
        50                  55                  60 ttc ttc ttc tcg gcc att ttc aac gcc ctg atg cgc acg tgg ctg gtc     240
Phe Phe Phe Ser Ala Ile Phe Asn Ala Leu Met Arg Thr Trp Leu Val
 65                 70                  75                  80 ata atc aag cgg cgc cag ttc gag gag ttt ctc ggc caa ctg gcc act     288
Ile Ile Lys Arg Arg Gln Phe Glu Glu Phe Leu Gly Gln Leu Ala Thr
                85                  90                  95 ctg ttc cat tcg att ctc gac tcc acc gac gag tgg ggg cgt ggc atc     336
Leu Phe His Ser Ile Leu Asp Ser Thr Asp Glu Trp Gly Arg Gly Ile
            100                 105                 110 ctg cgg agg gcg gaa cgg gag gct cgg aac ctg gcc atc ctt aat ttg     384
Leu Arg Arg Ala Glu Arg Glu Ala Arg Asn Leu Ala Ile Leu Asn Leu
        115                 120                 125 agt gcc tcc ttc ctg gac att gtc ggt gct ctg ttt ttc gaa tat aaa     432
Ser Ala Ser Phe Leu Asp Ile Val Gly Ala Leu Phe Phe Glu Tyr Lys
    130                 135                 140 ttc cca att ggt gtt gtc act ttt ttc ctt cca gct cat ccc ttc ggc     480
Phe Pro Ile Gly Val Val Thr Phe Phe Leu Pro Ala His Pro Phe Gly
145                 150                 155                 160 tta gct cta cca gga gtg agc atg acc agt tca ccc gtc tac gag gtt     528
Leu Ala Leu Pro Gly Val Ser Met Thr Ser Ser Pro Val Tyr Glu Val
                165                 170                 175 atc tac ttg gcc caa ctg cct acg ccc ctg ctg tcc atg atg tac         576
Ile Tyr Leu Ala Gln Leu Pro Thr Pro Leu Leu Ser Met Met Tyr
            180                 185                 190 atg cct ttc gtc agc ctt ttt gcc ggc ctg gcc atc ttt ggg aag gcc     624
Met Pro Phe Val Ser Leu Phe Ala Gly Leu Ala Ile Phe Gly Lys Ala
        195                 200                 205 atg ctg cag atc ctg gta cac agg ctg ggc cag att ggc gga gaa gag     672
Met Leu Gln Ile Leu Val His Arg Leu Gly Gln Ile Gly Gly Glu Glu
```

```
                210                 215                 220
cag tcg gag gag gag cgc ttc caa agg ctg gcc tcc tgc att gcg tac        720
Gln Ser Glu Glu Glu Arg Phe Gln Arg Leu Ala Ser Cys Ile Ala Tyr
225                 230                 235                 240 cac acg cag gtg atg cgc tat gtg tgg cag ctc aac aaa ctg gtg gcc        768
His Thr Gln Val Met Arg Tyr Val Trp Gln Leu Asn Lys Leu Val Ala
            245                 250                 255 aac att gtg gcg gtg gaa gca att att ttt ggc tcg ata atc tgc tca        816
Asn Ile Val Ala Val Glu Ala Ile Ile Phe Gly Ser Ile Ile Cys Ser
        260                 265                 270 ctg ctc ttc tgt ctg aat att ata acc tca ccc acc cag gtg atc tcg        864
Leu Leu Phe Cys Leu Asn Ile Ile Thr Ser Pro Thr Gln Val Ile Ser
    275                 280                 285 ata gtg atg tac att ctg acc atg ctg tac gtt ctc ttc acc tac tac        912
Ile Val Met Tyr Ile Leu Thr Met Leu Tyr Val Leu Phe Thr Tyr Tyr
290                 295                 300 aat cgg gcc aat gaa ata tgc ctc gag aac aac cgg gtg gcg gag gct        960
Asn Arg Ala Asn Glu Ile Cys Leu Glu Asn Asn Arg Val Ala Glu Ala
305                 310                 315                 320 gtt tac aat gtg ccc tgg tac gag gca gga act cgg ttt cgc aaa acc       1008
Val Tyr Asn Val Pro Trp Tyr Glu Ala Gly Thr Arg Phe Arg Lys Thr
            325                 330                 335 ctc ctg atc ttc ttg atg caa aca caa cac ccg atg gag ata aga gtc       1056
Leu Leu Ile Phe Leu Met Gln Thr Gln His Pro Met Glu Ile Arg Val
        340                 345                 350 ggc aac gtt tac ccc atg aca ttg gcc atg ttc cag agt ctg ttg aat       1104
Gly Asn Val Tyr Pro Met Thr Leu Ala Met Phe Gln Ser Leu Leu Asn
    355                 360                 365 gcg tcc tac tcc tac ttt acc atg ctg cgt ggc gtc acc ggc aaa tga       1152
Ala Ser Tyr Ser Tyr Phe Thr Met Leu Arg Gly Val Thr Gly Lys
370                 375                 380

<210> SEQ ID NO 18
<211> LENGTH: 383
<212> TYPE: PRT
<213> ORGANISM: Drosophila melanogaster

<400> SEQUENCE: 18

Met Thr Ile Glu Asp Ile Gly Leu Val Gly Ile Asn Val Arg Met Trp
1               5                   10                  15

Arg His Leu Ala Val Leu Tyr Pro Thr Pro Gly Ser Ser Trp Arg Lys
            20                  25                  30

Phe Ala Phe Val Leu Pro Val Thr Ala Met Asn Leu Met Gln Phe Val
        35                  40                  45

Tyr Leu Leu Arg Met Trp Gly Asp Leu Pro Ala Phe Ile Leu Asn Met
    50                  55                  60

Phe Phe Phe Ser Ala Ile Phe Asn Ala Leu Met Arg Thr Trp Leu Val
65                  70                  75                  80

Ile Ile Lys Arg Arg Gln Phe Glu Glu Phe Leu Gly Gln Leu Ala Thr
                85                  90                  95

Leu Phe His Ser Ile Leu Asp Ser Thr Asp Glu Trp Gly Arg Gly Ile
            100                 105                 110

Leu Arg Arg Ala Glu Arg Glu Ala Arg Asn Leu Ala Ile Leu Asn Leu
        115                 120                 125

Ser Ala Ser Phe Leu Asp Ile Val Gly Ala Leu Phe Phe Glu Tyr Lys
    130                 135                 140

Phe Pro Ile Gly Val Val Thr Phe Leu Pro Ala His Pro Phe Gly
145                 150                 155                 160
```

```
Leu Ala Leu Pro Gly Val Ser Met Thr Ser Ser Pro Val Tyr Glu Val
            165                 170                 175

Ile Tyr Leu Ala Gln Leu Pro Thr Pro Leu Leu Leu Ser Met Met Tyr
            180                 185                 190

Met Pro Phe Val Ser Leu Phe Ala Gly Leu Ala Ile Phe Gly Lys Ala
            195                 200                 205

Met Leu Gln Ile Leu Val His Arg Leu Gly Gln Ile Gly Gly Glu Glu
            210                 215                 220

Gln Ser Glu Glu Glu Arg Phe Gln Arg Leu Ala Ser Cys Ile Ala Tyr
225                 230                 235                 240

His Thr Gln Val Met Arg Tyr Val Trp Gln Leu Asn Lys Leu Val Ala
            245                 250                 255

Asn Ile Val Ala Val Glu Ala Ile Ile Phe Gly Ser Ile Ile Cys Ser
            260                 265                 270

Leu Leu Phe Cys Leu Asn Ile Ile Thr Ser Pro Thr Gln Val Ile Ser
            275                 280                 285

Ile Val Met Tyr Ile Leu Thr Met Leu Tyr Val Leu Phe Thr Tyr Tyr
            290                 295                 300

Asn Arg Ala Asn Glu Ile Cys Leu Glu Asn Asn Arg Val Ala Glu Ala
305                 310                 315                 320

Val Tyr Asn Val Pro Trp Tyr Glu Ala Gly Thr Arg Phe Arg Lys Thr
            325                 330                 335

Leu Leu Ile Phe Leu Met Gln Thr Gln His Pro Met Glu Ile Arg Val
            340                 345                 350

Gly Asn Val Tyr Pro Met Thr Leu Ala Met Phe Gln Ser Leu Leu Asn
            355                 360                 365

Ala Ser Tyr Ser Tyr Phe Thr Met Leu Arg Gly Val Thr Gly Lys
            370                 375                 380

<210> SEQ ID NO 19
<211> LENGTH: 1158
<212> TYPE: DNA
<213> ORGANISM: Drosophila melanogaster
<220> FEATURE:
<221> NAME/KEY: CDS
<222> LOCATION: (1)..(1155)
<223> OTHER INFORMATION: DOR 46F.1, a coding region on BDGP Clone No.
      AC005974

<400> SEQUENCE: 19 atg agc aaa gga gta gaa atc ttt tac aag ggc cag aag gca ttc ttg      48
Met Ser Lys Gly Val Glu Ile Phe Tyr Lys Gly Gln Lys Ala Phe Leu
 1               5                  10                  15 aac atc ctc tcg ttg tgg cct cag ata gaa cgc cgg tgg aga atc atc      96
Asn Ile Leu Ser Leu Trp Pro Gln Ile Glu Arg Arg Trp Arg Ile Ile
             20                  25                  30 cac cag gtg aac tat gtc cac gta att gtg ttt tgg gtg ctg ctc ttt     144
His Gln Val Asn Tyr Val His Val Ile Val Phe Trp Val Leu Leu Phe
         35                  40                  45 gat ctc ctc ttg gtg ctc cat gtg atg gct aat ttg agc tac atg tcc     192
Asp Leu Leu Leu Val Leu His Val Met Ala Asn Leu Ser Tyr Met Ser
     50                  55                  60 gag gtt gtg aaa gcc atc ttt atc ctg gcc acc agt gca ggg cac acc     240
Glu Val Val Lys Ala Ile Phe Ile Leu Ala Thr Ser Ala Gly His Thr
 65                  70                  75                  80 acc aag ctg ctg tcc ata aag gcg aac aat gtg cag atg gag gag ctc     288
Thr Lys Leu Leu Ser Ile Lys Ala Asn Asn Val Gln Met Glu Glu Leu
                 85                  90                  95
```

```
ttt agg aga ttg gat aac gaa gag ttc cgt cct aga ggc gcc aac gaa    336
Phe Arg Arg Leu Asp Asn Glu Glu Phe Arg Pro Arg Gly Ala Asn Glu
            100                 105                 110 gag ttg atc ttt gca gca gcc tgt gaa aga agt agg aag ctt cgg gac    384
Glu Leu Ile Phe Ala Ala Ala Cys Glu Arg Ser Arg Lys Leu Arg Asp
            115                 120                 125 ttc tat gga gcg ctt tcg ttt gcc gcc ttg agc atg att ctc ata ccc    432
Phe Tyr Gly Ala Leu Ser Phe Ala Ala Leu Ser Met Ile Leu Ile Pro
        130                 135                 140 cag ttc gcc ttg gac tgg tcc cac ctt ccg ctc aaa aca tac aat ccg    480
Gln Phe Ala Leu Asp Trp Ser His Leu Pro Leu Lys Thr Tyr Asn Pro
145                 150                 155                 160 ctt ggc gag aat acc ggc tca cct gct tat tgg ctc ctc tac tgc tat    528
Leu Gly Glu Asn Thr Gly Ser Pro Ala Tyr Trp Leu Leu Tyr Cys Tyr
                165                 170                 175 cag tgt ctg gcc ttg tcc gta tcc tgc atc acc aac ata gga ttc gac    576
Gln Cys Leu Ala Leu Ser Val Ser Cys Ile Thr Asn Ile Gly Phe Asp
            180                 185                 190 tca ctc tgc tcc tca ctg ttc atc ttc ctc aag tgc cag ctg gac att    624
Ser Leu Cys Ser Ser Leu Phe Ile Phe Leu Lys Cys Gln Leu Asp Ile
            195                 200                 205 ctg gcc gtg cga ctg gac aag atc ggt cgg tta atc act act tct ggt    672
Leu Ala Val Arg Leu Asp Lys Ile Gly Arg Leu Ile Thr Thr Ser Gly
210                 215                 220 ggc act gtg gaa cag caa ctt aag gaa aat atc cgc tat cac atg acc    720
Gly Thr Val Glu Gln Gln Leu Lys Glu Asn Ile Arg Tyr His Met Thr
225                 230                 235                 240 atc gtt gaa ctg tcg aaa acc gtg gag cgt cta ctt tgc aag ccg att    768
Ile Val Glu Leu Ser Lys Thr Val Glu Arg Leu Leu Cys Lys Pro Ile
                245                 250                 255 tcg gtg cag atc ttc tgc tcg gtt ttg gtg ctg act gcc aat ttc tat    816
Ser Val Gln Ile Phe Cys Ser Val Leu Val Leu Thr Ala Asn Phe Tyr
            260                 265                 270 gcc att gct gtg tta tct gac gag agg ctg gag ctc ttt aag tat gtg    864
Ala Ile Ala Val Leu Ser Asp Glu Arg Leu Glu Leu Phe Lys Tyr Val
        275                 280                 285 acc tat cag gcg tgc atg ttg att cag att ttt ata ttg tgc tac tat    912
Thr Tyr Gln Ala Cys Met Leu Ile Gln Ile Phe Ile Leu Cys Tyr Tyr
    290                 295                 300 gcc ggt gag gta acc cag cgc agc ctg gac ctt ccg cac gag ctg tac    960
Ala Gly Glu Val Thr Gln Arg Ser Leu Asp Leu Pro His Glu Leu Tyr
305                 310                 315                 320 aag acc tcc tgg gtg gac tgg gac tac agg agc cga agg att gcg ctc   1008
Lys Thr Ser Trp Val Asp Trp Asp Tyr Arg Ser Arg Arg Ile Ala Leu
                325                 330                 335 ctc ttt atg caa cgc ctt cac tcg acc ttg agg att agg aca ctt aat   1056
Leu Phe Met Gln Arg Leu His Ser Thr Leu Arg Ile Arg Thr Leu Asn
            340                 345                 350 cca agt ctt ggt ttt gac tta atg ctc ttc agc tcg gtg agt tct ttc   1104
Pro Ser Leu Gly Phe Asp Leu Met Leu Phe Ser Ser Val Ser Ser Phe
        355                 360                 365 cgt gtt ttg act ttt ttg tgc act gta gcc aat ttc cat aat gag gct   1152
Arg Val Leu Thr Phe Leu Cys Thr Val Ala Asn Phe His Asn Glu Ala
    370                 375                 380 cat tag                                                            1158
His
385

<210> SEQ ID NO 20
```

-continued

```
<211> LENGTH: 385
<212> TYPE: PRT
<213> ORGANISM: Drosophila melanogaster

<400> SEQUENCE: 20

Met Ser Lys Gly Val Glu Ile Phe Tyr Lys Gly Gln Lys Ala Phe Leu
 1               5                  10                  15

Asn Ile Leu Ser Leu Trp Pro Gln Ile Glu Arg Arg Trp Arg Ile Ile
            20                  25                  30

His Gln Val Asn Tyr Val His Val Ile Val Phe Trp Val Leu Leu Phe
        35                  40                  45

Asp Leu Leu Val Leu His Val Met Ala Asn Leu Ser Tyr Met Ser
    50                  55                  60

Glu Val Val Lys Ala Ile Phe Ile Leu Ala Thr Ser Ala Gly His Thr
 65                  70                  75                  80

Thr Lys Leu Leu Ser Ile Lys Ala Asn Asn Val Gln Met Glu Glu Leu
                85                  90                  95

Phe Arg Arg Leu Asp Asn Glu Glu Phe Arg Pro Arg Gly Ala Asn Glu
            100                 105                 110

Glu Leu Ile Phe Ala Ala Ala Cys Glu Arg Ser Arg Lys Leu Arg Asp
        115                 120                 125

Phe Tyr Gly Ala Leu Ser Phe Ala Ala Leu Ser Met Ile Leu Ile Pro
    130                 135                 140

Gln Phe Ala Leu Asp Trp Ser His Leu Pro Leu Lys Thr Tyr Asn Pro
145                 150                 155                 160

Leu Gly Glu Asn Thr Gly Ser Pro Ala Tyr Trp Leu Leu Tyr Cys Tyr
                165                 170                 175

Gln Cys Leu Ala Leu Ser Val Ser Cys Ile Thr Asn Ile Gly Phe Asp
            180                 185                 190

Ser Leu Cys Ser Ser Leu Phe Ile Phe Leu Lys Cys Gln Leu Asp Ile
        195                 200                 205

Leu Ala Val Arg Leu Asp Lys Ile Gly Arg Leu Ile Thr Thr Ser Gly
    210                 215                 220

Gly Thr Val Glu Gln Gln Leu Lys Glu Asn Ile Arg Tyr His Met Thr
225                 230                 235                 240

Ile Val Glu Leu Ser Lys Thr Val Glu Arg Leu Leu Cys Lys Pro Ile
                245                 250                 255

Ser Val Gln Ile Phe Cys Ser Val Leu Val Leu Thr Ala Asn Phe Tyr
            260                 265                 270

Ala Ile Ala Val Leu Ser Asp Glu Arg Leu Glu Leu Phe Lys Tyr Val
        275                 280                 285

Thr Tyr Gln Ala Cys Met Leu Ile Gln Ile Phe Ile Leu Cys Tyr Tyr
    290                 295                 300

Ala Gly Glu Val Thr Gln Arg Ser Leu Asp Leu Pro His Glu Leu Tyr
305                 310                 315                 320

Lys Thr Ser Trp Val Asp Trp Asp Tyr Arg Ser Arg Arg Ile Ala Leu
                325                 330                 335

Leu Phe Met Gln Arg Leu His Ser Thr Leu Arg Ile Arg Thr Leu Asn
            340                 345                 350

Pro Ser Leu Gly Phe Asp Leu Met Leu Phe Ser Ser Val Ser Ser Phe
        355                 360                 365

Arg Val Leu Thr Phe Leu Cys Thr Val Ala Asn Phe His Asn Glu Ala
    370                 375                 380

His
```

```
385

<210> SEQ ID NO 21
<211> LENGTH: 1155
<212> TYPE: DNA
<213> ORGANISM: Drosophila melanogaster
<220> FEATURE:
<221> NAME/KEY: CDS
<222> LOCATION: (1)..(1152)
<223> OTHER INFORMATION: DOR 46F.2, a coding region on BDGP Clone No.
      AC005974

<400> SEQUENCE: 21 atg gtt acg gag gac ttt tat aag tac cag gtg tgg tac ttc caa atc        48
Met Val Thr Glu Asp Phe Tyr Lys Tyr Gln Val Trp Tyr Phe Gln Ile
 1               5                  10                  15 ctt ggt gtt tgg cag ctc ccc act tgg gcc gca gac cac cag cgt cgt        96
Leu Gly Val Trp Gln Leu Pro Thr Trp Ala Ala Asp His Gln Arg Arg
             20                  25                  30 ttt cag tcc atg agg ttt ggc ttc atc ctg gtc atc ctg ttc atc atg       144
Phe Gln Ser Met Arg Phe Gly Phe Ile Leu Val Ile Leu Phe Ile Met
         35                  40                  45 ctg ctg ctt ttc tcc ttc gaa atg ttg aac aac att tcc caa gtt agg       192
Leu Leu Leu Phe Ser Phe Glu Met Leu Asn Asn Ile Ser Gln Val Arg
     50                  55                  60 gag atc cta aag gta ttc ttc atg ttc gcc acg gaa ata tcc tgc atg       240
Glu Ile Leu Lys Val Phe Phe Met Phe Ala Thr Glu Ile Ser Cys Met
 65                  70                  75                  80 gcc aaa tta ttg cat ttg aag ttg aag agc cgc aaa ctc gct ggc ttg       288
Ala Lys Leu Leu His Leu Lys Leu Lys Ser Arg Lys Leu Ala Gly Leu
                 85                  90                  95 gtt gat gcg atg ttg tcc cca gag ttc ggc gtt aaa agt gaa cag gaa       336
Val Asp Ala Met Leu Ser Pro Glu Phe Gly Val Lys Ser Glu Gln Glu
            100                 105                 110 atg cag atg ctg gaa ttg gat aga gtg gcg gtt gtc cgc atg agg aac       384
Met Gln Met Leu Glu Leu Asp Arg Val Ala Val Val Arg Met Arg Asn
        115                 120                 125 tcc tac ggc atc atg tcc ctg ggc gcg gct tcc ctg atc ctt ata gtt       432
Ser Tyr Gly Ile Met Ser Leu Gly Ala Ala Ser Leu Ile Leu Ile Val
    130                 135                 140 ccc tgt ttc gac aac ttt ggc gag cta cca ctg gcc atg ttg gag gta       480
Pro Cys Phe Asp Asn Phe Gly Glu Leu Pro Leu Ala Met Leu Glu Val
145                 150                 155                 160 tgc agc atc gag gga tgg atc tgc tat tgg tcg cag tac ctt ttc cac       528
Cys Ser Ile Glu Gly Trp Ile Cys Tyr Trp Ser Gln Tyr Leu Phe His
                165                 170                 175 tcg att tgc ctg ctg ccc act tgt gtg ctg aat ata acc tac gac tcg       576
Ser Ile Cys Leu Leu Pro Thr Cys Val Leu Asn Ile Thr Tyr Asp Ser
            180                 185                 190 gtg gcc tac tcg ttg ctc tgt ttc ttg aag gtt cag cta caa atg ctg       624
Val Ala Tyr Ser Leu Leu Cys Phe Leu Lys Val Gln Leu Gln Met Leu
        195                 200                 205 gtc ctg cga tta gaa aag ttg ggt cct gtg atc gaa ccc cag gat aat       672
Val Leu Arg Leu Glu Lys Leu Gly Pro Val Ile Glu Pro Gln Asp Asn
    210                 215                 220 gag aaa atc gca atg gaa ctg cgt gag tgt gcc gcc tac tac aac agg       720
Glu Lys Ile Ala Met Glu Leu Arg Glu Cys Ala Ala Tyr Tyr Asn Arg
225                 230                 235                 240 att gtt cgt ttc aag gac ctg gtg gag ctg ttc ata aag ggg cca gga       768
Ile Val Arg Phe Lys Asp Leu Val Glu Leu Phe Ile Lys Gly Pro Gly
                245                 250                 255
```

```
tct gtg cag ctc atg tgt tct gtt ctg gtg ctg gtg tcc aac ctg tac    816
Ser Val Gln Leu Met Cys Ser Val Leu Val Leu Val Ser Asn Leu Tyr
            260                 265                 270 gac atg tcc acc atg tcc att gca aac ggc gat gcc atc ttt atg ctc    864
Asp Met Ser Thr Met Ser Ile Ala Asn Gly Asp Ala Ile Phe Met Leu
        275                 280                 285 aag acc tgt atc tat cag ctg gtg atg ctc tgg cag atc ttc atc att    912
Lys Thr Cys Ile Tyr Gln Leu Val Met Leu Trp Gln Ile Phe Ile Ile
    290                 295                 300 tgc tac gcc tcc aac gag gta act gtc cag agc tct agg ttg tgt cac    960
Cys Tyr Ala Ser Asn Glu Val Thr Val Gln Ser Ser Arg Leu Cys His
305                 310                 315                 320 agc atc tac agc tcc caa tgg acg gga tgg aac agg gca aac cgc cgg   1008
Ser Ile Tyr Ser Ser Gln Trp Thr Gly Trp Asn Arg Ala Asn Arg Arg
                325                 330                 335 att gtc ctt ctc atg atg cag cgc ttt aat tcc ccg atg ctc ctg agc   1056
Ile Val Leu Leu Met Met Gln Arg Phe Asn Ser Pro Met Leu Leu Ser
            340                 345                 350 acc ttt aac ccc acc ttt gct ttc agc ttg gag gcc ttt ggt tct atc   1104
Thr Phe Asn Pro Thr Phe Ala Phe Ser Leu Glu Ala Phe Gly Ser Ile
        355                 360                 365 gtc aac tgc tcc tac agc tac ttc gca ctg ctg aag cgc gtc aac agt   1152
Val Asn Cys Ser Tyr Ser Tyr Phe Ala Leu Leu Lys Arg Val Asn Ser
    370                 375                 380 taa                                                                1155
```

<210> SEQ ID NO 22
<211> LENGTH: 384
<212> TYPE: PRT
<213> ORGANISM: Drosophila melanogaster

<400> SEQUENCE: 22

```
Met Val Thr Glu Asp Phe Tyr Lys Tyr Gln Val Trp Tyr Phe Gln Ile
 1               5                  10                  15

Leu Gly Val Trp Gln Leu Pro Thr Trp Ala Ala Asp His Gln Arg Arg
            20                  25                  30

Phe Gln Ser Met Arg Phe Gly Phe Ile Leu Val Ile Leu Phe Ile Met
        35                  40                  45

Leu Leu Leu Phe Ser Phe Glu Met Leu Asn Asn Ile Ser Gln Val Arg
    50                  55                  60

Glu Ile Leu Lys Val Phe Phe Met Phe Ala Thr Glu Ile Ser Cys Met
65                  70                  75                  80

Ala Lys Leu Leu His Leu Lys Leu Lys Ser Arg Lys Leu Ala Gly Leu
                85                  90                  95

Val Asp Ala Met Leu Ser Pro Glu Phe Gly Val Lys Ser Glu Gln Glu
            100                 105                 110

Met Gln Met Leu Glu Leu Asp Arg Val Ala Val Val Arg Met Arg Asn
        115                 120                 125

Ser Tyr Gly Ile Met Ser Leu Gly Ala Ala Ser Leu Ile Leu Ile Val
    130                 135                 140

Pro Cys Phe Asp Asn Phe Gly Glu Leu Pro Leu Ala Met Leu Glu Val
145                 150                 155                 160

Cys Ser Ile Glu Gly Trp Ile Cys Tyr Trp Ser Gln Tyr Leu Phe His
                165                 170                 175

Ser Ile Cys Leu Leu Pro Thr Cys Val Leu Asn Ile Thr Tyr Asp Ser
            180                 185                 190

Val Ala Tyr Ser Leu Leu Cys Phe Leu Lys Val Gln Leu Gln Met Leu
```

```
                195                 200                 205
Val Leu Arg Leu Glu Lys Leu Gly Pro Val Ile Glu Pro Gln Asp Asn
    210                 215                 220

Glu Lys Ile Ala Met Glu Leu Arg Glu Cys Ala Ala Tyr Tyr Asn Arg
225                 230                 235                 240

Ile Val Arg Phe Lys Asp Leu Val Glu Leu Phe Ile Lys Gly Pro Gly
                245                 250                 255

Ser Val Gln Leu Met Cys Ser Val Leu Val Leu Val Ser Asn Leu Tyr
                260                 265                 270

Asp Met Ser Thr Met Ser Ile Ala Asn Gly Asp Ala Ile Phe Met Leu
                275                 280                 285

Lys Thr Cys Ile Tyr Gln Leu Val Met Leu Trp Gln Ile Phe Ile Ile
                290                 295                 300

Cys Tyr Ala Ser Asn Glu Val Thr Val Gln Ser Ser Arg Leu Cys His
305                 310                 315                 320

Ser Ile Tyr Ser Ser Gln Trp Thr Gly Trp Asn Arg Ala Asn Arg Arg
                325                 330                 335

Ile Val Leu Leu Met Met Gln Arg Phe Asn Ser Pro Met Leu Leu Ser
                340                 345                 350

Thr Phe Asn Pro Thr Phe Ala Phe Ser Leu Glu Ala Phe Gly Ser Ile
                355                 360                 365

Val Asn Cys Ser Tyr Ser Tyr Phe Ala Leu Leu Lys Arg Val Asn Ser
                370                 375                 380

<210> SEQ ID NO 23
<211> LENGTH: 1158
<212> TYPE: DNA
<213> ORGANISM: Drosophila melanogaster
<220> FEATURE:
<221> NAME/KEY: CDS
<222> LOCATION: (1)..(1155)
<223> OTHER INFORMATION: DOR 47E.1, coding region of AF156880

<400> SEQUENCE: 23 atg gac agt ttt ctg caa gta cag aag agc acc att gcc ctt ctg ggc       48
Met Asp Ser Phe Leu Gln Val Gln Lys Ser Thr Ile Ala Leu Leu Gly
  1               5                  10                  15 ttt gat ctc ttt agt gaa aat cga gaa atg tgg aaa cgc ccc tat aga       96
Phe Asp Leu Phe Ser Glu Asn Arg Glu Met Trp Lys Arg Pro Tyr Arg
                 20                  25                  30 gca atg aat gtg ttt agc ata gct gcc att ttt ccc ttt atc ctg gca      144
Ala Met Asn Val Phe Ser Ile Ala Ala Ile Phe Pro Phe Ile Leu Ala
             35                  40                  45 gct gtg ctc cat aat tgg aag aat gta ttg ctg ctg gcc gat gcc atg      192
Ala Val Leu His Asn Trp Lys Asn Val Leu Leu Leu Ala Asp Ala Met
         50                  55                  60 gtg gcc cta cta ata acc att ctg ggc cta ttc aag ttt agc atg ata      240
Val Ala Leu Leu Ile Thr Ile Leu Gly Leu Phe Lys Phe Ser Met Ile
 65                  70                  75                  80 ctt tac tta cgt cgc gat ttc aag cga ctg att gac aaa ttt cgt ttg      288
Leu Tyr Leu Arg Arg Asp Phe Lys Arg Leu Ile Asp Lys Phe Arg Leu
                 85                  90                  95 ctc atg tcg aat gag gcg gaa cag ggc gag gaa tac gcc gag att ctc      336
Leu Met Ser Asn Glu Ala Glu Gln Gly Glu Glu Tyr Ala Glu Ile Leu
            100                 105                 110 aac gca gca aac aag cag gat caa cga atg tgc act ctg ttt agg act      384
Asn Ala Ala Asn Lys Gln Asp Gln Arg Met Cys Thr Leu Phe Arg Thr
        115                 120                 125
```

| | | |
|---|---|---|
| tgt ttc ctc ctc gcc tgg gcc ttg aat agt gtt ctg ccc ctc gtg aga<br>Cys Phe Leu Leu Ala Trp Ala Leu Asn Ser Val Leu Pro Leu Val Arg<br>130                       135                    140 | | 432 |
| atg ggt ctc agc tat tgg tta gca ggt cat gca gag ccc gag ttg cct<br>Met Gly Leu Ser Tyr Trp Leu Ala Gly His Ala Glu Pro Glu Leu Pro<br>145                   150               155               160 | | 480 |
| ttt ccc tgt ctt ttt ccc tgg aat atc cac atc att cgc aat tat gtt<br>Phe Pro Cys Leu Phe Pro Trp Asn Ile His Ile Ile Arg Asn Tyr Val<br>                165               170               175 | | 528 |
| ttg agc ttc atc tgg agc gct ttc gcc tcg aca ggt gtg gtt tta cct<br>Leu Ser Phe Ile Trp Ser Ala Phe Ala Ser Thr Gly Val Val Leu Pro<br>        180               185               190 | | 576 |
| gct gtc agc ttg gat acc ata ttc tgt tcc ttc acc agc aac ctg tgc<br>Ala Val Ser Leu Asp Thr Ile Phe Cys Ser Phe Thr Ser Asn Leu Cys<br>195                       200                    205 | | 624 |
| gcc ttc ttc aaa att gcg cag tac aag gtg gtt aga ttt aag ggc gga<br>Ala Phe Phe Lys Ile Ala Gln Tyr Lys Val Val Arg Phe Lys Gly Gly<br>210                       215                    220 | | 672 |
| tcc ctt aaa gaa tca cag gcc aca ttg aac aaa gtc ttt gcc ctg tac<br>Ser Leu Lys Glu Ser Gln Ala Thr Leu Asn Lys Val Phe Ala Leu Tyr<br>225                       230                       240 | | 720 |
| cag acc agc ttg gat atg tgc aac gat ctg aat cag tgc tac caa ccg<br>Gln Thr Ser Leu Asp Met Cys Asn Asp Leu Asn Gln Cys Tyr Gln Pro<br>                245               250               255 | | 768 |
| att atc tgc gcc cag ttc ttc att tca tct ctg caa ctc tgc atg ctg<br>Ile Ile Cys Ala Gln Phe Phe Ile Ser Ser Leu Gln Leu Cys Met Leu<br>        260             265               270 | | 816 |
| gga tat ctg ttc tcc att act ttt gcc cag aca gag ggc gtc tac tat<br>Gly Tyr Leu Phe Ser Ile Thr Phe Ala Gln Thr Glu Gly Val Tyr Tyr<br>275                       280                   285 | | 864 |
| gcc tca ttc ata gcc aca atc att ata caa gcc tat atc tac tgc tac<br>Ala Ser Phe Ile Ala Thr Ile Ile Ile Gln Ala Tyr Ile Tyr Cys Tyr<br>290                       295                    300 | | 912 |
| tgc ggg gag aac ctg aag acg gag agt gcc agc ttc gag tgg gcc atc<br>Cys Gly Glu Asn Leu Lys Thr Glu Ser Ala Ser Phe Glu Trp Ala Ile<br>305                       310                    315               320 | | 960 |
| tac gac agt ccg tgg cac gag agt ttg ggt gct ggt gga gcc tct acc<br>Tyr Asp Ser Pro Trp His Glu Ser Leu Gly Ala Gly Gly Ala Ser Thr<br>                325               330               335 | | 1008 |
| tcg atc tgc cga tcc ttg ctg atc agc atg atg cgg gct cat cgg gga<br>Ser Ile Cys Arg Ser Leu Leu Ile Ser Met Met Arg Ala His Arg Gly<br>        340             345               350 | | 1056 |
| ttc cgc att acg gga tac ttt ttc gag gca aac atg gag gcc ttc tca<br>Phe Arg Ile Thr Gly Tyr Phe Phe Glu Ala Asn Met Glu Ala Phe Ser<br>355                       360                    365 | | 1104 |
| tcg att gtt cgc acg gcg atg tcc tac atc aca atg ctg aga tca ttc<br>Ser Ile Val Arg Thr Ala Met Ser Tyr Ile Thr Met Leu Arg Ser Phe<br>370                       375                    380 | | 1152 |
| tcc taa<br>Ser<br>385 | | 1158 |

<210> SEQ ID NO 24
<211> LENGTH: 385
<212> TYPE: PRT
<213> ORGANISM: Drosophila melanogaster

<400> SEQUENCE: 24

Met Asp Ser Phe Leu Gln Val Gln Lys Ser Thr Ile Ala Leu Leu Gly
 1               5                  10                  15

```
Phe Asp Leu Phe Ser Glu Asn Arg Glu Met Trp Lys Arg Pro Tyr Arg
            20                  25                  30

Ala Met Asn Val Phe Ser Ile Ala Ala Ile Phe Pro Phe Ile Leu Ala
        35                  40                  45

Ala Val Leu His Asn Trp Lys Asn Val Leu Leu Ala Asp Ala Met
    50                  55                  60

Val Ala Leu Leu Ile Thr Ile Leu Gly Leu Phe Lys Phe Ser Met Ile
 65                  70                  75                  80

Leu Tyr Leu Arg Arg Asp Phe Lys Arg Leu Ile Asp Lys Phe Arg Leu
                85                  90                  95

Leu Met Ser Asn Glu Ala Glu Gln Gly Glu Tyr Ala Glu Ile Leu
            100                 105                 110

Asn Ala Ala Asn Lys Gln Asp Gln Arg Met Cys Thr Leu Phe Arg Thr
            115                 120                 125

Cys Phe Leu Leu Ala Trp Ala Leu Asn Ser Val Leu Pro Leu Val Arg
            130                 135                 140

Met Gly Leu Ser Tyr Trp Leu Ala Gly His Ala Glu Pro Glu Leu Pro
145                 150                 155                 160

Phe Pro Cys Leu Phe Pro Trp Asn Ile His Ile Ile Arg Asn Tyr Val
                165                 170                 175

Leu Ser Phe Ile Trp Ser Ala Phe Ala Ser Thr Gly Val Val Leu Pro
            180                 185                 190

Ala Val Ser Leu Asp Thr Ile Phe Cys Ser Phe Thr Ser Asn Leu Cys
        195                 200                 205

Ala Phe Phe Lys Ile Ala Gln Tyr Lys Val Val Arg Phe Lys Gly Gly
    210                 215                 220

Ser Leu Lys Glu Ser Gln Ala Thr Leu Asn Lys Val Phe Ala Leu Tyr
225                 230                 235                 240

Gln Thr Ser Leu Asp Met Cys Asn Asp Leu Asn Gln Cys Tyr Gln Pro
                245                 250                 255

Ile Ile Cys Ala Gln Phe Phe Ile Ser Ser Leu Gln Leu Cys Met Leu
            260                 265                 270

Gly Tyr Leu Phe Ser Ile Thr Phe Ala Gln Thr Glu Gly Val Tyr Tyr
            275                 280                 285

Ala Ser Phe Ile Ala Thr Ile Ile Gln Ala Tyr Ile Tyr Cys Tyr
        290                 295                 300

Cys Gly Glu Asn Leu Lys Thr Glu Ser Ala Ser Phe Glu Trp Ala Ile
305                 310                 315                 320

Tyr Asp Ser Pro Trp His Glu Ser Leu Gly Ala Gly Ala Ser Thr
                325                 330                 335

Ser Ile Cys Arg Ser Leu Leu Ile Ser Met Met Arg Ala His Arg Gly
            340                 345                 350

Phe Arg Ile Thr Gly Tyr Phe Phe Glu Ala Asn Met Glu Ala Phe Ser
            355                 360                 365

Ser Ile Val Arg Thr Ala Met Ser Tyr Ile Thr Met Leu Arg Ser Phe
    370                 375                 380

Ser
385

<210> SEQ ID NO 25
<211> LENGTH: 1203
<212> TYPE: DNA
<213> ORGANISM: Drosophila melanogaster
<220> FEATURE:
<221> NAME/KEY: CDS
```

-continued

```
<222> LOCATION: (1)..(1200)
<223> OTHER INFORMATION: DOR 47E.2, a coding region on BDGP Clone No.
      AC005638

<400> SEQUENCE: 25
```

| | | | | | | | | | | | | | | | | |
|---|---|---|---|---|---|---|---|---|---|---|---|---|---|---|---|---|
| atg | aac | gac | tcg | ggt | tat | caa | tca | aat | ctc | agc | ctt | ctg | cgg | gtt | ttt | 48 |
| Met | Asn | Asp | Ser | Gly | Tyr | Gln | Ser | Asn | Leu | Ser | Leu | Leu | Arg | Val | Phe | |
| 1 | | | | 5 | | | | | 10 | | | | | 15 | | |
| ctc | gac | gag | ttc | cga | tcg | gtt | ctg | cgg | cag | gaa | agt | ccc | ggt | ctc | atc | 96 |
| Leu | Asp | Glu | Phe | Arg | Ser | Val | Leu | Arg | Gln | Glu | Ser | Pro | Gly | Leu | Ile | |
| | | | 20 | | | | | 25 | | | | | 30 | | | |
| cca | cgc | ctg | gct | ttt | tac | tat | gtt | cgc | gcc | ttt | ctg | agc | ttg | ccc | ctg | 144 |
| Pro | Arg | Leu | Ala | Phe | Tyr | Tyr | Val | Arg | Ala | Phe | Leu | Ser | Leu | Pro | Leu | |
| | | 35 | | | | | 40 | | | | | 45 | | | | |
| tac | cga | tgg | atc | aac | ttg | ttc | atc | atg | tgc | aat | gtg | atg | acc | att | ttc | 192 |
| Tyr | Arg | Trp | Ile | Asn | Leu | Phe | Ile | Met | Cys | Asn | Val | Met | Thr | Ile | Phe | |
| | 50 | | | | | 55 | | | | | 60 | | | | | |
| tgg | acc | atg | ttc | gtg | gcc | ctg | ccc | gag | tcg | aag | aac | gtg | atc | gaa | atg | 240 |
| Trp | Thr | Met | Phe | Val | Ala | Leu | Pro | Glu | Ser | Lys | Asn | Val | Ile | Glu | Met | |
| 65 | | | | | 70 | | | | | 75 | | | | | 80 | |
| ggc | gac | gac | ttg | gtt | tgg | att | tcg | ggg | atg | gca | ctg | gtg | ttc | acc | aag | 288 |
| Gly | Asp | Asp | Leu | Val | Trp | Ile | Ser | Gly | Met | Ala | Leu | Val | Phe | Thr | Lys | |
| | | | | 85 | | | | | 90 | | | | | 95 | | |
| atc | ttt | tac | atg | cat | ttg | cgt | tgc | gac | gag | atc | gat | gaa | ctt | att | tcg | 336 |
| Ile | Phe | Tyr | Met | His | Leu | Arg | Cys | Asp | Glu | Ile | Asp | Glu | Leu | Ile | Ser | |
| | | | 100 | | | | | 105 | | | | | 110 | | | |
| gat | ttt | gaa | tac | tac | aac | cgg | gag | ctg | aga | ccc | cat | aat | atc | gat | gag | 384 |
| Asp | Phe | Glu | Tyr | Tyr | Asn | Arg | Glu | Leu | Arg | Pro | His | Asn | Ile | Asp | Glu | |
| | | 115 | | | | | 120 | | | | | 125 | | | | |
| gag | gtg | ttg | ggt | tgg | cag | aga | ctg | tgc | tac | gtg | ata | gaa | tcg | ggt | cta | 432 |
| Glu | Val | Leu | Gly | Trp | Gln | Arg | Leu | Cys | Tyr | Val | Ile | Glu | Ser | Gly | Leu | |
| | 130 | | | | | 135 | | | | | 140 | | | | | |
| tat | atc | aac | tgc | ttt | tgc | ctg | gtc | aac | ttc | ttc | agt | gcc | gct | att | ttc | 480 |
| Tyr | Ile | Asn | Cys | Phe | Cys | Leu | Val | Asn | Phe | Phe | Ser | Ala | Ala | Ile | Phe | |
| 145 | | | | | 150 | | | | | 155 | | | | | 160 | |
| ctg | caa | cct | ctg | ttg | ggc | gag | gga | aag | ctg | ccc | ttc | cac | agc | gtc | tat | 528 |
| Leu | Gln | Pro | Leu | Leu | Gly | Glu | Gly | Lys | Leu | Pro | Phe | His | Ser | Val | Tyr | |
| | | | | 165 | | | | | 170 | | | | | 175 | | |
| ccg | ttt | caa | tgg | cat | cgc | ttg | gat | ctg | cat | ccc | tac | acg | ttc | tgg | ttc | 576 |
| Pro | Phe | Gln | Trp | His | Arg | Leu | Asp | Leu | His | Pro | Tyr | Thr | Phe | Trp | Phe | |
| | | | 180 | | | | | 185 | | | | | 190 | | | |
| ctc | tac | atc | tgg | cag | agt | ctg | acc | tcg | cag | cac | aac | cta | atg | agc | att | 624 |
| Leu | Tyr | Ile | Trp | Gln | Ser | Leu | Thr | Ser | Gln | His | Asn | Leu | Met | Ser | Ile | |
| | | 195 | | | | | 200 | | | | | 205 | | | | |
| cta | atg | gtg | gat | atg | gta | ggc | att | tcc | acg | ttc | ctc | cag | acg | gcg | ctc | 672 |
| Leu | Met | Val | Asp | Met | Val | Gly | Ile | Ser | Thr | Phe | Leu | Gln | Thr | Ala | Leu | |
| | 210 | | | | | 215 | | | | | 220 | | | | | |
| aat | ctc | aag | ttg | ctt | tgc | atc | gag | ata | agg | aaa | ctg | ggg | gac | atg | gag | 720 |
| Asn | Leu | Lys | Leu | Leu | Cys | Ile | Glu | Ile | Arg | Lys | Leu | Gly | Asp | Met | Glu | |
| 225 | | | | | 230 | | | | | 235 | | | | | 240 | |
| gtc | agt | gat | aag | agg | ttc | cac | gag | gag | ttt | tgt | cgt | gtg | gtt | cgc | ttc | 768 |
| Val | Ser | Asp | Lys | Arg | Phe | His | Glu | Glu | Phe | Cys | Arg | Val | Val | Arg | Phe | |
| | | | | 245 | | | | | 250 | | | | | 255 | | |
| cac | cag | cac | att | atc | aaa | ttg | gtg | ggg | aaa | gcc | aat | aga | gct | ttc | aat | 816 |
| His | Gln | His | Ile | Ile | Lys | Leu | Val | Gly | Lys | Ala | Asn | Arg | Ala | Phe | Asn | |
| | | | 260 | | | | | 265 | | | | | 270 | | | |
| ggc | gcc | ttc | aat | gca | caa | tta | atg | gcc | agt | ttc | tcc | ctg | att | tcc | ata | 864 |
| Gly | Ala | Phe | Asn | Ala | Gln | Leu | Met | Ala | Ser | Phe | Ser | Leu | Ile | Ser | Ile | |
| | | 275 | | | | | 280 | | | | | 285 | | | | |
| tcc | act | ttc | gag | acc | atg | gct | gca | gcg | gct | gtg | gat | ccc | aaa | atg | gcc | 912 |
| Ser | Thr | Phe | Glu | Thr | Met | Ala | Ala | Ala | Val | Asp | Pro | Lys | Met | Ala | | |
| | 290 | | | | | 295 | | | | | 300 | | | | | |
| gcc | aag | ttc | gtg | ctt | ctc | atg | ctg | gtg | gca | ttc | att | caa | ctg | tcg | ctt | 960 |
| Ala | Lys | Phe | Val | Leu | Leu | Met | Leu | Val | Ala | Phe | Ile | Gln | Leu | Ser | Leu | |
| 305 | | | | | 310 | | | | | 315 | | | | | 320 | |
| tgg | tgc | gtc | tct | gga | act | ttg | gtt | tat | act | cag | tca | gtg | gag | gtg | gct | 1008 |
| Trp | Cys | Val | Ser | Gly | Thr | Leu | Val | Tyr | Thr | Gln | Ser | Val | Glu | Val | Ala | |
| | | | | 325 | | | | | 330 | | | | | 335 | | |
| cag | gct | gct | ttt | gat | atc | aac | gat | tgg | cac | acc | aaa | tcg | cca | ggc | atc | 1056 |
| Gln | Ala | Ala | Phe | Asp | Ile | Asn | Asp | Trp | His | Thr | Lys | Ser | Pro | Gly | Ile | |
| | | | 340 | | | | | 345 | | | | | 350 | | | |
| cag | agg | gat | ata | tcc | ttt | gtg | ata | cta | cga | gcc | cag | aaa | ccc | ctg | atg | 1104 |
| Gln | Arg | Asp | Ile | Ser | Phe | Val | Ile | Leu | Arg | Ala | Gln | Lys | Pro | Leu | Met | |
| | | 355 | | | | | 360 | | | | | 365 | | | | |
| tat | gtg | gcc | gaa | cca | ttt | ctg | ccc | ttc | acc | ctg | gga | acc | tat | atg | ctt | 1152 |
| Tyr | Val | Ala | Glu | Pro | Phe | Leu | Pro | Phe | Thr | Leu | Gly | Thr | Tyr | Met | Leu | |
| | 370 | | | | | 375 | | | | | 380 | | | | | |
| gtt | ctg | aag | aac | tgc | tat | cgt | ttg | ctg | gcc | ctg | atg | caa | gaa | tcg | atg | 1200 |

```
Val Leu Lys Asn Cys Tyr Arg Leu Leu Ala Leu Met Gln Glu Ser Met
385                 390                 395                 400
tag                                                              1203

<210> SEQ ID NO 26
<211> LENGTH: 400
<212> TYPE: PRT
<213> ORGANISM: Drosophila melanogaster

<400> SEQUENCE: 26

Met Asn Asp Ser Gly Tyr Gln Ser Asn Leu Ser Leu Leu Arg Val Phe
1               5                   10                  15

Leu Asp Glu Phe Arg Ser Val Leu Arg Gln Glu Ser Pro Gly Leu Ile
                20                  25                  30

Pro Arg Leu Ala Phe Tyr Tyr Val Arg Ala Phe Leu Ser Leu Pro Leu
            35                  40                  45

Tyr Arg Trp Ile Asn Leu Phe Ile Met Cys Asn Val Met Thr Ile Phe
        50                  55                  60

Trp Thr Met Phe Val Ala Leu Pro Glu Ser Lys Asn Val Ile Glu Met
65                  70                  75                  80

Gly Asp Asp Leu Val Trp Ile Ser Gly Met Ala Leu Val Phe Thr Lys
                85                  90                  95

Ile Phe Tyr Met His Leu Arg Cys Asp Glu Ile Asp Glu Leu Ile Ser
            100                 105                 110

Asp Phe Glu Tyr Tyr Asn Arg Glu Leu Arg Pro His Asn Ile Asp Glu
        115                 120                 125

Glu Val Leu Gly Trp Gln Arg Leu Cys Tyr Val Ile Glu Ser Gly Leu
130                 135                 140

Tyr Ile Asn Cys Phe Cys Leu Val Asn Phe Phe Ser Ala Ala Ile Phe
145                 150                 155                 160

Leu Gln Pro Leu Leu Gly Glu Gly Lys Leu Pro Phe His Ser Val Tyr
                165                 170                 175

Pro Phe Gln Trp His Arg Leu Asp Leu His Pro Tyr Thr Phe Trp Phe
            180                 185                 190

Leu Tyr Ile Trp Gln Ser Leu Thr Ser Gln His Asn Leu Met Ser Ile
        195                 200                 205

Leu Met Val Asp Met Val Gly Ile Ser Thr Phe Leu Gln Thr Ala Leu
    210                 215                 220

Asn Leu Lys Leu Leu Cys Ile Glu Ile Arg Lys Leu Gly Asp Met Glu
225                 230                 235                 240

Val Ser Asp Lys Arg Phe His Glu Glu Phe Cys Arg Val Val Arg Phe
                245                 250                 255

His Gln His Ile Ile Lys Leu Val Gly Lys Ala Asn Arg Ala Phe Asn
            260                 265                 270

Gly Ala Phe Asn Ala Gln Leu Met Ala Ser Phe Ser Leu Ile Ser Ile
        275                 280                 285

Ser Thr Phe Glu Thr Met Ala Ala Ala Val Asp Pro Lys Met Ala
    290                 295                 300

Ala Lys Phe Val Leu Leu Met Leu Val Ala Phe Ile Gln Leu Ser Leu
305                 310                 315                 320

Trp Cys Val Ser Gly Thr Leu Val Tyr Thr Gln Ser Val Glu Val Ala
                325                 330                 335

Gln Ala Ala Phe Asp Ile Asn Asp Trp His Thr Lys Ser Pro Gly Ile
            340                 345                 350

Gln Arg Asp Ile Ser Phe Val Ile Leu Arg Ala Gln Lys Pro Leu Met
```

```
              355                 360                      365
Tyr Val Ala Glu Pro Phe Leu Pro Phe Thr Leu Gly Thr Tyr Met Leu
            370                 375                 380

Val Leu Lys Asn Cys Tyr Arg Leu Leu Ala Leu Met Gln Glu Ser Met
385                 390                 395                 400

<210> SEQ ID NO 27
<211> LENGTH: 1140
<212> TYPE: DNA
<213> ORGANISM: Drosophila melanogaster
<220> FEATURE:
<221> NAME/KEY: CDS
<222> LOCATION: (1)..(1137)
<223> OTHER INFORMATION: DOR 59D.1, a coding region on BDGP Clone No.
      AC005672

<400> SEQUENCE: 27 atg gca gag gtc aga gtg gac agt ctg gag ttt ttc aag agc cat tgg      48
Met Ala Glu Val Arg Val Asp Ser Leu Glu Phe Phe Lys Ser His Trp
  1               5                  10                  15 acc gcc tgg cgg tac ttg gga gtg gct cat ttt cgg gtc gag aac tgg      96
Thr Ala Trp Arg Tyr Leu Gly Val Ala His Phe Arg Val Glu Asn Trp
             20                  25                  30 aag aac ctt tac gtg ttt tac agc att gtg tcg aat ctt ctc gtg acc     144
Lys Asn Leu Tyr Val Phe Tyr Ser Ile Val Ser Asn Leu Leu Val Thr
         35                  40                  45 ctg tgc tac ccc gtt cac ctg gga ata tcc ctc ttt cgc aac cgc acc     192
Leu Cys Tyr Pro Val His Leu Gly Ile Ser Leu Phe Arg Asn Arg Thr
     50                  55                  60 atc acc gag gac atc ctc aac ctg acc acc ttt gcg acc tgc aca gcc     240
Ile Thr Glu Asp Ile Leu Asn Leu Thr Thr Phe Ala Thr Cys Thr Ala
 65                  70                  75                  80 tgt tcg gtg aag tgc ctc ctc tac gcc tac aac atc aag gat gtg ctg     288
Cys Ser Val Lys Cys Leu Leu Tyr Ala Tyr Asn Ile Lys Asp Val Leu
                 85                  90                  95 gag atg gag cgg ctg ttg agg ctt ttg gat gaa cgc gtc gtg ggt ccg     336
Glu Met Glu Arg Leu Leu Arg Leu Leu Asp Glu Arg Val Val Gly Pro
            100                 105                 110 gag caa cgc agc atc tac gga caa gtg agg gtc cag ctg cga aat gtg     384
Glu Gln Arg Ser Ile Tyr Gly Gln Val Arg Val Gln Leu Arg Asn Val
        115                 120                 125 cta tac gtg ttc atc ggc atc tac atg ccg tgt gcc ctg ttc gcc gag     432
Leu Tyr Val Phe Ile Gly Ile Tyr Met Pro Cys Ala Leu Phe Ala Glu
    130                 135                 140 cta tcc ttt ctg ttc aag gag gag cgc ggt ctg atg tat ccc gcc tgg     480
Leu Ser Phe Leu Phe Lys Glu Glu Arg Gly Leu Met Tyr Pro Ala Trp
145                 150                 155                 160 ttt ccc ttc gac tgg ctg cac tcc acc agg aac tat tac ata gcg aac     528
Phe Pro Phe Asp Trp Leu His Ser Thr Arg Asn Tyr Tyr Ile Ala Asn
                165                 170                 175 gcc tat cag ata gtg ggc atc tcg ttt cag ctg ctg caa aac tat gtt     576
Ala Tyr Gln Ile Val Gly Ile Ser Phe Gln Leu Leu Gln Asn Tyr Val
            180                 185                 190 agc gac tgc ttt ccg gcg gtg gtg ctg tgc ctg atc tca tcc cac atc     624
Ser Asp Cys Phe Pro Ala Val Val Leu Cys Leu Ile Ser Ser His Ile
        195                 200                 205 aaa atg ttg tac aac aga ttc gag gag gtg ggc ctg gat cca gcc aga     672
Lys Met Leu Tyr Asn Arg Phe Glu Glu Val Gly Leu Asp Pro Ala Arg
    210                 215                 220 gat gcg gag aag gac ctg gag gcc tgc atc acc gat cac aag cat att     720
Asp Ala Glu Lys Asp Leu Glu Ala Cys Ile Thr Asp His Lys His Ile
```

```
                                                                -continued 225                 230                 235                 240
cta gaa cta ttc cga cgc atc gag gcc ttc att tcc ctg ccc atg cta     768
Leu Glu Leu Phe Arg Arg Ile Glu Ala Phe Ile Ser Leu Pro Met Leu
                245                 250                 255 att cag ttc aca gtg acc gcc ttg aat gtg tgc atc ggt tta gca gcc     816
Ile Gln Phe Thr Val Thr Ala Leu Asn Val Cys Ile Gly Leu Ala Ala
                260                 265                 270 ctg gtg ttt ttc gtc agc gag ccc atg gca cgg atg tac ttc atc ttc     864
Leu Val Phe Phe Val Ser Glu Pro Met Ala Arg Met Tyr Phe Ile Phe
                275                 280                 285 tac tcc ctg gcc atg ccg ctg cag atc ttt ccg tcc tgc ttt ttc ggc     912
Tyr Ser Leu Ala Met Pro Leu Gln Ile Phe Pro Ser Cys Phe Phe Gly
                290                 295                 300 acc gac aac gag tac tgg ttc gga cgc ctc cac tac gcg gcc ttc agt     960
Thr Asp Asn Glu Tyr Trp Phe Gly Arg Leu His Tyr Ala Ala Phe Ser
305                 310                 315                 320 tgc aat tgg cac aca cag aac agg agc ttt aag cgg aaa atg atg ctg    1008
Cys Asn Trp His Thr Gln Asn Arg Ser Phe Lys Arg Lys Met Met Leu
                325                 330                 335 ttc gtt gag caa tcg ttg aag aag agc acc gct gtg gct ggc gga atg    1056
Phe Val Glu Gln Ser Leu Lys Lys Ser Thr Ala Val Ala Gly Gly Met
                340                 345                 350 atg cgt atc cac ctg gac acg ttc ttt tcc acc cta aag ggg gcc tac    1104
Met Arg Ile His Leu Asp Thr Phe Phe Ser Thr Leu Lys Gly Ala Tyr
                355                 360                 365 tcc ctc ttt acc atc att att cgg atg aga aag tag                    1140
Ser Leu Phe Thr Ile Ile Ile Arg Met Arg Lys
                370                 375

<210> SEQ ID NO 28
<211> LENGTH: 379
<212> TYPE: PRT
<213> ORGANISM: Drosophila melanogaster

<400> SEQUENCE: 28

Met Ala Glu Val Arg Val Asp Ser Leu Glu Phe Phe Lys Ser His Trp
 1               5                  10                  15

Thr Ala Trp Arg Tyr Leu Gly Val Ala His Phe Arg Val Glu Asn Trp
                20                  25                  30

Lys Asn Leu Tyr Val Phe Tyr Ser Ile Val Ser Asn Leu Leu Val Thr
            35                  40                  45

Leu Cys Tyr Pro Val His Leu Gly Ile Ser Leu Phe Arg Asn Arg Thr
        50                  55                  60

Ile Thr Glu Asp Ile Leu Asn Leu Thr Thr Phe Ala Thr Cys Thr Ala
65                  70                  75                  80

Cys Ser Val Lys Cys Leu Leu Tyr Ala Tyr Asn Ile Lys Asp Val Leu
                85                  90                  95

Glu Met Glu Arg Leu Leu Arg Leu Leu Asp Glu Arg Val Val Gly Pro
            100                 105                 110

Glu Gln Arg Ser Ile Tyr Gly Gln Val Arg Val Gln Leu Arg Asn Val
        115                 120                 125

Leu Tyr Val Phe Ile Gly Ile Tyr Met Pro Cys Ala Leu Phe Ala Glu
130                 135                 140

Leu Ser Phe Leu Phe Lys Glu Glu Arg Gly Leu Met Tyr Pro Ala Trp
145                 150                 155                 160

Phe Pro Phe Asp Trp Leu His Ser Thr Arg Asn Tyr Tyr Ile Ala Asn
                165                 170                 175
```

```
Ala Tyr Gln Ile Val Gly Ile Ser Phe Gln Leu Leu Gln Asn Tyr Val
            180                 185                 190

Ser Asp Cys Phe Pro Ala Val Val Leu Cys Leu Ile Ser Ser His Ile
            195                 200                 205

Lys Met Leu Tyr Asn Arg Phe Glu Val Gly Leu Asp Pro Ala Arg
    210                 215                 220

Asp Ala Glu Lys Asp Leu Glu Ala Cys Ile Thr Asp His Lys His Ile
225                 230                 235                 240

Leu Glu Leu Phe Arg Arg Ile Glu Ala Phe Ile Ser Leu Pro Met Leu
                245                 250                 255

Ile Gln Phe Thr Val Thr Ala Leu Asn Val Cys Ile Gly Leu Ala Ala
            260                 265                 270

Leu Val Phe Val Ser Glu Pro Met Ala Arg Met Tyr Phe Ile Phe
        275                 280                 285

Tyr Ser Leu Ala Met Pro Leu Gln Ile Phe Pro Ser Cys Phe Gly
    290                 295                 300

Thr Asp Asn Glu Tyr Trp Phe Gly Arg Leu His Tyr Ala Ala Phe Ser
305                 310                 315                 320

Cys Asn Trp His Thr Gln Asn Arg Ser Phe Lys Arg Lys Met Met Leu
                325                 330                 335

Phe Val Glu Gln Ser Leu Lys Lys Ser Thr Ala Val Ala Gly Gly Met
                340                 345                 350

Met Arg Ile His Leu Asp Thr Phe Phe Ser Thr Leu Lys Gly Ala Tyr
                355                 360                 365

Ser Leu Phe Thr Ile Ile Ile Arg Met Arg Lys
    370                 375

<210> SEQ ID NO 29
<211> LENGTH: 1194
<212> TYPE: DNA
<213> ORGANISM: Drosophila melanogaster
<220> FEATURE:
<221> NAME/KEY: CDS
<222> LOCATION: (1)..(1194)
<223> OTHER INFORMATION: DOR 2F.1, coding region of NCBI Accession No.
      AL009195

<400> SEQUENCE: 29 atg gag aag caa gag gat ttc aaa ctg aac acc cac agt gct gtg tac        48
Met Glu Lys Gln Glu Asp Phe Lys Leu Asn Thr His Ser Ala Val Tyr
  1               5                  10                  15 tac cac tgg cgc gtt tgg gag ctc act ggc ctg atg cgt cct ccg ggc        96
Tyr His Trp Arg Val Trp Glu Leu Thr Gly Leu Met Arg Pro Pro Gly
             20                  25                  30 gtt tca agc ctg ctt tac gtg gta tac tcc att acg gtc aac ttg gtg       144
Val Ser Ser Leu Leu Tyr Val Val Tyr Ser Ile Thr Val Asn Leu Val
         35                  40                  45 gtc acc gtg ctg ttt ccc ttg agc ttg ctg gcc agg ctg ctg ttc acc       192
Val Thr Val Leu Phe Pro Leu Ser Leu Leu Ala Arg Leu Leu Phe Thr
     50                  55                  60 acc aac atg gcc gga ttg tgc gag aac ctg acc ata act att acc gat       240
Thr Asn Met Ala Gly Leu Cys Glu Asn Leu Thr Ile Thr Ile Thr Asp
 65                  70                  75                  80 att gtg gcc aat ttg aag ttt gcg aat gtg tac atg gtg agg aag cag       288
Ile Val Ala Asn Leu Lys Phe Ala Asn Val Tyr Met Val Arg Lys Gln
                 85                  90                  95 ctc cat gag att cgc tct ctc cta agg ctc atg gac gct aga gcc cgg       336
Leu His Glu Ile Arg Ser Leu Leu Arg Leu Met Asp Ala Arg Ala Arg
            100                 105                 110
```

```
ctg gtg ggc gat ccc gag gag att tct gcc ttg agg aag gaa gtg aat      384
Leu Val Gly Asp Pro Glu Glu Ile Ser Ala Leu Arg Lys Glu Val Asn
            115                 120                 125 atc gca cag ggc act ttc cgc acc ttt gcc agt att ttc gta ttt ggc      432
Ile Ala Gln Gly Thr Phe Arg Thr Phe Ala Ser Ile Phe Val Phe Gly
130                 135                 140 act act ttg agt tgc gtc cgc gtg gtc gtt cgc cca gat cga gag ctc      480
Thr Thr Leu Ser Cys Val Arg Val Val Val Arg Pro Asp Arg Glu Leu
145                 150                 155                 160 ctg tat ccg gcc tgg ttc ggc gtt gac tgg atg cac tcc acc aga aac      528
Leu Tyr Pro Ala Trp Phe Gly Val Asp Trp Met His Ser Thr Arg Asn
            165                 170                 175 tat gtg ctc atc aat atc tac cag ctc ttc ggc ttg ata gtg cag gct      576
Tyr Val Leu Ile Asn Ile Tyr Gln Leu Phe Gly Leu Ile Val Gln Ala
            180                 185                 190 ata cag aac tgc gct agt gac tcc tat ccg cct gcg ttt ctc tgc ctg      624
Ile Gln Asn Cys Ala Ser Asp Ser Tyr Pro Pro Ala Phe Leu Cys Leu
            195                 200                 205 ctc acg ggt cat atg cgt gct ttg gag ctg agg gtg cgg cgg att ggc      672
Leu Thr Gly His Met Arg Ala Leu Glu Leu Arg Val Arg Arg Ile Gly
210                 215                 220 tgc agg acg gaa aag tcc aat aaa ggg cag aca tat gaa gcc tgg cgg      720
Cys Arg Thr Glu Lys Ser Asn Lys Gly Gln Thr Tyr Glu Ala Trp Arg
225                 230                 235                 240 gag gag gtg tac cag gaa ctc atc gag tgc atc cgc gat ctg gcg cgg      768
Glu Glu Val Tyr Gln Glu Leu Ile Glu Cys Ile Arg Asp Leu Ala Arg
            245                 250                 255 gtc cat cgg ctg agg gag atc att cag cgg gtc ctt tca gtg ccc tgc      816
Val His Arg Leu Arg Glu Ile Ile Gln Arg Val Leu Ser Val Pro Cys
            260                 265                 270 atg gcc cag ttc gtc tgc tcc gcc gcc gtc cag tgt acc gtc gcc atg      864
Met Ala Gln Phe Val Cys Ser Ala Ala Val Gln Cys Thr Val Ala Met
            275                 280                 285 cac ttc ctg tac gta gcg gat gac cac gac cac acc gcc atg atc atc      912
His Phe Leu Tyr Val Ala Asp Asp His Asp His Thr Ala Met Ile Ile
            290                 295                 300 tcg att gta ttt ttc tcg gcc gtc acc ttg gag gtg ttt gta atc tgc      960
Ser Ile Val Phe Phe Ser Ala Val Thr Leu Glu Val Phe Val Ile Cys
305                 310                 315                 320 tat ttt ggg gac agg atg cgg aca cag agc gag gcg ctg tgc gat gcc     1008
Tyr Phe Gly Asp Arg Met Arg Thr Gln Ser Glu Ala Leu Cys Asp Ala
            325                 330                 335 ttc tac gat tgc aac tgg ata gaa cag ctg ccc aag ttc aag cgc gaa     1056
Phe Tyr Asp Cys Asn Trp Ile Glu Gln Leu Pro Lys Phe Lys Arg Glu
            340                 345                 350 ctg ctc ttc acc ctg gcc agg acg cag cgg cct tct ctt atc tac gca     1104
Leu Leu Phe Thr Leu Ala Arg Thr Gln Arg Pro Ser Leu Ile Tyr Ala
            355                 360                 365 ggc aac tac atc gca ctc tcg ctg gag acc ttc gag cag cag gtc atg     1152
Gly Asn Tyr Ile Ala Leu Ser Leu Glu Thr Phe Glu Gln Gln Val Met
370                 375                 380 agg ttc aca tac tct gtt ttc aca ctc ttg ctg agg gcc aag              1194
Arg Phe Thr Tyr Ser Val Phe Thr Leu Leu Leu Arg Ala Lys
385                 390                 395

<210> SEQ ID NO 30
<211> LENGTH: 398
<212> TYPE: PRT
<213> ORGANISM: Drosophila melanogaster
```

```
<400> SEQUENCE: 30

Met Glu Lys Gln Glu Asp Phe Lys Leu Asn Thr His Ser Ala Val Tyr
  1               5                  10                  15

Tyr His Trp Arg Val Trp Glu Leu Thr Gly Leu Met Arg Pro Pro Gly
             20                  25                  30

Val Ser Ser Leu Leu Tyr Val Tyr Ser Ile Thr Val Asn Leu Val
             35                  40                  45

Val Thr Val Leu Phe Pro Leu Ser Leu Leu Ala Arg Leu Leu Phe Thr
 50                  55                  60

Thr Asn Met Ala Gly Leu Cys Glu Asn Leu Thr Ile Thr Ile Thr Asp
 65                  70                  75                  80

Ile Val Ala Asn Leu Lys Phe Ala Asn Val Tyr Met Val Arg Lys Gln
                 85                  90                  95

Leu His Glu Ile Arg Ser Leu Leu Arg Leu Met Asp Ala Arg Ala Arg
                100                 105                 110

Leu Val Gly Asp Pro Glu Glu Ile Ser Ala Leu Arg Lys Glu Val Asn
                115                 120                 125

Ile Ala Gln Gly Thr Phe Arg Thr Phe Ala Ser Ile Phe Val Phe Gly
130                 135                 140

Thr Thr Leu Ser Cys Val Arg Val Val Arg Pro Asp Arg Glu Leu
145                 150                 155                 160

Leu Tyr Pro Ala Trp Phe Gly Val Asp Trp Met His Ser Thr Arg Asn
                165                 170                 175

Tyr Val Leu Ile Asn Ile Tyr Gln Leu Phe Gly Leu Ile Val Gln Ala
                180                 185                 190

Ile Gln Asn Cys Ala Ser Asp Ser Tyr Pro Pro Ala Phe Leu Cys Leu
                195                 200                 205

Leu Thr Gly His Met Arg Ala Leu Glu Leu Arg Val Arg Arg Ile Gly
210                 215                 220

Cys Arg Thr Glu Lys Ser Asn Lys Gly Gln Thr Tyr Glu Ala Trp Arg
225                 230                 235                 240

Glu Glu Val Tyr Gln Glu Leu Ile Glu Cys Ile Arg Asp Leu Ala Arg
                245                 250                 255

Val His Arg Leu Arg Glu Ile Ile Gln Arg Val Leu Ser Val Pro Cys
                260                 265                 270

Met Ala Gln Phe Val Cys Ser Ala Ala Val Gln Cys Thr Val Ala Met
                275                 280                 285

His Phe Leu Tyr Val Ala Asp Asp His Asp His Thr Ala Met Ile Ile
                290                 295                 300

Ser Ile Val Phe Phe Ser Ala Val Thr Leu Glu Val Phe Val Ile Cys
305                 310                 315                 320

Tyr Phe Gly Asp Arg Met Arg Thr Gln Ser Glu Ala Leu Cys Asp Ala
                325                 330                 335

Phe Tyr Asp Cys Asn Trp Ile Glu Gln Leu Pro Lys Phe Lys Arg Glu
                340                 345                 350

Leu Leu Phe Thr Leu Ala Arg Thr Gln Arg Pro Ser Leu Ile Tyr Ala
                355                 360                 365

Gly Asn Tyr Ile Ala Leu Ser Leu Glu Thr Phe Glu Gln Gln Val Met
370                 375                 380

Arg Phe Thr Tyr Ser Val Phe Thr Leu Leu Leu Arg Ala Lys
385                 390                 395

<210> SEQ ID NO 31
```

-continued

```
<211> LENGTH: 1191
<212> TYPE: DNA
<213> ORGANISM: Drosophila melanogaster
<220> FEATURE:
<221> NAME/KEY: CDS
<222> LOCATION: (1)..(1191)
<223> OTHER INFORMATION: DOR 22A.1, a coding region of BDGP Clone No.
      AC004121

<400> SEQUENCE: 31
```

| | | | | | | | | | | | | | | | | |
|---|---|---|---|---|---|---|---|---|---|---|---|---|---|---|---|---|
| atg | tta | agc | aag | ttt | ttt | ccc | cac | ata | aaa | gaa | aag | cca | ttg | agc | gag | 48 |
| Met | Leu | Ser | Lys | Phe | Phe | Pro | His | Ile | Lys | Glu | Lys | Pro | Leu | Ser | Glu | |
| 1 | | | | 5 | | | | | 10 | | | | | 15 | | |
| cgg | gtt | aag | tcc | cga | gat | gcc | ttc | att | tac | ttg | gat | cgg | gtg | atg | tgg | 96 |
| Arg | Val | Lys | Ser | Arg | Asp | Ala | Phe | Ile | Tyr | Leu | Asp | Arg | Val | Met | Trp | |
| | | | 20 | | | | | 25 | | | | | 30 | | | |
| tcc | ttt | ggc | tgg | aca | gag | cct | gaa | aac | aaa | agg | tgg | atc | ctt | cct | tat | 144 |
| Ser | Phe | Gly | Trp | Thr | Glu | Pro | Glu | Asn | Lys | Arg | Trp | Ile | Leu | Pro | Tyr | |
| | | 35 | | | | | 40 | | | | | 45 | | | | |
| aaa | ctg | tgg | tta | gcg | ttc | gtg | aac | ata | gta | atg | ctc | atc | ctt | ctg | ccg | 192 |
| Lys | Leu | Trp | Leu | Ala | Phe | Val | Asn | Ile | Val | Met | Leu | Ile | Leu | Leu | Pro | |
| | 50 | | | | | 55 | | | | | 60 | | | | | |
| atc | tcg | ata | agc | atc | gag | tac | ctc | cac | cga | ttt | aaa | acc | ttc | tcg | gcg | 240 |
| Ile | Ser | Ile | Ser | Ile | Glu | Tyr | Leu | His | Arg | Phe | Lys | Thr | Phe | Ser | Ala | |
| 65 | | | | | 70 | | | | | 75 | | | | | 80 | |
| ggg | gag | ttc | ctt | agt | tcc | ctc | gag | att | gga | gtc | aac | atg | tac | gga | agc | 288 |
| Gly | Glu | Phe | Leu | Ser | Ser | Leu | Glu | Ile | Gly | Val | Asn | Met | Tyr | Gly | Ser | |
| | | | | 85 | | | | | 90 | | | | | 95 | | |
| tct | ttt | aag | tgc | gcc | ttc | acc | ttg | att | gga | ttc | aag | aaa | aga | cag | gaa | 336 |
| Ser | Phe | Lys | Cys | Ala | Phe | Thr | Leu | Ile | Gly | Phe | Lys | Lys | Arg | Gln | Glu | |
| | | | 100 | | | | | 105 | | | | | 110 | | | |
| gct | aag | gtt | tta | ctg | gat | cag | ctg | gac | aag | aga | tgc | ctt | agc | gat | aag | 384 |
| Ala | Lys | Val | Leu | Leu | Asp | Gln | Leu | Asp | Lys | Arg | Cys | Leu | Ser | Asp | Lys | |
| | | 115 | | | | | 120 | | | | | 125 | | | | |
| gag | agg | tcc | act | gtt | cat | cgc | tat | gtc | gcc | atg | gga | aac | ttt | ttc | gat | 432 |
| Glu | Arg | Ser | Thr | Val | His | Arg | Tyr | Val | Ala | Met | Gly | Asn | Phe | Phe | Asp | |
| | 130 | | | | | 135 | | | | | 140 | | | | | |
| att | ttg | tat | cac | att | ttt | tac | tcc | acc | ttc | gtg | gta | atg | aac | ttc | ccg | 480 |
| Ile | Leu | Tyr | His | Ile | Phe | Tyr | Ser | Thr | Phe | Val | Val | Met | Asn | Phe | Pro | |
| 145 | | | | | 150 | | | | | 155 | | | | | 160 | |
| tat | ttt | ctg | ctt | gag | aga | cgc | cat | gct | tgg | cgc | atg | tac | ttt | cca | tat | 528 |
| Tyr | Phe | Leu | Leu | Glu | Arg | Arg | His | Ala | Trp | Arg | Met | Tyr | Phe | Pro | Tyr | |
| | | | | 165 | | | | | 170 | | | | | 175 | | |
| atc | gat | tcc | gac | gaa | cag | ttt | tac | atc | tcc | agc | atc | gcc | gag | tgt | ttt | 576 |
| Ile | Asp | Ser | Asp | Glu | Gln | Phe | Tyr | Ile | Ser | Ser | Ile | Ala | Glu | Cys | Phe | |
| | | | 180 | | | | | 185 | | | | | 190 | | | |
| ctg | atg | acg | gag | gcc | atc | tac | atg | gat | ctc | tgt | acg | gac | gtg | tgt | ccc | 624 |
| Leu | Met | Thr | Glu | Ala | Ile | Tyr | Met | Asp | Leu | Cys | Thr | Asp | Val | Cys | Pro | |
| | | 195 | | | | | 200 | | | | | 205 | | | | |
| ttg | atc | tcc | atg | ctt | atg | gct | cga | tgc | cac | att | agc | ctc | ctg | aaa | cag | 672 |
| Leu | Ile | Ser | Met | Leu | Met | Ala | Arg | Cys | His | Ile | Ser | Leu | Leu | Lys | Gln | |
| | 210 | | | | | 215 | | | | | 220 | | | | | |
| cga | ctg | aga | aat | ctc | cga | tcg | aag | cca | gga | agg | acc | gaa | gat | gag | tac | 720 |
| Arg | Leu | Arg | Asn | Leu | Arg | Ser | Lys | Pro | Gly | Arg | Thr | Glu | Asp | Glu | Tyr | |
| 225 | | | | | 230 | | | | | 235 | | | | | 240 | |
| ttg | gag | gag | ctc | acc | gag | tgc | att | cgg | gat | cat | cga | ttg | cta | ttg | gac | 768 |
| Leu | Glu | Glu | Leu | Thr | Glu | Cys | Ile | Arg | Asp | His | Arg | Leu | Leu | Leu | Asp | |
| | | | | 245 | | | | | 250 | | | | | 255 | | |
| tat | gtt | gac | gca | ttg | cga | ccc | gtc | ttt | tcg | gga | acc | att | ttt | gtg | cag | 816 |
| Tyr | Val | Asp | Ala | Leu | Arg | Pro | Val | Phe | Ser | Gly | Thr | Ile | Phe | Val | Gln | |
| | | | 260 | | | | | 265 | | | | | 270 | | | |

```
ttc ctc ctg atc ggt act gta ctg ggt ctc tca atg ata aat cta atg      864
Phe Leu Leu Ile Gly Thr Val Leu Gly Leu Ser Met Ile Asn Leu Met
        275                 280                 285 ttc ttc tcg aca ttt tgg act ggt gtc gcc act tgc ctt ttt atg ttc      912
Phe Phe Ser Thr Phe Trp Thr Gly Val Ala Thr Cys Leu Phe Met Phe
    290                 295                 300 gac gtg tcc atg gag acg ttc ccc ttt tgc tat ttg tgc aac atg att      960
Asp Val Ser Met Glu Thr Phe Pro Phe Cys Tyr Leu Cys Asn Met Ile
305                 310                 315                 320 atc gat gac tgc cag gaa atg tcc aat tgc ctc ttt caa tcg gac tgg     1008
Ile Asp Asp Cys Gln Glu Met Ser Asn Cys Leu Phe Gln Ser Asp Trp
            325                 330                 335 acc tct gcc gat cgt cgc tac aaa tcc acg ttg gta tac ttt ctt cac     1056
Thr Ser Ala Asp Arg Arg Tyr Lys Ser Thr Leu Val Tyr Phe Leu His
                340                 345                 350 aat ctt cag caa ccc att act ctc acg gct ggt gga gtg ttt cct att     1104
Asn Leu Gln Gln Pro Ile Thr Leu Thr Ala Gly Gly Val Phe Pro Ile
            355                 360                 365 tcc atg caa aca aat ttg gct atg gtg aag ctg gca ttt tct gtg gtt     1152
Ser Met Gln Thr Asn Leu Ala Met Val Lys Leu Ala Phe Ser Val Val
370                 375                 380 acg gta att aag caa ttt aac ttg gcc gaa agg ttt caa                 1191
Thr Val Ile Lys Gln Phe Asn Leu Ala Glu Arg Phe Gln
385                 390                 395

<210> SEQ ID NO 32
<211> LENGTH: 397
<212> TYPE: PRT
<213> ORGANISM: Drosophila melanogaster

<400> SEQUENCE: 32

Met Leu Ser Lys Phe Phe Pro His Ile Lys Glu Lys Pro Leu Ser Glu
  1               5                  10                  15

Arg Val Lys Ser Arg Asp Ala Phe Ile Tyr Leu Asp Arg Val Met Trp
                 20                  25                  30

Ser Phe Gly Trp Thr Glu Pro Glu Asn Lys Arg Trp Ile Leu Pro Tyr
             35                  40                  45

Lys Leu Trp Leu Ala Phe Val Asn Ile Val Met Leu Ile Leu Leu Pro
         50                  55                  60

Ile Ser Ile Ser Ile Glu Tyr Leu His Arg Phe Lys Thr Phe Ser Ala
 65                  70                  75                  80

Gly Glu Phe Leu Ser Ser Leu Glu Ile Gly Val Asn Met Tyr Gly Ser
                 85                  90                  95

Ser Phe Lys Cys Ala Phe Thr Leu Ile Gly Phe Lys Lys Arg Gln Glu
            100                 105                 110

Ala Lys Val Leu Leu Asp Gln Leu Asp Lys Arg Cys Leu Ser Asp Lys
        115                 120                 125

Glu Arg Ser Thr Val His Arg Tyr Val Ala Met Gly Asn Phe Phe Asp
    130                 135                 140

Ile Leu Tyr His Ile Phe Tyr Ser Thr Phe Val Val Met Asn Phe Pro
145                 150                 155                 160

Tyr Phe Leu Leu Glu Arg Arg His Ala Trp Arg Met Tyr Phe Pro Tyr
                165                 170                 175

Ile Asp Ser Asp Glu Gln Phe Tyr Ile Ser Ser Ile Ala Glu Cys Phe
            180                 185                 190

Leu Met Thr Glu Ala Ile Tyr Met Asp Leu Cys Thr Asp Val Cys Pro
        195                 200                 205
```

```
Leu Ile Ser Met Leu Met Ala Arg Cys His Ile Ser Leu Leu Lys Gln
    210                 215                 220

Arg Leu Arg Asn Leu Arg Ser Lys Pro Gly Arg Thr Glu Asp Glu Tyr
225                 230                 235                 240

Leu Glu Glu Leu Thr Glu Cys Ile Arg Asp His Arg Leu Leu Leu Asp
                245                 250                 255

Tyr Val Asp Ala Leu Arg Pro Val Phe Ser Gly Thr Ile Phe Val Gln
            260                 265                 270

Phe Leu Leu Ile Gly Thr Val Leu Gly Leu Ser Met Ile Asn Leu Met
        275                 280                 285

Phe Phe Ser Thr Phe Trp Thr Gly Val Ala Thr Cys Leu Phe Met Phe
    290                 295                 300

Asp Val Ser Met Glu Thr Phe Pro Phe Cys Tyr Leu Cys Asn Met Ile
305                 310                 315                 320

Ile Asp Asp Cys Gln Glu Met Ser Asn Cys Leu Phe Gln Ser Asp Trp
                325                 330                 335

Thr Ser Ala Asp Arg Arg Tyr Lys Ser Thr Leu Val Tyr Phe Leu His
                340                 345                 350

Asn Leu Gln Gln Pro Ile Thr Leu Thr Ala Gly Gly Val Phe Pro Ile
        355                 360                 365

Ser Met Gln Thr Asn Leu Ala Met Val Lys Leu Ala Phe Ser Val Val
    370                 375                 380

Thr Val Ile Lys Gln Phe Asn Leu Ala Glu Arg Phe Gln
385                 390                 395

<210> SEQ ID NO 33
<211> LENGTH: 1200
<212> TYPE: DNA
<213> ORGANISM: Drosophila melanogaster
<220> FEATURE:
<221> NAME/KEY: CDS
<222> LOCATION: (1)..(1200)
<223> OTHER INFORMATION: DOR 36E.1

<400> SEQUENCE: 33 atg gtt cgt tac gtg ccc cgg ttc gct gat ggt cag aaa gta aag ttg      48
Met Val Arg Tyr Val Pro Arg Phe Ala Asp Gly Gln Lys Val Lys Leu
  1               5                  10                  15 gct tgg ccc ttg gcg gtt ttt cgg tta aat cac ata ttc tgg cca ttg      96
Ala Trp Pro Leu Ala Val Phe Arg Leu Asn His Ile Phe Trp Pro Leu
             20                  25                  30 gat ccg agc aca ggg aaa tgg ggc cga tat ctg gac aag gtt cta gct     144
Asp Pro Ser Thr Gly Lys Trp Gly Arg Tyr Leu Asp Lys Val Leu Ala
         35                  40                  45 gtt gcg atg tcc ttg gtt ttt atg caa cac aac gat gca gag ctg agg     192
Val Ala Met Ser Leu Val Phe Met Gln His Asn Asp Ala Glu Leu Arg
     50                  55                  60 tac ttg cgc ttc gag gca agt aat cgg aat ttg gat gcc ttt ctc aca     240
Tyr Leu Arg Phe Glu Ala Ser Asn Arg Asn Leu Asp Ala Phe Leu Thr
 65                  70                  75                  80 gga atg cca acg tat tta atc ctc gtg gag gct caa ttt aga agt ctt     288
Gly Met Pro Thr Tyr Leu Ile Leu Val Glu Ala Gln Phe Arg Ser Leu
                 85                  90                  95 cac att cta ctg cac ttc gag aag ctt cag aag ttt tta gaa ata ttc     336
His Ile Leu Leu His Phe Glu Lys Leu Gln Lys Phe Leu Glu Ile Phe
            100                 105                 110 tac gca aat att tat att gat ccc cgt aag gaa ccc gaa atg ttt cga     384
Tyr Ala Asn Ile Tyr Ile Asp Pro Arg Lys Glu Pro Glu Met Phe Arg
        115                 120                 125
```

```
aaa gtg gat gga aag atg ata att aac aga tta gtt tcg gcc atg tac    432
Lys Val Asp Gly Lys Met Ile Ile Asn Arg Leu Val Ser Ala Met Tyr
    130                 135                 140 ggt gca gtt atc tct ctg tat cta atc gca ccc gtt ttt tcc atc att    480
Gly Ala Val Ile Ser Leu Tyr Leu Ile Ala Pro Val Phe Ser Ile Ile
145                 150                 155                 160 aac caa agc aaa gat ttt cta tac tct atg atc ttt ccg ttc gat tcg    528
Asn Gln Ser Lys Asp Phe Leu Tyr Ser Met Ile Phe Pro Phe Asp Ser
                165                 170                 175 gat ccc ttg tac ata ttt gtg cca ctg ctt ttg aca aac gta tgg gtt    576
Asp Pro Leu Tyr Ile Phe Val Pro Leu Leu Leu Thr Asn Val Trp Val
            180                 185                 190 ggc att gta ata gat acc atg atg ttc ggg gag acg aat ttg ttg tgt    624
Gly Ile Val Ile Asp Thr Met Met Phe Gly Glu Thr Asn Leu Leu Cys
        195                 200                 205 gaa cta att gtc cac cta aat ggt agt tat atg ttg ctc aag agg gac    672
Glu Leu Ile Val His Leu Asn Gly Ser Tyr Met Leu Leu Lys Arg Asp
210                 215                 220 ttg cag ttg gcc att gaa aag ata tta gtt gca agg gac cgt ccg cat    720
Leu Gln Leu Ala Ile Glu Lys Ile Leu Val Ala Arg Asp Arg Pro His
225                 230                 235                 240 atg gcc aaa cag cta aag gtt tta att aca aaa act ctc cga aag aat    768
Met Ala Lys Gln Leu Lys Val Leu Ile Thr Lys Thr Leu Arg Lys Asn
                245                 250                 255 gtg gct cta aat cag ttt ggc cag cag ctg gag gct cag tat act gtg    816
Val Ala Leu Asn Gln Phe Gly Gln Gln Leu Glu Ala Gln Tyr Thr Val
            260                 265                 270 cgg gtt ttt att atg ttt gca ttc gct gcg ggc ctt tta tgt gct ctt    864
Arg Val Phe Ile Met Phe Ala Phe Ala Ala Gly Leu Leu Cys Ala Leu
        275                 280                 285 tct ttt aag gct tat acg acg gat tcc ctc agc aca atg tac tac ctt    912
Ser Phe Lys Ala Tyr Thr Thr Asp Ser Leu Ser Thr Met Tyr Tyr Leu
    290                 295                 300 acc cat tgg gag caa atc ctg cag tac tct aca aat ccc agc gaa aat    960
Thr His Trp Glu Gln Ile Leu Gln Tyr Ser Thr Asn Pro Ser Glu Asn
305                 310                 315                 320 ctg cga tta cta aag ctc att aac ttg gcc att gag atg aac agc aag   1008
Leu Arg Leu Leu Lys Leu Ile Asn Leu Ala Ile Glu Met Asn Ser Lys
                325                 330                 335 ccc ttc tat gtg aca ggg cta aaa tat ttt cgc gtt agt ctg cag gct   1056
Pro Phe Tyr Val Thr Gly Leu Lys Tyr Phe Arg Val Ser Leu Gln Ala
            340                 345                 350 ggc tta aaa gta agt gaa aaa cga gtg caa aac cat ttc act gtc agc   1104
Gly Leu Lys Val Ser Glu Lys Arg Val Gln Asn His Phe Thr Val Ser
        355                 360                 365 tct ttc aca gat tct gca ggc atc ctt ctc gta ctt cac att cct cac   1152
Ser Phe Thr Asp Ser Ala Gly Ile Leu Leu Val Leu His Ile Pro His
    370                 375                 380 ttc gat gca gcg acg aca aat gag caa tta aat aat tca cat ttt ttt   1200
Phe Asp Ala Ala Thr Thr Asn Glu Gln Leu Asn Asn Ser His Phe Phe
385                 390                 395                 400
```

<210> SEQ ID NO 34
<211> LENGTH: 400
<212> TYPE: PRT
<213> ORGANISM: Drosophila melanogaster

<400> SEQUENCE: 34

```
Met Val Arg Tyr Val Pro Arg Phe Ala Asp Gly Gln Lys Val Lys Leu
 1               5                  10                  15
```

```
Ala Trp Pro Leu Ala Val Phe Arg Leu Asn His Ile Phe Trp Pro Leu
             20                  25                  30

Asp Pro Ser Thr Gly Lys Trp Gly Arg Tyr Leu Asp Lys Val Leu Ala
         35                  40                  45

Val Ala Met Ser Leu Val Phe Met Gln His Asn Asp Ala Glu Leu Arg
     50                  55                  60

Tyr Leu Arg Phe Glu Ala Ser Asn Arg Asn Leu Asp Ala Phe Leu Thr
 65                  70                  75                  80

Gly Met Pro Thr Tyr Leu Ile Leu Val Glu Ala Gln Phe Arg Ser Leu
                 85                  90                  95

His Ile Leu Leu His Phe Glu Lys Leu Gln Lys Phe Leu Glu Ile Phe
            100                 105                 110

Tyr Ala Asn Ile Tyr Ile Asp Pro Arg Lys Glu Pro Glu Met Phe Arg
        115                 120                 125

Lys Val Asp Gly Lys Met Ile Ile Asn Arg Leu Val Ser Ala Met Tyr
    130                 135                 140

Gly Ala Val Ile Ser Leu Tyr Leu Ile Ala Pro Val Phe Ser Ile Ile
145                 150                 155                 160

Asn Gln Ser Lys Asp Phe Leu Tyr Ser Met Ile Phe Pro Phe Asp Ser
                165                 170                 175

Asp Pro Leu Tyr Ile Phe Val Pro Leu Leu Leu Thr Asn Val Trp Val
            180                 185                 190

Gly Ile Val Ile Asp Thr Met Met Phe Gly Thr Asn Leu Leu Cys
        195                 200                 205

Glu Leu Ile Val His Leu Asn Gly Ser Tyr Met Leu Leu Lys Arg Asp
    210                 215                 220

Leu Gln Leu Ala Ile Glu Lys Ile Leu Val Ala Arg Asp Arg Pro His
225                 230                 235                 240

Met Ala Lys Gln Leu Lys Val Leu Ile Thr Lys Thr Leu Arg Lys Asn
                245                 250                 255

Val Ala Leu Asn Gln Phe Gly Gln Gln Leu Glu Ala Gln Tyr Thr Val
            260                 265                 270

Arg Val Phe Ile Met Phe Ala Phe Ala Ala Gly Leu Leu Cys Ala Leu
        275                 280                 285

Ser Phe Lys Ala Tyr Thr Thr Asp Ser Leu Ser Thr Met Tyr Tyr Leu
    290                 295                 300

Thr His Trp Glu Gln Ile Leu Gly Tyr Ser Thr Asn Pro Ser Glu Asn
305                 310                 315                 320

Leu Arg Leu Leu Lys Leu Ile Asn Leu Ala Ile Glu Met Asn Ser Lys
                325                 330                 335

Pro Phe Tyr Val Thr Gly Leu Lys Tyr Phe Arg Val Ser Leu Gln Ala
            340                 345                 350

Gly Leu Lys Val Ser Glu Lys Arg Val Gln Asn His Phe Thr Val Ser
        355                 360                 365

Ser Phe Thr Asp Ser Ala Gly Ile Leu Leu Val Leu His Ile Pro His
    370                 375                 380

Phe Asp Ala Ala Thr Thr Asn Glu Gln Leu Asn Asn Ser His Phe Phe
385                 390                 395                 400

<210> SEQ ID NO 35
<211> LENGTH: 1197
<212> TYPE: DNA
<213> ORGANISM: Drosophila melanogaster
<220> FEATURE:
```

-continued

```
<221> NAME/KEY: CDS
<222> LOCATION: (1)..(1197)
<223> OTHER INFORMATION: DOR 41E.1

<400> SEQUENCE: 35
```

| | | | | | | | | | | | | | | | | |
|---|---|---|---|---|---|---|---|---|---|---|---|---|---|---|---|---|
| atg | gtc | ttc | gag | cta | ata | cgt | ccc | gct | ccg | ctc | acg | gag | cag | aag | cgg | 48 |
| Met | Val | Phe | Glu | Leu | Ile | Arg | Pro | Ala | Pro | Leu | Thr | Glu | Gln | Lys | Arg | |
| 1 | | | | 5 | | | | | 10 | | | | | 15 | | |
| tcc | cga | gat | ggt | tgc | atc | tac | ctt | tac | cgc | gcc | atg | aag | ttt | att | gga | 96 |
| Ser | Arg | Asp | Gly | Cys | Ile | Tyr | Leu | Tyr | Arg | Ala | Met | Lys | Phe | Ile | Gly | |
| | | | 20 | | | | | 25 | | | | | 30 | | | |
| tgg | ctg | ccc | ccc | aag | cag | ggt | gtg | ctc | cgg | tat | gtg | tac | ctc | acc | tgg | 144 |
| Trp | Leu | Pro | Pro | Lys | Gln | Gly | Val | Leu | Arg | Tyr | Val | Tyr | Leu | Thr | Trp | |
| | 35 | | | | | 40 | | | | | 45 | | | | | |
| acg | cta | atg | acg | ttc | gtg | tgg | tgt | aca | acg | tac | ctg | ccg | ctt | ggc | ttc | 192 |
| Thr | Leu | Met | Thr | Phe | Val | Trp | Cys | Thr | Thr | Tyr | Leu | Pro | Leu | Gly | Phe | |
| 50 | | | | | 55 | | | | | 60 | | | | | | |
| ctt | ggt | agc | tac | atg | acg | cag | atc | aag | tcc | ttc | tcc | cct | gga | gag | ttt | 240 |
| Leu | Gly | Ser | Tyr | Met | Thr | Gln | Ile | Lys | Ser | Phe | Ser | Pro | Gly | Glu | Phe | |
| 65 | | | | | 70 | | | | | 75 | | | | | 80 | |
| ctc | act | tca | ctc | cag | gtg | tgc | att | aat | gcc | tac | ggc | tca | tcg | gta | aaa | 288 |
| Leu | Thr | Ser | Leu | Gln | Val | Cys | Ile | Asn | Ala | Tyr | Gly | Ser | Ser | Val | Lys | |
| | | | | 85 | | | | | 90 | | | | | 95 | | |
| gtt | gca | atc | aca | tac | tcc | atg | ctc | tgg | cgc | ctt | atc | aag | gcc | aag | aac | 336 |
| Val | Ala | Ile | Thr | Tyr | Ser | Met | Leu | Trp | Arg | Leu | Ile | Lys | Ala | Lys | Asn | |
| | | | 100 | | | | | 105 | | | | | 110 | | | |
| att | ttg | gac | cag | ctg | gac | ctg | cgc | tgc | acc | gcc | atg | gag | gag | cgc | gaa | 384 |
| Ile | Leu | Asp | Gln | Leu | Asp | Leu | Arg | Cys | Thr | Ala | Met | Glu | Glu | Arg | Glu | |
| | 115 | | | | | 120 | | | | | 125 | | | | | |
| aag | atc | cac | cta | gtg | gtg | gcc | cgc | agc | aac | cat | gcc | ttt | ctc | atc | ttc | 432 |
| Lys | Ile | His | Leu | Val | Val | Ala | Arg | Ser | Asn | His | Ala | Phe | Leu | Ile | Phe | |
| 130 | | | | | 135 | | | | | 140 | | | | | | |
| acc | ttt | gtc | tac | tgc | gga | tat | gcc | ggc | tcc | acc | tac | ctg | agc | tcg | gtt | 480 |
| Thr | Phe | Val | Tyr | Cys | Gly | Tyr | Ala | Gly | Ser | Thr | Tyr | Leu | Ser | Ser | Val | |
| 145 | | | | | 150 | | | | | 155 | | | | | 160 | |
| ctc | agc | ggg | cgt | ccg | ccc | tgg | cag | ctg | tac | aat | ccc | ttt | att | gat | tgg | 528 |
| Leu | Ser | Gly | Arg | Pro | Pro | Trp | Gln | Leu | Tyr | Asn | Pro | Phe | Ile | Asp | Trp | |
| | | | 165 | | | | | 170 | | | | | 175 | | | |
| cat | gac | ggc | aca | ctc | aag | ctc | tgg | gtg | gcc | tcc | acg | ttg | gag | tac | atg | 576 |
| His | Asp | Gly | Thr | Leu | Lys | Leu | Trp | Val | Ala | Ser | Thr | Leu | Glu | Tyr | Met | |
| | | 180 | | | | | 185 | | | | | 190 | | | | |
| gtg | atg | tca | ggc | gcc | gtt | ctg | cag | gat | caa | ctc | tcg | gac | tct | tac | cca | 624 |
| Val | Met | Ser | Gly | Ala | Val | Leu | Gln | Asp | Gln | Leu | Ser | Asp | Ser | Tyr | Pro | |
| | 195 | | | | | 200 | | | | | 205 | | | | | |
| ttg | atc | tat | acc | ctc | atc | ctt | cgt | gct | cac | ttg | gac | atg | cta | agg | gag | 672 |
| Leu | Ile | Tyr | Thr | Leu | Ile | Leu | Arg | Ala | His | Leu | Asp | Met | Leu | Arg | Glu | |
| 210 | | | | | 215 | | | | | 220 | | | | | | |
| cgc | atc | cga | cgc | ctc | cgt | tcc | gat | gag | aac | ctg | agc | gag | gcc | gag | agc | 720 |
| Arg | Ile | Arg | Arg | Leu | Arg | Ser | Asp | Glu | Asn | Leu | Ser | Glu | Ala | Glu | Ser | |
| 225 | | | | | 230 | | | | | 235 | | | | | 240 | |
| tat | gaa | gag | ctg | gtc | aaa | tgt | gtg | atg | gac | cac | aag | ctc | att | cta | aga | 768 |
| Tyr | Glu | Glu | Leu | Val | Lys | Cys | Val | Met | Asp | His | Lys | Leu | Ile | Leu | Arg | |
| | | | | 245 | | | | | 250 | | | | | 255 | | |
| tac | tgc | gcg | att | att | aaa | cca | gta | atc | cag | ggg | acc | atc | ttc | aca | cag | 816 |
| Tyr | Cys | Ala | Ile | Ile | Lys | Pro | Val | Ile | Gln | Gly | Thr | Ile | Phe | Thr | Gln | |
| | | | 260 | | | | | 265 | | | | | 270 | | | |
| ttt | ctg | ctg | atc | ggc | ctg | gtt | ctg | ggc | ttc | acg | ctg | atc | aac | gtg | ttt | 864 |
| Phe | Leu | Leu | Ile | Gly | Leu | Val | Leu | Gly | Phe | Thr | Leu | Ile | Asn | Val | Phe | |
| | 275 | | | | | 280 | | | | | 285 | | | | | |
| ttc | ttc | tca | gac | atc | tgg | acg | ggc | atc | gca | tca | ttt | atg | ttt | gtt | ata | 912 |

```
Phe Phe Ser Asp Ile Trp Thr Gly Ile Ala Ser Phe Met Phe Val Ile
        290                 295                 300 acc att ttg ctg cag acc ttc ccc ttc tgc tac aca tgc aac ctc atc      960
Thr Ile Leu Leu Gln Thr Phe Pro Phe Cys Tyr Thr Cys Asn Leu Ile
305                 310                 315                 320 atg gag gac tgc gag tcc ttg acc cat gct att ttc cag tcc aac tgg     1008
Met Glu Asp Cys Glu Ser Leu Thr His Ala Ile Phe Gln Ser Asn Trp
                325                 330                 335 gtg gat gcc agt cgt cgc tac aaa aca aca cta ctg tat ttt ctc caa     1056
Val Asp Ala Ser Arg Arg Tyr Lys Thr Thr Leu Leu Tyr Phe Leu Gln
            340                 345                 350 aac gtg cag cag cct atc gtt ttc att gca ggc ggt atc ttt cag ata     1104
Asn Val Gln Gln Pro Ile Val Phe Ile Ala Gly Gly Ile Phe Gln Ile
        355                 360                 365 tcc atg agc agc aac ata agt gtg gca aag ttt gct ttc tcc gtg ata     1152
Ser Met Ser Ser Asn Ile Ser Val Ala Lys Phe Ala Phe Ser Val Ile
370                 375                 380 acc att acc aag caa atg aat ata gct gac aaa ttt aag acg gac         1197
Thr Ile Thr Lys Gln Met Asn Ile Ala Asp Lys Phe Lys Thr Asp
385                 390                 395
```

<210> SEQ ID NO 36
<211> LENGTH: 399
<212> TYPE: PRT
<213> ORGANISM: Drosophila melanogaster

<400> SEQUENCE: 36

```
Met Val Phe Glu Leu Ile Arg Pro Ala Pro Leu Thr Glu Gln Lys Arg
  1               5                  10                  15

Ser Arg Asp Gly Cys Ile Tyr Leu Tyr Arg Ala Met Lys Phe Ile Gly
                 20                  25                  30

Trp Leu Pro Pro Lys Gln Gly Val Leu Arg Tyr Val Tyr Leu Thr Trp
             35                  40                  45

Thr Leu Met Thr Phe Val Trp Cys Thr Thr Tyr Leu Pro Leu Gly Phe
 50                  55                  60

Leu Gly Ser Tyr Met Thr Gln Ile Lys Ser Phe Ser Pro Gly Glu Phe
 65                  70                  75                  80

Leu Thr Ser Leu Gln Val Cys Ile Asn Ala Tyr Gly Ser Ser Val Lys
                 85                  90                  95

Val Ala Ile Thr Tyr Ser Met Leu Trp Arg Leu Ile Lys Ala Lys Asn
                100                 105                 110

Ile Leu Asp Gln Leu Asp Leu Arg Cys Thr Ala Met Glu Glu Arg Glu
            115                 120                 125

Lys Ile His Leu Val Val Ala Arg Ser Asn His Ala Phe Leu Ile Phe
130                 135                 140

Thr Phe Val Tyr Cys Gly Tyr Ala Gly Ser Thr Tyr Leu Ser Ser Val
145                 150                 155                 160

Leu Ser Gly Arg Pro Pro Trp Gln Leu Tyr Asn Pro Phe Ile Asp Trp
                165                 170                 175

His Asp Gly Thr Leu Lys Leu Trp Val Ala Ser Thr Leu Glu Tyr Met
            180                 185                 190

Val Met Ser Gly Ala Val Leu Gln Asp Gln Leu Ser Asp Ser Tyr Pro
        195                 200                 205

Leu Ile Tyr Thr Leu Ile Leu Arg Ala His Leu Asp Met Leu Arg Glu
    210                 215                 220

Arg Ile Arg Arg Leu Arg Ser Asp Glu Asn Leu Ser Glu Ala Glu Ser
225                 230                 235                 240
```

```
Tyr Glu Glu Leu Val Lys Cys Val Met Asp His Lys Leu Ile Leu Arg
                245                 250                 255

Tyr Cys Ala Ile Ile Lys Pro Val Ile Gln Gly Thr Ile Phe Thr Gln
            260                 265                 270

Phe Leu Leu Ile Gly Leu Val Leu Gly Phe Thr Leu Ile Asn Val Phe
        275                 280                 285

Phe Phe Ser Asp Ile Trp Thr Gly Ile Ala Ser Phe Met Phe Val Ile
    290                 295                 300

Thr Ile Leu Leu Gln Thr Phe Pro Phe Cys Tyr Thr Cys Asn Leu Ile
305                 310                 315                 320

Met Glu Asp Cys Glu Ser Leu Thr His Ala Ile Phe Gln Ser Asn Trp
                325                 330                 335

Val Asp Ala Ser Arg Arg Tyr Lys Thr Thr Leu Leu Tyr Phe Leu Gln
            340                 345                 350

Asn Val Gln Gln Pro Ile Val Phe Ile Ala Gly Gly Ile Phe Gln Ile
        355                 360                 365

Ser Met Ser Ser Asn Ile Ser Val Ala Lys Phe Ala Phe Ser Val Ile
    370                 375                 380

Thr Ile Thr Lys Gln Met Asn Ile Ala Asp Lys Phe Lys Thr Asp
385                 390                 395
```

<210> SEQ ID NO 37
<211> LENGTH: 1218
<212> TYPE: DNA
<213> ORGANISM: Drosophila melanogaster
<220> FEATURE:
<221> NAME/KEY: CDS
<222> LOCATION: (1)..(1218)
<223> OTHER INFORMATION: DOR 41E.2

<400> SEQUENCE: 37

```
atg gat ctg cga agg tgg ttt ccg acc ttg tac acc cag tcg aag gat        48
Met Asp Leu Arg Arg Trp Phe Pro Thr Leu Tyr Thr Gln Ser Lys Asp
 1               5                  10                  15 tcg cca gtt cgc tcc cga gac gcg acc ctg tac ctc cta cgc tgc gtc        96
Ser Pro Val Arg Ser Arg Asp Ala Thr Leu Tyr Leu Leu Arg Cys Val
             20                  25                  30 ttc tta atg ggc gtc cgc aag cca cct gcc aag ttt ttc gtg gcc tac       144
Phe Leu Met Gly Val Arg Lys Pro Pro Ala Lys Phe Phe Val Ala Tyr
         35                  40                  45 gtg ctc tgg tcc ttc gca ctg aat ttc tgc tca aca ttt tat cag cca       192
Val Leu Trp Ser Phe Ala Leu Asn Phe Cys Ser Thr Phe Tyr Gln Pro
     50                  55                  60 att ggc ttt ctc aca ggc tat ata agc cat tta tca gag ttc tcc ccg       240
Ile Gly Phe Leu Thr Gly Tyr Ile Ser His Leu Ser Glu Phe Ser Pro
 65                  70                  75                  80 gga gag ttt cta act tcg ctg cag gtg gcc ttt aat gct tgg tcc tgc       288
Gly Glu Phe Leu Thr Ser Leu Gln Val Ala Phe Asn Ala Trp Ser Cys
                 85                  90                  95 tct aca aaa gtc ctg ata gtg tgg gca cta gtt aag cgc ttt gac gag       336
Ser Thr Lys Val Leu Ile Val Trp Ala Leu Val Lys Arg Phe Asp Glu
            100                 105                 110 gct aat aac ctt ctc gac gag atg gat agg cgt atc aca gac ccc gga       384
Ala Asn Asn Leu Leu Asp Glu Met Asp Arg Arg Ile Thr Asp Pro Gly
        115                 120                 125 gag cgt ctt cag att cat cgc gct gtc tcc ctc agt aac cgt ata ttc       432
Glu Arg Leu Gln Ile His Arg Ala Val Ser Leu Ser Asn Arg Ile Phe
    130                 135                 140
```

```
ttc ttt ttc atg gca gtc tac atg gtt tat gcc act aat acg ttt ctg        480
Phe Phe Phe Met Ala Val Tyr Met Val Tyr Ala Thr Asn Thr Phe Leu
145                 150                 155                 160 tcg gcg atc ttc att gga agg cca ccg tac caa aat tac tac cct ttt        528
Ser Ala Ile Phe Ile Gly Arg Pro Pro Tyr Gln Asn Tyr Tyr Pro Phe
            165                 170                 175 ctg gac tgg cga tct agc act ctg cat cta gct ctg cag gcc ggt ctg        576
Leu Asp Trp Arg Ser Ser Thr Leu His Leu Ala Leu Gln Ala Gly Leu
        180                 185                 190 gaa tac ttc gcc atg gct ggc gcc tgc ttc cag gac gtt tgc gtt gat        624
Glu Tyr Phe Ala Met Ala Gly Ala Cys Phe Gln Asp Val Cys Val Asp
    195                 200                 205 tgc tac cca gtc aat ttc gtt ttg gtc ctg cgt gcc cac atg tcg atc        672
Cys Tyr Pro Val Asn Phe Val Leu Val Leu Arg Ala His Met Ser Ile
210                 215                 220 ttc gcg gag cgc ctt cga cgt ttg gga act tat cct tat gaa agc cag        720
Phe Ala Glu Arg Leu Arg Arg Leu Gly Thr Tyr Pro Tyr Glu Ser Gln
225                 230                 235                 240 gag cag aaa tat gaa cga ttg gtt cag tgc ata caa gat cac aaa gta        768
Glu Gln Lys Tyr Glu Arg Leu Val Gln Cys Ile Gln Asp His Lys Val
            245                 250                 255 att ttg cga ttt gtt gac tgc ctg cgt cct gtt att tct ggt acc atc        816
Ile Leu Arg Phe Val Asp Cys Leu Arg Pro Val Ile Ser Gly Thr Ile
        260                 265                 270 ttc gtg caa ttc ttg gtt gtg ggg ttg gtg ctg ggc ttt acc cta att        864
Phe Val Gln Phe Leu Val Val Gly Leu Val Leu Gly Phe Thr Leu Ile
    275                 280                 285 aac att gtc ctg ttc gcc aac ttg gga tcg gcc atc gca gcg ctc tcg        912
Asn Ile Val Leu Phe Ala Asn Leu Gly Ser Ala Ile Ala Ala Leu Ser
290                 295                 300 ttt atg gcc gca gtg ctt cta gag acg act ccc ttc tgc ata ttg tgc        960
Phe Met Ala Ala Val Leu Leu Glu Thr Thr Pro Phe Cys Ile Leu Cys
305                 310                 315                 320 aat tat ctc aca gaa gac tgc tac aag ctg gcc gat gcc ctg ttt cag       1008
Asn Tyr Leu Thr Glu Asp Cys Tyr Lys Leu Ala Asp Ala Leu Phe Gln
            325                 330                 335 tca aac tgg att gat gag gag aaa cga tac caa aag aca ctc atg tac       1056
Ser Asn Trp Ile Asp Glu Glu Lys Arg Tyr Gln Lys Thr Leu Met Tyr
        340                 345                 350 ttc cta cag aaa ctg cag cag cct ata acc ttc atg gct atg aac gtg       1104
Phe Leu Gln Lys Leu Gln Gln Pro Ile Thr Phe Met Ala Met Asn Val
    355                 360                 365 ttt cca ata tct gtg gga act aac atc agt gtc aca aaa ttt tcg ttc       1152
Phe Pro Ile Ser Val Gly Thr Asn Ile Ser Val Thr Lys Phe Ser Phe
370                 375                 380 tcc gtc ttt act ctc gta aaa caa atg aac ata tct gag aaa ctt gcc       1200
Ser Val Phe Thr Leu Val Lys Gln Met Asn Ile Ser Glu Lys Leu Ala
385                 390                 395                 400 aaa tct gaa atg gaa gag                                                1218
Lys Ser Glu Met Glu Glu
            405

<210> SEQ ID NO 38
<211> LENGTH: 406
<212> TYPE: PRT
<213> ORGANISM: Drosophila melanogaster

<400> SEQUENCE: 38

Met Asp Leu Arg Arg Trp Phe Pro Thr Leu Tyr Thr Gln Ser Lys Asp
1               5                   10                  15
```

-continued

```
Ser Pro Val Arg Ser Arg Asp Ala Thr Leu Tyr Leu Arg Cys Val
         20                  25                  30
Phe Leu Met Gly Val Arg Lys Pro Ala Lys Phe Val Ala Tyr
     35                  40                  45
Val Leu Trp Ser Phe Ala Leu Asn Phe Cys Ser Thr Phe Tyr Gln Pro
 50                  55                  60
Ile Gly Phe Leu Thr Gly Tyr Ile Ser His Leu Ser Glu Phe Ser Pro
 65                  70                  75                  80
Gly Glu Phe Leu Thr Ser Leu Gln Val Ala Phe Asn Ala Trp Ser Cys
                 85                  90                  95
Ser Thr Lys Val Leu Ile Val Trp Ala Leu Val Lys Arg Phe Asp Glu
            100                 105                 110
Ala Asn Asn Leu Leu Asp Glu Met Asp Arg Arg Ile Thr Asp Pro Gly
            115                 120                 125
Glu Arg Leu Gln Ile His Arg Ala Val Ser Leu Ser Asn Arg Ile Phe
        130                 135                 140
Phe Phe Phe Met Ala Val Tyr Met Val Tyr Ala Thr Asn Thr Phe Leu
145                 150                 155                 160
Ser Ala Ile Phe Ile Gly Arg Pro Pro Tyr Gln Asn Tyr Tyr Pro Phe
                165                 170                 175
Leu Asp Trp Arg Ser Ser Thr Leu His Leu Ala Leu Gln Ala Gly Leu
            180                 185                 190
Glu Tyr Phe Ala Met Ala Gly Ala Cys Phe Gln Asp Val Cys Val Asp
        195                 200                 205
Cys Tyr Pro Val Asn Phe Val Leu Val Leu Arg Ala His Met Ser Ile
    210                 215                 220
Phe Ala Glu Arg Leu Arg Arg Leu Gly Thr Tyr Pro Tyr Glu Ser Gln
225                 230                 235                 240
Glu Gln Lys Tyr Glu Arg Leu Val Gln Cys Ile Gln Asp His Lys Val
                245                 250                 255
Ile Leu Arg Phe Val Asp Cys Leu Arg Pro Val Ile Ser Gly Thr Ile
            260                 265                 270
Phe Val Gln Phe Leu Val Val Gly Leu Val Leu Gly Phe Thr Leu Ile
        275                 280                 285
Asn Ile Val Leu Phe Ala Asn Leu Gly Ser Ala Ile Ala Ala Leu Ser
    290                 295                 300
Phe Met Ala Ala Val Leu Leu Glu Thr Thr Pro Phe Cys Ile Leu Cys
305                 310                 315                 320
Asn Tyr Leu Thr Glu Asp Cys Tyr Lys Leu Ala Asp Ala Leu Phe Gln
                325                 330                 335
Ser Asn Trp Ile Asp Glu Glu Lys Arg Tyr Gln Lys Thr Leu Met Tyr
            340                 345                 350
Phe Leu Gln Lys Leu Gln Gln Pro Ile Thr Phe Met Ala Met Asn Val
        355                 360                 365
Phe Pro Ile Ser Val Gly Thr Asn Ile Ser Val Thr Lys Phe Ser Phe
    370                 375                 380
Ser Val Phe Thr Leu Val Lys Gln Met Asn Ile Ser Glu Lys Leu Ala
385                 390                 395                 400
Lys Ser Glu Met Glu Glu
                405
```

<210> SEQ ID NO 39
<211> LENGTH: 1188
<212> TYPE: DNA

-continued

```
<213> ORGANISM: Drosophila melanogaster
<220> FEATURE:
<221> NAME/KEY: CDS
<222> LOCATION: (1)..(1188)
<223> OTHER INFORMATION: DOR 45F.1

<400> SEQUENCE: 39
```

| | | | | | | | | | | | | | | | | |
|---|---|---|---|---|---|---|---|---|---|---|---|---|---|---|---|---|
| atg | tat | ccg | cga | ttc | ctc | agc | cgt | aac | tat | ccg | ctg | gcc | aag | cat | ttg | 48 |
| Met | Tyr | Pro | Arg | Phe | Leu | Ser | Arg | Asn | Tyr | Pro | Leu | Ala | Lys | His | Leu | |
| 1 | | | | 5 | | | | | 10 | | | | | 15 | | |
| ttc | ttc | gtc | acc | aga | tac | tcc | ttt | ggc | ctg | ctg | ggc | ctg | aga | ttt | ggc | 96 |
| Phe | Phe | Val | Thr | Arg | Tyr | Ser | Phe | Gly | Leu | Leu | Gly | Leu | Arg | Phe | Gly | |
| | | | 20 | | | | | 25 | | | | | 30 | | | |
| aaa | gag | caa | tcg | tgg | ctt | cac | ctc | ttg | tgg | ctg | gtg | ttc | aat | ttc | gtt | 144 |
| Lys | Glu | Gln | Ser | Trp | Leu | His | Leu | Leu | Trp | Leu | Val | Phe | Asn | Phe | Val | |
| | | 35 | | | | | 40 | | | | | 45 | | | | |
| aac | ctg | gcg | cac | tgc | tgc | cag | gcg | gag | ttc | gtc | ttc | ggc | tgg | agt | cac | 192 |
| Asn | Leu | Ala | His | Cys | Cys | Gln | Ala | Glu | Phe | Val | Phe | Gly | Trp | Ser | His | |
| | 50 | | | | | 55 | | | | | 60 | | | | | |
| ttg | cgc | acc | agt | ccc | gtg | gat | gcc | atg | gac | gcc | ttt | tgt | cct | ctg | gcc | 240 |
| Leu | Arg | Thr | Ser | Pro | Val | Asp | Ala | Met | Asp | Ala | Phe | Cys | Pro | Leu | Ala | |
| 65 | | | | | 70 | | | | | 75 | | | | | 80 | |
| tgc | agt | ttc | acc | acg | ctc | ttc | aag | ctg | gga | tgg | atg | tgg | tgg | cgt | cgc | 288 |
| Cys | Ser | Phe | Thr | Thr | Leu | Phe | Lys | Leu | Gly | Trp | Met | Trp | Trp | Arg | Arg | |
| | | | | 85 | | | | | 90 | | | | | 95 | | |
| cag | gaa | gta | gct | gat | cta | atg | gac | cgc | atc | cgc | ttg | ctc | atc | ggg | gag | 336 |
| Gln | Glu | Val | Ala | Asp | Leu | Met | Asp | Arg | Ile | Arg | Leu | Leu | Ile | Gly | Glu | |
| | | | | 100 | | | | | 105 | | | | | 110 | | |
| cag | gag | aag | agg | gag | gac | tcc | cgg | aga | aag | gtg | gct | caa | agg | agc | tac | 384 |
| Gln | Glu | Lys | Arg | Glu | Asp | Ser | Arg | Arg | Lys | Val | Ala | Gln | Arg | Ser | Tyr | |
| | | | 115 | | | | | 120 | | | | | 125 | | | |
| tat | ctc | atg | gtc | acc | agg | tgc | ggt | atg | ctg | gtc | ttc | acc | ctg | ggc | agc | 432 |
| Tyr | Leu | Met | Val | Thr | Arg | Cys | Gly | Met | Leu | Val | Phe | Thr | Leu | Gly | Ser | |
| | 130 | | | | | 135 | | | | | 140 | | | | | |
| att | acc | act | gga | gcc | ttc | gtt | ctg | cgt | tcc | ctt | tgg | gaa | atg | tgg | gtg | 480 |
| Ile | Thr | Thr | Gly | Ala | Phe | Val | Leu | Arg | Ser | Leu | Trp | Glu | Met | Trp | Val | |
| 145 | | | | | 150 | | | | | 155 | | | | | 160 | |
| cgt | cgt | cat | cag | gag | ttc | aaa | ttc | gat | atg | ccc | ttt | cgc | atg | ctg | ttc | 528 |
| Arg | Arg | His | Gln | Glu | Phe | Lys | Phe | Asp | Met | Pro | Phe | Arg | Met | Leu | Phe | |
| | | | | 165 | | | | | 170 | | | | | 175 | | |
| cac | gac | ttt | gcg | cat | cgc | atg | ccc | tgg | ttt | cca | gtt | ttc | tat | ctc | tac | 576 |
| His | Asp | Phe | Ala | His | Arg | Met | Pro | Trp | Phe | Pro | Val | Phe | Tyr | Leu | Tyr | |
| | | | | 180 | | | | | 185 | | | | | 190 | | |
| tcc | aca | tgg | agt | ggc | cag | gtc | act | gtg | tac | gcc | ttt | gct | ggt | aca | gat | 624 |
| Ser | Thr | Trp | Ser | Gly | Gln | Val | Thr | Val | Tyr | Ala | Phe | Ala | Gly | Thr | Asp | |
| | | | 195 | | | | | 200 | | | | | 205 | | | |
| ggt | ttc | ttc | ttt | ggc | ttt | acc | ctc | tac | atg | gcc | ttc | ttg | ctg | cag | gcc | 672 |
| Gly | Phe | Phe | Phe | Gly | Phe | Thr | Leu | Tyr | Met | Ala | Phe | Leu | Leu | Gln | Ala | |
| | 210 | | | | | 215 | | | | | 220 | | | | | |
| tta | aga | tac | gat | atc | cag | gat | gcc | ctc | aag | cca | ata | aga | gat | ccc | tcg | 720 |
| Leu | Arg | Tyr | Asp | Ile | Gln | Asp | Ala | Leu | Lys | Pro | Ile | Arg | Asp | Pro | Ser | |
| 225 | | | | | 230 | | | | | 235 | | | | | 240 | |
| ctt | agg | gaa | tcc | aaa | atc | tgc | tgt | cag | cga | ttg | gcg | gac | atc | gtg | gat | 768 |
| Leu | Arg | Glu | Ser | Lys | Ile | Cys | Cys | Gln | Arg | Leu | Ala | Asp | Ile | Val | Asp | |
| | | | | 245 | | | | | 250 | | | | | 255 | | |
| cgc | cac | aat | gag | ata | gag | aag | ata | gtc | aag | gaa | ttt | tct | gga | att | atg | 816 |
| Arg | His | Asn | Glu | Ile | Glu | Lys | Ile | Val | Lys | Glu | Phe | Ser | Gly | Ile | Met | |
| | | | | 260 | | | | | 265 | | | | | 270 | | |
| gct | gct | cca | act | ttt | gtt | cac | ttc | gta | tca | gcc | agc | tta | gtg | ata | gcc | 864 |
| Ala | Ala | Pro | Thr | Phe | Val | His | Phe | Val | Ser | Ala | Ser | Leu | Val | Ile | Ala | |
| | | | 275 | | | | | 280 | | | | | 285 | | | |

```
acc agc gtc att gat ata cta ttg tat tcc ggc tat aac atc atc cgt      912
Thr Ser Val Ile Asp Ile Leu Leu Tyr Ser Gly Tyr Asn Ile Ile Arg
    290                 295                 300 tac gtg gtg tac acc ttc acg gtt tcc tcg gcc atc ttc ctc tat tgc      960
Tyr Val Val Tyr Thr Phe Thr Val Ser Ser Ala Ile Phe Leu Tyr Cys
305                 310                 315                 320 tac gga ggc aca gaa atg tca act gag agc ctt tcc ttg gga gaa gca     1008
Tyr Gly Gly Thr Glu Met Ser Thr Glu Ser Leu Ser Leu Gly Glu Ala
                325                 330                 335 gcc tac agc agt gcc tgg tat act tgg gat cga gag acc cgc agg cgg     1056
Ala Tyr Ser Ser Ala Trp Tyr Thr Trp Asp Arg Glu Thr Arg Arg Arg
            340                 345                 350 gtc ttt ctc att atc ctg cgt gct caa cga ccc att acg gtg agg gtg     1104
Val Phe Leu Ile Ile Leu Arg Ala Gln Arg Pro Ile Thr Val Arg Val
        355                 360                 365 ccc ttt ttt gca cca tcg tta cca gtc ttc aca tcg gtc atc aag ttt     1152
Pro Phe Phe Ala Pro Ser Leu Pro Val Phe Thr Ser Val Ile Lys Phe
    370                 375                 380 aca ggt tcg att gtg gca ctg gct aag acg ata ctg                     1188
Thr Gly Ser Ile Val Ala Leu Ala Lys Thr Ile Leu
385                 390                 395

<210> SEQ ID NO 40
<211> LENGTH: 396
<212> TYPE: PRT
<213> ORGANISM: Drosophila melanogaster

<400> SEQUENCE: 40

Met Tyr Pro Arg Phe Leu Ser Arg Asn Tyr Pro Leu Ala Lys His Leu
1               5                   10                  15

Phe Phe Val Thr Arg Tyr Ser Phe Gly Leu Leu Gly Leu Arg Phe Gly
                20                  25                  30

Lys Glu Gln Ser Trp Leu His Leu Leu Trp Leu Val Phe Asn Phe Val
            35                  40                  45

Asn Leu Ala His Cys Cys Gln Ala Glu Phe Val Phe Gly Trp Ser His
        50                  55                  60

Leu Arg Thr Ser Pro Val Asp Ala Met Asp Ala Phe Cys Pro Leu Ala
65                  70                  75                  80

Cys Ser Phe Thr Thr Leu Phe Lys Leu Gly Trp Met Trp Arg Arg
                85                  90                  95

Gln Glu Val Ala Asp Leu Met Arg Ile Arg Leu Leu Ile Gly Glu
            100                 105                 110

Gln Glu Lys Arg Glu Asp Ser Arg Arg Lys Val Ala Gln Arg Ser Tyr
        115                 120                 125

Tyr Leu Met Val Thr Arg Cys Gly Met Leu Val Phe Thr Leu Gly Ser
    130                 135                 140

Ile Thr Thr Gly Ala Phe Val Leu Arg Ser Leu Trp Glu Met Trp Val
145                 150                 155                 160

Arg Arg His Gln Glu Phe Lys Phe Asp Met Pro Phe Arg Met Leu Phe
                165                 170                 175

His Asp Phe Ala His Arg Met Pro Trp Phe Pro Val Phe Tyr Leu Tyr
            180                 185                 190

Ser Thr Trp Ser Gly Gln Val Thr Val Tyr Ala Phe Ala Gly Thr Asp
        195                 200                 205

Gly Phe Phe Phe Gly Phe Thr Leu Tyr Met Ala Phe Leu Leu Gln Ala
    210                 215                 220
```

```
Leu Arg Tyr Asp Ile Gln Asp Ala Leu Lys Pro Ile Arg Asp Pro Ser
225                 230                 235                 240

Leu Arg Glu Ser Lys Ile Cys Cys Gln Arg Leu Ala Asp Ile Val Asp
            245                 250                 255

Arg His Asn Glu Ile Glu Lys Ile Val Lys Glu Phe Ser Gly Ile Met
                260                 265                 270

Ala Ala Pro Thr Phe Val His Phe Val Ser Ala Ser Leu Val Ile Ala
            275                 280                 285

Thr Ser Val Ile Asp Ile Leu Leu Tyr Ser Gly Tyr Asn Ile Ile Arg
        290                 295                 300

Tyr Val Val Tyr Thr Phe Thr Val Ser Ser Ala Ile Phe Leu Tyr Cys
305                 310                 315                 320

Tyr Gly Gly Thr Glu Met Ser Thr Glu Ser Leu Ser Leu Gly Glu Ala
                325                 330                 335

Ala Tyr Ser Ser Ala Trp Tyr Thr Trp Asp Arg Glu Thr Arg Arg Arg
            340                 345                 350

Val Phe Leu Ile Ile Leu Arg Ala Gln Arg Pro Ile Thr Val Arg Val
        355                 360                 365

Pro Phe Phe Ala Pro Ser Leu Pro Val Phe Thr Ser Val Ile Lys Phe
370                 375                 380

Thr Gly Ser Ile Val Ala Leu Ala Lys Thr Ile Leu
385                 390                 395
```

<210> SEQ ID NO 41
<211> LENGTH: 1158
<212> TYPE: DNA
<213> ORGANISM: Drosophila melanogaster
<220> FEATURE:
<221> NAME/KEY: CDS
<222> LOCATION: (1)..(1158)
<223> OTHER INFORMATION: DOR 49D.1

<400> SEQUENCE: 41

```
atg ttt gaa gac att cag cta atc tac atg aat atc aag ata ttg cga      48
Met Phe Glu Asp Ile Gln Leu Ile Tyr Met Asn Ile Lys Ile Leu Arg
 1               5                  10                  15 ttc tgg gcc ctg ctc tat gac aaa aac ttg agg cgt tat gtg tgc att      96
Phe Trp Ala Leu Leu Tyr Asp Lys Asn Leu Arg Arg Tyr Val Cys Ile
             20                  25                  30 gga ctg gcc tca ttc cac atc ttc acc caa atc gtc tac atg atg agt     144
Gly Leu Ala Ser Phe His Ile Phe Thr Gln Ile Val Tyr Met Met Ser
         35                  40                  45 acc aat gaa gga cta acc ggg ata att cgt aac tca tat atg ctc gtc     192
Thr Asn Glu Gly Leu Thr Gly Ile Ile Arg Asn Ser Tyr Met Leu Val
     50                  55                  60 ctt tgg att aat acg gtg ctg cga gct tat ctc ttg ctg gcg gat cac     240
Leu Trp Ile Asn Thr Val Leu Arg Ala Tyr Leu Leu Leu Ala Asp His
 65                  70                  75                  80 gac aga tat ttg gct ttg atc caa aaa cta act gag gcc tat tac gat     288
Asp Arg Tyr Leu Ala Leu Ile Gln Lys Leu Thr Glu Ala Tyr Tyr Asp
                 85                  90                  95 tta ctg aat ctg aac gat tcg tat ata tcg gaa ata ttg gac cag gtg     336
Leu Leu Asn Leu Asn Asp Ser Tyr Ile Ser Glu Ile Leu Asp Gln Val
            100                 105                 110 aac aag gtg gga aag ttg atg gct agg ggc aat ctg ttc ttt ggc atg     384
Asn Lys Val Gly Lys Leu Met Ala Arg Gly Asn Leu Phe Phe Gly Met
        115                 120                 125 ctc aca tcc atg gga ttc ggt ctg tac cca ttg tcc tcc agc gaa aga     432
Leu Thr Ser Met Gly Phe Gly Leu Tyr Pro Leu Ser Ser Ser Glu Arg
```

```
            130                 135                 140
gct ctt aat ttt aaa acc cac ttt cct ttt gca gtc ctg cca ttt ggc    480
Ala Leu Asn Phe Lys Thr His Phe Pro Phe Ala Val Leu Pro Phe Gly
145                 150                 155                 160 agc aaa att cct ggt cta aat gag tac gag agt ccg tac tat gag atg    528
Ser Lys Ile Pro Gly Leu Asn Glu Tyr Glu Ser Pro Tyr Tyr Glu Met
                165                 170                 175 tgg tac atc ttt cag atg ctc atc acc ccg atg ggc tgt tgc atg tac    576
Trp Tyr Ile Phe Gln Met Leu Ile Thr Pro Met Gly Cys Cys Met Tyr
            180                 185                 190 att ccg tac acc agt ctg att gtg ggc ttg ata atg ttc ggc att gtg    624
Ile Pro Tyr Thr Ser Leu Ile Val Gly Leu Ile Met Phe Gly Ile Val
        195                 200                 205 agg tgc aag gct ttg cag cat cgc ctc cgc cag gtg gcg ctt aag cat    672
Arg Cys Lys Ala Leu Gln His Arg Leu Arg Gln Val Ala Leu Lys His
    210                 215                 220 ccg tac gga gat cgc gat ccc cgt gaa ctg agg gag gag atc ata gcc    720
Pro Tyr Gly Asp Arg Asp Pro Arg Glu Leu Arg Glu Glu Ile Ile Ala
225                 230                 235                 240 tgc ata cgt tac cag cag agc att atc gag tac atg gat cac ata aac    768
Cys Ile Arg Tyr Gln Gln Ser Ile Ile Glu Tyr Met Asp His Ile Asn
                245                 250                 255 gag ctg acc acc atg atg ttc cta ttc gaa ctg atg gcc ttt tcg gcg    816
Glu Leu Thr Thr Met Met Phe Leu Phe Glu Leu Met Ala Phe Ser Ala
            260                 265                 270 ctc ctc tgt gcg ctg ctc ttt atg ctg att atc gtc agc ggc acc agt    864
Leu Leu Cys Ala Leu Leu Phe Met Leu Ile Ile Val Ser Gly Thr Ser
        275                 280                 285 cag ctg ata att gtt tgc atg tac att aac atg att ctg gcc caa ata    912
Gln Leu Ile Ile Val Cys Met Tyr Ile Asn Met Ile Leu Ala Gln Ile
    290                 295                 300 ctg gcc ctc tat tgg tat gca aat gag tta agg gaa cag aat ctg gcg    960
Leu Ala Leu Tyr Trp Tyr Ala Asn Glu Leu Arg Glu Gln Asn Leu Ala
305                 310                 315                 320 gtg gcc acc gca gcc tac gaa acg gag tgg ttc acc ttc gac gtt cca   1008
Val Ala Thr Ala Ala Tyr Glu Thr Glu Trp Phe Thr Phe Asp Val Pro
                325                 330                 335 ctg cgc aaa aac atc ctg ttc atg atg atg agg gca cag cgg cca gct   1056
Leu Arg Lys Asn Ile Leu Phe Met Met Met Arg Ala Gln Arg Pro Ala
            340                 345                 350 gca ata cta ctg ggc aat ata cgc ccc atc act ttg gaa ctg ttc caa   1104
Ala Ile Leu Leu Gly Asn Ile Arg Pro Ile Thr Leu Glu Leu Phe Gln
        355                 360                 365 aac cta ctg aac aca acc tat aca ttt ttt acg gtt ctc aag cga gtc   1152
Asn Leu Leu Asn Thr Thr Tyr Thr Phe Phe Thr Val Leu Lys Arg Val
    370                 375                 380 tac gga                                                            1158
Tyr Gly
385

<210> SEQ ID NO 42
<211> LENGTH: 386
<212> TYPE: PRT
<213> ORGANISM: Drosophila melanogaster

<400> SEQUENCE: 42

Met Phe Glu Asp Ile Gln Leu Ile Tyr Met Asn Ile Lys Ile Leu Arg
 1               5                  10                  15

Phe Trp Ala Leu Leu Tyr Asp Lys Asn Leu Arg Arg Tyr Val Cys Ile
            20                  25                  30
```

Gly Leu Ala Ser Phe His Ile Phe Thr Gln Ile Val Tyr Met Met Ser
        35                  40                  45

Thr Asn Glu Gly Leu Thr Gly Ile Ile Arg Asn Ser Tyr Met Leu Val
    50                  55                  60

Leu Trp Ile Asn Thr Val Leu Arg Ala Tyr Leu Leu Ala Asp His
65                  70                  75                  80

Asp Arg Tyr Leu Ala Leu Ile Gln Lys Leu Thr Glu Ala Tyr Tyr Asp
                85                  90                  95

Leu Leu Asn Leu Asn Asp Ser Tyr Ile Ser Glu Ile Leu Asp Gln Val
            100                 105                 110

Asn Lys Val Gly Lys Leu Met Ala Arg Gly Asn Leu Phe Phe Gly Met
        115                 120                 125

Leu Thr Ser Met Gly Phe Gly Leu Tyr Pro Leu Ser Ser Ser Glu Arg
    130                 135                 140

Ala Leu Asn Phe Lys Thr His Phe Pro Phe Ala Val Leu Pro Phe Gly
145                 150                 155                 160

Ser Lys Ile Pro Gly Leu Asn Glu Tyr Glu Ser Pro Tyr Tyr Glu Met
                165                 170                 175

Trp Tyr Ile Phe Gln Met Leu Ile Thr Pro Met Gly Cys Cys Met Tyr
            180                 185                 190

Ile Pro Tyr Thr Ser Leu Ile Val Gly Leu Ile Met Phe Gly Ile Val
        195                 200                 205

Arg Cys Lys Ala Leu Gln His Arg Leu Arg Gln Val Ala Leu Lys His
    210                 215                 220

Pro Tyr Gly Asp Arg Asp Pro Arg Glu Leu Arg Glu Glu Ile Ile Ala
225                 230                 235                 240

Cys Ile Arg Tyr Gln Gln Ser Ile Ile Glu Tyr Met Asp His Ile Asn
                245                 250                 255

Glu Leu Thr Thr Met Met Phe Leu Phe Glu Leu Met Ala Phe Ser Ala
            260                 265                 270

Leu Leu Cys Ala Leu Leu Phe Met Leu Ile Ile Val Ser Gly Thr Ser
        275                 280                 285

Gln Leu Ile Ile Val Cys Met Tyr Ile Asn Met Ile Leu Ala Gln Ile
    290                 295                 300

Leu Ala Leu Tyr Trp Tyr Ala Asn Glu Leu Arg Glu Gln Asn Leu Ala
305                 310                 315                 320

Val Ala Thr Ala Ala Tyr Glu Thr Glu Trp Phe Thr Phe Asp Val Pro
                325                 330                 335

Leu Arg Lys Asn Ile Leu Phe Met Met Met Arg Ala Gln Arg Pro Ala
            340                 345                 350

Ala Ile Leu Leu Gly Asn Ile Arg Pro Ile Thr Leu Glu Leu Phe Gln
        355                 360                 365

Asn Leu Leu Asn Thr Thr Tyr Thr Phe Phe Thr Val Leu Lys Arg Val
    370                 375                 380

Tyr Gly
385

<210> SEQ ID NO 43
<211> LENGTH: 1359
<212> TYPE: DNA
<213> ORGANISM: Drosophila melanogaster
<220> FEATURE:
<221> NAME/KEY: CDS
<222> LOCATION: (1)..(1359)
<223> OTHER INFORMATION: DOR 56E.1

-continued

```
<400> SEQUENCE: 43 atg gtt aac gct aaa cag ttt aac atg ttt aaa gtt aag gat ctg ttg      48
Met Val Asn Ala Lys Gln Phe Asn Met Phe Lys Val Lys Asp Leu Leu
1               5                   10                  15 ctt tcg ccg aca act ttc gag gat cca att ttt gga acc cac ctg cga      96
Leu Ser Pro Thr Thr Phe Glu Asp Pro Ile Phe Gly Thr His Leu Arg
                20                  25                  30 tac ttc caa tgg tac gga tat gtg gcc tcc aag gat cag aat agg cct     144
Tyr Phe Gln Trp Tyr Gly Tyr Val Ala Ser Lys Asp Gln Asn Arg Pro
            35                  40                  45 ttg tta agt ctt ata cgg tgc acc att ttg acg gca tcg att tgg ctt     192
Leu Leu Ser Leu Ile Arg Cys Thr Ile Leu Thr Ala Ser Ile Trp Leu
        50                  55                  60 agc tgt gct tta atg ctg gcg aga gtg ttt cgt ggt tac gaa aac ctc     240
Ser Cys Ala Leu Met Leu Ala Arg Val Phe Arg Gly Tyr Glu Asn Leu
65                  70                  75                  80 aat gat ggg gcc aca agt tac gcc acc gca gtc cag tat ttc gcg gta     288
Asn Asp Gly Ala Thr Ser Tyr Ala Thr Ala Val Gln Tyr Phe Ala Val
                85                  90                  95 tcg att gcc atg ttt aat gct tac gta caa aga gat aga tat gtt ctt     336
Ser Ile Ala Met Phe Asn Ala Tyr Val Gln Arg Asp Arg Tyr Val Leu
            100                 105                 110 tta tac tta cac att gtt tta gaa gta ata tcc ctt ttg cga gtt gcc     384
Leu Tyr Leu His Ile Val Leu Glu Val Ile Ser Leu Leu Arg Val Ala
        115                 120                 125 cac tcg gat atc cag aac ttg atg cac gaa gca gat aat cgg gag atg     432
His Ser Asp Ile Gln Asn Leu Met His Glu Ala Asp Asn Arg Glu Met
130                 135                 140 gaa ctt ttg gtc gcc act cag gct tat aca cga acc att acc ctg ttg     480
Glu Leu Leu Val Ala Thr Gln Ala Tyr Thr Arg Thr Ile Thr Leu Leu
145                 150                 155                 160 atc tgg ata cca tcg gtt att gct ggc cta atg gcc tat tca gac tgc     528
Ile Trp Ile Pro Ser Val Ile Ala Gly Leu Met Ala Tyr Ser Asp Cys
                165                 170                 175 atc tac agg agt ctg ttt ctg ccg aaa tcg gtt ttc aat gtg cca gct     576
Ile Tyr Arg Ser Leu Phe Leu Pro Lys Ser Val Phe Asn Val Pro Ala
            180                 185                 190 gtg cga cgt ggt gag gag cat ccc att ctg cta ttt cag ctg ttt ccc     624
Val Arg Arg Gly Glu Glu His Pro Ile Leu Leu Phe Gln Leu Phe Pro
        195                 200                 205 ttc gga gaa ctt tgc gat aac ttc gtt gtt gga tac ttg gga cct tgg     672
Phe Gly Glu Leu Cys Asp Asn Phe Val Val Gly Tyr Leu Gly Pro Trp
210                 215                 220 tat gct ctg ggc ctg gga atc acg gct atc cca ttg tgg cac acc ttt     720
Tyr Ala Leu Gly Leu Gly Ile Thr Ala Ile Pro Leu Trp His Thr Phe
225                 230                 235                 240 atc act tgc ctc atg aag tac gta aat ctc aag ctg caa ata ctc aac     768
Ile Thr Cys Leu Met Lys Tyr Val Asn Leu Lys Leu Gln Ile Leu Asn
                245                 250                 255 aag cga gtg gag gag atg gat att acc cga ctt aat tcc aaa ttg gta     816
Lys Arg Val Glu Glu Met Asp Ile Thr Arg Leu Asn Ser Lys Leu Val
            260                 265                 270 att ggt cgc cta act gcc agt gag tta acc ttc tgg caa atg caa ctc     864
Ile Gly Arg Leu Thr Ala Ser Glu Leu Thr Phe Trp Gln Met Gln Leu
        275                 280                 285 ttc aag gaa ttt gta aag gaa cag ctg agg att cga aaa ttt gtc cag     912
Phe Lys Glu Phe Val Lys Glu Gln Leu Arg Ile Arg Lys Phe Val Gln
290                 295                 300
```

-continued

```
gaa cta cag tat ctg att tgc gtg cct gtg atg gca gat ttc att atc      960
Glu Leu Gln Tyr Leu Ile Cys Val Pro Val Met Ala Asp Phe Ile Ile
305                 310                 315                 320 ttc tcg gtt ctc att tgc ttt ctc ttt ttt gcc ttg aca gtt ggc gtt     1008
Phe Ser Val Leu Ile Cys Phe Leu Phe Phe Ala Leu Thr Val Gly Val
                325                 330                 335 cca agc aaa atg gat tac ttc ttc atg ttc att tac ctt ttt gtg atg    1056
Pro Ser Lys Met Asp Tyr Phe Phe Met Phe Ile Tyr Leu Phe Val Met
            340                 345                 350 gct ggt ata ttg tgg att tat cat tgg cat gcc acg ttg att gtt gaa    1104
Ala Gly Ile Leu Trp Ile Tyr His Trp His Ala Thr Leu Ile Val Glu
        355                 360                 365 tgt cac gat gaa ctg agc ctt gct tac ttt tct tgc gga tgg tac aac    1152
Cys His Asp Glu Leu Ser Leu Ala Tyr Phe Ser Cys Gly Trp Tyr Asn
    370                 375                 380 ttc gaa atg cct ttg cag aaa atg ctg gtt ttt atg atg atg cat gcc    1200
Phe Glu Met Pro Leu Gln Lys Met Leu Val Phe Met Met Met His Ala
385                 390                 395                 400 caa agg ccg atg aag atg cgc gcc ctg ctg gtc gat ttg aat ctg agg    1248
Gln Arg Pro Met Lys Met Arg Ala Leu Leu Val Asp Leu Asn Leu Arg
                405                 410                 415 acc ttc ata gac gta agg ctg cta act gct aac tcg ata ttg gat tta    1296
Thr Phe Ile Asp Val Arg Leu Leu Thr Ala Asn Ser Ile Leu Asp Leu
            420                 425                 430 tcg aat tca agc ctt tcc ttt cca gat tgg ccg tgg agc cta cag cta    1344
Ser Asn Ser Ser Leu Ser Phe Pro Asp Trp Pro Trp Ser Leu Gln Leu
        435                 440                 445 ctt caa ttt gct gcg                                                 1359
Leu Gln Phe Ala Ala
    450
```

<210> SEQ ID NO 44
<211> LENGTH: 453
<212> TYPE: PRT
<213> ORGANISM: Drosophila melanogaster

<400> SEQUENCE: 44

```
Met Val Asn Ala Lys Gln Phe Asn Met Phe Lys Val Lys Asp Leu Leu
1               5                   10                  15

Leu Ser Pro Thr Thr Phe Glu Asp Pro Ile Phe Gly Thr His Leu Arg
            20                  25                  30

Tyr Phe Gln Trp Tyr Gly Tyr Val Ala Ser Lys Asp Gln Asn Arg Pro
        35                  40                  45

Leu Leu Ser Leu Ile Arg Cys Thr Ile Leu Thr Ala Ser Ile Trp Leu
    50                  55                  60

Ser Cys Ala Leu Met Leu Ala Arg Val Phe Arg Gly Tyr Glu Asn Leu
65                  70                  75                  80

Asn Asp Gly Ala Thr Ser Tyr Ala Thr Ala Val Gln Tyr Phe Ala Val
                85                  90                  95

Ser Ile Ala Met Phe Asn Ala Tyr Val Gln Arg Asp Arg Tyr Val Leu
            100                 105                 110

Leu Tyr Leu His Ile Val Leu Glu Val Ile Ser Leu Leu Arg Val Ala
        115                 120                 125

His Ser Asp Ile Gln Asn Leu Met His Glu Ala Asp Asn Arg Glu Met
    130                 135                 140

Glu Leu Leu Val Ala Thr Gln Ala Tyr Thr Arg Thr Ile Thr Leu Leu
145                 150                 155                 160

Ile Trp Ile Pro Ser Val Ile Ala Gly Leu Met Ala Tyr Ser Asp Cys
```

-continued

```
                         165                 170                 175
        Ile Tyr Arg Ser Leu Phe Leu Pro Lys Ser Val Phe Asn Val Pro Ala
                        180                 185                 190

Val Arg Arg Gly Glu Glu His Pro Ile Leu Leu Phe Gln Leu Phe Pro
                    195                 200                 205

Phe Gly Glu Leu Cys Asp Asn Phe Val Val Gly Tyr Leu Gly Pro Trp
                    210                 215                 220

Tyr Ala Leu Gly Leu Gly Ile Thr Ala Ile Pro Leu Trp His Thr Phe
        225                 230                 235                 240

Ile Thr Cys Leu Met Lys Tyr Val Asn Lys Leu Gln Ile Leu Asn
                        245                 250                 255

Lys Arg Val Glu Glu Met Asp Ile Thr Arg Leu Asn Ser Lys Leu Val
                    260                 265                 270

Ile Gly Arg Leu Thr Ala Ser Glu Leu Thr Phe Trp Gln Met Gln Leu
                    275                 280                 285

Phe Lys Glu Phe Val Lys Glu Gln Leu Arg Ile Arg Lys Phe Val Gln
                    290                 295                 300

Glu Leu Gln Tyr Leu Ile Cys Val Pro Val Met Ala Asp Phe Ile Ile
        305                 310                 315                 320

Phe Ser Val Leu Ile Cys Phe Leu Phe Ala Leu Thr Val Gly Val
                        325                 330                 335

Pro Ser Lys Met Asp Tyr Phe Met Phe Ile Tyr Leu Phe Val Met
                        340                 345                 350

Ala Gly Ile Leu Trp Ile Tyr His Trp Ala Thr Leu Ile Val Glu
                    355                 360                 365

Cys His Asp Glu Leu Ser Leu Ala Tyr Phe Ser Cys Gly Trp Tyr Asn
                    370                 375                 380

Phe Glu Met Pro Leu Gln Lys Met Leu Val Phe Met Met His Ala
        385                 390                 395                 400

Gln Arg Pro Met Lys Met Arg Ala Leu Leu Val Asp Leu Asn Leu Arg
                    405                 410                 415

Thr Phe Ile Asp Val Arg Leu Leu Thr Ala Asn Ser Ile Leu Asp Leu
                    420                 425                 430

Ser Asn Ser Ser Leu Ser Phe Pro Asp Trp Pro Trp Ser Leu Gln Leu
                    435                 440                 445

Leu Gln Phe Ala Ala
            450

<210> SEQ ID NO 45
<211> LENGTH: 1278
<212> TYPE: DNA
<213> ORGANISM: Drosophila melanogaster
<220> FEATURE:
<221> NAME/KEY: CDS
<222> LOCATION: (1)..(1278)
<223> OTHER INFORMATION: DOR 69F.1

<400> SEQUENCE: 45 atg cag ttg cac gac cat atg aag tac ata gac ttg ggt tgc aag atg      48
Met Gln Leu His Asp His Met Lys Tyr Ile Asp Leu Gly Cys Lys Met
  1               5                  10                  15 gca tgc ata cca aga tat caa tgg aaa gga cgc cct act gaa aga cag      96
Ala Cys Ile Pro Arg Tyr Gln Trp Lys Gly Arg Pro Thr Glu Arg Gln
                 20                  25                  30 ttc tac gct tcg gag caa agg ata gtg ttc ctt ctt gga acc att tgc     144
Phe Tyr Ala Ser Glu Gln Arg Ile Val Phe Leu Leu Gly Thr Ile Cys
             35                  40                  45
```

-continued

```
cag ata ttc cag att act gga gtg ctt atc tat tgg tat tgc aat ggc      192
Gln Ile Phe Gln Ile Thr Gly Val Leu Ile Tyr Trp Tyr Cys Asn Gly
     50                  55                  60 cgt ctt gcc acg gaa acg ggc acc ttt gtg gca caa tta tct gaa atg      240
Arg Leu Ala Thr Glu Thr Gly Thr Phe Val Ala Gln Leu Ser Glu Met
 65                  70                  75                  80 tgc agt tct ttt tgt cta aca ttt gtg gga ttc tgt aac gtt tat gcg      288
Cys Ser Ser Phe Cys Leu Thr Phe Val Gly Phe Cys Asn Val Tyr Ala
                 85                  90                  95 atc tct aca aac cgc aat caa att gaa aca tta ctc gag gag ctt cat      336
Ile Ser Thr Asn Arg Asn Gln Ile Glu Thr Leu Leu Glu Glu Leu His
            100                 105                 110 cag ata tat ccg aga tac agg aaa aat cac tat cgc tgc cag cat tat      384
Gln Ile Tyr Pro Arg Tyr Arg Lys Asn His Tyr Arg Cys Gln His Tyr
        115                 120                 125 ttt gac atg gcc atg aca ata atg aga att gag ttt ctt ttc tat atg      432
Phe Asp Met Ala Met Thr Ile Met Arg Ile Glu Phe Leu Phe Tyr Met
    130                 135                 140 atc ttg tac gtg tac tac aat agt gca cca tta tgg gtg ctt ctt tgg      480
Ile Leu Tyr Val Tyr Tyr Asn Ser Ala Pro Leu Trp Val Leu Leu Trp
145                 150                 155                 160 gaa cac ttg cac gag gaa tat gat ctt agc ttc aag acg cag acc aac      528
Glu His Leu His Glu Glu Tyr Asp Leu Ser Phe Lys Thr Gln Thr Asn
                165                 170                 175 act tgg ttt cca tgg aaa gtc cat ggg tcg gca ctt gga ttt ggt atg      576
Thr Trp Phe Pro Trp Lys Val His Gly Ser Ala Leu Gly Phe Gly Met
            180                 185                 190 gct gta cta agc ata acc gtg gga tcc ttt gtg ggc gta ggt ttc agt      624
Ala Val Leu Ser Ile Thr Val Gly Ser Phe Val Gly Val Gly Phe Ser
        195                 200                 205 att gtc acc cag aat ctt atc tgt ttg tta acc ttc caa cta aag ttg      672
Ile Val Thr Gln Asn Leu Ile Cys Leu Leu Thr Phe Gln Leu Lys Leu
    210                 215                 220 cac tac gat gga ata tcc agt cag tta gta tct ctc gat tgc cgt cgt      720
His Tyr Asp Gly Ile Ser Ser Gln Leu Val Ser Leu Asp Cys Arg Arg
225                 230                 235                 240 cct gga gct cat aag gag ttg agc atc ctc atc gcc cac cac agc cga      768
Pro Gly Ala His Lys Glu Leu Ser Ile Leu Ile Ala His His Ser Arg
                245                 250                 255 atc ctt cag ctg ggc gac caa gtc aat gac ata atg aac ttt gta ttc      816
Ile Leu Gln Leu Gly Asp Gln Val Asn Asp Ile Met Asn Phe Val Phe
            260                 265                 270 ggc tct agc cta gta ggt gcc act att gcc att tgt atg tca agt gtt      864
Gly Ser Ser Leu Val Gly Ala Thr Ile Ala Ile Cys Met Ser Ser Val
        275                 280                 285 tct ata atg cta ctg gac tta gca tct gcc ttc aaa tat gcc agt ggt      912
Ser Ile Met Leu Leu Asp Leu Ala Ser Ala Phe Lys Tyr Ala Ser Gly
    290                 295                 300 cta gtg gca ttc gtc ctc tac aac ttt gtc atc tgc tac atg gga acc      960
Leu Val Ala Phe Val Leu Tyr Asn Phe Val Ile Cys Tyr Met Gly Thr
305                 310                 315                 320 gag gtc act tta gct cgt ata aag gtc ggt aat atg ggg caa ata cga     1008
Glu Val Thr Leu Ala Arg Ile Lys Val Gly Asn Met Gly Gln Ile Arg
                325                 330                 335 cag cca cgt ttt aga gca gga tgg aat ttg aga act act tta agt att     1056
Gln Pro Arg Phe Arg Ala Gly Trp Asn Leu Arg Thr Thr Leu Ser Ile
            340                 345                 350 ttg aca gca ttt tgc gtc tgg cga tgt ttc cac gag gaa gat ttg tat     1104
Leu Thr Ala Phe Cys Val Trp Arg Cys Phe His Glu Glu Asp Leu Tyr
```

```
                355                 360                 365
cca acg ttt cga agg gca ttc ttt ttg cta ggt aac ttt tgc ctg gct       1152
Pro Thr Phe Arg Arg Ala Phe Phe Leu Leu Gly Asn Phe Cys Leu Ala
    370                 375                 380 tac caa tgt att gga gta att ata gat tgt ata gat tgg ttc ata tat       1200
Tyr Gln Cys Ile Gly Val Ile Ile Asp Cys Ile Asp Trp Phe Ile Tyr
385                 390                 395                 400 gga cgg aag gcg gtg gat acc caa aga ttc gtt gct gag atc tca gag       1248
Gly Arg Lys Ala Val Asp Thr Gln Arg Phe Val Ala Glu Ile Ser Glu
                405                 410                 415 gct aca ggt gct cgt cgc agt tgg att ttt                               1278
Ala Thr Gly Ala Arg Arg Ser Trp Ile Phe
            420                 425

<210> SEQ ID NO 46
<211> LENGTH: 426
<212> TYPE: PRT
<213> ORGANISM: Drosophila melanogaster

<400> SEQUENCE: 46

Met Gln Leu His Asp His Met Lys Tyr Ile Asp Leu Gly Cys Lys Met
 1               5                  10                  15

Ala Cys Ile Pro Arg Tyr Gln Trp Lys Gly Arg Pro Thr Glu Arg Gln
                20                  25                  30

Phe Tyr Ala Ser Glu Gln Arg Ile Val Phe Leu Gly Thr Ile Cys
            35                  40                  45

Gln Ile Phe Gln Ile Thr Gly Val Leu Ile Tyr Trp Tyr Cys Asn Gly
        50                  55                  60

Arg Leu Ala Thr Glu Thr Gly Thr Phe Val Ala Gln Leu Ser Glu Met
65                  70                  75                  80

Cys Ser Ser Phe Cys Leu Thr Phe Val Gly Phe Cys Asn Val Tyr Ala
                85                  90                  95

Ile Ser Thr Asn Arg Asn Gln Ile Glu Thr Leu Leu Glu Glu Leu His
                100                 105                 110

Gln Ile Tyr Pro Arg Tyr Arg Lys Asn His Tyr Arg Cys Gln His Tyr
            115                 120                 125

Phe Asp Met Ala Met Thr Ile Met Arg Ile Glu Phe Leu Phe Tyr Met
130                 135                 140

Ile Leu Tyr Val Tyr Tyr Asn Ser Ala Pro Leu Trp Val Leu Leu Trp
145                 150                 155                 160

Glu His Leu His Glu Glu Tyr Asp Leu Ser Phe Lys Thr Gln Thr Asn
                165                 170                 175

Thr Trp Phe Pro Trp Lys Val His Gly Ser Ala Leu Gly Phe Gly Met
            180                 185                 190

Ala Val Leu Ser Ile Thr Val Gly Ser Phe Val Gly Val Gly Phe Ser
        195                 200                 205

Ile Val Thr Gln Asn Leu Ile Cys Leu Leu Thr Phe Gln Leu Lys Leu
210                 215                 220

His Tyr Asp Gly Ile Ser Ser Gln Leu Val Ser Leu Asp Cys Arg Arg
225                 230                 235                 240

Pro Gly Ala His Lys Glu Leu Ser Ile Leu Ile Ala His His Ser Arg
                245                 250                 255

Ile Leu Gln Leu Gly Asp Gln Val Asn Asp Ile Met Asn Phe Val Phe
            260                 265                 270

Gly Ser Ser Leu Val Gly Ala Thr Ile Ala Ile Cys Met Ser Ser Val
        275                 280                 285
```

-continued

```
                Ser Ile Met Leu Leu Asp Leu Ala Ser Ala Phe Lys Tyr Ala Ser Gly
                    290                 295                 300

Leu Val Ala Phe Val Leu Tyr Asn Phe Val Ile Cys Tyr Met Gly Thr
                305                 310                 315                 320

Glu Val Thr Leu Ala Arg Ile Lys Val Gly Asn Met Gly Gln Ile Arg
                                325                 330                 335

Gln Pro Arg Phe Arg Ala Gly Trp Asn Leu Arg Thr Thr Leu Ser Ile
                            340                 345                 350

Leu Thr Ala Phe Cys Val Trp Arg Cys Phe His Glu Glu Asp Leu Tyr
                            355                 360                 365

Pro Thr Phe Arg Arg Ala Phe Phe Leu Leu Gly Asn Phe Cys Leu Ala
                        370                 375                 380

Tyr Gln Cys Ile Gly Val Ile Ile Asp Cys Ile Asp Trp Phe Ile Tyr
                385                 390                 395                 400

Gly Arg Lys Ala Val Asp Thr Gln Arg Phe Val Ala Glu Ile Ser Glu
                                405                 410                 415

Ala Thr Gly Ala Arg Arg Ser Trp Ile Phe
                            420                 425

<210> SEQ ID NO 47
<211> LENGTH: 1242
<212> TYPE: DNA
<213> ORGANISM: Drosophila melanogaster
<220> FEATURE:
<221> NAME/KEY: CDS
<222> LOCATION: (1)..(1242)
<223> OTHER INFORMATION: DOR 69F.2

<400> SEQUENCE: 47 atg cag ttg gag gac ttt atg cgg tac ccg gac ctc gtg tgt caa gcg        48
Met Gln Leu Glu Asp Phe Met Arg Tyr Pro Asp Leu Val Cys Gln Ala
 1               5                  10                  15 gcc caa ctt ccc aga tac acg tgg aat ggc aga cga tcc ttg gaa gtt        96
Ala Gln Leu Pro Arg Tyr Thr Trp Asn Gly Arg Arg Ser Leu Glu Val
                20                  25                  30 aaa cgc aac ttg gca aaa cgc att atc ttc tgg ctt gga gca gta aat       144
Lys Arg Asn Leu Ala Lys Arg Ile Ile Phe Trp Leu Gly Ala Val Asn
            35                  40                  45 ttg gtt tat cac aat att ggc tgc gtc atg tat ggc tat ttc ggt gat       192
Leu Val Tyr His Asn Ile Gly Cys Val Met Tyr Gly Tyr Phe Gly Asp
        50                  55                  60 gga aga aca aag gat cca att gcg tat tta gct gaa ttg gca tct gtg       240
Gly Arg Thr Lys Asp Pro Ile Ala Tyr Leu Ala Glu Leu Ala Ser Val
 65                  70                  75                  80 gcc agc atg ctt ggt ttc acc att gtg ggc acc ctc aac ttg tgg aag       288
Ala Ser Met Leu Gly Phe Thr Ile Val Gly Thr Leu Asn Leu Trp Lys
                85                  90                  95 atg ctg agc ctt aag acc cat ttt gag aac cta cta aat gaa ttc gag       336
Met Leu Ser Leu Lys Thr His Phe Glu Asn Leu Leu Asn Glu Phe Glu
            100                 105                 110 gaa tta ttt caa cta atc aag cac agg gcg tat cgc ata cac cac tat       384
Glu Leu Phe Gln Leu Ile Lys His Arg Ala Tyr Arg Ile His His Tyr
        115                 120                 125 caa gaa aag tat acg cgt cat ata cga aat aca ttt att ttc cat acc       432
Gln Glu Lys Tyr Thr Arg His Ile Arg Asn Thr Phe Ile Phe His Thr
130                 135                 140 tct gcc gtt gtc tac tac aac tca cta cca att ctt cta atg att cgg       480
Ser Ala Val Val Tyr Tyr Asn Ser Leu Pro Ile Leu Leu Met Ile Arg
145                 150                 155                 160
```

```
gaa cat ttc tcg aac tca cag cag ttg ggc tat aga att cag agt aat    528
Glu His Phe Ser Asn Ser Gln Gln Leu Gly Tyr Arg Ile Gln Ser Asn
            165                 170                 175 acc tgg tat ccc tgg cag gtt cag gga tca att cct gga ttt ttt gct    576
Thr Trp Tyr Pro Trp Gln Val Gln Gly Ser Ile Pro Gly Phe Phe Ala
            180                 185                 190 gca gtc gcc tgt caa atc ttt tcg tgc caa acc aat atg tgc gtc aat    624
Ala Val Ala Cys Gln Ile Phe Ser Cys Gln Thr Asn Met Cys Val Asn
            195                 200                 205 atg ttt atc cag ttt ctg atc aac ttt ttt ggt atc cag cta gaa ata    672
Met Phe Ile Gln Phe Leu Ile Asn Phe Phe Gly Ile Gln Leu Glu Ile
    210                 215                 220 cac ttc gat ggt ttg gcc agg cag ctg gag acc atc gat gcc cgc aat    720
His Phe Asp Gly Leu Ala Arg Gln Leu Glu Thr Ile Asp Ala Arg Asn
225                 230                 235                 240 ccc cat gcc aag gat caa ttg aag tat ctg att gta tat cac aca aaa    768
Pro His Ala Lys Asp Gln Leu Lys Tyr Leu Ile Val Tyr His Thr Lys
                245                 250                 255 ttg ctt aat cta gcc gac aga gtt aat cga tcg ttt aac ttt acg ttt    816
Leu Leu Asn Leu Ala Asp Arg Val Asn Arg Ser Phe Asn Phe Thr Phe
            260                 265                 270 ctc ata agt ctg tcg gta tcc atg ata tcc aac tgt ttt ctg gca ttt    864
Leu Ile Ser Leu Ser Val Ser Met Ile Ser Asn Cys Phe Leu Ala Phe
            275                 280                 285 tcc atg acc atg ttc gac ttt ggc acc tct cta aaa cat tta ctc gga    912
Ser Met Thr Met Phe Asp Phe Gly Thr Ser Leu Lys His Leu Leu Gly
    290                 295                 300 ctt ttg cta ttc atc aca tat aat ttt tca atg tgc cgc agt ggt acg    960
Leu Leu Leu Phe Ile Thr Tyr Asn Phe Ser Met Cys Arg Ser Gly Thr
305                 310                 315                 320 cac ttg att tta acg agt ggc aaa gta ttg cca gcg gcc ttt tat aac   1008
His Leu Ile Leu Thr Ser Gly Lys Val Leu Pro Ala Ala Phe Tyr Asn
                325                 330                 335 aat tgg tat gaa ggc gat ctt gtt tat cga agg atg ctc ctc atc ctg   1056
Asn Trp Tyr Glu Gly Asp Leu Val Tyr Arg Arg Met Leu Leu Ile Leu
            340                 345                 350 atg atg cgt gct acg aaa cct tat atg tgg aaa acc tac aag ctg gca   1104
Met Met Arg Ala Thr Lys Pro Tyr Met Trp Lys Thr Tyr Lys Leu Ala
            355                 360                 365 cct gta tcc ata act aca tat atg gca gtg agt ttt tcc tta ctt aca   1152
Pro Val Ser Ile Thr Thr Tyr Met Ala Val Ser Phe Ser Leu Leu Thr
    370                 375                 380 tgg cat tta tta ttc aat ttt aat tca tgt gtt ggc ttt cag aca ttg   1200
Trp His Leu Leu Phe Asn Phe Asn Ser Cys Val Gly Phe Gln Thr Leu
385                 390                 395                 400 aag ttt tca tat caa atg ttt acc tgt gtg cgg tcc ctt aaa             1242
Lys Phe Ser Tyr Gln Met Phe Thr Cys Val Arg Ser Leu Lys
                405                 410

<210> SEQ ID NO 48
<211> LENGTH: 414
<212> TYPE: PRT
<213> ORGANISM: Drosophila melanogaster

<400> SEQUENCE: 48

Met Gln Leu Glu Asp Phe Met Arg Tyr Pro Asp Leu Val Cys Gln Ala
 1               5                  10                  15

Ala Gln Leu Pro Arg Tyr Thr Trp Asn Gly Arg Arg Ser Leu Glu Val
            20                  25                  30
```

```
Lys Arg Asn Leu Ala Lys Arg Ile Ile Phe Trp Leu Gly Ala Val Asn
         35                  40                  45

Leu Val Tyr His Asn Ile Gly Cys Val Met Tyr Gly Tyr Phe Gly Asp
     50                  55                  60

Gly Arg Thr Lys Asp Pro Ile Ala Tyr Leu Ala Glu Leu Ala Ser Val
 65                  70                  75                  80

Ala Ser Met Leu Gly Phe Thr Ile Val Gly Thr Leu Asn Leu Trp Lys
                 85                  90                  95

Met Leu Ser Leu Lys Thr His Phe Glu Asn Leu Leu Asn Glu Phe Glu
             100                 105                 110

Glu Leu Phe Gln Leu Ile Lys His Arg Ala Tyr Arg Ile His His Tyr
         115                 120                 125

Gln Glu Lys Tyr Thr Arg His Ile Arg Asn Thr Phe Ile Phe His Thr
     130                 135                 140

Ser Ala Val Val Tyr Tyr Asn Ser Leu Pro Ile Leu Leu Met Ile Arg
145                 150                 155                 160

Glu His Phe Ser Asn Ser Gln Gln Leu Gly Tyr Arg Ile Gln Ser Asn
                 165                 170                 175

Thr Trp Tyr Pro Trp Gln Val Gln Gly Ser Ile Pro Gly Phe Phe Ala
             180                 185                 190

Ala Val Ala Cys Gln Ile Phe Ser Cys Gln Thr Asn Met Cys Val Asn
         195                 200                 205

Met Phe Ile Gln Phe Leu Ile Asn Phe Gly Ile Gln Leu Glu Ile
     210                 215                 220

His Phe Asp Gly Leu Ala Arg Gln Leu Glu Thr Ile Asp Ala Arg Asn
225                 230                 235                 240

Pro His Ala Lys Asp Gln Leu Lys Tyr Leu Ile Val Tyr His Thr Lys
                 245                 250                 255

Leu Leu Asn Leu Ala Asp Arg Val Asn Arg Ser Phe Asn Phe Thr Phe
             260                 265                 270

Leu Ile Ser Leu Ser Val Ser Met Ile Ser Asn Cys Phe Leu Ala Phe
         275                 280                 285

Ser Met Thr Met Phe Asp Phe Gly Thr Ser Leu Lys His Leu Leu Gly
     290                 295                 300

Leu Leu Leu Phe Ile Thr Tyr Asn Phe Ser Met Cys Arg Ser Gly Thr
305                 310                 315                 320

His Leu Ile Leu Thr Ser Gly Lys Val Leu Pro Ala Ala Phe Tyr Asn
                 325                 330                 335

Asn Trp Tyr Glu Gly Asp Leu Val Tyr Arg Arg Met Leu Leu Ile Leu
             340                 345                 350

Met Met Arg Ala Thr Lys Pro Tyr Met Trp Lys Thr Tyr Lys Leu Ala
         355                 360                 365

Pro Val Ser Ile Thr Thr Tyr Met Ala Val Ser Phe Ser Leu Leu Thr
     370                 375                 380

Trp His Leu Leu Phe Asn Phe Asn Ser Cys Val Gly Phe Gln Thr Leu
385                 390                 395                 400

Lys Phe Ser Tyr Gln Met Phe Thr Cys Val Arg Ser Leu Lys
                 405                 410
```

<210> SEQ ID NO 49
<211> LENGTH: 1170
<212> TYPE: DNA
<213> ORGANISM: Drosophila melanogaster
<220> FEATURE:
<221> NAME/KEY: CDS

<222> LOCATION: (1)..(1170)
<223> OTHER INFORMATION: DOR 85A.1

<400> SEQUENCE: 49

```
atg gaa gag cta atg aag tac gct agc ttc ttt aca cag cag tgg gca        48
Met Glu Glu Leu Met Lys Tyr Ala Ser Phe Phe Thr Gln Gln Trp Ala
 1               5                  10                  15 tac ggg cat ata cca atg ggt gaa gaa tcc aaa agg aac aaa ctt ata        96
Tyr Gly His Ile Pro Met Gly Glu Glu Ser Lys Arg Asn Lys Leu Ile
             20                  25                  30 ttt cac ata gtt ttt tgg tcc aat gtg att aac ctg agc ttc gtt gga       144
Phe His Ile Val Phe Trp Ser Asn Val Ile Asn Leu Ser Phe Val Gly
         35                  40                  45 tta ttt gag agc att tac gtt tac agt gcc ttc atg gat aat aag ttc       192
Leu Phe Glu Ser Ile Tyr Val Tyr Ser Ala Phe Met Asp Asn Lys Phe
     50                  55                  60 ctg gaa gca gtc act gcg ttg tcc tac att ggc ttc gta acc gta ggc       240
Leu Glu Ala Val Thr Ala Leu Ser Tyr Ile Gly Phe Val Thr Val Gly
 65                  70                  75                  80 atg agc aag atg ttc ttc atc cgg tgg aag aaa acg gct ata act gaa       288
Met Ser Lys Met Phe Phe Ile Arg Trp Lys Lys Thr Ala Ile Thr Glu
                 85                  90                  95 ctg att aat gaa ttg aag gag atc tat ccg aat ggt ttg atc cga gag       336
Leu Ile Asn Glu Leu Lys Glu Ile Tyr Pro Asn Gly Leu Ile Arg Glu
            100                 105                 110 gaa aga tac aat ctg ccg atg tat ctg ggc acc tgc tcc aga atc agc       384
Glu Arg Tyr Asn Leu Pro Met Tyr Leu Gly Thr Cys Ser Arg Ile Ser
        115                 120                 125 ctt ata tat tcc ttg ctc tac tct gtt ctc atc tgg aca ttc aac ttg       432
Leu Ile Tyr Ser Leu Leu Tyr Ser Val Leu Ile Trp Thr Phe Asn Leu
    130                 135                 140 ttt tgt gta atg gag tat tgg gtc tat gac aag tgg ctc aac att cga       480
Phe Cys Val Met Glu Tyr Trp Val Tyr Asp Lys Trp Leu Asn Ile Arg
145                 150                 155                 160 gtg gtg ggc aaa cag ttg ccg tac ctc atg tac att cct tgg aaa tgg       528
Val Val Gly Lys Gln Leu Pro Tyr Leu Met Tyr Ile Pro Trp Lys Trp
                165                 170                 175 cag gat aac tgg tcg tac tat cca ctg tta ttc tcc cag aat ttt gca       576
Gln Asp Asn Trp Ser Tyr Tyr Pro Leu Leu Phe Ser Gln Asn Phe Ala
            180                 185                 190 gga tac aca tct gca gct ggt caa att tca acc gat gtc ttg ctc tgc       624
Gly Tyr Thr Ser Ala Ala Gly Gln Ile Ser Thr Asp Val Leu Leu Cys
        195                 200                 205 gcg gtg gcc act cag ttg gta atg cac ttc gac ttt ctc tca aat agt       672
Ala Val Ala Thr Gln Leu Val Met His Phe Asp Phe Leu Ser Asn Ser
    210                 215                 220 atg gaa cgc cac gaa ttg agt gga gat tgg aag aag gac tcc cga ttt       720
Met Glu Arg His Glu Leu Ser Gly Asp Trp Lys Lys Asp Ser Arg Phe
225                 230                 235                 240 ctg gtg gac att gtt agg tat cac gaa cgt ata ctc cgc ctt tca gat       768
Leu Val Asp Ile Val Arg Tyr His Glu Arg Ile Leu Arg Leu Ser Asp
                245                 250                 255 gca gtg aac gat ata ttt gga att cca cta ctc aac ttc atg gta           816
Ala Val Asn Asp Ile Phe Gly Ile Pro Leu Leu Asn Phe Met Val
            260                 265                 270 tcc tcg ttc gtc atc tgc ttc gtg gga ttc cag atg act gtt gga gtt       864
Ser Ser Phe Val Ile Cys Phe Val Gly Phe Gln Met Thr Val Gly Val
        275                 280                 285 ccg ccg gat ata gtt gtg aag ctc ttc ctc ttc ctt gtc tct tcg atg       912
Pro Pro Asp Ile Val Val Lys Leu Phe Leu Phe Leu Val Ser Ser Met
```

|  |  |  |  |  |  |  |  |  |  |  |  |  |  |  |  |  |
|---|---|---|---|---|---|---|---|---|---|---|---|---|---|---|---|---|
| | 290 | | | | 295 | | | | | 300 | | | | | | |
| agt | cag | gtc | tat | ttg | att | tgt | cac | tat | ggt | caa | ctg | gtg | gcc | gat | gct | 960 |
| Ser | Gln | Val | Tyr | Leu | Ile | Cys | His | Tyr | Gly | Gln | Leu | Val | Ala | Asp | Ala | |
| 305 | | | | 310 | | | | | 315 | | | | 320 | | | |
| agc | tac | gga | ttt | tcg | gtt | gcc | acc | tac | aat | cag | aag | tgg | tat | aaa | gcc | 1008 |
| Ser | Tyr | Gly | Phe | Ser | Val | Ala | Thr | Tyr | Asn | Gln | Lys | Trp | Tyr | Lys | Ala | |
| | | | 325 | | | | | 330 | | | | | 335 | | | |
| gat | gtg | cgc | tat | aaa | cga | gcc | ttg | gtt | att | att | ata | gct | aga | tcg | cag | 1056 |
| Asp | Val | Arg | Tyr | Lys | Arg | Ala | Leu | Val | Ile | Ile | Ile | Ala | Arg | Ser | Gln | |
| | | 340 | | | | | 345 | | | | | 350 | | | | |
| aag | gta | act | ttt | cta | aag | gcc | act | ata | ttc | ttg | gat | att | acc | agg | tcc | 1104 |
| Lys | Val | Thr | Phe | Leu | Lys | Ala | Thr | Ile | Phe | Leu | Asp | Ile | Thr | Arg | Ser | |
| | | 355 | | | | | 360 | | | | | 365 | | | | |
| act | atg | aca | gat | ctg | ctt | caa | ata | tca | tac | aaa | ttc | ttc | gcc | ctg | ctg | 1152 |
| Thr | Met | Thr | Asp | Leu | Leu | Gln | Ile | Ser | Tyr | Lys | Phe | Phe | Ala | Leu | Leu | |
| 370 | | | | 375 | | | | | 380 | | | | | | | |
| cgc | aca | atg | tat | acc | caa | | | | | | | | | | | 1170 |
| Arg | Thr | Met | Tyr | Thr | Gln | | | | | | | | | | | |
| 385 | | | | 390 | | | | | | | | | | | | |

<210> SEQ ID NO 50
<211> LENGTH: 390
<212> TYPE: PRT
<213> ORGANISM: Drosophila melanogaster

<400> SEQUENCE: 50

| Met | Glu | Glu | Leu | Met | Lys | Tyr | Ala | Ser | Phe | Phe | Thr | Gln | Gln | Trp | Ala |
|---|---|---|---|---|---|---|---|---|---|---|---|---|---|---|---|
| 1 | | | | 5 | | | | | 10 | | | | | 15 | |

| Tyr | Gly | His | Ile | Pro | Met | Gly | Glu | Glu | Ser | Lys | Arg | Asn | Lys | Leu | Ile |
|---|---|---|---|---|---|---|---|---|---|---|---|---|---|---|---|
| | | | 20 | | | | | 25 | | | | | 30 | | |

| Phe | His | Ile | Val | Phe | Trp | Ser | Asn | Val | Ile | Asn | Leu | Ser | Phe | Val | Gly |
|---|---|---|---|---|---|---|---|---|---|---|---|---|---|---|---|
| | | 35 | | | | | 40 | | | | | 45 | | | |

| Leu | Phe | Glu | Ser | Ile | Tyr | Val | Tyr | Ser | Ala | Phe | Met | Asp | Asn | Lys | Phe |
|---|---|---|---|---|---|---|---|---|---|---|---|---|---|---|---|
| | 50 | | | | | 55 | | | | | 60 | | | | |

| Leu | Glu | Ala | Val | Thr | Ala | Leu | Ser | Tyr | Ile | Gly | Phe | Val | Thr | Val | Gly |
|---|---|---|---|---|---|---|---|---|---|---|---|---|---|---|---|
| 65 | | | | | 70 | | | | | 75 | | | | | 80 |

| Met | Ser | Lys | Met | Phe | Phe | Ile | Arg | Trp | Lys | Lys | Thr | Ala | Ile | Thr | Glu |
|---|---|---|---|---|---|---|---|---|---|---|---|---|---|---|---|
| | | | | 85 | | | | | 90 | | | | | 95 | |

| Leu | Ile | Asn | Glu | Leu | Lys | Glu | Ile | Tyr | Pro | Asn | Gly | Leu | Ile | Arg | Glu |
|---|---|---|---|---|---|---|---|---|---|---|---|---|---|---|---|
| | | | 100 | | | | | 105 | | | | | 110 | | |

| Glu | Arg | Tyr | Asn | Leu | Pro | Met | Tyr | Leu | Gly | Thr | Cys | Ser | Arg | Ile | Ser |
|---|---|---|---|---|---|---|---|---|---|---|---|---|---|---|---|
| | | | 115 | | | | | 120 | | | | | 125 | | |

| Leu | Ile | Tyr | Ser | Leu | Leu | Tyr | Ser | Val | Leu | Ile | Trp | Thr | Phe | Asn | Leu |
|---|---|---|---|---|---|---|---|---|---|---|---|---|---|---|---|
| | 130 | | | | | 135 | | | | | 140 | | | | |

| Phe | Cys | Val | Met | Glu | Tyr | Trp | Val | Tyr | Asp | Lys | Trp | Leu | Asn | Ile | Arg |
|---|---|---|---|---|---|---|---|---|---|---|---|---|---|---|---|
| 145 | | | | | 150 | | | | | 155 | | | | | 160 |

| Val | Val | Gly | Lys | Gln | Leu | Pro | Tyr | Leu | Met | Tyr | Ile | Pro | Trp | Lys | Trp |
|---|---|---|---|---|---|---|---|---|---|---|---|---|---|---|---|
| | | | | 165 | | | | | 170 | | | | | 175 | |

| Gln | Asp | Asn | Trp | Ser | Tyr | Tyr | Pro | Leu | Leu | Phe | Ser | Gln | Asn | Phe | Ala |
|---|---|---|---|---|---|---|---|---|---|---|---|---|---|---|---|
| | | | 180 | | | | | 185 | | | | | 190 | | |

| Gly | Tyr | Thr | Ser | Ala | Ala | Gly | Gln | Ile | Ser | Thr | Asp | Val | Leu | Leu | Cys |
|---|---|---|---|---|---|---|---|---|---|---|---|---|---|---|---|
| | | | 195 | | | | | 200 | | | | | 205 | | |

| Ala | Val | Ala | Thr | Gln | Leu | Val | Met | His | Phe | Asp | Phe | Leu | Ser | Asn | Ser |
|---|---|---|---|---|---|---|---|---|---|---|---|---|---|---|---|
| | 210 | | | | | 215 | | | | | 220 | | | | |

| Met | Glu | Arg | His | Glu | Leu | Ser | Gly | Asp | Trp | Lys | Lys | Asp | Ser | Arg | Phe |
|---|---|---|---|---|---|---|---|---|---|---|---|---|---|---|---|
| 225 | | | | | 230 | | | | | 235 | | | | | 240 |

```
Leu Val Asp Ile Val Arg Tyr His Glu Arg Ile Leu Arg Leu Ser Asp
            245                 250                 255

Ala Val Asn Asp Ile Phe Gly Ile Pro Leu Leu Leu Asn Phe Met Val
            260                 265                 270

Ser Ser Phe Val Ile Cys Phe Gly Phe Gln Met Thr Val Gly Val
        275                 280                 285

Pro Pro Asp Ile Val Val Lys Leu Phe Leu Phe Leu Val Ser Ser Met
        290                 295                 300

Ser Gln Val Tyr Leu Ile Cys His Tyr Gly Gln Leu Val Ala Asp Ala
305                 310                 315                 320

Ser Tyr Gly Phe Ser Val Ala Thr Tyr Asn Gln Lys Trp Tyr Lys Ala
                325                 330                 335

Asp Val Arg Tyr Lys Arg Ala Leu Val Ile Ile Ile Ala Arg Ser Gln
                340                 345                 350

Lys Val Thr Phe Leu Lys Ala Thr Ile Phe Leu Asp Ile Thr Arg Ser
                355                 360                 365

Thr Met Thr Asp Leu Leu Gln Ile Ser Tyr Lys Phe Phe Ala Leu Leu
        370                 375                 380

Arg Thr Met Tyr Thr Gln
385                 390

<210> SEQ ID NO 51
<211> LENGTH: 1167
<212> TYPE: DNA
<213> ORGANISM: Drosophila melanogaster
<220> FEATURE:
<221> NAME/KEY: CDS
<222> LOCATION: (1)..(1167)
<223> OTHER INFORMATION: DOR 85A.3

<400> SEQUENCE: 51 atg aag ttc atg aag tac gca gtt ttc ttt tac aca tcg gtg ggc att       48
Met Lys Phe Met Lys Tyr Ala Val Phe Phe Tyr Thr Ser Val Gly Ile
  1               5                  10                  15 gag ccg tat acg att gac tcg cgg tcc aaa aaa gcg agc cta tgg tca       96
Glu Pro Tyr Thr Ile Asp Ser Arg Ser Lys Lys Ala Ser Leu Trp Ser
                 20                  25                  30 cat ctt ctc ttc tgg gcc aat gtg atc aat tta agt gtc att gtt ttc      144
His Leu Leu Phe Trp Ala Asn Val Ile Asn Leu Ser Val Ile Val Phe
             35                  40                  45 gga gag atc ctc tat ctg gga gtg gcc tat tcc gat gga aag ttc att      192
Gly Glu Ile Leu Tyr Leu Gly Val Ala Tyr Ser Asp Gly Lys Phe Ile
         50                  55                  60 gat gcc gtc act gta ctg tca tat atc gga ttc gta atc gtg ggc atg      240
Asp Ala Val Thr Val Leu Ser Tyr Ile Gly Phe Val Ile Val Gly Met
 65                  70                  75                  80 agc aag atg ttc ttc ata tgg tgg aag aag acc gat cta agc gat ttg      288
Ser Lys Met Phe Phe Ile Trp Trp Lys Lys Thr Asp Leu Ser Asp Leu
                 85                  90                  95 gtt aag gaa ttg gag cac atc tat cca aat ggc aaa gct gag gag gag      336
Val Lys Glu Leu Glu His Ile Tyr Pro Asn Gly Lys Ala Glu Glu Glu
            100                 105                 110 atg tat cgg ttg gat agg tat ctg cga tct tgt tca cga att agc att      384
Met Tyr Arg Leu Asp Arg Tyr Leu Arg Ser Cys Ser Arg Ile Ser Ile
        115                 120                 125 acc tat gca cta ctc tac tcc gta ctc atc tgg acc ttc aat ctg ttc      432
Thr Tyr Ala Leu Leu Tyr Ser Val Leu Ile Trp Thr Phe Asn Leu Phe
    130                 135                 140 agt atc atg caa ttc ctt gtc tat gaa aag ttg ctt aaa atc cga gtg      480
```

| | | | | | | | | | | | |
|---|---|---|---|---|---|---|---|---|---|---|---|
| Ser | Ile | Met | Gln | Phe | Leu | Val | Tyr | Glu | Lys | Leu | Leu | Lys | Ile | Arg | Val |
| 145 | | | | | 150 | | | | | 155 | | | | | 160 |

```
gtc ggc caa acg ctg cca tat ttg atg tac ttt ccc tgg aac tgg cat    528
Val Gly Gln Thr Leu Pro Tyr Leu Met Tyr Phe Pro Trp Asn Trp His
            165                 170                 175 gaa aac tgg acg tat tat gtg ctg ctg ttc tgt caa aac ttc gca gga    576
Glu Asn Trp Thr Tyr Tyr Val Leu Leu Phe Cys Gln Asn Phe Ala Gly
        180                 185                 190 cat act tcg gca tcg gga cag atc tct acg gat ctt ttg ctt tgt gct    624
His Thr Ser Ala Ser Gly Gln Ile Ser Thr Asp Leu Leu Leu Cys Ala
            195                 200                 205 gtt gct acc cag gtg gta atg cac ttc gat tac ttg gcc aga gtg gtg    672
Val Ala Thr Gln Val Val Met His Phe Asp Tyr Leu Ala Arg Val Val
        210                 215                 220 gaa aaa caa gtg tta gat cgc gat tgg agc gaa aac tcc aga ttt ttg    720
Glu Lys Gln Val Leu Asp Arg Asp Trp Ser Glu Asn Ser Arg Phe Leu
225                 230                 235                 240 gca aaa act gta caa tat cat cag cgc att ctt cgg cta atg gac gtt    768
Ala Lys Thr Val Gln Tyr His Gln Arg Ile Leu Arg Leu Met Asp Val
            245                 250                 255 ctc aac gat ata ttc ggg ata ccg cta ctg ctt aac ttt atg gtc tcc    816
Leu Asn Asp Ile Phe Gly Ile Pro Leu Leu Leu Asn Phe Met Val Ser
        260                 265                 270 aca ttt gtc atc tgc ttt gtg gga ttc caa atg acc gtg ggt gtc ccg    864
Thr Phe Val Ile Cys Phe Val Gly Phe Gln Met Thr Val Gly Val Pro
            275                 280                 285 ccg gac atc atg att aag ctc ttc ttg ttc ctg ttc tcg tcc ttg tcg    912
Pro Asp Ile Met Ile Lys Leu Phe Leu Phe Leu Phe Ser Ser Leu Ser
        290                 295                 300 caa gtg tac ttg ata tgc cac tac ggc cag ctg att gcc gat gcg agc    960
Gln Val Tyr Leu Ile Cys His Tyr Gly Gln Leu Ile Ala Asp Ala Ser
305                 310                 315                 320 tct agc tta tcg att tct gca tat aag cag aat tgg caa aat gct gac   1008
Ser Ser Leu Ser Ile Ser Ala Tyr Lys Gln Asn Trp Gln Asn Ala Asp
            325                 330                 335 att cgc tat cgt cgg gct ctg gta ttc ttt ata gct cga cct cag agg   1056
Ile Arg Tyr Arg Arg Ala Leu Val Phe Phe Ile Ala Arg Pro Gln Arg
        340                 345                 350 aca act tat cta aaa gct aca att ttc atg aat ata aca agg gcc acc   1104
Thr Thr Tyr Leu Lys Ala Thr Ile Phe Met Asn Ile Thr Arg Ala Thr
            355                 360                 365 atg acg gac ctt ctt caa gta tcc tac aaa ttt ttc gct ctg ctt cgt   1152
Met Thr Asp Leu Leu Gln Val Ser Tyr Lys Phe Phe Ala Leu Leu Arg
370                 375                 380 acc atg tac ata aag                                              1167
Thr Met Tyr Ile Lys
385

<210> SEQ ID NO 52
<211> LENGTH: 389
<212> TYPE: PRT
<213> ORGANISM: Drosophila melanogaster

<400> SEQUENCE: 52

Met Lys Phe Met Lys Tyr Ala Val Phe Tyr Thr Ser Val Gly Ile
  1               5                  10                  15

Glu Pro Tyr Thr Ile Asp Ser Arg Ser Lys Lys Ala Ser Leu Trp Ser
                 20                  25                  30

His Leu Leu Phe Trp Ala Asn Val Ile Asn Leu Ser Val Ile Val Phe
             35                  40                  45
```

```
Gly Glu Ile Leu Tyr Leu Gly Val Ala Tyr Ser Asp Gly Lys Phe Ile
 50                  55                  60

Asp Ala Val Thr Val Leu Ser Tyr Ile Gly Phe Val Ile Val Gly Met
 65                  70                  75                  80

Ser Lys Met Phe Phe Ile Trp Trp Lys Thr Asp Leu Ser Asp Leu
                 85                  90                  95

Val Lys Glu Leu Glu His Ile Tyr Pro Asn Gly Lys Ala Glu Glu Glu
                100                 105                 110

Met Tyr Arg Leu Asp Arg Tyr Leu Arg Ser Cys Ser Arg Ile Ser Ile
                115                 120                 125

Thr Tyr Ala Leu Leu Tyr Ser Val Leu Ile Trp Thr Phe Asn Leu Phe
        130                 135                 140

Ser Ile Met Gln Phe Leu Val Tyr Glu Lys Leu Leu Lys Ile Arg Val
145                 150                 155                 160

Val Gly Gln Thr Leu Pro Tyr Leu Met Tyr Phe Pro Trp Asn Trp His
                165                 170                 175

Glu Asn Trp Thr Tyr Tyr Val Leu Leu Phe Cys Gln Asn Phe Ala Gly
                180                 185                 190

His Thr Ser Ala Ser Gly Gln Ile Ser Thr Asp Leu Leu Cys Ala
        195                 200                 205

Val Ala Thr Gln Val Val Met His Phe Asp Tyr Leu Ala Arg Val Val
210                 215                 220

Glu Lys Gln Val Leu Asp Arg Asp Trp Ser Glu Asn Ser Arg Phe Leu
225                 230                 235                 240

Ala Lys Thr Val Gln Tyr His Gln Arg Ile Leu Arg Leu Met Asp Val
                245                 250                 255

Leu Asn Asp Ile Phe Gly Ile Pro Leu Leu Leu Asn Phe Met Val Ser
                260                 265                 270

Thr Phe Val Ile Cys Phe Val Gly Phe Gln Met Thr Val Gly Val Pro
        275                 280                 285

Pro Asp Ile Met Ile Lys Leu Phe Leu Phe Leu Phe Ser Ser Leu Ser
        290                 295                 300

Gln Val Tyr Leu Ile Cys His Tyr Gly Gln Leu Ile Ala Asp Ala Ser
305                 310                 315                 320

Ser Ser Leu Ser Ile Ser Ala Tyr Lys Gln Asn Trp Gln Asn Ala Asp
                325                 330                 335

Ile Arg Tyr Arg Arg Ala Leu Val Phe Phe Ile Ala Arg Pro Gln Arg
                340                 345                 350

Thr Thr Tyr Leu Lys Ala Thr Ile Phe Met Asn Ile Thr Arg Ala Thr
            355                 360                 365

Met Thr Asp Leu Leu Gln Val Ser Tyr Lys Phe Phe Ala Leu Leu Arg
370                 375                 380

Thr Met Tyr Ile Lys
385

<210> SEQ ID NO 53
<211> LENGTH: 1305
<212> TYPE: DNA
<213> ORGANISM: Drosophila melanogaster
<220> FEATURE:
<221> NAME/KEY: CDS
<222> LOCATION: (1)..(1305)
<223> OTHER INFORMATION: DOR 85B.1

<400> SEQUENCE: 53
```

```
                                                              -continued atg gga ctc cag ttg gcg aat ggc acg aag cca tcg ccg cgg tta ccc      48
Met Gly Leu Gln Leu Ala Asn Gly Thr Lys Pro Ser Pro Arg Leu Pro
 1               5                  10                  15 aaa tgg tgg cca aag cgg ctg gaa atg att ggt aaa gtg ctg ccc aaa      96
Lys Trp Trp Pro Lys Arg Leu Glu Met Ile Gly Lys Val Leu Pro Lys
            20                  25                  30 gcc tat tgt tcc atg gtg att ttc acc tcc ctg cat ttg ggt gtc ctg     144
Ala Tyr Cys Ser Met Val Ile Phe Thr Ser Leu His Leu Gly Val Leu
         35                  40                  45 ttc acg aaa acc aca ctg gat gtc ctg ccg acg ggg gag ctg cag gcc     192
Phe Thr Lys Thr Thr Leu Asp Val Leu Pro Thr Gly Glu Leu Gln Ala
     50                  55                  60 ata acg gat gcc ctc acc atg acc ata ata tac ttt ttc acg ggc tac     240
Ile Thr Asp Ala Leu Thr Met Thr Ile Ile Tyr Phe Phe Thr Gly Tyr
 65                  70                  75                  80 ggc acc atc tac tgg tgc ctg cgc tcc cgg cgc ctc ttg gcc tac atg     288
Gly Thr Ile Tyr Trp Cys Leu Arg Ser Arg Arg Leu Leu Ala Tyr Met
                 85                  90                  95 gag cac atg aac cgg gag tat cgc cat cat tcg ctg gcc ggg gtg acc     336
Glu His Met Asn Arg Glu Tyr Arg His His Ser Leu Ala Gly Val Thr
            100                 105                 110 ttt gtg agt agc cat gcg gcc ttt agg atg tcc aga aac ttc acg gtg     384
Phe Val Ser Ser His Ala Ala Phe Arg Met Ser Arg Asn Phe Thr Val
        115                 120                 125 gtg tgg ata atg tcc tgc ctg ctg ggc gtg att tcc tgg ggc gtt tcg     432
Val Trp Ile Met Ser Cys Leu Leu Gly Val Ile Ser Trp Gly Val Ser
130                 135                 140 cca ctg atg ctg ggc atc cgg atg ctg ccg ctc caa tgt tgg tat ccc     480
Pro Leu Met Leu Gly Ile Arg Met Leu Pro Leu Gln Cys Trp Tyr Pro
145                 150                 155                 160 ttc gac gcc ctg ggt ccc ggc aca tat acg gcg gtc tat gct aca caa     528
Phe Asp Ala Leu Gly Pro Gly Thr Tyr Thr Ala Val Tyr Ala Thr Gln
                165                 170                 175 ctt ttc ggt cag atc atg gtg ggc atg acc ttt gga ttc ggg gga tca     576
Leu Phe Gly Gln Ile Met Val Gly Met Thr Phe Gly Phe Gly Gly Ser
            180                 185                 190 ctg ttt gtc acc ctg agc ctg cta ctc ctg gga caa ttc gat gtg ctc     624
Leu Phe Val Thr Leu Ser Leu Leu Leu Leu Gly Gln Phe Asp Val Leu
        195                 200                 205 tac tgc agc ctg aag aac ctg gat gcc cat acc aag ttg ctg ggc ggg     672
Tyr Cys Ser Leu Lys Asn Leu Asp Ala His Thr Lys Leu Leu Gly Gly
    210                 215                 220 gag tct gta aat ggc ctg agt tcg ctg caa gag gag ttg ctg ctg ggg     720
Glu Ser Val Asn Gly Leu Ser Ser Leu Gln Glu Glu Leu Leu Leu Gly
225                 230                 235                 240 gac tcg aag agg gaa tta aat cag tac gtt ttg ctc cag gag cat ccg     768
Asp Ser Lys Arg Glu Leu Asn Gln Tyr Val Leu Leu Gln Glu His Pro
                245                 250                 255 acg gat ctg ctg aga ttg tcg gca gga cga aaa tgt cct gac caa gga     816
Thr Asp Leu Leu Arg Leu Ser Ala Gly Arg Lys Cys Pro Asp Gln Gly
            260                 265                 270 aat gcg ttt cac aac gcc ttg gtg gaa tgc att cgc ttg cat cgc ttc     864
Asn Ala Phe His Asn Ala Leu Val Glu Cys Ile Arg Leu His Arg Phe
        275                 280                 285 att ctg cac tgc tca cag gag ttg gag aat cta ttc agt cca tat tgt     912
Ile Leu His Cys Ser Gln Glu Leu Glu Asn Leu Phe Ser Pro Tyr Cys
    290                 295                 300 ctg gtc aag tca ctg cag atc acc ttt cag ctt tgc ctg ctg gtc ttt     960
Leu Val Lys Ser Leu Gln Ile Thr Phe Gln Leu Cys Leu Leu Val Phe
305                 310                 315                 320
```

```
gtg ggc gtt tcg ggt act cga gag gtc ctg cgg att gtc aac cag cta          1008
Val Gly Val Ser Gly Thr Arg Glu Val Leu Arg Ile Val Asn Gln Leu
                325                 330                 335 cag tac ttg gga ctg acc atc ttc gag ctc cta atg ttc acc tat tgt          1056
Gln Tyr Leu Gly Leu Thr Ile Phe Glu Leu Leu Met Phe Thr Tyr Cys
            340                 345                 350 ggc gaa ctc ctc agt cgg cat agt att cga tct ggc gac gcc ttt tgg          1104
Gly Glu Leu Leu Ser Arg His Ser Ile Arg Ser Gly Asp Ala Phe Trp
        355                 360                 365 agg ggt gcg tgg tgg aag cac gcc cat ttc atc cgc cag gac atc ctc          1152
Arg Gly Ala Trp Trp Lys His Ala His Phe Ile Arg Gln Asp Ile Leu
    370                 375                 380 atc ttt ctg gtc aat agt aga cgt gca gtt cac gtg act gcc ggc aag          1200
Ile Phe Leu Val Asn Ser Arg Arg Ala Val His Val Thr Ala Gly Lys
385                 390                 395                 400 ttt tat gtg atg gat gtg aat cgt cta aga tcg gtt ata acg cag gcg          1248
Phe Tyr Val Met Asp Val Asn Arg Leu Arg Ser Val Ile Thr Gln Ala
                405                 410                 415 ttc agc ttc ttg act ttg ctg caa aag ttg gct gcc aag aag acg gaa          1296
Phe Ser Phe Leu Thr Leu Leu Gln Lys Leu Ala Ala Lys Lys Thr Glu
            420                 425                 430 tcg gag ctc                                                              1305
Ser Glu Leu
        435

<210> SEQ ID NO 54
<211> LENGTH: 435
<212> TYPE: PRT
<213> ORGANISM: Drosophila melanogaster

<400> SEQUENCE: 54

Met Gly Leu Gln Leu Ala Asn Gly Thr Lys Pro Ser Pro Arg Leu Pro
 1               5                  10                  15

Lys Trp Trp Pro Lys Arg Leu Glu Met Ile Gly Lys Val Leu Pro Lys
            20                  25                  30

Ala Tyr Cys Ser Met Val Ile Phe Thr Ser Leu His Leu Gly Val Leu
        35                  40                  45

Phe Thr Lys Thr Thr Leu Asp Val Leu Pro Thr Gly Glu Leu Gln Ala
    50                  55                  60

Ile Thr Asp Ala Leu Thr Met Thr Ile Ile Tyr Phe Thr Gly Tyr
65                  70                  75                  80

Gly Thr Ile Tyr Trp Cys Leu Arg Ser Arg Arg Leu Leu Ala Tyr Met
                85                  90                  95

Glu His Met Asn Arg Glu Tyr Arg His His Ser Leu Ala Gly Val Thr
            100                 105                 110

Phe Val Ser Ser His Ala Ala Phe Arg Met Ser Arg Asn Phe Thr Val
        115                 120                 125

Val Trp Ile Met Ser Cys Leu Leu Gly Val Ile Ser Trp Gly Val Ser
    130                 135                 140

Pro Leu Met Leu Gly Ile Arg Met Leu Pro Gln Cys Trp Tyr Pro
145                 150                 155                 160

Phe Asp Ala Leu Gly Pro Gly Thr Tyr Thr Ala Val Tyr Ala Thr Gln
                165                 170                 175

Leu Phe Gly Gln Ile Met Val Gly Met Thr Phe Gly Phe Gly Ser
            180                 185                 190

Leu Phe Val Thr Leu Ser Leu Leu Leu Gly Gln Phe Asp Val Leu
        195                 200                 205
```

-continued

```
        Tyr Cys Ser Leu Lys Asn Leu Asp Ala His Thr Lys Leu Leu Gly Gly
            210                 215                 220

Glu Ser Val Asn Gly Leu Ser Ser Leu Gln Glu Leu Leu Leu Gly
        225                 230                 235                 240

Asp Ser Lys Arg Glu Leu Asn Gln Tyr Val Leu Leu Gln Glu His Pro
                        245                 250                 255

Thr Asp Leu Leu Arg Leu Ser Ala Gly Arg Lys Cys Pro Asp Gln Gly
                        260                 265                 270

Asn Ala Phe His Asn Ala Leu Val Glu Cys Ile Arg Leu His Arg Phe
                    275                 280                 285

Ile Leu His Cys Ser Gln Glu Leu Glu Asn Leu Phe Ser Pro Tyr Cys
            290                 295                 300

Leu Val Lys Ser Leu Gln Ile Thr Phe Gln Leu Cys Leu Leu Val Phe
        305                 310                 315                 320

Val Gly Val Ser Gly Thr Arg Glu Val Leu Arg Ile Val Asn Gln Leu
                        325                 330                 335

Gln Tyr Leu Gly Leu Thr Ile Phe Glu Leu Leu Met Phe Thr Tyr Cys
                        340                 345                 350

Gly Glu Leu Leu Ser Arg His Ser Ile Arg Ser Gly Asp Ala Phe Trp
                    355                 360                 365

Arg Gly Ala Trp Trp Lys His Ala His Phe Ile Arg Gln Asp Ile Leu
            370                 375                 380

Ile Phe Leu Val Asn Ser Arg Arg Ala Val His Val Thr Ala Gly Lys
        385                 390                 395                 400

Phe Tyr Val Met Asp Val Asn Arg Leu Arg Ser Val Ile Thr Gln Ala
                        405                 410                 415

Phe Ser Phe Leu Thr Leu Leu Gln Lys Leu Ala Ala Lys Lys Thr Glu
                        420                 425                 430

Ser Glu Leu
                435

<210> SEQ ID NO 55
<211> LENGTH: 1203
<212> TYPE: DNA
<213> ORGANISM: Drosophila melanogaster
<220> FEATURE:
<221> NAME/KEY: CDS
<222> LOCATION: (1)..(1203)

<400> SEQUENCE: 55 atg aag cca acg gaa atc aaa aaa ccc tat cga atg gag gag ttt ctg      48
Met Lys Pro Thr Glu Ile Lys Lys Pro Tyr Arg Met Glu Glu Phe Leu
 1               5                  10                  15 cgt ccg cag atg ttc cag gag gtg gct cag atg gtg cat ttc cag tgg      96
Arg Pro Gln Met Phe Gln Glu Val Ala Gln Met Val His Phe Gln Trp
                20                  25                  30 cgg aga aat ccg gtg gac aac agc atg gtg aac gca tcc atg gtc ccc     144
Arg Arg Asn Pro Val Asp Asn Ser Met Val Asn Ala Ser Met Val Pro
            35                  40                  45 ttc tgc ttg tcg gcg ttt ctt aat gtc ctg ttt ttc ggc tgc aat ggt     192
Phe Cys Leu Ser Ala Phe Leu Asn Val Leu Phe Phe Gly Cys Asn Gly
        50                  55                  60 tgg gac atc ata gga cat ttt tgg ctg gga cat cct gcc aac cag aat     240
Trp Asp Ile Ile Gly His Phe Trp Leu Gly His Pro Ala Asn Gln Asn
 65                  70                  75                  80 ccg ccc gtg ctt agc atc acc att tac ttc tcg atc agg gga ttg atg     288
Pro Pro Val Leu Ser Ile Thr Ile Tyr Phe Ser Ile Arg Gly Leu Met
                85                  90                  95
```

|     |     |     |     |     |     |     |     |     |     |     |     |     |     |     |     |
| --- | --- | --- | --- | --- | --- | --- | --- | --- | --- | --- | --- | --- | --- | --- | --- |
|     |     |     | 85  |     |     |     | 90  |     |     |     | 95  |     |     |     |     |
| cta | tac | ctg | aaa | cga | aag | gaa | atc | gtt | gag | ttt | gtt | aac | gac | ttg | gat | 336 |
| Leu | Tyr | Leu | Lys | Arg | Lys | Glu | Ile | Val | Glu | Phe | Val | Asn | Asp | Leu | Asp |     |
|     |     |     | 100 |     |     |     | 105 |     |     |     | 110 |     |     |     |     |
| cgg | gag | tgt | ccg | cgg | gac | ttg | gtc | agc | cag | ttg | gac | atg | caa | atg | gat | 384 |
| Arg | Glu | Cys | Pro | Arg | Asp | Leu | Val | Ser | Gln | Leu | Asp | Met | Gln | Met | Asp |     |
|     |     |     | 115 |     |     |     | 120 |     |     |     | 125 |     |     |     |     |
| gag | acg | tac | cga | aac | ttt | tgg | cag | cgc | tat | cgc | ttc | atc | cgt | atc | tac | 432 |
| Glu | Thr | Tyr | Arg | Asn | Phe | Trp | Gln | Arg | Tyr | Arg | Phe | Ile | Arg | Ile | Tyr |     |
|     | 130 |     |     |     |     | 135 |     |     |     |     | 140 |     |     |     |     |
| tcc | cat | ttg | ggt | ggt | ccg | atg | ttc | tgc | gtt | gtg | cca | tta | gct | cta | ttc | 480 |
| Ser | His | Leu | Gly | Gly | Pro | Met | Phe | Cys | Val | Val | Pro | Leu | Ala | Leu | Phe |     |
| 145 |     |     |     |     | 150 |     |     |     |     | 155 |     |     |     |     | 160 |
| ctc | ctg | acc | cac | gag | ggt | aaa | gat | act | cct | gtt | gcc | cag | cac | gag | cag | 528 |
| Leu | Leu | Thr | His | Glu | Gly | Lys | Asp | Thr | Pro | Val | Ala | Gln | His | Glu | Gln |     |
|     |     |     |     | 165 |     |     |     |     | 170 |     |     |     |     | 175 |     |
| ctc | ctt | gga | gga | tgg | ctg | cca | tgc | ggt | gtg | cga | aag | gac | cca | aat | ttc | 576 |
| Leu | Leu | Gly | Gly | Trp | Leu | Pro | Cys | Gly | Val | Arg | Lys | Asp | Pro | Asn | Phe |     |
|     |     |     | 180 |     |     |     | 185 |     |     |     | 190 |     |     |     |     |
| tac | ctt | tta | gtc | tgg | tcc | ttc | gac | ctg | atg | tgc | acc | act | tgc | ggc | gtc | 624 |
| Tyr | Leu | Leu | Val | Trp | Ser | Phe | Asp | Leu | Met | Cys | Thr | Thr | Cys | Gly | Val |     |
|     |     | 195 |     |     |     |     | 200 |     |     |     |     | 205 |     |     |     |
| tcc | ttt | ttc | gtt | acc | ttc | gac | aac | cta | ttc | aat | gtg | atg | cag | gga | cat | 672 |
| Ser | Phe | Phe | Val | Thr | Phe | Asp | Asn | Leu | Phe | Asn | Val | Met | Gln | Gly | His |     |
| 210 |     |     |     |     | 215 |     |     |     |     | 220 |     |     |     |     |     |
| ttg | gtc | atg | cat | ttg | ggc | cat | ctt | gct | cgc | cag | ttt | tcg | gcc | atc | gat | 720 |
| Leu | Val | Met | His | Leu | Gly | His | Leu | Ala | Arg | Gln | Phe | Ser | Ala | Ile | Asp |     |
| 225 |     |     |     |     | 230 |     |     |     |     | 235 |     |     |     |     | 240 |
| cct | cga | cag | agt | ttg | acc | gat | gag | aag | cga | ttc | ttt | gtg | gat | ctt | agg | 768 |
| Pro | Arg | Gln | Ser | Leu | Thr | Asp | Glu | Lys | Arg | Phe | Phe | Val | Asp | Leu | Arg |     |
|     |     |     |     | 245 |     |     |     |     | 250 |     |     |     |     | 255 |     |
| tta | tta | gtt | cag | agg | cag | cag | ctt | ctt | aat | gga | ttg | tgc | aga | aaa | tac | 816 |
| Leu | Leu | Val | Gln | Arg | Gln | Gln | Leu | Leu | Asn | Gly | Leu | Cys | Arg | Lys | Tyr |     |
|     |     |     | 260 |     |     |     | 265 |     |     |     | 270 |     |     |     |     |
| aac | gac | atc | ttt | aaa | gtg | gcc | ttc | ctg | gtg | agc | aat | ttt | gta | ggc | gcc | 864 |
| Asn | Asp | Ile | Phe | Lys | Val | Ala | Phe | Leu | Val | Ser | Asn | Phe | Val | Gly | Ala |     |
|     |     | 275 |     |     |     |     | 280 |     |     |     |     | 285 |     |     |     |
| ggt | tcc | ctc | tgc | ttc | tac | ctc | ttt | atg | ctc | tcg | gag | aca | tca | gat | gtc | 912 |
| Gly | Ser | Leu | Cys | Phe | Tyr | Leu | Phe | Met | Leu | Ser | Glu | Thr | Ser | Asp | Val |     |
|     | 290 |     |     |     |     | 295 |     |     |     |     | 300 |     |     |     |     |
| ctt | atc | atc | gcc | cag | tat | ata | tta | ccc | act | ttg | gtc | ctg | gtg | ggc | ttc | 960 |
| Leu | Ile | Ile | Ala | Gln | Tyr | Ile | Leu | Pro | Thr | Leu | Val | Leu | Val | Gly | Phe |     |
| 305 |     |     |     |     | 310 |     |     |     |     | 315 |     |     |     |     | 320 |
| aca | ttt | gag | att | tgt | cta | cgg | gga | acc | caa | ctg | gaa | aag | gcg | tcg | gag | 1008 |
| Thr | Phe | Glu | Ile | Cys | Leu | Arg | Gly | Thr | Gln | Leu | Glu | Lys | Ala | Ser | Glu |     |
|     |     |     |     | 325 |     |     |     |     | 330 |     |     |     |     | 335 |     |
| gga | ctg | gaa | tcg | tcg | ttg | cga | agc | cag | gaa | tgg | tat | ttg | gga | agt | agg | 1056 |
| Gly | Leu | Glu | Ser | Ser | Leu | Arg | Ser | Gln | Glu | Trp | Tyr | Leu | Gly | Ser | Arg |     |
|     |     |     | 340 |     |     |     | 345 |     |     |     | 350 |     |     |     |     |
| cgg | tac | cgg | aag | ttc | tat | ttg | ctc | tgg | acg | caa | tat | tgc | cag | cga | aca | 1104 |
| Arg | Tyr | Arg | Lys | Phe | Tyr | Leu | Leu | Trp | Thr | Gln | Tyr | Cys | Gln | Arg | Thr |     |
|     |     | 355 |     |     |     |     | 360 |     |     |     |     | 365 |     |     |     |
| cag | caa | ctg | ggc | gcc | ttt | ggg | cta | atc | caa | gtc | aat | atg | gtg | cac | ttc | 1152 |
| Gln | Gln | Leu | Gly | Ala | Phe | Gly | Leu | Ile | Gln | Val | Asn | Met | Val | His | Phe |     |
| 370 |     |     |     |     | 375 |     |     |     |     | 380 |     |     |     |     |     |
| act | gaa | ata | atg | cag | ctg | gcc | tat | aga | ctc | ttc | act | ttt | ctc | aaa | tct | 1200 |
| Thr | Glu | Ile | Met | Gln | Leu | Ala | Tyr | Arg | Leu | Phe | Thr | Phe | Leu | Lys | Ser |     |
| 385 |     |     |     |     | 390 |     |     |     |     | 395 |     |     |     |     | 400 |
| cat |     |     |     |     |     |     |     |     |     |     |     |     |     |     |     | 1203 |

His

<210> SEQ ID NO 56
<211> LENGTH: 401
<212> TYPE: PRT
<213> ORGANISM: Drosophila melanogaster

<400> SEQUENCE: 56

```
Met Lys Pro Thr Glu Ile Lys Lys Pro Tyr Arg Met Glu Glu Phe Leu
 1               5                  10                  15
Arg Pro Gln Met Phe Gln Glu Val Ala Gln Met Val His Phe Gln Trp
            20                  25                  30
Arg Arg Asn Pro Val Asp Asn Ser Met Val Asn Ala Ser Met Val Pro
        35                  40                  45
Phe Cys Leu Ser Ala Phe Leu Asn Val Leu Phe Phe Gly Cys Asn Gly
    50                  55                  60
Trp Asp Ile Ile Gly His Phe Trp Leu Gly His Pro Ala Asn Gln Asn
 65                  70                  75                  80
Pro Pro Val Leu Ser Ile Thr Ile Tyr Phe Ser Ile Arg Gly Leu Met
                85                  90                  95
Leu Tyr Leu Lys Arg Lys Glu Ile Val Glu Phe Val Asn Asp Leu Asp
            100                 105                 110
Arg Glu Cys Pro Arg Asp Leu Val Ser Gln Leu Asp Met Gln Met Asp
        115                 120                 125
Glu Thr Tyr Arg Asn Phe Trp Gln Arg Tyr Arg Phe Ile Arg Ile Tyr
    130                 135                 140
Ser His Leu Gly Gly Pro Met Phe Cys Val Val Pro Leu Ala Leu Phe
145                 150                 155                 160
Leu Leu Thr His Glu Gly Lys Asp Thr Pro Val Ala Gln His Glu Gln
                165                 170                 175
Leu Leu Gly Gly Trp Leu Pro Cys Gly Val Arg Lys Asp Pro Asn Phe
            180                 185                 190
Tyr Leu Leu Val Trp Ser Phe Asp Leu Met Cys Thr Thr Cys Gly Val
        195                 200                 205
Ser Phe Phe Val Thr Phe Asp Asn Leu Phe Asn Val Met Gln Gly His
    210                 215                 220
Leu Val Met His Leu Gly His Leu Ala Arg Gln Phe Ser Ala Ile Asp
225                 230                 235                 240
Pro Arg Gln Ser Leu Thr Asp Glu Lys Arg Phe Phe Val Asp Leu Arg
                245                 250                 255
Leu Leu Val Gln Arg Gln Gln Leu Leu Asn Gly Leu Cys Arg Lys Tyr
            260                 265                 270
Asn Asp Ile Phe Lys Val Ala Phe Leu Val Ser Asn Phe Val Gly Ala
        275                 280                 285
Gly Ser Leu Cys Phe Tyr Leu Phe Met Leu Ser Glu Thr Ser Asp Val
    290                 295                 300
Leu Ile Ile Ala Gln Tyr Ile Leu Pro Thr Leu Val Leu Val Gly Phe
305                 310                 315                 320
Thr Phe Glu Ile Cys Leu Arg Gly Thr Gln Leu Glu Lys Ala Ser Glu
                325                 330                 335
Gly Leu Glu Ser Ser Leu Arg Ser Gln Glu Trp Tyr Leu Gly Ser Arg
            340                 345                 350
Arg Tyr Arg Lys Phe Tyr Leu Leu Trp Thr Gln Tyr Cys Gln Arg Thr
        355                 360                 365
```

```
Gln Gln Leu Gly Ala Phe Gly Leu Ile Gln Val Asn Met Val His Phe
        370                 375                 380

Thr Glu Ile Met Gln Leu Ala Tyr Arg Leu Phe Thr Phe Leu Lys Ser
385                 390                 395                 400

His

<210> SEQ ID NO 57
<211> LENGTH: 1131
<212> TYPE: DNA
<213> ORGANISM: Drosophila melanogaster
<220> FEATURE:
<221> NAME/KEY: CDS
<222> LOCATION: (1)..(1131)
<223> OTHER INFORMATION: DOR 92E.1

<400> SEQUENCE: 57 atg act ttc tac aag acc atc ggc gag gat ctg tac tcc gat agg gat     48
Met Thr Phe Tyr Lys Thr Ile Gly Glu Asp Leu Tyr Ser Asp Arg Asp
  1               5                  10                  15 ccg aat gtg ata agg cgt tac ctg cta cgt ttt tat ctg gta ctc ggt     96
Pro Asn Val Ile Arg Arg Tyr Leu Leu Arg Phe Tyr Leu Val Leu Gly
             20                  25                  30 ttt ctc aac ttc aat gcc tat gtg gtg ggc gaa atc gcg tac ttt ata    144
Phe Leu Asn Phe Asn Ala Tyr Val Val Gly Glu Ile Ala Tyr Phe Ile
         35                  40                  45 gtc cat ata atg tcg acg act act ctt ttg gag gcc act gca gtg gca    192
Val His Ile Met Ser Thr Thr Thr Leu Leu Glu Ala Thr Ala Val Ala
     50                  55                  60 ccg tgc att ggt ttc agc ttc atg gcc gac ttt aag cag ttc ggt ctc    240
Pro Cys Ile Gly Phe Ser Phe Met Ala Asp Phe Lys Gln Phe Gly Leu
 65                  70                  75                  80 aca gtg aat aga aag cga ttg gtc aga ttg ctg gat gat ctc aag gag    288
Thr Val Asn Arg Lys Arg Leu Val Arg Leu Leu Asp Asp Leu Lys Glu
                 85                  90                  95 ata ttt cct tta gat tta gaa gcg cag cgg aag tat aac gta tcg ttt    336
Ile Phe Pro Leu Asp Leu Glu Ala Gln Arg Lys Tyr Asn Val Ser Phe
            100                 105                 110 tac cgg aaa cac atg aac agg gtc atg acc cta ttc acc atc ctc tgc    384
Tyr Arg Lys His Met Asn Arg Val Met Thr Leu Phe Thr Ile Leu Cys
        115                 120                 125 atg acc tac acc tcg tca ttt agc ttt tat cca gcc atc aag tcg acc    432
Met Thr Tyr Thr Ser Ser Phe Ser Phe Tyr Pro Ala Ile Lys Ser Thr
    130                 135                 140 ata aag tat tac ctt atg gga tcg gaa atc ttt gag cgc aac tac gga    480
Ile Lys Tyr Tyr Leu Met Gly Ser Glu Ile Phe Glu Arg Asn Tyr Gly
145                 150                 155                 160 ttt cac att ttg ttt ccc tac gac gca gaa acg gat ctg acg gtc tac    528
Phe His Ile Leu Phe Pro Tyr Asp Ala Glu Thr Asp Leu Thr Val Tyr
                165                 170                 175 tgg ttt tcc tac tgg gga ttg gct cat tgt gcc tat gtg gcc gga gtt    576
Trp Phe Ser Tyr Trp Gly Leu Ala His Cys Ala Tyr Val Ala Gly Val
            180                 185                 190 tcc tac gtc tgc gtg gat ctc ctg ctg atc gcg acc ata acc cag ctg    624
Ser Tyr Val Cys Val Asp Leu Leu Leu Ile Ala Thr Ile Thr Gln Leu
        195                 200                 205 acc atg cac ttc aac ttt ata gcg aat gat ttg gag gcc tac gaa gga    672
Thr Met His Phe Asn Phe Ile Ala Asn Asp Leu Glu Ala Tyr Glu Gly
    210                 215                 220 ggt gat cat acg gat gaa gaa aat atc aaa tac ctg cac aac ttg gtc    720
Gly Asp His Thr Asp Glu Glu Asn Ile Lys Tyr Leu His Asn Leu Val
225                 230                 235                 240
```

```
gtc tat cat gcc agg gcg ctg gac ctc agc gag gag gtc aac aac ata      768
Val Tyr His Ala Arg Ala Leu Asp Leu Ser Glu Glu Val Asn Asn Ile
            245                 250                 255 ttc agc ttc ctg atc ctg tgg aac ttt att gcc gca tcg ctc gtg att      816
Phe Ser Phe Leu Ile Leu Trp Asn Phe Ile Ala Ala Ser Leu Val Ile
                260                 265                 270 tgc ttc gct ggc ttt cag att aca gcc tca aat gtg gag gac ata ggg      864
Cys Phe Ala Gly Phe Gln Ile Thr Ala Ser Asn Val Glu Asp Ile Gly
        275                 280                 285 gtg tac ttc ata ttt ttt tca gct tcg ctg gtt caa gtc ttt aaa tgt      912
Val Tyr Phe Ile Phe Phe Ser Ala Ser Leu Val Gln Val Phe Lys Cys
    290                 295                 300 tct ttt cag agc tct cgg att ggc cat tcg gca ttt aat cag aac tgg      960
Ser Phe Gln Ser Ser Arg Ile Gly His Ser Ala Phe Asn Gln Asn Trp
305                 310                 315                 320 ttg cca tgc agc acc aaa tac aaa cgc atc ctg cag ttt att atc gcg     1008
Leu Pro Cys Ser Thr Lys Tyr Lys Arg Ile Leu Gln Phe Ile Ile Ala
                325                 330                 335 cgc agc cag aag ccc gcc tct ata aga ccg cct acc ttt cca ccc ata     1056
Arg Ser Gln Lys Pro Ala Ser Ile Arg Pro Pro Thr Phe Pro Pro Ile
            340                 345                 350 tct ttt aat acc ttt atg aag gta atc agc atg tcg tat cag ttt ttt     1104
Ser Phe Asn Thr Phe Met Lys Val Ile Ser Met Ser Tyr Gln Phe Phe
        355                 360                 365 gca ctg ctc cgc acc aca tat tat ggt                                 1131
Ala Leu Leu Arg Thr Thr Tyr Tyr Gly
    370                 375

<210> SEQ ID NO 58
<211> LENGTH: 377
<212> TYPE: PRT
<213> ORGANISM: Drosophila melanogaster

<400> SEQUENCE: 58

Met Thr Phe Tyr Lys Thr Ile Gly Glu Asp Leu Tyr Ser Asp Arg Asp
 1               5                  10                  15

Pro Asn Val Ile Arg Arg Tyr Leu Leu Arg Phe Tyr Leu Val Leu Gly
            20                  25                  30

Phe Leu Asn Phe Asn Ala Tyr Val Val Gly Glu Ile Ala Tyr Phe Ile
        35                  40                  45

Val His Ile Met Ser Thr Thr Thr Leu Leu Glu Ala Thr Ala Val Ala
    50                  55                  60

Pro Cys Ile Gly Phe Ser Phe Met Ala Asp Phe Lys Gln Phe Gly Leu
65                  70                  75                  80

Thr Val Asn Arg Lys Arg Leu Val Arg Leu Leu Asp Asp Leu Lys Glu
                85                  90                  95

Ile Phe Pro Leu Asp Leu Glu Ala Gln Arg Lys Tyr Asn Val Ser Phe
            100                 105                 110

Tyr Arg Lys His Met Asn Arg Val Met Thr Leu Phe Thr Ile Leu Cys
        115                 120                 125

Met Thr Tyr Thr Ser Ser Phe Ser Phe Tyr Pro Ala Ile Lys Ser Thr
    130                 135                 140

Ile Lys Tyr Tyr Leu Met Gly Ser Glu Ile Phe Glu Arg Asn Tyr Gly
145                 150                 155                 160

Phe His Ile Leu Phe Pro Tyr Asp Ala Glu Thr Asp Leu Thr Val Tyr
                165                 170                 175

Trp Phe Ser Tyr Trp Gly Leu Ala His Cys Ala Tyr Val Ala Gly Val
```

```
                180                 185                 190
Ser Tyr Val Cys Val Asp Leu Leu Ile Ala Thr Ile Thr Gln Leu
            195                 200                 205

Thr Met His Phe Asn Phe Ile Ala Asn Asp Leu Glu Ala Tyr Glu Gly
    210                 215                 220

Gly Asp His Thr Asp Glu Glu Asn Ile Lys Tyr Leu His Asn Leu Val
225                 230                 235                 240

Val Tyr His Ala Arg Ala Leu Asp Leu Ser Glu Glu Val Asn Asn Ile
            245                 250                 255

Phe Ser Phe Leu Ile Leu Trp Asn Phe Ile Ala Ala Ser Leu Val Ile
            260                 265                 270

Cys Phe Ala Gly Phe Gln Ile Thr Ala Ser Asn Val Glu Asp Ile Gly
            275                 280                 285

Val Tyr Phe Ile Phe Ser Ala Ser Leu Val Gln Val Phe Lys Cys
290                 295                 300

Ser Phe Gln Ser Ser Arg Ile Gly His Ser Ala Phe Asn Gln Asn Trp
305                 310                 315                 320

Leu Pro Cys Ser Thr Lys Tyr Lys Arg Ile Leu Gln Phe Ile Ile Ala
                325                 330                 335

Arg Ser Gln Lys Pro Ala Ser Ile Arg Pro Pro Thr Phe Pro Pro Ile
            340                 345                 350

Ser Phe Asn Thr Phe Met Lys Val Ile Ser Met Ser Tyr Gln Phe Phe
            355                 360                 365

Ala Leu Leu Arg Thr Thr Tyr Tyr Gly
            370                 375

<210> SEQ ID NO 59
<211> LENGTH: 1161
<212> TYPE: DNA
<213> ORGANISM: Drosophila melanogaster
<220> FEATURE:
<221> NAME/KEY: CDS
<222> LOCATION: (1)..(1161)
<223> OTHER INFORMATION: DOR 94D.1

<400> SEQUENCE: 59 atg gat aaa cac aag gat cgc att gaa tcc atg cgc cta att ctt cag      48
Met Asp Lys His Lys Asp Arg Ile Glu Ser Met Arg Leu Ile Leu Gln
 1               5                  10                  15 gtc atg caa cta ttt ggc ctc tgg ccg tgg tcc ttg aaa tcg gaa gag      96
Val Met Gln Leu Phe Gly Leu Trp Pro Trp Ser Leu Lys Ser Glu Glu
             20                  25                  30 gag tgg act ttc acc ggt ttt gta aag cgc aac tat cgc ttc ctg ctc     144
Glu Trp Thr Phe Thr Gly Phe Val Lys Arg Asn Tyr Arg Phe Leu Leu
         35                  40                  45 cat ctg ccc att acc ttc acc ttt att gga ctc atg tgg ctg gag gcc     192
His Leu Pro Ile Thr Phe Thr Phe Ile Gly Leu Met Trp Leu Glu Ala
     50                  55                  60 ttc atc tcg agc aat ctg gag cag gct ggc cag gtt ctg tac atg tcc     240
Phe Ile Ser Ser Asn Leu Glu Gln Ala Gly Gln Val Leu Tyr Met Ser
 65                  70                  75                  80 atc acc gag atg gct ttg gtg gtg aaa atc ctg agc att tgg cac tat     288
Ile Thr Glu Met Ala Leu Val Val Lys Ile Leu Ser Ile Trp His Tyr
                 85                  90                  95 cgc acc gaa gct tgg cgg ctg atg tac gaa ctc caa cat gct ccg gac     336
Arg Thr Glu Ala Trp Arg Leu Met Tyr Glu Leu Gln His Ala Pro Asp
            100                 105                 110 tac caa ctc cac aac cag gag gag gta gac ttt tgg cgc cgg gag caa     384
```

```
Tyr Gln Leu His Asn Gln Glu Glu Val Asp Phe Trp Arg Arg Glu Gln
        115                 120                 125 cga ttc ttc aag tgg ttc ttc tac atc tac att ctg att agc ttg ggc      432
Arg Phe Phe Lys Trp Phe Phe Tyr Ile Tyr Ile Leu Ile Ser Leu Gly
    130                 135                 140 gtg gta tat agt ggc tgc act gga gta ctt ttt ctg gag ggc tac gaa      480
Val Val Tyr Ser Gly Cys Thr Gly Val Leu Phe Leu Glu Gly Tyr Glu
145                 150                 155                 160 ctg ccc ttt gcc tac tac gtg ccc ttc gaa tgg cag aac gag aga agg      528
Leu Pro Phe Ala Tyr Tyr Val Pro Phe Glu Trp Gln Asn Glu Arg Arg
                165                 170                 175 tac tgg ttc gcc tat ggt tac gat atg gcg ggc atg acg ctg acc tgc      576
Tyr Trp Phe Ala Tyr Gly Tyr Asp Met Ala Gly Met Thr Leu Thr Cys
                180                 185                 190 atc tca aac att acc ctg gac acc ctg ggt tgc tat ttc ctg ttc cat      624
Ile Ser Asn Ile Thr Leu Asp Thr Leu Gly Cys Tyr Phe Leu Phe His
                195                 200                 205 atc tct ctt ttg tac cga ctg ctt ggt ctg cga ttg agg gaa acg aag      672
Ile Ser Leu Leu Tyr Arg Leu Leu Gly Leu Arg Leu Arg Glu Thr Lys
        210                 215                 220 aat atg aag aat gat acc att ttt ggc cag cag ttg cgt gcc atc ttc      720
Asn Met Lys Asn Asp Thr Ile Phe Gly Gln Gln Leu Arg Ala Ile Phe
225                 230                 235                 240 att atg cat cag agg att aga agc cta acc ctg acc tgc cag aga atc      768
Ile Met His Gln Arg Ile Arg Ser Leu Thr Leu Thr Cys Gln Arg Ile
                245                 250                 255 gta tct ccc tat atc cta tct cag atc att ttg agt gcc ctg atc atc      816
Val Ser Pro Tyr Ile Leu Ser Gln Ile Ile Leu Ser Ala Leu Ile Ile
                260                 265                 270 tgc ttt agt gga tac cgc ttg cag cat gtg gga att cgc gat aat ccc      864
Cys Phe Ser Gly Tyr Arg Leu Gln His Val Gly Ile Arg Asp Asn Pro
                275                 280                 285 ggc cag ttt ata tcc atg ttg cag ttt gtc agt gtg atg atc ctg cag      912
Gly Gln Phe Ile Ser Met Leu Gln Phe Val Ser Val Met Ile Leu Gln
        290                 295                 300 att tac ttg ccc tgc tac tat gga aac gag ata acc gtg tat gcc aat      960
Ile Tyr Leu Pro Cys Tyr Tyr Gly Asn Glu Ile Thr Val Tyr Ala Asn
305                 310                 315                 320 cag ctg acc aac gag gtt tac cat acc aat tgg ctg gaa tgt cgg cca     1008
Gln Leu Thr Asn Glu Val Tyr His Thr Asn Trp Leu Glu Cys Arg Pro
                325                 330                 335 ccg att cga aag tta ctc aat gcc tac atg gag cac ctg aag aaa ccg     1056
Pro Ile Arg Lys Leu Leu Asn Ala Tyr Met Glu His Leu Lys Lys Pro
                340                 345                 350 gtg acc atc cgg gct ggc aac tac ttc gcc gtg gga cta cca att ttt     1104
Val Thr Ile Arg Ala Gly Asn Tyr Phe Ala Val Gly Leu Pro Ile Phe
        355                 360                 365 gtt aag acc atc aac aac gcc tac agt ttc ttg gct tta tta cta aat     1152
Val Lys Thr Ile Asn Asn Ala Tyr Ser Phe Leu Ala Leu Leu Leu Asn
370                 375                 380 gta tcg aat                                                          1161
Val Ser Asn
385

<210> SEQ ID NO 60
<211> LENGTH: 387
<212> TYPE: PRT
<213> ORGANISM: Drosophila melanogaster

<400> SEQUENCE: 60
```

-continued

```
Met Asp Lys His Lys Asp Arg Ile Glu Ser Met Arg Leu Ile Leu Gln
 1               5                  10                  15

Val Met Gln Leu Phe Gly Leu Trp Pro Trp Ser Leu Lys Ser Glu Glu
                20                  25                  30

Glu Trp Thr Phe Thr Gly Phe Val Lys Arg Asn Tyr Arg Phe Leu Leu
            35                  40                  45

His Leu Pro Ile Thr Phe Thr Phe Ile Gly Leu Met Trp Leu Glu Ala
        50                  55                  60

Phe Ile Ser Ser Asn Leu Glu Gln Ala Gly Gln Val Leu Tyr Met Ser
 65                  70                  75                  80

Ile Thr Glu Met Ala Leu Val Val Lys Ile Leu Ser Ile Trp His Tyr
                85                  90                  95

Arg Thr Glu Ala Trp Arg Leu Met Tyr Glu Leu Gln His Ala Pro Asp
            100                 105                 110

Tyr Gln Leu His Asn Gln Glu Val Asp Phe Trp Arg Arg Glu Gln
        115                 120                 125

Arg Phe Phe Lys Trp Phe Phe Tyr Ile Tyr Ile Leu Ile Ser Leu Gly
    130                 135                 140

Val Val Tyr Ser Gly Cys Thr Gly Val Leu Phe Leu Glu Gly Tyr Glu
145                 150                 155                 160

Leu Pro Phe Ala Tyr Tyr Val Pro Phe Glu Trp Gln Asn Glu Arg Arg
                165                 170                 175

Tyr Trp Phe Ala Tyr Gly Tyr Asp Met Ala Gly Met Thr Leu Thr Cys
            180                 185                 190

Ile Ser Asn Ile Thr Leu Asp Thr Leu Gly Cys Tyr Phe Leu Phe His
        195                 200                 205

Ile Ser Leu Leu Tyr Arg Leu Leu Gly Leu Arg Leu Arg Glu Thr Lys
    210                 215                 220

Asn Met Lys Asn Asp Thr Ile Phe Gly Gln Gln Leu Arg Ala Ile Phe
225                 230                 235                 240

Ile Met His Gln Arg Ile Arg Ser Leu Thr Leu Thr Cys Gln Arg Ile
                245                 250                 255

Val Ser Pro Tyr Ile Leu Ser Gln Ile Ile Leu Ser Ala Leu Ile Ile
            260                 265                 270

Cys Phe Ser Gly Tyr Arg Leu Gln His Val Gly Ile Arg Asp Asn Pro
        275                 280                 285

Gly Gln Phe Ile Ser Met Leu Gln Phe Val Ser Val Met Ile Leu Gln
    290                 295                 300

Ile Tyr Leu Pro Cys Tyr Tyr Gly Asn Glu Ile Thr Val Tyr Ala Asn
305                 310                 315                 320

Gln Leu Thr Asn Glu Val Tyr His Thr Asn Trp Leu Glu Cys Arg Pro
                325                 330                 335

Pro Ile Arg Lys Leu Leu Asn Ala Tyr Met Glu His Leu Lys Lys Pro
            340                 345                 350

Val Thr Ile Arg Ala Gly Asn Tyr Phe Ala Val Gly Leu Pro Ile Phe
        355                 360                 365

Val Lys Thr Ile Asn Asn Ala Tyr Ser Phe Leu Ala Leu Leu Leu Asn
    370                 375                 380

Val Ser Asn
385
```

<210> SEQ ID NO 61
<211> LENGTH: 1101
<212> TYPE: DNA

```
<213> ORGANISM: Drosophila melanogaster
<220> FEATURE:
<221> NAME/KEY: CDS
<222> LOCATION: (1)..(1101)

<400> SEQUENCE: 61 atg gag tct aca aat cgc cta agt gcc atc caa aca ctt tta gta atc      48
Met Glu Ser Thr Asn Arg Leu Ser Ala Ile Gln Thr Leu Leu Val Ile
 1               5                  10                  15 caa cgt tgg ata gga ctt ctt aaa tgg gaa aac gag ggc gag gat gga      96
Gln Arg Trp Ile Gly Leu Leu Lys Trp Glu Asn Glu Gly Glu Asp Gly
             20                  25                  30 gta tta acc tgg cta aaa cga ata tat cct ttt gta ctg cac ctt cca     144
Val Leu Thr Trp Leu Lys Arg Ile Tyr Pro Phe Val Leu His Leu Pro
         35                  40                  45 ctg acc ttc acg tat att gcc tta atg tgg tat gaa gct att aca tcg     192
Leu Thr Phe Thr Tyr Ile Ala Leu Met Trp Tyr Glu Ala Ile Thr Ser
     50                  55                  60 tca gat ttt gag gaa gct ggt caa gtt ctg tac atg tcc atc acc gaa     240
Ser Asp Phe Glu Glu Ala Gly Gln Val Leu Tyr Met Ser Ile Thr Glu
 65                  70                  75                  80 ctg gca ttg gtc act aaa ctg ctg aat att tgg tat cgt cgt cat gaa     288
Leu Ala Leu Val Thr Lys Leu Leu Asn Ile Trp Tyr Arg Arg His Glu
                 85                  90                  95 gct gct agt cta atc cac gaa ttg caa cac gat ccc gca ttt aat ctg     336
Ala Ala Ser Leu Ile His Glu Leu Gln His Asp Pro Ala Phe Asn Leu
            100                 105                 110 cgc aat tcg gag gaa atc aaa ttc tgg cag caa aat cag agg aac ttt     384
Arg Asn Ser Glu Glu Ile Lys Phe Trp Gln Gln Asn Gln Arg Asn Phe
        115                 120                 125 aag aga ata ttt tac tgg tac atc tgg ggc agc ctt ttc gtg gct gta     432
Lys Arg Ile Phe Tyr Trp Tyr Ile Trp Gly Ser Leu Phe Val Ala Val
    130                 135                 140 atg ggt tat ata agc gtg ttt ttc cag gag gat tac gag ctg ccc ttt     480
Met Gly Tyr Ile Ser Val Phe Phe Gln Glu Asp Tyr Glu Leu Pro Phe
145                 150                 155                 160 ggc tac tac gtg cca ttc gag tgg cgc acc agg gaa cga tac ttc tac     528
Gly Tyr Tyr Val Pro Phe Glu Trp Arg Thr Arg Glu Arg Tyr Phe Tyr
                165                 170                 175 gct tgg ggc tat aat gtg gtg gcc atg acc ctg tgc tgt cta tcc aac     576
Ala Trp Gly Tyr Asn Val Val Ala Met Thr Leu Cys Cys Leu Ser Asn
            180                 185                 190 atc cta ctg gac aca cta ggc tgt tat ttc atg ttc cac atc gcc tcg     624
Ile Leu Leu Asp Thr Leu Gly Cys Tyr Phe Met Phe His Ile Ala Ser
        195                 200                 205 ctt ttc agg ctt ttg gga atg cga ctg gag gcc ttg aaa aat gca gcc     672
Leu Phe Arg Leu Leu Gly Met Arg Leu Glu Ala Leu Lys Asn Ala Ala
    210                 215                 220 gaa gag aaa gcc aga ccg gag ttg cgc cgc att ttc caa ctg cac act     720
Glu Glu Lys Ala Arg Pro Glu Leu Arg Arg Ile Phe Gln Leu His Thr
225                 230                 235                 240 aaa gtc cgc cga ttg acg agg gaa tgc gaa gtg tta gtt tca ccc tat     768
Lys Val Arg Arg Leu Thr Arg Glu Cys Glu Val Leu Val Ser Pro Tyr
                245                 250                 255 gtt cta tcc caa gtg gtc ttc agt gcc ttc atc atc tgc ttc agt gcc     816
Val Leu Ser Gln Val Val Phe Ser Ala Phe Ile Ile Cys Phe Ser Ala
            260                 265                 270 tat cga ctg gtg cac atg ggc ttc aag cag cga cct gga ctc ttc gtg     864
Tyr Arg Leu Val His Met Gly Phe Lys Gln Arg Pro Gly Leu Phe Val
        275                 280                 285
```

```
acc acc gtg caa ttc gtg gcc gtc atg atc gtc cag att ttc ttg ccc    912
Thr Thr Val Gln Phe Val Ala Val Met Ile Val Gln Ile Phe Leu Pro
    290                 295                 300 tgt tac tac ggc aat gag ttg acc ttt cat gcc aat gca ctc act aat    960
Cys Tyr Tyr Gly Asn Glu Leu Thr Phe His Ala Asn Ala Leu Thr Asn
305                 310                 315                 320 agt gtc ttc ggt acc aat tgg ctg gag tac tcc gtg ggc act cgc aag   1008
Ser Val Phe Gly Thr Asn Trp Leu Glu Tyr Ser Val Gly Thr Arg Lys
                325                 330                 335 ctg ctt aac tgc tac atg gag ttc ctc aag cga ccg gtt aaa acc atc   1056
Leu Leu Asn Cys Tyr Met Glu Phe Leu Lys Arg Pro Val Lys Thr Ile
            340                 345                 350 aac aat gcc tac agt ttc ttc gcc ctg ctg cta aag ata tcc aag        1101
Asn Asn Ala Tyr Ser Phe Phe Ala Leu Leu Leu Lys Ile Ser Lys
        355                 360                 365

<210> SEQ ID NO 62
<211> LENGTH: 367
<212> TYPE: PRT
<213> ORGANISM: Drosophila melanogaster

<400> SEQUENCE: 62

Met Glu Ser Thr Asn Arg Leu Ser Ala Ile Gln Thr Leu Leu Val Ile
1               5                   10                  15

Gln Arg Trp Ile Gly Leu Leu Lys Trp Glu Asn Glu Gly Glu Asp Gly
            20                  25                  30

Val Leu Thr Trp Leu Lys Arg Ile Tyr Pro Phe Val Leu His Leu Pro
        35                  40                  45

Leu Thr Phe Thr Tyr Ile Ala Leu Met Trp Tyr Glu Ala Ile Thr Ser
    50                  55                  60

Ser Asp Phe Glu Glu Ala Gly Gln Val Leu Tyr Met Ser Ile Thr Glu
65              70                  75                  80

Leu Ala Leu Val Thr Lys Leu Leu Asn Ile Trp Tyr Arg Arg His Glu
                85                  90                  95

Ala Ala Ser Leu Ile His Glu Leu Gln His Asp Pro Ala Phe Asn Leu
            100                 105                 110

Arg Asn Ser Glu Glu Ile Lys Phe Trp Gln Gln Asn Gln Arg Asn Phe
        115                 120                 125

Lys Arg Ile Phe Tyr Trp Tyr Ile Trp Gly Ser Leu Phe Val Ala Val
    130                 135                 140

Met Gly Tyr Ile Ser Val Phe Phe Gln Glu Asp Tyr Glu Leu Pro Phe
145                 150                 155                 160

Gly Tyr Tyr Val Pro Phe Glu Trp Arg Thr Arg Glu Arg Tyr Phe Tyr
                165                 170                 175

Ala Trp Gly Tyr Asn Val Val Ala Met Thr Leu Cys Cys Leu Ser Asn
            180                 185                 190

Ile Leu Leu Asp Thr Leu Gly Cys Tyr Phe Met Phe His Ile Ala Ser
        195                 200                 205

Leu Phe Arg Leu Leu Gly Met Arg Leu Glu Ala Leu Lys Asn Ala Ala
    210                 215                 220

Glu Glu Lys Ala Arg Pro Glu Leu Arg Arg Ile Phe Gln Leu His Thr
225                 230                 235                 240

Lys Val Arg Arg Leu Thr Arg Glu Cys Glu Val Leu Val Ser Pro Tyr
                245                 250                 255

Val Leu Ser Gln Val Val Phe Ser Ala Phe Ile Ile Cys Phe Ser Ala
            260                 265                 270
```

```
Tyr Arg Leu Val His Met Gly Phe Lys Gln Arg Pro Gly Leu Phe Val
         275                 280                 285

Thr Thr Val Gln Phe Val Ala Val Met Ile Val Gln Ile Phe Leu Pro
     290                 295                 300

Cys Tyr Tyr Gly Asn Glu Leu Thr Phe His Ala Asn Ala Leu Thr Asn
305                 310                 315                 320

Ser Val Phe Gly Thr Asn Trp Leu Glu Tyr Ser Val Gly Thr Arg Lys
                 325                 330                 335

Leu Leu Asn Cys Tyr Met Glu Phe Leu Lys Arg Pro Val Lys Thr Ile
             340                 345                 350

Asn Asn Ala Tyr Ser Phe Phe Ala Leu Leu Leu Lys Ile Ser Lys
             355                 360                 365

<210> SEQ ID NO 63
<211> LENGTH: 1095
<212> TYPE: DNA
<213> ORGANISM: Drosophila melanogaster
<220> FEATURE:
<221> NAME/KEY: CDS
<222> LOCATION: (1)..(1095)
<223> OTHER INFORMATION: DORLU 1.1

<400> SEQUENCE: 63 atg tgg ctc atc gga tgg att ccg ccg aag gag gga gtc ctg cgc tac      48
Met Trp Leu Ile Gly Trp Ile Pro Pro Lys Glu Gly Val Leu Arg Tyr
 1               5                  10                  15 gtg tat ctc ttc tgg acc tgc gtg ccc ttc gcc ttc ggg gtg ttt tac      96
Val Tyr Leu Phe Trp Thr Cys Val Pro Phe Ala Phe Gly Val Phe Tyr
             20                  25                  30 ctg ccc gtg ggc ttc atc atc agc tac gtg cag gag ttc aag aac ttc     144
Leu Pro Val Gly Phe Ile Ile Ser Tyr Val Gln Glu Phe Lys Asn Phe
         35                  40                  45 acg ccg ggc gag ttc ctt acc tcg ctg cag gtg tgc atc aat gtg tat     192
Thr Pro Gly Glu Phe Leu Thr Ser Leu Gln Val Cys Ile Asn Val Tyr
     50                  55                  60 ggc gcc tcg gtg aag tcc acc atc acc tac ctc ttc ctc tgg cga ctg     240
Gly Ala Ser Val Lys Ser Thr Ile Thr Tyr Leu Phe Leu Trp Arg Leu
 65                  70                  75                  80 cgc aag acg gag atc ctt ctg gac tcc ctg gac aag agg ctg gcg aac     288
Arg Lys Thr Glu Ile Leu Leu Asp Ser Leu Asp Lys Arg Leu Ala Asn
                 85                  90                  95 gac agc gat cgc gag agg atc cac aat atg gtg gcg cgc tgc aac tac     336
Asp Ser Asp Arg Glu Arg Ile His Asn Met Val Ala Arg Cys Asn Tyr
            100                 105                 110 gcc ttt ctc atc tac agc ttc atc tac tgc gga tac gcg ggt tcc act     384
Ala Phe Leu Ile Tyr Ser Phe Ile Tyr Cys Gly Tyr Ala Gly Ser Thr
        115                 120                 125 ttc ctg tcc tac gcc ctc agt ggt cgt cct ccg tgg tcc gtc tac aat     432
Phe Leu Ser Tyr Ala Leu Ser Gly Arg Pro Pro Trp Ser Val Tyr Asn
    130                 135                 140 ccc ttc atc gat tgg cgc gat ggc atg ggc agc ctg tgg atc cag gcc     480
Pro Phe Ile Asp Trp Arg Asp Gly Met Gly Ser Leu Trp Ile Gln Ala
145                 150                 155                 160 ata ttc gag tac atc acc atg tcc ttc gcc gtg ctg cag gac cag cta     528
Ile Phe Glu Tyr Ile Thr Met Ser Phe Ala Val Leu Gln Asp Gln Leu
                165                 170                 175 tcc gac acg tat ccc ctg atg ttc acc att atg ttc cgg gcc cac atg     576
Ser Asp Thr Tyr Pro Leu Met Phe Thr Ile Met Phe Arg Ala His Met
            180                 185                 190 gag gtc ctc aag gat cac gtg cgg agc ctg cgc atg gat ccc gag cgc     624
```

-continued

```
                Glu Val Leu Lys Asp His Val Arg Ser Leu Arg Met Asp Pro Glu Arg
                            195                 200                 205 agt gag gca gac aac tat cag gat ctg gtg aac tgc gtg ctg gac cac          672
Ser Glu Ala Asp Asn Tyr Gln Asp Leu Val Asn Cys Val Leu Asp His
    210                 215                 220 aag act ata ctg aaa tgc tgt gac atg att cgc ccc atg ata tcc cgc          720
Lys Thr Ile Leu Lys Cys Cys Asp Met Ile Arg Pro Met Ile Ser Arg
225                 230                 235                 240 acc atc ttc gtg caa ttc gcg ctg att ggt tcc gtt ttg ggc ctg acc          768
Thr Ile Phe Val Gln Phe Ala Leu Ile Gly Ser Val Leu Gly Leu Thr
                245                 250                 255 ctg gtg aac gtg ttc ttc ttc tcg aac ttc tgg aag ggc gtg gcc tcg          816
Leu Val Asn Val Phe Phe Phe Ser Asn Phe Trp Lys Gly Val Ala Ser
            260                 265                 270 ctc ctg ttc gtc atc acc atc ctg ctg cag acc ttc ccg ttc tgc tac          864
Leu Leu Phe Val Ile Thr Ile Leu Leu Gln Thr Phe Pro Phe Cys Tyr
        275                 280                 285 acc tgc aac atg ctg atc gac gat gcc cag gat ctg tcc aac gag att          912
Thr Cys Asn Met Leu Ile Asp Asp Ala Gln Asp Leu Ser Asn Glu Ile
    290                 295                 300 ttc cag tcc aac tgg gtg gac gcg gag ccg cgc tac aag gcg acg ctg          960
Phe Gln Ser Asn Trp Val Asp Ala Glu Pro Arg Tyr Lys Ala Thr Leu
305                 310                 315                 320 gtg ctc ttc atg cac cat gtt cag cag ccc ata atc ttc att gcc gga         1008
Val Leu Phe Met His His Val Gln Gln Pro Ile Ile Phe Ile Ala Gly
                325                 330                 335 ggc atc ttt ccc atc tct atg aac agc aac ata acc gta agg att act         1056
Gly Ile Phe Pro Ile Ser Met Asn Ser Asn Ile Thr Val Arg Ile Thr
            340                 345                 350 tct ttc ctg cca act gcc tac ttc aca ttt gac cca ttt                     1095
Ser Phe Leu Pro Thr Ala Tyr Phe Thr Phe Asp Pro Phe
        355                 360                 365

<210> SEQ ID NO 64
<211> LENGTH: 365
<212> TYPE: PRT
<213> ORGANISM: Drosophila melanogaster

<400> SEQUENCE: 64

Met Trp Leu Ile Gly Trp Ile Pro Pro Lys Glu Gly Val Leu Arg Tyr
 1               5                  10                  15

Val Tyr Leu Phe Trp Thr Cys Val Pro Phe Ala Phe Gly Val Phe Tyr
            20                  25                  30

Leu Pro Val Gly Phe Ile Ile Ser Tyr Val Gln Glu Phe Lys Asn Phe
        35                  40                  45

Thr Pro Gly Glu Phe Leu Thr Ser Leu Gln Val Cys Ile Asn Val Tyr
    50                  55                  60

Gly Ala Ser Val Lys Ser Thr Ile Thr Tyr Leu Phe Leu Trp Arg Leu
65                  70                  75                  80

Arg Lys Thr Glu Ile Leu Leu Asp Ser Leu Asp Lys Arg Leu Ala Asn
                85                  90                  95

Asp Ser Asp Arg Glu Arg Ile His Asn Met Val Ala Arg Cys Asn Tyr
            100                 105                 110

Ala Phe Leu Ile Tyr Ser Phe Ile Tyr Cys Gly Tyr Ala Gly Ser Thr
        115                 120                 125

Phe Leu Ser Tyr Ala Leu Ser Gly Arg Pro Pro Trp Ser Val Tyr Asn
    130                 135                 140

Pro Phe Ile Asp Trp Arg Asp Gly Met Gly Ser Leu Trp Ile Gln Ala
```

```
145                 150                 155                 160
Ile Phe Glu Tyr Ile Thr Met Ser Phe Ala Val Leu Gln Asp Gln Leu
                165                 170                 175

Ser Asp Thr Tyr Pro Leu Met Phe Thr Ile Met Phe Arg Ala His Met
            180                 185                 190

Glu Val Leu Lys Asp His Val Arg Ser Leu Arg Met Asp Pro Glu Arg
        195                 200                 205

Ser Glu Ala Asp Asn Tyr Gln Asp Leu Val Asn Cys Val Leu Asp His
    210                 215                 220

Lys Thr Ile Leu Lys Cys Cys Asp Met Ile Arg Pro Met Ile Ser Arg
225                 230                 235                 240

Thr Ile Phe Val Gln Phe Ala Leu Ile Gly Ser Val Leu Gly Leu Thr
                245                 250                 255

Leu Val Asn Val Phe Phe Ser Asn Phe Trp Lys Gly Val Ala Ser
            260                 265                 270

Leu Leu Phe Val Ile Thr Ile Leu Leu Gln Thr Phe Pro Phe Cys Tyr
        275                 280                 285

Thr Cys Asn Met Leu Ile Asp Asp Ala Gln Asp Leu Ser Asn Glu Ile
    290                 295                 300

Phe Gln Ser Asn Trp Val Asp Ala Glu Pro Arg Tyr Lys Ala Thr Leu
305                 310                 315                 320

Val Leu Phe Met His His Val Gln Gln Pro Ile Ile Phe Ile Ala Gly
                325                 330                 335

Gly Ile Phe Pro Ile Ser Met Asn Ser Asn Ile Thr Val Arg Ile Thr
            340                 345                 350

Ser Phe Leu Pro Thr Ala Tyr Phe Thr Phe Asp Pro Phe
        355                 360                 365

<210> SEQ ID NO 65
<211> LENGTH: 1233
<212> TYPE: DNA
<213> ORGANISM: Drosophila melanogaster
<220> FEATURE:
<221> NAME/KEY: CDS
<222> LOCATION: (1)..(1233)
<223> OTHER INFORMATION: DORLU 2.1

<400> SEQUENCE: 65 atg acc aag ttc ttc ttc aag cgc ctg caa act gct cca ctt gat cag    48
Met Thr Lys Phe Phe Phe Lys Arg Leu Gln Thr Ala Pro Leu Asp Gln
 1               5                  10                  15 gag gtg agt tcc ctt gat gcc agc gac tac tac tac cgc atc gca ttt    96
Glu Val Ser Ser Leu Asp Ala Ser Asp Tyr Tyr Tyr Arg Ile Ala Phe
             20                  25                  30 ttc ctg ggc tgg acc ccg ccc aag ggg gct ctg ctc cga tgg atc tac   144
Phe Leu Gly Trp Thr Pro Pro Lys Gly Ala Leu Leu Arg Trp Ile Tyr
         35                  40                  45 tcc ctg tgg act ctg acc acg atg tgg ctg ggt atc gtg tac ctg ccg   192
Ser Leu Trp Thr Leu Thr Thr Met Trp Leu Gly Ile Val Tyr Leu Pro
     50                  55                  60 ctc gga ctg agc ctc acc tat gtg aag cac ttc gat aga ttc acg ccg   240
Leu Gly Leu Ser Leu Thr Tyr Val Lys His Phe Asp Arg Phe Thr Pro
 65                  70                  75                  80 acg gag ttc ctg acc tcc ctg cag gtg gat atc aac tgc atc ggg aac   288
Thr Glu Phe Leu Thr Ser Leu Gln Val Asp Ile Asn Cys Ile Gly Asn
                 85                  90                  95 gtg atc aag tca tgc gta act tat tcc cag atg tgg cgt ttt cgc cgg   336
Val Ile Lys Ser Cys Val Thr Tyr Ser Gln Met Trp Arg Phe Arg Arg
            100                 105                 110
```

-continued

```
              100               105               110
atg aat gag ctt atc tcg tcc ctg gac aag aga tgt gtg act acg aca    384
Met Asn Glu Leu Ile Ser Ser Leu Asp Lys Arg Cys Val Thr Thr Thr
            115               120               125 cag cgt cga att ttc cat aag atg gtg gca cgg gtt aat ctc atc gtg    432
Gln Arg Arg Ile Phe His Lys Met Val Ala Arg Val Asn Leu Ile Val
    130               135               140 att ctg ttc ttg tcc acg tac ttg ggc ttc tgc ttt cta act ctg ttc    480
Ile Leu Phe Leu Ser Thr Tyr Leu Gly Phe Cys Phe Leu Thr Leu Phe
145               150               155               160 act tcg gtt ttc gct ggc aaa gct cct tgg cag ctg tac aac cca ctg    528
Thr Ser Val Phe Ala Gly Lys Ala Pro Trp Gln Leu Tyr Asn Pro Leu
                165               170               175 gtg gac tgg cgg aaa ggc cat tgg cag cta tgg att gcc tcc atc ctg    576
Val Asp Trp Arg Lys Gly His Trp Gln Leu Trp Ile Ala Ser Ile Leu
            180               185               190 gag tac tgt gtg gtc tcc att ggc acc atg cag gag ttg atg tcc gac    624
Glu Tyr Cys Val Val Ser Ile Gly Thr Met Gln Glu Leu Met Ser Asp
        195               200               205 acc tac gcc ata gtg ttc atc tcc ttg ttc cgc tgc cac ctg gct att    672
Thr Tyr Ala Ile Val Phe Ile Ser Leu Phe Arg Cys His Leu Ala Ile
210               215               220 ctc aga gat cgc ata gct aat ctg cgg cag gat ccg aaa ctc agt gag    720
Leu Arg Asp Arg Ile Ala Asn Leu Arg Gln Asp Pro Lys Leu Ser Glu
225               230               235               240 atg gaa cac tat gag cag atg gtg gcc tgc att cag gat cat cga acc    768
Met Glu His Tyr Glu Gln Met Val Ala Cys Ile Gln Asp His Arg Thr
            245               250               255 atc ata cag tgc tcc cag att att cga ccc atc ctg tcg atc act atc    816
Ile Ile Gln Cys Ser Gln Ile Ile Arg Pro Ile Leu Ser Ile Thr Ile
        260               265               270 ttt gcc cag ttc atg ctg gtt ggc att gac ttg ggt ctg gcg gcc atc    864
Phe Ala Gln Phe Met Leu Val Gly Ile Asp Leu Gly Leu Ala Ala Ile
    275               280               285 agc atc ctc ttc ttt ccg aac acc att tgg acg atc atg gca aac gtg    912
Ser Ile Leu Phe Phe Pro Asn Thr Ile Trp Thr Ile Met Ala Asn Val
    290               295               300 tcg ttc atc gtg gcc atc tgt aca gag tcc ttt cca tgc tgc atg ctc    960
Ser Phe Ile Val Ala Ile Cys Thr Glu Ser Phe Pro Cys Cys Met Leu
305               310               315               320 tgc gag cat ctg atc gag gac tcc gtc cat gtg agc aac gcc ctg ttc    1008
Cys Glu His Leu Ile Glu Asp Ser Val His Val Ser Asn Ala Leu Phe
            325               330               335 cac tca aac tgg ata acc gcg gac agg agc tac aag tcg gcg gtt ctg    1056
His Ser Asn Trp Ile Thr Ala Asp Arg Ser Tyr Lys Ser Ala Val Leu
        340               345               350 tat ttc ctg cac cgg gct cag caa ccc att caa ttc acg gcc ggc tcc    1104
Tyr Phe Leu His Arg Ala Gln Gln Pro Ile Gln Phe Thr Ala Gly Ser
    355               360               365 ata ttt ccc att tcg gtg cag agc aac ata gcc gtg gcc aag ttc gcg    1152
Ile Phe Pro Ile Ser Val Gln Ser Asn Ile Ala Val Ala Lys Phe Ala
370               375               380 ttc aca atc atc aca atc gtg aac caa atg aat ctg ggc gag aag ttc    1200
Phe Thr Ile Ile Thr Ile Val Asn Gln Met Asn Leu Gly Glu Lys Phe
385               390               395               400 ttc agt gac agg agc aat ggc gat ata aat cct                        1233
Phe Ser Asp Arg Ser Asn Gly Asp Ile Asn Pro
            405               410
```

```
<210> SEQ ID NO 66
<211> LENGTH: 411
<212> TYPE: PRT
<213> ORGANISM: Drosophila melanogaster

<400> SEQUENCE: 66

Met Thr Lys Phe Phe Phe Lys Arg Leu Gln Thr Ala Pro Leu Asp Gln
  1               5                  10                  15

Glu Val Ser Ser Leu Asp Ala Ser Asp Tyr Tyr Arg Ile Ala Phe
                 20                  25                  30

Phe Leu Gly Trp Thr Pro Pro Lys Gly Ala Leu Leu Arg Trp Ile Tyr
             35                  40                  45

Ser Leu Trp Thr Leu Thr Thr Met Trp Leu Gly Ile Val Tyr Leu Pro
         50                  55                  60

Leu Gly Leu Ser Leu Thr Tyr Val Lys His Phe Asp Arg Phe Thr Pro
 65                  70                  75                  80

Thr Glu Phe Leu Thr Ser Leu Gln Val Asp Ile Asn Cys Ile Gly Asn
                 85                  90                  95

Val Ile Lys Ser Cys Val Thr Tyr Ser Gln Met Trp Arg Phe Arg Arg
             100                 105                 110

Met Asn Glu Leu Ile Ser Ser Leu Asp Lys Arg Cys Val Thr Thr Thr
         115                 120                 125

Gln Arg Arg Ile Phe His Lys Met Val Ala Arg Val Asn Leu Ile Val
                 130                 135                 140

Ile Leu Phe Leu Ser Thr Tyr Leu Gly Phe Cys Phe Leu Thr Leu Phe
145                 150                 155                 160

Thr Ser Val Phe Ala Gly Lys Ala Pro Trp Gln Leu Tyr Asn Pro Leu
                 165                 170                 175

Val Asp Trp Arg Lys Gly His Trp Gln Leu Trp Ile Ala Ser Ile Leu
             180                 185                 190

Glu Tyr Cys Val Val Ser Ile Gly Thr Met Gln Glu Leu Met Ser Asp
         195                 200                 205

Thr Tyr Ala Ile Val Phe Ile Ser Leu Phe Arg Cys His Leu Ala Ile
     210                 215                 220

Leu Arg Asp Arg Ile Ala Asn Leu Arg Gln Asp Pro Lys Leu Ser Glu
225                 230                 235                 240

Met Glu His Tyr Glu Gln Met Val Ala Cys Ile Gln Asp His Arg Thr
                 245                 250                 255

Ile Ile Gln Cys Ser Gln Ile Ile Arg Pro Ile Leu Ser Ile Thr Ile
             260                 265                 270

Phe Ala Gln Phe Met Leu Val Gly Ile Asp Leu Gly Leu Ala Ala Ile
         275                 280                 285

Ser Ile Leu Phe Phe Pro Asn Thr Ile Trp Thr Ile Met Ala Asn Val
     290                 295                 300

Ser Phe Ile Val Ala Ile Cys Thr Glu Ser Phe Pro Cys Cys Met Leu
305                 310                 315                 320

Cys Glu His Leu Ile Glu Asp Ser Val His Val Ser Asn Ala Leu Phe
                 325                 330                 335

His Ser Asn Trp Ile Thr Ala Asp Arg Ser Tyr Lys Ser Ala Val Leu
             340                 345                 350

Tyr Phe Leu His Arg Ala Gln Gln Pro Ile Gln Phe Thr Ala Gly Ser
         355                 360                 365

Ile Phe Pro Ile Ser Val Gln Ser Asn Ile Ala Val Ala Lys Phe Ala
     370                 375                 380
```

```
Phe Thr Ile Ile Thr Ile Val Asn Gln Met Asn Leu Gly Glu Lys Phe
385                 390                 395                 400

Phe Ser Asp Arg Ser Asn Gly Asp Ile Asn Pro
                405                 410

<210> SEQ ID NO 67
<211> LENGTH: 1191
<212> TYPE: DNA
<213> ORGANISM: Drosophila melanogaster
<220> FEATURE:
<221> NAME/KEY: CDS
<222> LOCATION: (1)..(1191)
<223> OTHER INFORMATION: DORLU 4.1

<400> SEQUENCE: 67 atg att ttt aag tac att caa gag cca gtc ctt gga tcc tta ttt cga      48
Met Ile Phe Lys Tyr Ile Gln Glu Pro Val Leu Gly Ser Leu Phe Arg
  1               5                  10                  15 tcc cgg gat tcg ctg atc tac tta aac aga tcc ata gat caa atg gga     96
Ser Arg Asp Ser Leu Ile Tyr Leu Asn Arg Ser Ile Asp Gln Met Gly
             20                  25                  30 tgg aga ctg ccg cca cga act aag ccg tac tgg tgg ctc tat tac att    144
Trp Arg Leu Pro Pro Arg Thr Lys Pro Tyr Trp Trp Leu Tyr Tyr Ile
         35                  40                  45 tgg aca ttg gtg gtc ata gta ctc gtc ttt atc ttt ata ccc tat gga    192
Trp Thr Leu Val Val Ile Val Leu Val Phe Ile Phe Ile Pro Tyr Gly
     50                  55                  60 ctg ata atg act gga ata aag gag ttc aag aac ttc acg acc acg gat    240
Leu Ile Met Thr Gly Ile Lys Glu Phe Lys Asn Phe Thr Thr Thr Asp
 65                  70                  75                  80 ctg ttt acg tat gtc cag gtg ccg gtt aac acc aat gct tcg atc atg    288
Leu Phe Thr Tyr Val Gln Val Pro Val Asn Thr Asn Ala Ser Ile Met
                 85                  90                  95 aag ggc att ata gtg ttg ttt atg cgg cgg cga ttt tca agg gct cag    336
Lys Gly Ile Ile Val Leu Phe Met Arg Arg Arg Phe Ser Arg Ala Gln
            100                 105                 110 aag atg atg gac gcc atg gac att cga tgc acc aag atg gag gag aaa    384
Lys Met Met Asp Ala Met Asp Ile Arg Cys Thr Lys Met Glu Glu Lys
        115                 120                 125 gtc cag gtg cac cga gca gca gcc tta tgc aat cgt gtt gtt gtg att    432
Val Gln Val His Arg Ala Ala Ala Leu Cys Asn Arg Val Val Val Ile
    130                 135                 140 tac cat tgc ata tac ttc ggc tat cta tcc atg gcc tta acc gga gct    480
Tyr His Cys Ile Tyr Phe Gly Tyr Leu Ser Met Ala Leu Thr Gly Ala
145                 150                 155                 160 ctg gtg att ggg aag act cca ttc tgt ttg tac aat cca ctg gtt aac    528
Leu Val Ile Gly Lys Thr Pro Phe Cys Leu Tyr Asn Pro Leu Val Asn
                165                 170                 175 ccc gac gat cat ttc tat ctg gcc act gcc att gaa tcg gtc acc atg    576
Pro Asp Asp His Phe Tyr Leu Ala Thr Ala Ile Glu Ser Val Thr Met
            180                 185                 190 gct ggc att att ctg gcc aat ctc att ttg gac gta tat ccc atc ata    624
Ala Gly Ile Ile Leu Ala Asn Leu Ile Leu Asp Val Tyr Pro Ile Ile
        195                 200                 205 tat gtg gtc gtt ctg cgg atc cac atg gag ctc ttg agt gag cga atc    672
Tyr Val Val Val Leu Arg Ile His Met Glu Leu Leu Ser Glu Arg Ile
    210                 215                 220 aag acg ctg cgt act gat gtg gaa aaa ggc gac gat caa cat tat gcc    720
Lys Thr Leu Arg Thr Asp Val Glu Lys Gly Asp Asp Gln His Tyr Ala
225                 230                 235                 240 gag ctg gtg gag tgt gta aag gat cac aag cta att gtc gaa tat gga    768
```

```
                                                            -continued

Glu Leu Val Glu Cys Val Lys Asp His Lys Leu Ile Val Glu Tyr Gly
                245                 250                 255 aac act ctg cgt ccc atg ata tcc gcc acg atg ttc atc caa cta cta         816
Asn Thr Leu Arg Pro Met Ile Ser Ala Thr Met Phe Ile Gln Leu Leu
            260                 265                 270 tcc gtt ggc tta ctt ttg ggt ctg gca gcg gtg tcc atg cag ttc tat         864
Ser Val Gly Leu Leu Leu Gly Leu Ala Ala Val Ser Met Gln Phe Tyr
        275                 280                 285 aac acc gta atg gag cgt gtt gtc tcc ggg gtc tac acc ata gcc att         912
Asn Thr Val Met Glu Arg Val Val Ser Gly Val Tyr Thr Ile Ala Ile
    290                 295                 300 cta tcc cag acc ttt cca ttt tgc tat gtc tgt gag cag ctg agc agc         960
Leu Ser Gln Thr Phe Pro Phe Cys Tyr Val Cys Glu Gln Leu Ser Ser
305                 310                 315                 320 gat tgc gaa tcc ctg acc aac aca ctg ttc cat tcc aag tgg att gga         1008
Asp Cys Glu Ser Leu Thr Asn Thr Leu Phe His Ser Lys Trp Ile Gly
                325                 330                 335 gct gag cga cga tac aga acc acg atg ttg tac ttc att cac aat gtt         1056
Ala Glu Arg Arg Tyr Arg Thr Thr Met Leu Tyr Phe Ile His Asn Val
            340                 345                 350 cag cag tcg att ttg ttc act gcg ggc gga att ttc ccc ata tgt cta         1104
Gln Gln Ser Ile Leu Phe Thr Ala Gly Gly Ile Phe Pro Ile Cys Leu
        355                 360                 365 aac acc aat ata aag atg gcc aag ttc gct ttc tca gtg gtg acc att         1152
Asn Thr Asn Ile Lys Met Ala Lys Phe Ala Phe Ser Val Val Thr Ile
    370                 375                 380 gta aat gag atg gac ttg gcc gag aaa ttg aga agg gag                     1191
Val Asn Glu Met Asp Leu Ala Glu Lys Leu Arg Arg Glu
385                 390                 395

<210> SEQ ID NO 68
<211> LENGTH: 397
<212> TYPE: PRT
<213> ORGANISM: Drosophila melanogaster

<400> SEQUENCE: 68

Met Ile Phe Lys Tyr Ile Gln Glu Pro Val Leu Gly Ser Leu Phe Arg
 1               5                  10                  15

Ser Arg Asp Ser Leu Ile Tyr Leu Asn Arg Ser Ile Asp Gln Met Gly
            20                  25                  30

Trp Arg Leu Pro Pro Arg Thr Lys Pro Tyr Trp Trp Leu Tyr Tyr Ile
        35                  40                  45

Trp Thr Leu Val Val Ile Val Leu Val Phe Ile Phe Ile Pro Tyr Gly
    50                  55                  60

Leu Ile Met Thr Gly Ile Lys Glu Phe Lys Asn Phe Thr Thr Thr Asp
65                  70                  75                  80

Leu Phe Thr Tyr Val Gln Val Pro Val Asn Thr Asn Ala Ser Ile Met
                85                  90                  95

Lys Gly Ile Ile Val Leu Phe Met Arg Arg Phe Ser Arg Ala Gln
            100                 105                 110

Lys Met Met Asp Ala Met Asp Ile Arg Cys Thr Lys Met Glu Glu Lys
        115                 120                 125

Val Gln Val His Arg Ala Ala Ala Leu Cys Asn Arg Val Val Ile
    130                 135                 140

Tyr His Cys Ile Tyr Phe Gly Tyr Leu Ser Met Ala Leu Thr Gly Ala
145                 150                 155                 160

Leu Val Ile Gly Lys Thr Pro Phe Cys Leu Tyr Asn Pro Leu Val Asn
                165                 170                 175
```

-continued

```
Pro Asp Asp His Phe Tyr Leu Ala Thr Ala Ile Glu Ser Val Thr Met
            180                 185                 190

Ala Gly Ile Ile Leu Ala Asn Leu Ile Leu Asp Val Tyr Pro Ile Ile
            195                 200                 205

Tyr Val Val Leu Arg Ile His Met Glu Leu Leu Ser Glu Arg Ile
    210                 215                 220

Lys Thr Leu Arg Thr Asp Val Glu Lys Gly Asp Asp Gln His Tyr Ala
225                 230                 235                 240

Glu Leu Val Glu Cys Val Lys Asp His Lys Leu Ile Val Glu Tyr Gly
                245                 250                 255

Asn Thr Leu Arg Pro Met Ile Ser Ala Thr Met Phe Ile Gln Leu Leu
            260                 265                 270

Ser Val Gly Leu Leu Leu Gly Leu Ala Ala Val Ser Met Gln Phe Tyr
            275                 280                 285

Asn Thr Val Met Glu Arg Val Val Ser Gly Val Tyr Thr Ile Ala Ile
            290                 295                 300

Leu Ser Gln Thr Phe Pro Phe Cys Tyr Val Cys Glu Gln Leu Ser Ser
305                 310                 315                 320

Asp Cys Glu Ser Leu Thr Asn Thr Leu Phe His Ser Lys Trp Ile Gly
                325                 330                 335

Ala Glu Arg Arg Tyr Arg Thr Thr Met Leu Tyr Phe Ile His Asn Val
                340                 345                 350

Gln Gln Ser Ile Leu Phe Thr Ala Gly Gly Ile Phe Pro Ile Cys Leu
            355                 360                 365

Asn Thr Asn Ile Lys Met Ala Lys Phe Ala Phe Ser Val Val Thr Ile
            370                 375                 380

Val Asn Glu Met Asp Leu Ala Glu Lys Leu Arg Arg Glu
385                 390                 395
```

<210> SEQ ID NO 69
<211> LENGTH: 1191
<212> TYPE: DNA
<213> ORGANISM: Drosophila melanogaster
<220> FEATURE:
<221> NAME/KEY: CDS
<222> LOCATION: (1)..(1191)
<223> OTHER INFORMATION: DORLU 5.1

<400> SEQUENCE: 69

```
atg ttg ttc aac tat ctg cga aag ccg aat ccg aca aac ctt ttg act      48
Met Leu Phe Asn Tyr Leu Arg Lys Pro Asn Pro Thr Asn Leu Leu Thr
  1               5                  10                  15 tct ccg gac tca ttt aga tac ttt gag tat gga atg ttt tgc atg gga      96
Ser Pro Asp Ser Phe Arg Tyr Phe Glu Tyr Gly Met Phe Cys Met Gly
             20                  25                  30 tgg cac aca cca gca acg cat aag ata atc tac tat ata aca tcc tgt     144
Trp His Thr Pro Ala Thr His Lys Ile Ile Tyr Tyr Ile Thr Ser Cys
         35                  40                  45 ttg att ttt gct tgg tgt gcc gta tac ttg cca atc gga atc atc att     192
Leu Ile Phe Ala Trp Cys Ala Val Tyr Leu Pro Ile Gly Ile Ile Ile
     50                  55                  60 agt ttc aaa acg gat att aac aca ttc aca ccg aat gaa ctg ttg aca     240
Ser Phe Lys Thr Asp Ile Asn Thr Phe Thr Pro Asn Glu Leu Leu Thr
 65                  70                  75                  80 gtt atg caa tta ttt ttc aat tca gtg gga atg cca ttc aag gtt ctg     288
Val Met Gln Leu Phe Phe Asn Ser Val Gly Met Pro Phe Lys Val Leu
                 85                  90                  95
```

```
ttc ttc aat ttg tat att tct gga ttt tac aag gcc aaa aag ctc ctt      336
Phe Phe Asn Leu Tyr Ile Ser Gly Phe Tyr Lys Ala Lys Lys Leu Leu
            100                 105                 110 agc gaa atg gac aaa cgt tgc acc act ttg aag gag cga gtg gaa gtg      384
Ser Glu Met Asp Lys Arg Cys Thr Thr Leu Lys Glu Arg Val Glu Val
        115                 120                 125 cac caa ggt gtg gtc cgt tgc aac aag gcc tac ctc att tac cag ttc      432
His Gln Gly Val Val Arg Cys Asn Lys Ala Tyr Leu Ile Tyr Gln Phe
    130                 135                 140 att tat acc gcg tac act att tca aca ttt cta tcg gcg gct ctt agt      480
Ile Tyr Thr Ala Tyr Thr Ile Ser Thr Phe Leu Ser Ala Ala Leu Ser
145                 150                 155                 160 gga aaa ttg cca tgg cgc atc tat aat cct ttt gtg gat ttt cga gaa      528
Gly Lys Leu Pro Trp Arg Ile Tyr Asn Pro Phe Val Asp Phe Arg Glu
                165                 170                 175 agt aga tcc agt ttt tgg aaa gct gcc ctc aac gag aca gca ctt atg      576
Ser Arg Ser Ser Phe Trp Lys Ala Ala Leu Asn Glu Thr Ala Leu Met
            180                 185                 190 cta ttt gct gtg act caa acc cta atg agt gat ata tat cca ctg ctt      624
Leu Phe Ala Val Thr Gln Thr Leu Met Ser Asp Ile Tyr Pro Leu Leu
        195                 200                 205 tat ggt ttg atc ctg aga gtt cac ctc aaa ctt tgc gac cta aga gtg      672
Tyr Gly Leu Ile Leu Arg Val His Leu Lys Leu Leu Arg Leu Arg Val
    210                 215                 220 gag agc ctg tgc aca gat tct gga aaa agc gat gct gaa aac gag caa      720
Glu Ser Leu Cys Thr Asp Ser Gly Lys Ser Asp Ala Glu Asn Glu Gln
225                 230                 235                 240 gat ttg att aag tgc atc aag gat cac aat ctc att att gac tat gct      768
Asp Leu Ile Lys Cys Ile Lys Asp His Asn Leu Ile Ile Asp Tyr Ala
                245                 250                 255 gca gca ata cga cca gcg gtt acc cgc aca att ttc gtt caa ttc ctc      816
Ala Ala Ile Arg Pro Ala Val Thr Arg Thr Ile Phe Val Gln Phe Leu
            260                 265                 270 ttg atc gga att tgc ctt ggc ctt tca atg atc aat cta ctc ttc ttt      864
Leu Ile Gly Ile Cys Leu Gly Leu Ser Met Ile Asn Leu Leu Phe Phe
        275                 280                 285 gcc gac atc tgg aca gga ttg gcc aca gtg gct tac atc aat ggt cta      912
Ala Asp Ile Trp Thr Gly Leu Ala Thr Val Ala Tyr Ile Asn Gly Leu
    290                 295                 300 atg gtg cag aca ttt cca ttt tgc ttc gtt tgt gat cta ctc aaa aag      960
Met Val Gln Thr Phe Pro Phe Cys Phe Val Cys Asp Leu Leu Lys Lys
305                 310                 315                 320 gat tgt gaa ctt ctt gtg tcg gcc ata ttt cat tcc aac tgg att aat     1008
Asp Cys Glu Leu Leu Val Ser Ala Ile Phe His Ser Asn Trp Ile Asn
                325                 330                 335 tca agc cgc agt tac aag tca tct ttg aga tat ttt ctg aag aac gcc     1056
Ser Ser Arg Ser Tyr Lys Ser Ser Leu Arg Tyr Phe Leu Lys Asn Ala
            340                 345                 350 cag aaa tca att gct ttt aca gcc ggc tct att ttt ccc att tct act     1104
Gln Lys Ser Ile Ala Phe Thr Ala Gly Ser Ile Phe Pro Ile Ser Thr
        355                 360                 365 ggc tcg aat att aag gtg gct aag ctg gca ttt tcg gtg gtt act ttt     1152
Gly Ser Asn Ile Lys Val Ala Lys Leu Ala Phe Ser Val Val Thr Phe
    370                 375                 380 gtc aat caa ctt aac ata gct gac aga ttg aca aag aac                 1191
Val Asn Gln Leu Asn Ile Ala Asp Arg Leu Thr Lys Asn
385                 390                 395

<210> SEQ ID NO 70
<211> LENGTH: 397
```

-continued

```
<212> TYPE: PRT
<213> ORGANISM: Drosophila melanogaster

<400> SEQUENCE: 70

Met Leu Phe Asn Tyr Leu Arg Lys Pro Asn Pro Thr Asn Leu Leu Thr
 1               5                  10                  15

Ser Pro Asp Ser Phe Arg Tyr Phe Glu Tyr Gly Met Phe Cys Met Gly
            20                  25                  30

Trp His Thr Pro Ala Thr His Lys Ile Ile Tyr Tyr Ile Thr Ser Cys
        35                  40                  45

Leu Ile Phe Ala Trp Cys Ala Val Tyr Leu Pro Ile Gly Ile Ile Ile
    50                  55                  60

Ser Phe Lys Thr Asp Ile Asn Thr Phe Thr Pro Asn Glu Leu Leu Thr
65                  70                  75                  80

Val Met Gln Leu Phe Phe Asn Ser Val Gly Met Pro Phe Lys Val Leu
                85                  90                  95

Phe Phe Asn Leu Tyr Ile Ser Gly Phe Tyr Lys Ala Lys Lys Leu Leu
                100                 105                 110

Ser Glu Met Asp Lys Arg Cys Thr Thr Leu Lys Glu Arg Val Glu Val
            115                 120                 125

His Gln Gly Val Val Arg Cys Asn Lys Ala Tyr Leu Ile Tyr Gln Phe
    130                 135                 140

Ile Tyr Thr Ala Tyr Thr Ile Ser Thr Phe Leu Ser Ala Ala Leu Ser
145                 150                 155                 160

Gly Lys Leu Pro Trp Arg Ile Tyr Asn Pro Phe Val Asp Phe Arg Glu
                165                 170                 175

Ser Arg Ser Ser Phe Trp Lys Ala Ala Leu Asn Glu Thr Ala Leu Met
            180                 185                 190

Leu Phe Ala Val Thr Gln Thr Leu Met Ser Asp Ile Tyr Pro Leu Leu
    195                 200                 205

Tyr Gly Leu Ile Leu Arg Val His Leu Lys Leu Leu Arg Leu Arg Val
    210                 215                 220

Glu Ser Leu Cys Thr Asp Ser Gly Lys Ser Asp Ala Glu Asn Glu Gln
225                 230                 235                 240

Asp Leu Ile Lys Cys Ile Lys Asp His Asn Leu Ile Ile Asp Tyr Ala
                245                 250                 255

Ala Ala Ile Arg Pro Ala Val Thr Arg Thr Ile Phe Val Gln Phe Leu
            260                 265                 270

Leu Ile Gly Ile Cys Leu Gly Leu Ser Met Ile Asn Leu Leu Phe Phe
    275                 280                 285

Ala Asp Ile Trp Thr Gly Leu Ala Thr Val Ala Tyr Ile Asn Gly Leu
    290                 295                 300

Met Val Gln Thr Phe Pro Phe Cys Phe Val Cys Asp Leu Leu Lys Lys
305                 310                 315                 320

Asp Cys Glu Leu Leu Val Ser Ala Ile Phe His Ser Asn Trp Ile Asn
                325                 330                 335

Ser Ser Arg Ser Tyr Lys Ser Ser Leu Arg Tyr Phe Leu Lys Asn Ala
            340                 345                 350

Gln Lys Ser Ile Ala Phe Thr Ala Gly Ser Ile Phe Pro Ile Ser Thr
        355                 360                 365

Gly Ser Asn Ile Lys Val Ala Lys Leu Ala Phe Ser Val Val Thr Phe
    370                 375                 380

Val Asn Gln Leu Asn Ile Ala Asp Arg Leu Thr Lys Asn
385                 390                 395
```

```
<210> SEQ ID NO 71
<211> LENGTH: 1239
<212> TYPE: DNA
<213> ORGANISM: Drosophila melanogaster
<220> FEATURE:
<221> NAME/KEY: CDS
<222> LOCATION: (1)..(1239)
<223> OTHER INFORMATION: DORLU 6.1

<400> SEQUENCE: 71 atg gcg gtg agc act cgt gtg gcc aca aag cag gaa gtg ccc gaa tcc      48
Met Ala Val Ser Thr Arg Val Ala Thr Lys Gln Glu Val Pro Glu Ser
 1               5                  10                  15 cgg cga gcg ttt agg aat ctc ttc aat tgc ttc tat gcc ctt ggc atg      96
Arg Arg Ala Phe Arg Asn Leu Phe Asn Cys Phe Tyr Ala Leu Gly Met
             20                  25                  30 cag gca ccg gat ggc agt cga ccg acc acg agc agc aca tgg caa cgc     144
Gln Ala Pro Asp Gly Ser Arg Pro Thr Thr Ser Ser Thr Trp Gln Arg
         35                  40                  45 atc tac gcc tgc ttc tcg gtg gtc atg tac gtg tgg caa ctg ctg ctg     192
Ile Tyr Ala Cys Phe Ser Val Val Met Tyr Val Trp Gln Leu Leu Leu
     50                  55                  60 gtg ccc aca ttc ttt gtg atc agc tat cgg tac atg ggc ggc atg gag     240
Val Pro Thr Phe Phe Val Ile Ser Tyr Arg Tyr Met Gly Gly Met Glu
 65                  70                  75                  80 att acc cag gtg ctg acc tcc gcc cag gtg gcc atc gat gcg gtc att     288
Ile Thr Gln Val Leu Thr Ser Ala Gln Val Ala Ile Asp Ala Val Ile
                 85                  90                  95 ctg ccg gcc aag att gtg gca ctg gcg tgg aat ttg cca ttg ctg cgc     336
Leu Pro Ala Lys Ile Val Ala Leu Ala Trp Asn Leu Pro Leu Leu Arg
            100                 105                 110 aga gca gag cat cat ctg gcc gcc ttg gat gcg cgg tgc agg gaa cag     384
Arg Ala Glu His His Leu Ala Ala Leu Asp Ala Arg Cys Arg Glu Gln
        115                 120                 125 gag gag ttc caa ttg atc ctc gat gcg gtg agg ttt tgc aac tat ctg     432
Glu Glu Phe Gln Leu Ile Leu Asp Ala Val Arg Phe Cys Asn Tyr Leu
    130                 135                 140 gta tgg ttc tac cag atc tgc tat gcc atc tac tcc tcg tcg aca ttt     480
Val Trp Phe Tyr Gln Ile Cys Tyr Ala Ile Tyr Ser Ser Ser Thr Phe
145                 150                 155                 160 gtg tgc gcc ttc ctg ctg ggc caa ccg cca tat gcc ctc tat ttg cct     528
Val Cys Ala Phe Leu Leu Gly Gln Pro Pro Tyr Ala Leu Tyr Leu Pro
                165                 170                 175 ggc ctc gat tgg cag cgt tcc cag atg cag ttc tgc atc cag gcc tgg     576
Gly Leu Asp Trp Gln Arg Ser Gln Met Gln Phe Cys Ile Gln Ala Trp
            180                 185                 190 att gag ttc ctt atc atg aac tgg acg tgc ctg cac caa gct agc gat     624
Ile Glu Phe Leu Ile Met Asn Trp Thr Cys Leu His Gln Ala Ser Asp
        195                 200                 205 gat gtg tac gcc gtt atc tat ctg tat gtg gtc cgg att caa gtg caa     672
Asp Val Tyr Ala Val Ile Tyr Leu Tyr Val Val Arg Ile Gln Val Gln
    210                 215                 220 ttg ctg gcc agg cgg gtg gag aag ctg gcg acg gat gat agt ggc cag     720
Leu Leu Ala Arg Arg Val Glu Lys Leu Gly Thr Asp Asp Ser Gly Gln
225                 230                 235                 240 gtg gag atc tat ccc gat gag cgg cgg cag gag gag cat tgc gcg gaa     768
Val Glu Ile Tyr Pro Asp Glu Arg Arg Gln Glu Glu His Cys Ala Glu
                245                 250                 255 ctg cag cgc tgc att gta gat cac cag acg atg ctg cag ctg ctc gac     816
Leu Gln Arg Cys Ile Val Asp His Gln Thr Met Leu Gln Leu Leu Asp
```

|  |  |  |  |  |  |  |  |  |  |  |  |  |  |  |  |
|---|---|---|---|---|---|---|---|---|---|---|---|---|---|---|---|
|  |  |  |  | 260 |  |  |  |  | 265 |  |  |  |  | 270 |  |

```
tgc att agt ccc gtc atc tcg cgt acc ata ttc gtt cag ttc ctg atc      864
Cys Ile Ser Pro Val Ile Ser Arg Thr Ile Phe Val Gln Phe Leu Ile
        275                 280                 285 acc gcc gcc atc atg ggc acc acc atg atc aac att ttc att ttc gcc      912
Thr Ala Ala Ile Met Gly Thr Thr Met Ile Asn Ile Phe Ile Phe Ala
    290                 295                 300 aat acg aac acg aag atc gca tcg atc att tac ctg ctg gcg gtg acc      960
Asn Thr Asn Thr Lys Ile Ala Ser Ile Ile Tyr Leu Leu Ala Val Thr
305                 310                 315                 320 ctg cag acg gct cca tgt tgc tat cag gcc acc tcg ctg atg ttg gac     1008
Leu Gln Thr Ala Pro Cys Cys Tyr Gln Ala Thr Ser Leu Met Leu Asp
                325                 330                 335 aac gag agg ctg gcc ctg gcc atc ttc cag tgc cag tgg ctg ggc cag     1056
Asn Glu Arg Leu Ala Leu Ala Ile Phe Gln Cys Gln Trp Leu Gly Gln
            340                 345                 350 agt gcc cgg ttc cgt aag atg ctg ctc tac tat ctt cat cgc gcc cag     1104
Ser Ala Arg Phe Arg Lys Met Leu Leu Tyr Tyr Leu His Arg Ala Gln
        355                 360                 365 cag ccc atc acg ctg acc gcc atg aag ctg ttt ccc atc aat ctg gcc     1152
Gln Pro Ile Thr Leu Thr Ala Met Lys Leu Phe Pro Ile Asn Leu Ala
    370                 375                 380 acg tac ttc agt ata gcc aag ttc tcg ttt tcg ctc tac acg ctc atc     1200
Thr Tyr Phe Ser Ile Ala Lys Phe Ser Phe Ser Leu Tyr Thr Leu Ile
385                 390                 395                 400 aag ggg atg aat ctc ggc gag cga ttc aac agg aca aat                  1239
Lys Gly Met Asn Leu Gly Glu Arg Phe Asn Arg Thr Asn
                405                 410
```

<210> SEQ ID NO 72
<211> LENGTH: 413
<212> TYPE: PRT
<213> ORGANISM: Drosophila melanogaster

<400> SEQUENCE: 72

```
Met Ala Val Ser Thr Arg Val Ala Thr Lys Gln Glu Val Pro Glu Ser
 1               5                  10                  15

Arg Arg Ala Phe Arg Asn Leu Phe Asn Cys Phe Tyr Ala Leu Gly Met
             20                  25                  30

Gln Ala Pro Asp Gly Ser Arg Pro Thr Thr Ser Ser Thr Trp Gln Arg
         35                  40                  45

Ile Tyr Ala Cys Phe Ser Val Val Met Tyr Val Trp Gln Leu Leu Leu
     50                  55                  60

Val Pro Thr Phe Phe Val Ile Ser Tyr Arg Tyr Met Gly Gly Met Glu
 65                  70                  75                  80

Ile Thr Gln Val Leu Thr Ser Ala Gln Val Ala Ile Asp Ala Val Ile
                 85                  90                  95

Leu Pro Ala Lys Ile Val Ala Leu Ala Trp Asn Leu Pro Leu Leu Arg
            100                 105                 110

Arg Ala Glu His His Leu Ala Ala Leu Asp Ala Arg Cys Arg Glu Gln
        115                 120                 125

Glu Glu Phe Gln Leu Ile Leu Asp Ala Val Arg Phe Cys Asn Tyr Leu
    130                 135                 140

Val Trp Phe Tyr Gln Ile Cys Tyr Ala Ile Tyr Ser Ser Ser Thr Phe
145                 150                 155                 160

Val Cys Ala Phe Leu Leu Gly Gln Pro Pro Tyr Ala Leu Tyr Leu Pro
                165                 170                 175
```

```
Gly Leu Asp Trp Gln Arg Ser Gln Met Gln Phe Cys Ile Gln Ala Trp
            180                 185                 190

Ile Glu Phe Leu Ile Met Asn Trp Thr Cys Leu His Gln Ala Ser Asp
        195                 200                 205

Asp Val Tyr Ala Val Ile Tyr Leu Tyr Val Arg Ile Gln Val Gln
    210                 215                 220

Leu Leu Ala Arg Arg Val Glu Lys Leu Gly Thr Asp Ser Gly Gln
225                 230                 235                 240

Val Glu Ile Tyr Pro Asp Glu Arg Arg Gln Glu His Cys Ala Glu
                245                 250                 255

Leu Gln Arg Cys Ile Val Asp His Gln Thr Met Leu Gln Leu Leu Asp
            260                 265                 270

Cys Ile Ser Pro Val Ile Ser Arg Thr Ile Phe Val Gln Phe Leu Ile
            275                 280                 285

Thr Ala Ala Ile Met Gly Thr Thr Met Ile Asn Ile Phe Ile Phe Ala
        290                 295                 300

Asn Thr Asn Thr Lys Ile Ala Ser Ile Ile Tyr Leu Leu Ala Val Thr
305                 310                 315                 320

Leu Gln Thr Ala Pro Cys Cys Tyr Gln Ala Thr Ser Leu Met Leu Asp
                325                 330                 335

Asn Glu Arg Leu Ala Leu Ala Ile Phe Gln Cys Gln Trp Leu Gly Gln
            340                 345                 350

Ser Ala Arg Phe Arg Lys Met Leu Leu Tyr Tyr Leu His Arg Ala Gln
            355                 360                 365

Gln Pro Ile Thr Leu Thr Ala Met Lys Leu Phe Pro Ile Asn Leu Ala
        370                 375                 380

Thr Tyr Phe Ser Ile Ala Lys Phe Ser Phe Ser Leu Tyr Thr Leu Ile
385                 390                 395                 400

Lys Gly Met Asn Leu Gly Glu Arg Phe Asn Arg Thr Asn
                405                 410
```

<210> SEQ ID NO 73
<211> LENGTH: 1089
<212> TYPE: DNA
<213> ORGANISM: Drosophila melanogaster
<220> FEATURE:
<221> NAME/KEY: CDS
<222> LOCATION: (1)..(1089)
<223> OTHER INFORMATION: DORLU 7.1

<400> SEQUENCE: 73

```
atg gac tac gat cga att cga ccg gtg cga ttt ttg acg gga gtg ctg      48
Met Asp Tyr Asp Arg Ile Arg Pro Val Arg Phe Leu Thr Gly Val Leu
1               5                   10                  15 aaa tgg tgg cgt ctc tgg ccg agg aag gaa tcg gtg tcc aca ccg gac      96
Lys Trp Trp Arg Leu Trp Pro Arg Lys Glu Ser Val Ser Thr Pro Asp
            20                  25                  30 tgg act aac tgg cag gca tat gcc ttg cac gtt cca ttt aca ttc ttg     144
Trp Thr Asn Trp Gln Ala Tyr Ala Leu His Val Pro Phe Thr Phe Leu
        35                  40                  45 ttt gtg ttg ctt ttg tgg ttg gag gca atc aag agc agg gat ata cag     192
Phe Val Leu Leu Leu Trp Leu Glu Ala Ile Lys Ser Arg Asp Ile Gln
50                  55                  60 cat acc gcc gat gtc ctt ttg att tgc cta acc acc act gcc ttg gga     240
His Thr Ala Asp Val Leu Leu Ile Cys Leu Thr Thr Thr Ala Leu Gly
65                  70                  75                  80 ggt aaa gtt atc aat atc tgg aag tat gcc cat gtg gcc caa ggc att     288
Gly Lys Val Ile Asn Ile Trp Lys Tyr Ala His Val Ala Gln Gly Ile
```

```
                    85                      90                      95
ttg tcc gag tgg agc acg tgg gat ctt ttc gag ctg agg agc aaa cag        336
Leu Ser Glu Trp Ser Thr Trp Asp Leu Phe Glu Leu Arg Ser Lys Gln
            100                     105                     110 gaa gtg gat atg tgg cga ttc gag cat cga cgt ttc aat cgt gtt ttt        384
Glu Val Asp Met Trp Arg Phe Glu His Arg Arg Phe Asn Arg Val Phe
            115                     120                     125 atg ttt tac tgt ttg tgc agt gct ggt gta atc cca ttt att gtg att        432
Met Phe Tyr Cys Leu Cys Ser Ala Gly Val Ile Pro Phe Ile Val Ile
    130                     135                     140 caa ccg ttg ttt gat atc cca aat cga ttg ccc ttc tgg atg tgg aca        480
Gln Pro Leu Phe Asp Ile Pro Asn Arg Leu Pro Phe Trp Met Trp Thr
145                     150                     155                 160 cca ttc gat tgg cag cag cct gtt ctc tta tgg tat gca ttc atc tat        528
Pro Phe Asp Trp Gln Gln Pro Val Leu Leu Trp Tyr Ala Phe Ile Tyr
                165                     170                     175 cag gcc aca acc att cct att gcc tgt gct tgc aac gta acc atg gac        576
Gln Ala Thr Thr Ile Pro Ile Ala Cys Ala Cys Asn Val Thr Met Asp
            180                     185                     190 gct gtt aat tgg tac ttg atg ctg cat ctg tcc ttg tgt ttg cgt atg        624
Ala Val Asn Trp Tyr Leu Met Leu His Leu Ser Leu Cys Leu Arg Met
    195                     200                     205 ttg ggc cag cga ttg agt aag ctt cag cat gat gac aag gat ctg agg        672
Leu Gly Gln Arg Leu Ser Lys Leu Gln His Asp Asp Lys Asp Leu Arg
210                     215                     220 gag aag ttc ctg gaa ctg atc cat ctg cac cag cga ctc aag caa cag        720
Glu Lys Phe Leu Glu Leu Ile His Leu His Gln Arg Leu Lys Gln Gln
225                     230                     235                 240 gcc ttg agc att gaa atc ttt att tcg aag agc acg ttc acc caa att        768
Ala Leu Ser Ile Glu Ile Phe Ile Ser Lys Ser Thr Phe Thr Gln Ile
                245                     250                     255 ctg gtc agt tcc ctt atc att tgc ttc acc att tac agc atg cag atg        816
Leu Val Ser Ser Leu Ile Ile Cys Phe Thr Ile Tyr Ser Met Gln Met
            260                     265                     270 tac cta gtg gcc atg atc atg cag gtc atg ctg ccc acc ata tat ggt        864
Tyr Leu Val Ala Met Ile Met Gln Val Met Leu Pro Thr Ile Tyr Gly
    275                     280                     285 aac gcc gtc atc gat tct gca aat atg ttg acc gat tcc atg tac aat        912
Asn Ala Val Ile Asp Ser Ala Asn Met Leu Thr Asp Ser Met Tyr Asn
290                     295                     300 tcg gat tgg ccg gat atg aat tgc cga atg cgt cgc cta gtt tta atg        960
Ser Asp Trp Pro Asp Met Asn Cys Arg Met Arg Arg Leu Val Leu Met
305                     310                     315                 320 ttt atg gtg tac tta aat cga ccg gtg acc tta aaa gcc ggt ggc ttt       1008
Phe Met Val Tyr Leu Asn Arg Pro Val Thr Leu Lys Ala Gly Gly Phe
                325                     330                     335 ttt cat att ggt tta cct ctg ttt acc aag acc atg aat caa gca tac       1056
Phe His Ile Gly Leu Pro Leu Phe Thr Lys Thr Met Asn Gln Ala Tyr
            340                     345                     350 agt ttg ctg gcc ttg ctg ctc aac atg aac caa                           1089
Ser Leu Leu Ala Leu Leu Leu Asn Met Asn Gln
    355                     360
```

<210> SEQ ID NO 74
<211> LENGTH: 363
<212> TYPE: PRT
<213> ORGANISM: Drosophila melanogaster

<400> SEQUENCE: 74

Met Asp Tyr Asp Arg Ile Arg Pro Val Arg Phe Leu Thr Gly Val Leu

-continued

```
          1               5                   10                  15
Lys Trp Trp Arg Leu Trp Pro Arg Lys Glu Ser Val Ser Thr Pro Asp
                    20                  25              30

Trp Thr Asn Trp Gln Ala Tyr Ala Leu His Val Pro Phe Thr Phe Leu
            35                  40                  45

Phe Val Leu Leu Leu Trp Leu Glu Ala Ile Lys Ser Arg Asp Ile Gln
        50                  55                  60

His Thr Ala Asp Val Leu Leu Ile Cys Leu Thr Thr Ala Leu Gly
65                      70                  75                  80

Gly Lys Val Ile Asn Ile Trp Lys Tyr Ala His Val Ala Gln Gly Ile
                        85                  90                  95

Leu Ser Glu Trp Ser Thr Trp Asp Leu Phe Glu Leu Arg Ser Lys Gln
                    100                 105                 110

Glu Val Asp Met Trp Arg Phe Glu His Arg Arg Phe Asn Arg Val Phe
                115                 120                 125

Met Phe Tyr Cys Leu Cys Ser Ala Gly Val Ile Pro Phe Ile Val Ile
            130                 135                 140

Gln Pro Leu Phe Asp Ile Pro Asn Arg Leu Pro Phe Trp Met Trp Thr
145                 150                 155                 160

Pro Phe Asp Trp Gln Gln Pro Val Leu Leu Trp Tyr Ala Phe Ile Tyr
                    165                 170                 175

Gln Ala Thr Thr Ile Pro Ile Ala Cys Ala Cys Asn Val Thr Met Asp
                180                 185                 190

Ala Val Asn Trp Tyr Leu Met Leu His Leu Ser Leu Cys Leu Arg Met
            195                 200                 205

Leu Gly Gln Arg Leu Ser Lys Leu Gln His Asp Asp Lys Asp Leu Arg
210                 215                 220

Glu Lys Phe Leu Glu Leu Ile His Leu His Gln Arg Leu Lys Gln Gln
225                 230                 235                 240

Ala Leu Ser Ile Glu Ile Phe Ile Ser Lys Ser Thr Phe Thr Gln Ile
                245                 250                 255

Leu Val Ser Ser Leu Ile Ile Cys Phe Thr Ile Tyr Ser Met Gln Met
                260                 265                 270

Tyr Leu Val Ala Met Ile Met Gln Val Met Leu Pro Thr Ile Tyr Gly
            275                 280                 285

Asn Ala Val Ile Asp Ser Ala Asn Met Leu Thr Asp Ser Met Tyr Asn
290                 295                 300

Ser Asp Trp Pro Asp Met Asn Cys Arg Met Arg Leu Val Leu Met
305                 310                 315                 320

Phe Met Val Tyr Leu Asn Arg Pro Val Thr Leu Lys Ala Gly Gly Phe
                325                 330                 335

Phe His Ile Gly Leu Pro Leu Phe Thr Lys Thr Met Asn Gln Ala Tyr
            340                 345                 350

Ser Leu Leu Ala Leu Leu Leu Asn Met Asn Gln
        355                 360
```

<210> SEQ ID NO 75
<211> LENGTH: 1176
<212> TYPE: DNA
<213> ORGANISM: Drosophila melanogaster
<220> FEATURE:
<221> NAME/KEY: CDS
<222> LOCATION: (1)..(1176)
<223> OTHER INFORMATION: DORLU 9.1

<400> SEQUENCE: 75

```
atg agc gac aag gtg aag gga aaa aag cag gag gaa aag gat caa tcc    48
Met Ser Asp Lys Val Lys Gly Lys Lys Gln Glu Glu Lys Asp Gln Ser
 1               5                  10                  15 ttg cgg gtg caa att ctc gtt tat cgc tgc atg ggc atc gat ttg tgg    96
Leu Arg Val Gln Ile Leu Val Tyr Arg Cys Met Gly Ile Asp Leu Trp
                20                  25                  30 agc ccc acg atg gcg aat gac cgc ccg tgg ctg acc ttt gtc aca atg   144
Ser Pro Thr Met Ala Asn Asp Arg Pro Trp Leu Thr Phe Val Thr Met
            35                  40                  45 gga cca ctt ttc ctg ttt atg gtg ccc atg ttc ctg gcc gcc cac gag   192
Gly Pro Leu Phe Leu Phe Met Val Pro Met Phe Leu Ala Ala His Glu
        50                  55                  60 tac atc acc cag gtg agc ctg ctc tcc gac acc ctg ggc tcc acc ttc   240
Tyr Ile Thr Gln Val Ser Leu Leu Ser Asp Thr Leu Gly Ser Thr Phe
 65                  70                  75                  80 gcc agc atg ctc acc ctg gtc aaa ttc ctg ctc ttc tgc tat cat cgc   288
Ala Ser Met Leu Thr Leu Val Lys Phe Leu Leu Phe Cys Tyr His Arg
                85                  90                  95 aag gag ttc gtc ggc ctg atc tac cac atc agg gcc att ctg gct aaa   336
Lys Glu Phe Val Gly Leu Ile Tyr His Ile Arg Ala Ile Leu Ala Lys
                100                 105                 110 gaa atc gaa gtg tgg cct gat gcg cgg gaa atc atc gag gtg gag aac   384
Glu Ile Glu Val Trp Pro Asp Ala Arg Glu Ile Ile Glu Val Glu Asn
            115                 120                 125 caa agt gac caa atg ctc agt ctt acg tac act cgc tgt ttt gga ctg   432
Gln Ser Asp Gln Met Leu Ser Leu Thr Tyr Thr Arg Cys Phe Gly Leu
        130                 135                 140 gct gga atc ttt gcg gcc ctg aag ccc ttt gtg ggc atc ata ctc tcc   480
Ala Gly Ile Phe Ala Ala Leu Lys Pro Phe Val Gly Ile Ile Leu Ser
145                 150                 155                 160 tcg att cgc ggc gac gag att cac ctg gag ctg ccc cac aac ggc gtt   528
Ser Ile Arg Gly Asp Glu Ile His Leu Glu Leu Pro His Asn Gly Val
                165                 170                 175 tac ccg tac gat ctc cag gtg gtc atg ttt tat gtg ccc acc tat ctg   576
Tyr Pro Tyr Asp Leu Gln Val Val Met Phe Tyr Val Pro Thr Tyr Leu
            180                 185                 190 tgg aat gtg atg gcc agc tat agt gct gta acc atg gca ctc tgc gtg   624
Trp Asn Val Met Ala Ser Tyr Ser Ala Val Thr Met Ala Leu Cys Val
        195                 200                 205 gac tcg ctg ctc ttc ttt ttc acc tac aac gtg tgc gcc att ttc aag   672
Asp Ser Leu Leu Phe Phe Phe Thr Tyr Asn Val Cys Ala Ile Phe Lys
    210                 215                 220 atc gcc aag cac cgg atg atc cat ctg ccg gcg gtg ggc gga aag gag   720
Ile Ala Lys His Arg Met Ile His Leu Pro Ala Val Gly Gly Lys Glu
225                 230                 235                 240 gag ctg gag ggg ctc gtc cag gtg ctg ctg cac cag aag ggc ctc       768
Glu Leu Glu Gly Leu Val Gln Val Leu Leu His Gln Lys Gly Leu
                245                 250                 255 cag atc gcc gat cac att gcg gac aag tac cgg ccg ctg atc ttt ttg   816
Gln Ile Ala Asp His Ile Ala Asp Lys Tyr Arg Pro Leu Ile Phe Leu
            260                 265                 270 cag ttc ttt ctg tcc gcc ttg cag atc tgc ttc att gga ttc cag gtg   864
Gln Phe Phe Leu Ser Ala Leu Gln Ile Cys Phe Ile Gly Phe Gln Val
        275                 280                 285 gct gat ctg ttt ccc aat ccg cag agt ctc tac ttt atc gcc ttt gtg   912
Ala Asp Leu Phe Pro Asn Pro Gln Ser Leu Tyr Phe Ile Ala Phe Val
    290                 295                 300 ggc tcg ctg ctc atc gca ctg ttc atc tac tcg aag tgc ggc gaa aat   960
Gly Ser Leu Leu Ile Ala Leu Phe Ile Tyr Ser Lys Cys Gly Glu Asn
```

```
                305                 310                 315                 320
atc aag agt gcc agc ctg gat ttc gga aac ggg ctc tac gag acc aac     1008
Ile Lys Ser Ala Ser Leu Asp Phe Gly Asn Gly Leu Tyr Glu Thr Asn
                    325                 330                 335 tgg acc gac ttc tcg cca ccc act aaa aga gcc ctc ctc att gcc gcc     1056
Trp Thr Asp Phe Ser Pro Pro Thr Lys Arg Ala Leu Leu Ile Ala Ala
                    340                 345                 350 atg cgc gcc cag cga cct tgc cag atg aag ggc tac ttt ttc gag gcc     1104
Met Arg Ala Gln Arg Pro Cys Gln Met Lys Gly Tyr Phe Phe Glu Ala
                    355                 360                 365 agc atg gcc acc ttc tcg acg att gtt cgc tct gcc gtg tcg tac atc     1152
Ser Met Ala Thr Phe Ser Thr Ile Val Arg Ser Ala Val Ser Tyr Ile
                    370                 375                 380 atg atg ttg cgc tcc ttt aat gcc                                     1176
Met Met Leu Arg Ser Phe Asn Ala
385                 390

<210> SEQ ID NO 76
<211> LENGTH: 392
<212> TYPE: PRT
<213> ORGANISM: Drosophila melanogaster

<400> SEQUENCE: 76

Met Ser Asp Lys Val Lys Gly Lys Lys Gln Glu Glu Lys Asp Gln Ser
 1               5                  10                  15

Leu Arg Val Gln Ile Leu Val Tyr Arg Cys Met Gly Ile Asp Leu Trp
                20                  25                  30

Ser Pro Thr Met Ala Asn Asp Arg Pro Trp Leu Thr Phe Val Thr Met
            35                  40                  45

Gly Pro Leu Phe Leu Phe Met Val Pro Met Phe Leu Ala Ala His Glu
        50                  55                  60

Tyr Ile Thr Gln Val Ser Leu Leu Ser Asp Thr Leu Gly Ser Thr Phe
65                  70                  75                  80

Ala Ser Met Leu Thr Leu Val Lys Phe Leu Leu Phe Cys Tyr His Arg
                85                  90                  95

Lys Glu Phe Val Gly Leu Ile Tyr His Ile Arg Ala Ile Leu Ala Lys
                100                 105                 110

Glu Ile Glu Val Trp Pro Asp Ala Arg Glu Ile Ile Glu Val Glu Asn
            115                 120                 125

Gln Ser Asp Gln Met Leu Ser Leu Thr Tyr Thr Arg Cys Phe Gly Leu
        130                 135                 140

Ala Gly Ile Phe Ala Ala Leu Lys Pro Phe Val Gly Ile Ile Leu Ser
145                 150                 155                 160

Ser Ile Arg Gly Asp Glu Ile His Leu Glu Leu Pro His Asn Gly Val
                165                 170                 175

Tyr Pro Tyr Asp Leu Gln Val Val Met Phe Tyr Val Pro Thr Tyr Leu
            180                 185                 190

Trp Asn Val Met Ala Ser Tyr Ser Ala Val Thr Met Ala Leu Cys Val
        195                 200                 205

Asp Ser Leu Leu Phe Phe Thr Tyr Asn Val Cys Ala Ile Phe Lys
        210                 215                 220

Ile Ala Lys His Arg Met Ile His Leu Pro Ala Val Gly Gly Lys Glu
225                 230                 235                 240

Glu Leu Glu Gly Leu Val Gln Val Leu Leu His Gln Lys Gly Leu
                245                 250                 255

Gln Ile Ala Asp His Ile Ala Asp Lys Tyr Arg Pro Leu Ile Phe Leu
```

```
                    260                  265                   270
Gln Phe Phe Leu Ser Ala Leu Gln Ile Cys Phe Ile Gly Phe Gln Val
            275                  280                  285
Ala Asp Leu Phe Pro Asn Pro Gln Ser Leu Tyr Phe Ile Ala Phe Val
        290                  295                  300
Gly Ser Leu Leu Ile Ala Leu Phe Ile Tyr Ser Lys Cys Gly Glu Asn
305                  310                  315                  320
Ile Lys Ser Ala Ser Leu Asp Phe Gly Asn Gly Leu Tyr Glu Thr Asn
                325                  330                  335
Trp Thr Asp Phe Ser Pro Pro Thr Lys Arg Ala Leu Leu Ile Ala Ala
            340                  345                  350
Met Arg Ala Gln Arg Pro Cys Gln Met Lys Gly Tyr Phe Phe Glu Ala
        355                  360                  365
Ser Met Ala Thr Phe Ser Thr Ile Val Arg Ser Ala Val Ser Tyr Ile
    370                  375                  380
Met Met Leu Arg Ser Phe Asn Ala
385                 390

<210> SEQ ID NO 77
<211> LENGTH: 1221
<212> TYPE: DNA
<213> ORGANISM: Drosophila melanogaster
<220> FEATURE:
<221> NAME/KEY: CDS
<222> LOCATION: (1)..(1221)
<223> OTHER INFORMATION: DORLU 12.1

<400> SEQUENCE: 77 atg gat aac gtc gcg gaa atg cct gaa gaa aag tat gtc gaa gtc gat     48
Met Asp Asn Val Ala Glu Met Pro Glu Glu Lys Tyr Val Glu Val Asp
  1               5                  10                  15 gat ttt ttg agg cta gct gtg aaa ttc tac aat act ttg ggc att gat     96
Asp Phe Leu Arg Leu Ala Val Lys Phe Tyr Asn Thr Leu Gly Ile Asp
             20                  25                  30 ccc tat gaa act gga cga aaa cga act att tgg ttt caa ata tat ttc    144
Pro Tyr Glu Thr Gly Arg Lys Arg Thr Ile Trp Phe Gln Ile Tyr Phe
         35                  40                  45 gca ttg aat atg ttt aat atg gtg ttt agt ttt tat gcc gag gta gcg    192
Ala Leu Asn Met Phe Asn Met Val Phe Ser Phe Tyr Ala Glu Val Ala
     50                  55                  60 act ctg gtg gac agg tta cgc gat aat gaa aat ttt ctc gag agc tgc    240
Thr Leu Val Asp Arg Leu Arg Asp Asn Glu Asn Phe Leu Glu Ser Cys
 65                  70                  75                  80 atc tta ctg agc tac gtg tcc ttt gtg gtc atg ggc ctc tcc aag ata    288
Ile Leu Leu Ser Tyr Val Ser Phe Val Val Met Gly Leu Ser Lys Ile
                 85                  90                  95 ggt gct gta atg aaa aaa aag cca aaa atg aca gct ttg gtc agg caa    336
Gly Ala Val Met Lys Lys Lys Pro Lys Met Thr Ala Leu Val Arg Gln
            100                  105                  110 ttg gag acc tgc ttt ccg tcg cca agt gca aag gtt caa gag gaa tat    384
Leu Glu Thr Cys Phe Pro Ser Pro Ser Ala Lys Val Gln Glu Glu Tyr
        115                  120                  125 gct gtg aag tcc tgg ctg aaa cgc tgc cat ata tac aca aag gga ttt    432
Ala Val Lys Ser Trp Leu Lys Arg Cys His Ile Tyr Thr Lys Gly Phe
    130                  135                  140 ggt ggt ctc ttc atg atc atg tat ttc gct cac gct ctg att ccc tta    480
Gly Gly Leu Phe Met Ile Met Tyr Phe Ala His Ala Leu Ile Pro Leu
145                  150                  155                  160 ttc ata tac ttc att caa aga gtg ctg ctc cac tat ccg gat gcc aag    528
```

```
Phe Ile Tyr Phe Ile Gln Arg Val Leu Leu His Tyr Pro Asp Ala Lys
                165                 170                 175 cag att atg ccg ttt tac caa ctc gaa cct tgg gaa ttt cgc gac tcc      576
Gln Ile Met Pro Phe Tyr Gln Leu Glu Pro Trp Glu Phe Arg Asp Ser
            180                 185                 190 tgg ttg ttt tat cca agc tat ttt cac cag tcg tcg gcc gga tat acg      624
Trp Leu Phe Tyr Pro Ser Tyr Phe His Gln Ser Ser Ala Gly Tyr Thr
        195                 200                 205 gct aca tgt gga tcc att gcc ggt gac cta atg atc ttc gct gtg gtc      672
Ala Thr Cys Gly Ser Ile Ala Gly Asp Leu Met Ile Phe Ala Val Val
    210                 215                 220 ctg cag gtc atc atg cac tac gaa aga ctg gcc aag gtt ctt agg gag      720
Leu Gln Val Ile Met His Tyr Glu Arg Leu Ala Lys Val Leu Arg Glu
225                 230                 235                 240 ttt aag att caa gcc cat aac gca ccc aat gga gct aag gag gat ata      768
Phe Lys Ile Gln Ala His Asn Ala Pro Asn Gly Ala Lys Glu Asp Ile
                245                 250                 255 agg aag ttg cag tcc cta gtc gcc aat cac att gat ata ctt cga ctc      816
Arg Lys Leu Gln Ser Leu Val Ala Asn His Ile Asp Ile Leu Arg Leu
            260                 265                 270 act gat ctg atg aac gag gtc ttt gga att ccc ttg ttg cta aac ttt      864
Thr Asp Leu Met Asn Glu Val Phe Gly Ile Pro Leu Leu Leu Asn Phe
        275                 280                 285 att gca tct gcg ctg ctg gtc tgc ctg gtg gga gtt caa tta acc atc      912
Ile Ala Ser Ala Leu Leu Val Cys Leu Val Gly Val Gln Leu Thr Ile
    290                 295                 300 gct tta agt cca gag tat ttt tgc aag cag atg cta ttt ctg att tcc      960
Ala Leu Ser Pro Glu Tyr Phe Cys Lys Gln Met Leu Phe Leu Ile Ser
305                 310                 315                 320 gta ctg ctt gag gtc tat ctc ctt tgc tcc ttc agc cag agg tta ata     1008
Val Leu Leu Glu Val Tyr Leu Leu Cys Ser Phe Ser Gln Arg Leu Ile
                325                 330                 335 gat gct agc gaa aac gtg ggc cat gcg gca tac gat atg gat tgg tta     1056
Asp Ala Ser Glu Asn Val Gly His Ala Ala Tyr Asp Met Asp Trp Leu
            340                 345                 350 ggt tcc gac aaa cga ttc aag aaa att tta att ttt ata tct atg cga     1104
Gly Ser Asp Lys Arg Phe Lys Lys Ile Leu Ile Phe Ile Ser Met Arg
        355                 360                 365 tcc cag aag cca gtt tgc ctt aaa gcc aca gtt gtc ttg gac tta tcc     1152
Ser Gln Lys Pro Val Cys Leu Lys Ala Thr Val Val Leu Asp Leu Ser
    370                 375                 380 atg cca act atg agc atc ttt ctt ggt atg tcg tat aag ttt ttc tgc     1200
Met Pro Thr Met Ser Ile Phe Leu Gly Met Ser Tyr Lys Phe Phe Cys
385                 390                 395                 400 gct gtg agg act atg tat caa                                         1221
Ala Val Arg Thr Met Tyr Gln
                405

<210> SEQ ID NO 78
<211> LENGTH: 407
<212> TYPE: PRT
<213> ORGANISM: Drosophila melanogaster

<400> SEQUENCE: 78

Met Asp Asn Val Ala Glu Met Pro Glu Glu Lys Tyr Val Glu Val Asp
  1               5                  10                  15

Asp Phe Leu Arg Leu Ala Val Lys Phe Tyr Asn Thr Leu Gly Ile Asp
                 20                  25                  30

Pro Tyr Glu Thr Gly Arg Lys Arg Thr Ile Trp Phe Gln Ile Tyr Phe
             35                  40                  45
```

```
Ala Leu Asn Met Phe Asn Met Val Phe Ser Phe Tyr Ala Glu Val Ala
     50                  55                  60

Thr Leu Val Asp Arg Leu Arg Asp Asn Glu Asn Phe Leu Glu Ser Cys
 65                  70                  75                  80

Ile Leu Leu Ser Tyr Val Ser Phe Val Val Met Gly Leu Ser Lys Ile
                 85                  90                  95

Gly Ala Val Met Lys Lys Pro Lys Met Thr Ala Leu Val Arg Gln
                100             105             110

Leu Glu Thr Cys Phe Pro Ser Pro Ser Ala Lys Val Gln Glu Glu Tyr
            115             120             125

Ala Val Lys Ser Trp Leu Lys Arg Cys His Ile Tyr Thr Lys Gly Phe
    130             135             140

Gly Gly Leu Phe Met Ile Met Tyr Phe Ala His Ala Leu Ile Pro Leu
145             150             155             160

Phe Ile Tyr Phe Ile Gln Arg Val Leu Leu His Tyr Pro Asp Ala Lys
                165             170             175

Gln Ile Met Pro Phe Tyr Gln Leu Glu Pro Trp Glu Phe Arg Asp Ser
                180             185             190

Trp Leu Phe Tyr Pro Ser Tyr Phe His Gln Ser Ser Ala Gly Tyr Thr
                195             200             205

Ala Thr Cys Gly Ser Ile Ala Gly Asp Leu Met Ile Phe Ala Val Val
    210             215             220

Leu Gln Val Ile Met His Tyr Glu Arg Leu Ala Lys Val Leu Arg Glu
225             230             235             240

Phe Lys Ile Gln Ala His Asn Ala Pro Asn Gly Ala Lys Glu Asp Ile
                245             250             255

Arg Lys Leu Gln Ser Leu Val Ala Asn His Ile Asp Ile Leu Arg Leu
                260             265             270

Thr Asp Leu Met Asn Glu Val Phe Gly Ile Pro Leu Leu Asn Phe
        275             280             285

Ile Ala Ser Ala Leu Leu Val Cys Leu Val Gly Val Gln Leu Thr Ile
    290             295             300

Ala Leu Ser Pro Glu Tyr Phe Cys Lys Gln Met Leu Phe Leu Ile Ser
305             310             315             320

Val Leu Glu Val Tyr Leu Leu Cys Ser Phe Ser Gln Arg Leu Ile
                325             330             335

Asp Ala Ser Glu Asn Val Gly His Ala Ala Tyr Asp Met Asp Trp Leu
            340             345             350

Gly Ser Asp Lys Arg Phe Lys Lys Ile Leu Ile Phe Ile Ser Met Arg
            355             360             365

Ser Gln Lys Pro Val Cys Leu Lys Ala Thr Val Val Leu Asp Leu Ser
    370             375             380

Met Pro Thr Met Ser Ile Phe Leu Gly Met Ser Tyr Lys Phe Phe Cys
385             390             395             400

Ala Val Arg Thr Met Tyr Gln
                405

<210> SEQ ID NO 79
<211> LENGTH: 1212
<212> TYPE: DNA
<213> ORGANISM: Drosophila melanogaster
<220> FEATURE:
<221> NAME/KEY: CDS
<222> LOCATION: (1)..(1212)
<223> OTHER INFORMATION: DORLU 13.1
```

<400> SEQUENCE: 79

```
atg gaa aca gcg aag gat aat aca gcc agg act ttt atg gaa ttg atg      48
Met Glu Thr Ala Lys Asp Asn Thr Ala Arg Thr Phe Met Glu Leu Met
 1               5                  10                  15 cga gtg cca gta cag ttt tac aga acg att gga gag gat atc tac gcc      96
Arg Val Pro Val Gln Phe Tyr Arg Thr Ile Gly Glu Asp Ile Tyr Ala
             20                  25                  30 cat cga tcc acg aat ccc cta aaa tcg ctt ctc ttc aag atc tat cta     144
His Arg Ser Thr Asn Pro Leu Lys Ser Leu Leu Phe Lys Ile Tyr Leu
         35                  40                  45 tat gcg gga ttc ata aat ttt aat ctg ttg gta atc ggt gaa ctg gtg     192
Tyr Ala Gly Phe Ile Asn Phe Asn Leu Leu Val Ile Gly Glu Leu Val
 50                  55                  60 ttc ttc tac aac tca att cag gac ttt gaa acc att cga ttg gcc atc     240
Phe Phe Tyr Asn Ser Ile Gln Asp Phe Glu Thr Ile Arg Leu Ala Ile
 65                  70                  75                  80 gcg gtg gct cca tgt atc gga ttt tct ctg gtt gct gat ttt aaa caa     288
Ala Val Ala Pro Cys Ile Gly Phe Ser Leu Val Ala Asp Phe Lys Gln
                 85                  90                  95 gct gcc atg att aga ggc aag aaa aca cta att atg cta ctc gat gat     336
Ala Ala Met Ile Arg Gly Lys Lys Thr Leu Ile Met Leu Leu Asp Asp
            100                 105                 110 ttg gag aac atg cat ccg aaa acc ctg gca aag caa atg gaa tac aaa     384
Leu Glu Asn Met His Pro Lys Thr Leu Ala Lys Gln Met Glu Tyr Lys
        115                 120                 125 ttg ccg gac ttt gaa aag acc atg aaa cgt gtg atc aat ata ttc acc     432
Leu Pro Asp Phe Glu Lys Thr Met Lys Arg Val Ile Asn Ile Phe Thr
    130                 135                 140 ttt ctc tgc ttg gcc tat acg act acg ttc tcc ttt tat ccg gcc atc     480
Phe Leu Cys Leu Ala Tyr Thr Thr Thr Phe Ser Phe Tyr Pro Ala Ile
145                 150                 155                 160 aag gca tcc gtg aaa ttt aat ttc ttg ggc tac gac acc ttt gat cga     528
Lys Ala Ser Val Lys Phe Asn Phe Leu Gly Tyr Asp Thr Phe Asp Arg
                165                 170                 175 aat ttt ggt ttc ctc atc tgg ttt ccc ttc gat gca aca agg aat aat     576
Asn Phe Gly Phe Leu Ile Trp Phe Pro Phe Asp Ala Thr Arg Asn Asn
            180                 185                 190 ttg ata tac tgg atc atg tac tgg gac ata gcc cat ggg gcc tat cta     624
Leu Ile Tyr Trp Ile Met Tyr Trp Asp Ile Ala His Gly Ala Tyr Leu
        195                 200                 205 gcg ggt att gct ttt ctc tgc gcc gat ctt ttg ctc gtc gta gtc att     672
Ala Gly Ile Ala Phe Leu Cys Ala Asp Leu Leu Leu Val Val Val Ile
    210                 215                 220 acc cag att tgt atg cac ttt aac tat ata tct atg cga tta gag gat     720
Thr Gln Ile Cys Met His Phe Asn Tyr Ile Ser Met Arg Leu Glu Asp
225                 230                 235                 240 cat cca tgt aat tcg aat gag gac aaa gag aat ata gag ttt ctt att     768
His Pro Cys Asn Ser Asn Glu Asp Lys Glu Asn Ile Glu Phe Leu Ile
                245                 250                 255 ggc att atc aga tac cat gac aag tgc ctt aaa cta tgc gaa cat gtc     816
Gly Ile Ile Arg Tyr His Asp Lys Cys Leu Lys Leu Cys Glu His Val
            260                 265                 270 aac gat ctg tat agt ttc tct ttg ctg ctt aat ttc ctt atg gca tcc     864
Asn Asp Leu Tyr Ser Phe Ser Leu Leu Leu Asn Phe Leu Met Ala Ser
        275                 280                 285 atg cag att tgt ttc ata gcc ttt cag gtc acc gaa tca aca gtg gaa     912
Met Gln Ile Cys Phe Ile Ala Phe Gln Val Thr Glu Ser Thr Val Glu
    290                 295                 300
```

```
gtg att att att tac tgc att ttt ttg atg acc tcg atg gtt cag gta      960
Val Ile Ile Ile Tyr Cys Ile Phe Leu Met Thr Ser Met Val Gln Val
305                 310                 315                 320 ttt atg gtg tgc tac tat ggg gat act tta att gcc gcg agc ttg aaa     1008
Phe Met Val Cys Tyr Tyr Gly Asp Thr Leu Ile Ala Ala Ser Leu Lys
                325                 330                 335 gtg ggc gat gcc gct tac aac caa aag tgg ttt cag tgc agc aaa tcc     1056
Val Gly Asp Ala Ala Tyr Asn Gln Lys Trp Phe Gln Cys Ser Lys Ser
            340                 345                 350 tat tgc acc atg ttg aag ttg cta atc atg agg agt cag aaa cca gct     1104
Tyr Cys Thr Met Leu Lys Leu Leu Ile Met Arg Ser Gln Lys Pro Ala
        355                 360                 365 tca ata aga ccg ccg act ttt ccc ccc ata tcc ttg gtt acc tat atg     1152
Ser Ile Arg Pro Pro Thr Phe Pro Pro Ile Ser Leu Val Thr Tyr Met
370                 375                 380 aag gtc atc agc atg tcg tat caa ttt ttt gcc tta ctt aga acc aca     1200
Lys Val Ile Ser Met Ser Tyr Gln Phe Phe Ala Leu Leu Arg Thr Thr
385                 390                 395                 400 tac agc aat aat                                                      1212
Tyr Ser Asn Asn <210> SEQ ID NO 80
<211> LENGTH: 404
<212> TYPE: PRT
<213> ORGANISM: Drosophila melanogaster

<400> SEQUENCE: 80

Met Glu Thr Ala Lys Asp Asn Thr Ala Arg Thr Phe Met Glu Leu Met
1               5                   10                  15

Arg Val Pro Val Gln Phe Tyr Arg Thr Ile Gly Glu Asp Ile Tyr Ala
            20                  25                  30

His Arg Ser Thr Asn Pro Leu Lys Ser Leu Leu Phe Lys Ile Tyr Leu
        35                  40                  45

Tyr Ala Gly Phe Ile Asn Phe Asn Leu Leu Val Ile Gly Glu Leu Val
    50                  55                  60

Phe Phe Tyr Asn Ser Ile Gln Asp Phe Glu Thr Ile Arg Leu Ala Ile
65                  70                  75                  80

Ala Val Ala Pro Cys Ile Gly Phe Ser Leu Val Ala Asp Phe Lys Gln
                85                  90                  95

Ala Ala Met Ile Arg Gly Lys Lys Thr Leu Ile Met Leu Leu Asp Asp
            100                 105                 110

Leu Glu Asn Met His Pro Lys Thr Leu Ala Lys Gln Met Glu Tyr Lys
        115                 120                 125

Leu Pro Asp Phe Glu Lys Thr Met Lys Arg Val Ile Asn Ile Phe Thr
    130                 135                 140

Phe Leu Cys Leu Ala Tyr Thr Thr Thr Phe Ser Phe Tyr Pro Ala Ile
145                 150                 155                 160

Lys Ala Ser Val Lys Phe Asn Phe Leu Gly Tyr Asp Thr Phe Asp Arg
                165                 170                 175

Asn Phe Gly Phe Leu Ile Trp Phe Pro Phe Asp Ala Thr Arg Asn Asn
            180                 185                 190

Leu Ile Tyr Trp Ile Met Tyr Trp Asp Ile Ala His Gly Ala Tyr Leu
        195                 200                 205

Ala Gly Ile Ala Phe Leu Cys Ala Asp Leu Leu Leu Val Val Val Ile
    210                 215                 220

Thr Gln Ile Cys Met His Phe Asn Tyr Ile Ser Met Arg Leu Glu Asp
225                 230                 235                 240
```

```
His Pro Cys Asn Ser Asn Glu Asp Lys Glu Asn Ile Glu Phe Leu Ile
            245                 250                 255

Gly Ile Ile Arg Tyr His Asp Lys Cys Leu Lys Leu Cys Glu His Val
            260                 265                 270

Asn Asp Leu Tyr Ser Phe Ser Leu Leu Asn Phe Leu Met Ala Ser
            275                 280             285

Met Gln Ile Cys Phe Ile Ala Phe Gln Val Thr Glu Ser Thr Val Glu
        290                 295                 300

Val Ile Ile Ile Tyr Cys Ile Phe Leu Met Thr Ser Met Val Gln Val
305                 310                 315                 320

Phe Met Val Cys Tyr Tyr Gly Asp Thr Leu Ile Ala Ala Ser Leu Lys
                325                 330                 335

Val Gly Asp Ala Ala Tyr Asn Gln Lys Trp Phe Gln Cys Ser Lys Ser
            340                 345                 350

Tyr Cys Thr Met Leu Lys Leu Leu Ile Met Arg Ser Gln Lys Pro Ala
            355                 360                 365

Ser Ile Arg Pro Pro Thr Phe Pro Pro Ile Ser Leu Val Thr Tyr Met
370                 375                 380

Lys Val Ile Ser Met Ser Tyr Gln Phe Phe Ala Leu Leu Arg Thr Thr
385                 390                 395                 400

Tyr Ser Asn Asn

<210> SEQ ID NO 81
<211> LENGTH: 1179
<212> TYPE: DNA
<213> ORGANISM: Drosophila melanogaster
<220> FEATURE:
<221> NAME/KEY: CDS
<222> LOCATION: (1)..(1179)
<223> OTHER INFORMATION: DORLU 14.1

<400> SEQUENCE: 81 atg gaa cct gtg cag tac agc tac gag gat ttc gct cga ttg ccc acg      48
Met Glu Pro Val Gln Tyr Ser Tyr Glu Asp Phe Ala Arg Leu Pro Thr
 1               5                  10                  15 acg gtg ttc tgg atc atg ggc tac gac atg ctg ggc gtt ccg aag acc      96
Thr Val Phe Trp Ile Met Gly Tyr Asp Met Leu Gly Val Pro Lys Thr
             20                  25                  30 cgc tct cgc agg ata cta tac tgg ata tat cgt ttc ctc tgt ctc gcc     144
Arg Ser Arg Arg Ile Leu Tyr Trp Ile Tyr Arg Phe Leu Cys Leu Ala
         35                  40                  45 agc cat ggg gtc tgt gta gga gtc atg gta ttt cgt atg gtg gag gca     192
Ser His Gly Val Cys Val Gly Val Met Val Phe Arg Met Val Glu Ala
     50                  55                  60 aag acc att gac aat gtt tcg ctg atc atg cgg tat gcc act ctg gtc     240
Lys Thr Ile Asp Asn Val Ser Leu Ile Met Arg Tyr Ala Thr Leu Val
 65                  70                  75                  80 acc tat atc atc aac tcg gat acg aaa ttc gca act gtc tta caa agg     288
Thr Tyr Ile Ile Asn Ser Asp Thr Lys Phe Ala Thr Val Leu Gln Arg
                 85                  90                  95 agt gca att caa agt cta aac tca aaa ctg gcc gaa cta tat ccg aag     336
Ser Ala Ile Gln Ser Leu Asn Ser Lys Leu Ala Glu Leu Tyr Pro Lys
            100                 105                 110 acc acg ctg gac agg atc tat cac cgg gtg aat gat cac tat tgg acc     384
Thr Thr Leu Asp Arg Ile Tyr His Arg Val Asn Asp His Tyr Trp Thr
        115                 120                 125 aag tca ttt gta tat ttg gtt att atc tac att ggt tcg tcg att atg     432
Lys Ser Phe Val Tyr Leu Val Ile Ile Tyr Ile Gly Ser Ser Ile Met
```

|  |  |
|---|---|
| gtt gtt att gga ccg att att acg tcg att ata gct tac ttc acg cac<br>Val Val Ile Gly Pro Ile Ile Thr Ser Ile Ile Ala Tyr Phe Thr His<br>145                   150                  155                  160 | 480 |
| aac gtt ttc acc tac atg cac tgc tat ccg tac ttt ttg tat gat cct<br>Asn Val Phe Thr Tyr Met His Cys Tyr Pro Tyr Phe Leu Tyr Asp Pro<br>                  165                  170                  175 | 528 |
| gag aag gat ccg gtt tgg atc tac atc agc atc tat gct ctg gaa tgg<br>Glu Lys Asp Pro Val Trp Ile Tyr Ile Ser Ile Tyr Ala Leu Glu Trp<br>              180                  185                  190 | 576 |
| ttg cac agc aca cag atg gtc att tcg aac att ggc gcg gat atc tgg<br>Leu His Ser Thr Gln Met Val Ile Ser Asn Ile Gly Ala Asp Ile Trp<br>           195                  200                  205 | 624 |
| ctg ctg tac ttt cag gtg cag ata aat ctc cac ttc agg ggc att ata<br>Leu Leu Tyr Phe Gln Val Gln Ile Asn Leu His Phe Arg Gly Ile Ile<br>210                  215                  220 | 672 |
| cga tca ctg gcg gat cac aag ccc agt gtg aag cac gac cag gag gac<br>Arg Ser Leu Ala Asp His Lys Pro Ser Val Lys His Asp Gln Glu Asp<br>225                  230                  235                  240 | 720 |
| agg aaa ttc att gcg aaa att gtc gac aag cag gtg cac ctg gtc agt<br>Arg Lys Phe Ile Ala Lys Ile Val Asp Lys Gln Val His Leu Val Ser<br>                  245                  250                  255 | 768 |
| ttg caa aac gat ctg aat ggt atc ttt gga aaa tcg ctg ctt cta agc<br>Leu Gln Asn Asp Leu Asn Gly Ile Phe Gly Lys Ser Leu Leu Leu Ser<br>           260                  265                  270 | 816 |
| ctg ctg acc acc gca gcg gtt atc tgc acg gtg gcg gtg tac act ctg<br>Leu Leu Thr Thr Ala Ala Val Ile Cys Thr Val Ala Val Tyr Thr Leu<br>           275                  280                  285 | 864 |
| att cag ggt ccc acc ttg gag ggc ttc acc tat gtg atc ttc atc ggg<br>Ile Gln Gly Pro Thr Leu Glu Gly Phe Thr Tyr Val Ile Phe Ile Gly<br>290                  295                  300 | 912 |
| act tct gtg atg cag gtc tac ctg gtg tgc tat tac ggt cag caa gtt<br>Thr Ser Val Met Gln Val Tyr Leu Val Cys Tyr Tyr Gly Gln Gln Val<br>305                  310                  315                  320 | 960 |
| ctc gac ttg gtg gag cgc gag gtg gcc cac gcc gtg tac aat cat gat<br>Leu Asp Leu Val Glu Arg Glu Val Ala His Ala Val Tyr Asn His Asp<br>                  325                  330                  335 | 1008 |
| ttt cac gat gct tct ata gcg tac aag agg tac ctg ctc ata atc att<br>Phe His Asp Ala Ser Ile Ala Tyr Lys Arg Tyr Leu Leu Ile Ile Ile<br>           340                  345                  350 | 1056 |
| atc agg gcg cag cag ccc gtg gaa ctt aat gcc atg ggc tac ctg tcc<br>Ile Arg Ala Gln Gln Pro Val Glu Leu Asn Ala Met Gly Tyr Leu Ser<br>           355                  360                  365 | 1104 |
| att tcg ctg gac acc ttt aaa cag ctg atg agc gtc tcc tac cgg gtt<br>Ile Ser Leu Asp Thr Phe Lys Gln Leu Met Ser Val Ser Tyr Arg Val<br>           370                  375                  380 | 1152 |
| ata acc atg ctc atg cag atg att cag<br>Ile Thr Met Leu Met Gln Met Ile Gln<br>385                  390 | 1179 |

<210> SEQ ID NO 82
<211> LENGTH: 393
<212> TYPE: PRT
<213> ORGANISM: Drosophila melanogaster

<400> SEQUENCE: 82

Met Glu Pro Val Gln Tyr Ser Tyr Glu Asp Phe Ala Arg Leu Pro Thr
1                 5                   10                 15

Thr Val Phe Trp Ile Met Gly Tyr Asp Met Leu Gly Val Pro Lys Thr
                20                  25                 30

```
Arg Ser Arg Arg Ile Leu Tyr Trp Ile Tyr Arg Phe Leu Cys Leu Ala
        35                  40                  45

Ser His Gly Val Cys Val Gly Val Met Val Phe Arg Met Val Glu Ala
    50                  55                  60

Lys Thr Ile Asp Asn Val Ser Leu Ile Met Arg Tyr Ala Thr Leu Val
65                  70                  75                  80

Thr Tyr Ile Ile Asn Ser Asp Thr Lys Phe Ala Thr Val Leu Gln Arg
                85                  90                  95

Ser Ala Ile Gln Ser Leu Asn Ser Lys Leu Ala Glu Leu Tyr Pro Lys
            100                 105                 110

Thr Thr Leu Asp Arg Ile Tyr His Arg Val Asn Asp His Tyr Trp Thr
        115                 120                 125

Lys Ser Phe Val Tyr Leu Val Ile Tyr Ile Gly Ser Ser Ile Met
    130                 135                 140

Val Val Ile Gly Pro Ile Ile Thr Ser Ile Ile Ala Tyr Phe Thr His
145                 150                 155                 160

Asn Val Phe Thr Tyr Met His Cys Tyr Pro Tyr Phe Leu Tyr Asp Pro
                165                 170                 175

Glu Lys Asp Pro Val Trp Ile Tyr Ile Ser Ile Tyr Ala Leu Glu Trp
            180                 185                 190

Leu His Ser Thr Gln Met Val Ile Ser Asn Ile Gly Ala Asp Ile Trp
        195                 200                 205

Leu Leu Tyr Phe Gln Val Gln Ile Asn Leu His Phe Arg Gly Ile Ile
    210                 215                 220

Arg Ser Leu Ala Asp His Lys Pro Ser Val Lys His Asp Gln Glu Asp
225                 230                 235                 240

Arg Lys Phe Ile Ala Lys Ile Val Asp Lys Gln Val His Leu Val Ser
                245                 250                 255

Leu Gln Asn Asp Leu Asn Gly Ile Phe Gly Lys Ser Leu Leu Leu Ser
            260                 265                 270

Leu Leu Thr Thr Ala Ala Val Ile Cys Thr Val Ala Val Tyr Thr Leu
        275                 280                 285

Ile Gln Gly Pro Thr Leu Glu Gly Phe Thr Tyr Val Ile Phe Ile Gly
    290                 295                 300

Thr Ser Val Met Gln Val Tyr Leu Val Cys Tyr Tyr Gly Gln Gln Val
305                 310                 315                 320

Leu Asp Leu Val Glu Arg Glu Val Ala His Ala Val Tyr Asn His Asp
                325                 330                 335

Phe His Asp Ala Ser Ile Ala Tyr Lys Arg Tyr Leu Leu Ile Ile Ile
            340                 345                 350

Ile Arg Ala Gln Gln Pro Val Glu Leu Asn Ala Met Gly Tyr Leu Ser
        355                 360                 365

Ile Ser Leu Asp Thr Phe Lys Gln Leu Met Ser Val Ser Tyr Arg Val
    370                 375                 380

Ile Thr Met Leu Met Gln Met Ile Gln
385                 390

<210> SEQ ID NO 83
<211> LENGTH: 1134
<212> TYPE: DNA
<213> ORGANISM: Drosophila melanogaster
<220> FEATURE:
<221> NAME/KEY: CDS
<222> LOCATION: (1)..(1134)
<223> OTHER INFORMATION: DORLU 15.1
```

```
<400> SEQUENCE: 83 atg gac gcc agc tac ttt gcc gtc cag aga aga gct ctg gaa ata gtt      48
Met Asp Ala Ser Tyr Phe Ala Val Gln Arg Arg Ala Leu Glu Ile Val
 1               5                  10                  15 gga ttc gat ccc agt act ccg caa ctg agt ctg aaa cat ccc atc tgg      96
Gly Phe Asp Pro Ser Thr Pro Gln Leu Ser Leu Lys His Pro Ile Trp
             20                  25                  30 gcc ggg att ctc atc ctg tcc ttg atc tct cac aac tgg ccc atg gta     144
Ala Gly Ile Leu Ile Leu Ser Leu Ile Ser His Asn Trp Pro Met Val
         35                  40                  45 gtc tat gcc ctg cag gat ctc tcc gac ttg acc cgt ctg acg gac aac     192
Val Tyr Ala Leu Gln Asp Leu Ser Asp Leu Thr Arg Leu Thr Asp Asn
     50                  55                  60 ttt gcg gtg ttt atg caa gga tca cag agc acc ttc aag ttc ctg gtc     240
Phe Ala Val Phe Met Gln Gly Ser Gln Ser Thr Phe Lys Phe Leu Val
 65                  70                  75                  80 atg atg gcg aaa cga agg cgc att gga tcg ttg att cac cgt ttg cat     288
Met Met Ala Lys Arg Arg Arg Ile Gly Ser Leu Ile His Arg Leu His
                 85                  90                  95 aag cta aac cag gcg gcc agt gcc acg ccc aat cac ctg gag aag atc     336
Lys Leu Asn Gln Ala Ala Ser Ala Thr Pro Asn His Leu Glu Lys Ile
            100                 105                 110 gag agg gaa aac caa ctg gat agg tat gtc gcc agg tcc ttt aga aat     384
Glu Arg Glu Asn Gln Leu Asp Arg Tyr Val Ala Arg Ser Phe Arg Asn
        115                 120                 125 gcc gcc tac gga gtg att tgt gcc tcg gcc ata gcg ccc atg ttg ctt     432
Ala Ala Tyr Gly Val Ile Cys Ala Ser Ala Ile Ala Pro Met Leu Leu
    130                 135                 140 ggc ctg tgg gga tat gtg gag acg ggt gta ttt acc ccg acc aca ccc     480
Gly Leu Trp Gly Tyr Val Glu Thr Gly Val Phe Thr Pro Thr Thr Pro
145                 150                 155                 160 atg gag ttc aac ttc tgg ctg gac gag cga aag cct cac ttt tat tgg     528
Met Glu Phe Asn Phe Trp Leu Asp Glu Arg Lys Pro His Phe Tyr Trp
                165                 170                 175 ccc atc tac gtt tgg ggc gta ctg ggc gtg gca gct gcc gcc tgg ttg     576
Pro Ile Tyr Val Trp Gly Val Leu Gly Val Ala Ala Ala Ala Trp Leu
            180                 185                 190 gcc att gca acg gac acc ctg ttc tcc tgg ctg act cac aat gtg gtg     624
Ala Ile Ala Thr Asp Thr Leu Phe Ser Trp Leu Thr His Asn Val Val
        195                 200                 205 att cag ttc caa cta ctg gag ctt gtt ctc gaa gag aag gat ctg aat     672
Ile Gln Phe Gln Leu Leu Glu Leu Val Leu Glu Glu Lys Asp Leu Asn
    210                 215                 220 ggc gga gac tct cgc ctg acc ggg ttt gtt agt cgt cat cgt ata gct     720
Gly Gly Asp Ser Arg Leu Thr Gly Phe Val Ser Arg His Arg Ile Ala
225                 230                 235                 240 ctg gat ttg gcc aag gaa cta agt tcg att ttc ggg gag atc gtc ttt     768
Leu Asp Leu Ala Lys Glu Leu Ser Ser Ile Phe Gly Glu Ile Val Phe
                245                 250                 255 gtg aaa tac atg ctc agt tac ctg caa ctc tgc atg ttg gcc ttt cgc     816
Val Lys Tyr Met Leu Ser Tyr Leu Gln Leu Cys Met Leu Ala Phe Arg
            260                 265                 270 ttc agc cgc agt ggc tgg agt gcc cag gtg cca ttt aga gcc acc ttc     864
Phe Ser Arg Ser Gly Trp Ser Ala Gln Val Pro Phe Arg Ala Thr Phe
        275                 280                 285 cta gtg gcc atc atc atc caa ctg agt tcg tat tgc tat gga ggc gag     912
Leu Val Ala Ile Ile Ile Gln Leu Ser Ser Tyr Cys Tyr Gly Gly Glu
    290                 295                 300
```

-continued

```
tat ata aag cag caa agt ttg gcc atc gca caa gcc gtt tat ggt caa    960
Tyr Ile Lys Gln Gln Ser Leu Ala Ile Ala Gln Ala Val Tyr Gly Gln
305                 310                 315                 320 atc aat tgg cca gaa atg acg cca aag aaa aga aga ctc tgg caa atg   1008
Ile Asn Trp Pro Glu Met Thr Pro Lys Lys Arg Arg Leu Trp Gln Met
            325                 330                 335 gtg atc atg agg gcg cag cga ccg gct aag att ttt gga ttc atg ttc   1056
Val Ile Met Arg Ala Gln Arg Pro Ala Lys Ile Phe Gly Phe Met Phe
        340                 345                 350 gtt gtg gac ttg cca ctg ctg ctt tgg gtc atc aga act gcg ggc tca   1104
Val Val Asp Leu Pro Leu Leu Leu Trp Val Ile Arg Thr Ala Gly Ser
    355                 360                 365 ttt ctg gcc atg ctt agg act ttc gag cgt                           1134
Phe Leu Ala Met Leu Arg Thr Phe Glu Arg
370                 375

<210> SEQ ID NO 84
<211> LENGTH: 378
<212> TYPE: PRT
<213> ORGANISM: Drosophila melanogaster

<400> SEQUENCE: 84

Met Asp Ala Ser Tyr Phe Ala Val Gln Arg Arg Ala Leu Glu Ile Val
  1               5                  10                  15

Gly Phe Asp Pro Ser Thr Pro Gln Leu Ser Leu Lys His Pro Ile Trp
                 20                  25                  30

Ala Gly Ile Leu Ile Leu Ser Leu Ile Ser His Asn Trp Pro Met Val
             35                  40                  45

Val Tyr Ala Leu Gln Asp Leu Ser Asp Leu Thr Arg Leu Thr Asp Asn
         50                  55                  60

Phe Ala Val Phe Met Gln Gly Ser Gln Ser Thr Phe Lys Phe Leu Val
 65                  70                  75                  80

Met Met Ala Lys Arg Arg Ile Gly Ser Leu Ile His Arg Leu His
                 85                  90                  95

Lys Leu Asn Gln Ala Ala Ser Ala Thr Pro Asn His Leu Glu Lys Ile
            100                 105                 110

Glu Arg Glu Asn Gln Leu Asp Arg Tyr Val Ala Arg Ser Phe Arg Asn
        115                 120                 125

Ala Ala Tyr Gly Val Ile Cys Ala Ser Ala Ile Ala Pro Met Leu Leu
    130                 135                 140

Gly Leu Trp Gly Tyr Val Glu Thr Gly Val Phe Thr Pro Thr Pro
145                 150                 155                 160

Met Glu Phe Asn Phe Trp Leu Asp Glu Arg Lys Pro His Phe Tyr Trp
                165                 170                 175

Pro Ile Tyr Val Trp Gly Val Leu Gly Val Ala Ala Ala Trp Leu
            180                 185                 190

Ala Ile Ala Thr Asp Thr Leu Phe Ser Trp Leu Thr His Asn Val Val
        195                 200                 205

Ile Gln Phe Gln Leu Leu Glu Leu Val Leu Glu Glu Lys Asp Leu Asn
    210                 215                 220

Gly Gly Asp Ser Arg Leu Thr Gly Phe Val Ser Arg His Arg Ile Ala
225                 230                 235                 240

Leu Asp Leu Ala Lys Glu Leu Ser Ser Ile Phe Gly Glu Ile Val Phe
                245                 250                 255

Val Lys Tyr Met Leu Ser Tyr Leu Gln Leu Cys Met Leu Ala Phe Arg
            260                 265                 270
```

```
Phe Ser Arg Ser Gly Trp Ser Ala Gln Val Pro Phe Arg Ala Thr Phe
            275                 280                 285

Leu Val Ala Ile Ile Gln Leu Ser Ser Tyr Cys Tyr Gly Gly Glu
        290                 295                 300

Tyr Ile Lys Gln Gln Ser Leu Ala Ile Ala Gln Ala Val Tyr Gly Gln
305                 310                 315                 320

Ile Asn Trp Pro Glu Met Thr Pro Lys Lys Arg Arg Leu Trp Gln Met
                325                 330                 335

Val Ile Met Arg Ala Gln Arg Pro Ala Lys Ile Phe Gly Phe Met Phe
            340                 345                 350

Val Val Asp Leu Pro Leu Leu Leu Trp Val Ile Arg Thr Ala Gly Ser
            355                 360                 365

Phe Leu Ala Met Leu Arg Thr Phe Glu Arg
        370                 375

<210> SEQ ID NO 85
<211> LENGTH: 1065
<212> TYPE: DNA
<213> ORGANISM: Drosophila melanogaster
<220> FEATURE:
<221> NAME/KEY: CDS
<222> LOCATION: (1)..(1065)
<223> OTHER INFORMATION: DORLU 16.1

<400> SEQUENCE: 85 atg gaa aaa cta cgt tcc tat gag gat ttc atc ttc atg gcc aac atg      48
Met Glu Lys Leu Arg Ser Tyr Glu Asp Phe Ile Phe Met Ala Asn Met
  1               5                  10                  15 atg ttc aag acc ctt ggc tac gat cta ttc cat aca ccc aaa ccc tgg      96
Met Phe Lys Thr Leu Gly Tyr Asp Leu Phe His Thr Pro Lys Pro Trp
                 20                  25                  30 tgg cgc tat ctg ctt gtg cga gga tac ttc gtt ttg tgc acg atc agc     144
Trp Arg Tyr Leu Leu Val Arg Gly Tyr Phe Val Leu Cys Thr Ile Ser
             35                  40                  45 aac ttt tac gag gct tcc atg gtg acg aca agg ata att gag tgg gaa     192
Asn Phe Tyr Glu Ala Ser Met Val Thr Thr Arg Ile Ile Glu Trp Glu
         50                  55                  60 tcc ttg gcc gga agt ccc tcc aaa ata atg cga cag ggt ctg cac ttc     240
Ser Leu Ala Gly Ser Pro Ser Lys Ile Met Arg Gln Gly Leu His Phe
 65                  70                  75                  80 ttt tac atg ttg agt agc caa ttg aaa ttt atc aca ttc atg ata aat     288
Phe Tyr Met Leu Ser Ser Gln Leu Lys Phe Ile Thr Phe Met Ile Asn
                 85                  90                  95 cgc aaa cgc cta ctg cag ctg agc cat cgt ttg aaa gag ttg tat cct     336
Arg Lys Arg Leu Leu Gln Leu Ser His Arg Leu Lys Glu Leu Tyr Pro
            100                 105                 110 cat aaa gag caa aat caa agg aag tac gag gtg aat aaa tac tac cta     384
His Lys Glu Gln Asn Gln Arg Lys Tyr Glu Val Asn Lys Tyr Tyr Leu
        115                 120                 125 tcc tgt tcc acg cgc aat gtt ttg tac gtg tac tac ttt gta atg gtc     432
Ser Cys Ser Thr Arg Asn Val Leu Tyr Val Tyr Tyr Phe Val Met Val
    130                 135                 140 gtc atg gca ctg gaa ccc ctc gtt cag tcg tgc att atc cag ttc ata     480
Val Met Ala Leu Glu Pro Leu Val Gln Ser Cys Ile Ile Gln Phe Ile
145                 150                 155                 160 gtg aat gtg agc ctg ggc aca gat ctg tgg atg atg tgc gtc tca agc     528
Val Asn Val Ser Leu Gly Thr Asp Leu Trp Met Met Cys Val Ser Ser
                165                 170                 175 caa ata tcg atg cac ttg ggc tat ctg gcc aat atg ttg gcc tcc att     576
Gln Ile Ser Met His Leu Gly Tyr Leu Ala Asn Met Leu Ala Ser Ile
```

-continued

```
               180                 185                 190
cga cca agt cca gaa acg gaa caa caa gac tgt gac ttc ttg gcc agc     624
Arg Pro Ser Pro Glu Thr Glu Gln Gln Asp Cys Asp Phe Leu Ala Ser
        195                 200                 205 att ata aag aga cat caa cta atg atc agg ctt caa aag gac gtg aac     672
Ile Ile Lys Arg His Gln Leu Met Ile Arg Leu Gln Lys Asp Val Asn
    210                 215                 220 tat gtt ttt gga ctc tta ttg gca tct aat ctg ttt acc aca tcc tgt     720
Tyr Val Phe Gly Leu Leu Leu Ala Ser Asn Leu Phe Thr Thr Ser Cys
225                 230                 235                 240 tta ctt tgc tgc atg gcg tac tat acc gtc gtc gaa ggt ttc aat tgg     768
Leu Leu Cys Cys Met Ala Tyr Tyr Thr Val Val Glu Gly Phe Asn Trp
                245                 250                 255 gag ggc att tcc tat atg atg ctc ttt gct agt gta gct gcc cag ttc     816
Glu Gly Ile Ser Tyr Met Met Leu Phe Ala Ser Val Ala Ala Gln Phe
            260                 265                 270 tac gtt gtc agc tca cac gga caa atg tta ata gat ttg agt aca aat     864
Tyr Val Val Ser Ser His Gly Gln Met Leu Ile Asp Leu Ser Thr Asn
        275                 280                 285 tta gcc aag gct gcc ttt gaa agc aag tgg tat gaa gga tct ttg cga     912
Leu Ala Lys Ala Ala Phe Glu Ser Lys Trp Tyr Glu Gly Ser Leu Arg
    290                 295                 300 tac aaa aag gag ata ctc att cta atg gca cag gct caa cga cct ttg     960
Tyr Lys Lys Glu Ile Leu Ile Leu Met Ala Gln Ala Gln Arg Pro Leu
305                 310                 315                 320 gag att tca gcc agg gga gta att atc ata tcc ctc gac acc ttt aaa    1008
Glu Ile Ser Ala Arg Gly Val Ile Ile Ile Ser Leu Asp Thr Phe Lys
                325                 330                 335 ata ttg atg acc atc aca tac aga ttt ttc gcg gtt ata cga caa act    1056
Ile Leu Met Thr Ile Thr Tyr Arg Phe Phe Ala Val Ile Arg Gln Thr
            340                 345                 350 gta gaa aag                                                        1065
Val Glu Lys
        355
```

<210> SEQ ID NO 86
<211> LENGTH: 355
<212> TYPE: PRT
<213> ORGANISM: Drosophila melanogaster

<400> SEQUENCE: 86

```
Met Glu Lys Leu Arg Ser Tyr Glu Asp Phe Ile Phe Met Ala Asn Met
  1               5                  10                  15

Met Phe Lys Thr Leu Gly Tyr Asp Leu Phe His Thr Pro Lys Pro Trp
                 20                  25                  30

Trp Arg Tyr Leu Leu Val Arg Gly Tyr Phe Val Leu Cys Thr Ile Ser
             35                  40                  45

Asn Phe Tyr Glu Ala Ser Met Val Thr Thr Arg Ile Ile Glu Trp Glu
         50                  55                  60

Ser Leu Ala Gly Ser Pro Ser Lys Ile Met Arg Gln Gly Leu His Phe
 65                  70                  75                  80

Phe Tyr Met Leu Ser Ser Gln Leu Lys Phe Ile Thr Phe Met Ile Asn
                 85                  90                  95

Arg Lys Arg Leu Leu Gln Leu Ser His Arg Leu Lys Glu Leu Tyr Pro
            100                 105                 110

His Lys Glu Gln Asn Gln Arg Lys Tyr Glu Val Asn Lys Tyr Tyr Leu
        115                 120                 125

Ser Cys Ser Thr Arg Asn Val Leu Tyr Val Tyr Tyr Phe Val Met Val
```

```
        130                 135                 140
Val Met Ala Leu Glu Pro Leu Val Gln Ser Cys Ile Ile Gln Phe Ile
145                 150                 155                 160

Val Asn Val Ser Leu Gly Thr Asp Leu Trp Met Met Cys Val Ser Ser
                165                 170                 175

Gln Ile Ser Met His Leu Gly Tyr Leu Ala Asn Met Leu Ala Ser Ile
            180                 185                 190

Arg Pro Ser Pro Glu Thr Glu Gln Gln Asp Cys Asp Phe Leu Ala Ser
        195                 200                 205

Ile Ile Lys Arg His Gln Leu Met Ile Arg Leu Gln Lys Asp Val Asn
    210                 215                 220

Tyr Val Phe Gly Leu Leu Leu Ala Ser Asn Leu Phe Thr Thr Ser Cys
225                 230                 235                 240

Leu Leu Cys Cys Met Ala Tyr Tyr Thr Val Val Glu Gly Phe Asn Trp
                245                 250                 255

Glu Gly Ile Ser Tyr Met Met Leu Phe Ala Ser Val Ala Ala Gln Phe
            260                 265                 270

Tyr Val Ser Ser His Gly Gln Met Leu Ile Asp Leu Ser Thr Asn
        275                 280                 285

Leu Ala Lys Ala Ala Phe Glu Ser Lys Trp Tyr Glu Gly Ser Leu Arg
    290                 295                 300

Tyr Lys Lys Glu Ile Leu Ile Leu Met Ala Gln Ala Gln Arg Pro Leu
305                 310                 315                 320

Glu Ile Ser Ala Arg Gly Val Ile Ile Ser Leu Asp Thr Phe Lys
                325                 330                 335

Ile Leu Met Thr Ile Thr Tyr Arg Phe Phe Ala Val Ile Arg Gln Thr
            340                 345                 350

Val Glu Lys
      355

<210> SEQ ID NO 87
<211> LENGTH: 1272
<212> TYPE: DNA
<213> ORGANISM: Drosophila melanogaster
<220> FEATURE:
<221> NAME/KEY: CDS
<222> LOCATION: (1)..(1272)
<223> OTHER INFORMATION: DORLU 22.1

<400> SEQUENCE: 87 atg ctg acg gac aag ttc ctc cga ctg cag tcc gct tta ttt cgc ctt        48
Met Leu Thr Asp Lys Phe Leu Arg Leu Gln Ser Ala Leu Phe Arg Leu
  1               5                  10                  15 ctc gga ctc gaa ttg ttg cac gag cag gat gtt ggc cat cga tat cct       96
Leu Gly Leu Glu Leu Leu His Glu Gln Asp Val Gly His Arg Tyr Pro
             20                  25                  30 tgg cgc agc atc tgc tgc att ctc tcg gtg gcc agt ttc atg ccc ctg      144
Trp Arg Ser Ile Cys Cys Ile Leu Ser Val Ala Ser Phe Met Pro Leu
         35                  40                  45 acc att gcg ttt ggc ctg caa aac gtc caa aat gtg gag caa tta acc      192
Thr Ile Ala Phe Gly Leu Gln Asn Val Gln Asn Val Glu Gln Leu Thr
     50                  55                  60 gac tca ctc tgc tcg gtt ctc gtg gat ttg ctg gcc ctg tgc aaa atc      240
Asp Ser Leu Cys Ser Val Leu Val Asp Leu Leu Ala Leu Cys Lys Ile
 65                  70                  75                  80 ggg ctt ttc ctt tgg ctt tac aag gac ttc aag ttc cta ata ggg cag      288
Gly Leu Phe Leu Trp Leu Tyr Lys Asp Phe Lys Phe Leu Ile Gly Gln
                 85                  90                  95
```

```
ttc tat tgt gtt ttg caa acg gaa acc cac acc gct gtc gct gaa atg       336
Phe Tyr Cys Val Leu Gln Thr Glu Thr His Thr Ala Val Ala Glu Met
            100                 105                 110 ata gtg acc agg gaa agt cgt cgg gat cag ttc atc agt gct atg tat       384
Ile Val Thr Arg Glu Ser Arg Arg Asp Gln Phe Ile Ser Ala Met Tyr
        115                 120                 125 gcc tac tgt ttc att acg gct ggc ctt tcg gcc tgc ctg atg tcc cct       432
Ala Tyr Cys Phe Ile Thr Ala Gly Leu Ser Ala Cys Leu Met Ser Pro
    130                 135                 140 cta tcc atg ctg att agc tac cac gaa cag gtg aat tgc agc cga aat       480
Leu Ser Met Leu Ile Ser Tyr His Glu Gln Val Asn Cys Ser Arg Asn
145                 150                 155                 160 ttc cat ttc cca gtg tgt aag aaa aag tac tgc tta ata tcc aga ata       528
Phe His Phe Pro Val Cys Lys Lys Lys Tyr Cys Leu Ile Ser Arg Ile
                165                 170                 175 tta aga tac agt ttc tgc aga tat ccc tgg gac aat atg aag ctg tcc       576
Leu Arg Tyr Ser Phe Cys Arg Tyr Pro Trp Asp Asn Met Lys Leu Ser
            180                 185                 190 aac tac atc att tcc tat ttc tgg aat gtg tgt gct gca ttg ggc gtg       624
Asn Tyr Ile Ile Ser Tyr Phe Trp Asn Val Cys Ala Ala Leu Gly Val
        195                 200                 205 gca ctg ccc acc gtt tgt gtg gac aca ctg ttc tgt tct ctg agc cat       672
Ala Leu Pro Thr Val Cys Val Asp Thr Leu Phe Cys Ser Leu Ser His
    210                 215                 220 aat ctc tgt gcc cta ttc cag att gcc agg cac aaa atg atg cac ttt       720
Asn Leu Cys Ala Leu Phe Gln Ile Ala Arg His Lys Met Met His Phe
225                 230                 235                 240 gag ggc aga aat acc aaa gag act cat gag aac tta aag cac gtg ttt       768
Glu Gly Arg Asn Thr Lys Glu Thr His Glu Asn Leu Lys His Val Phe
                245                 250                 255 caa cta tat gcg ttg tgt ttg aac ctg ggc cat ttc tta aac gaa tat       816
Gln Leu Tyr Ala Leu Cys Leu Asn Leu Gly His Phe Leu Asn Glu Tyr
            260                 265                 270 ttc aga ccg ctc atc tgc cag ttt gtg gca gcc tca ctg cac ttg tgt       864
Phe Arg Pro Leu Ile Cys Gln Phe Val Ala Ala Ser Leu His Leu Cys
        275                 280                 285 gtc ctg tgc tac caa ctg tct gcc aat atc ctg cag cca gcg tta ctc       912
Val Leu Cys Tyr Gln Leu Ser Ala Asn Ile Leu Gln Pro Ala Leu Leu
    290                 295                 300 ttc tat gcc gca ttt acg gca gca gtt gtt ggc cag gtg tct ata tac       960
Phe Tyr Ala Ala Phe Thr Ala Ala Val Val Gly Gln Val Ser Ile Tyr
305                 310                 315                 320 tgc ttc tgc gga tcg agc atc cat tcg gag tgt cag cta ttt ggc cag      1008
Cys Phe Cys Gly Ser Ser Ile His Ser Glu Cys Gln Leu Phe Gly Gln
                325                 330                 335 gcc atc tac gag tcc agc tgg ccc cat ctg ctg cag gaa aac ctg cag      1056
Ala Ile Tyr Glu Ser Ser Trp Pro His Leu Leu Gln Glu Asn Leu Gln
            340                 345                 350 ctt gta agc tcc tta aaa att gcc atg atg cga tcg agt ttg gga tgt      1104
Leu Val Ser Ser Leu Lys Ile Ala Met Met Arg Ser Ser Leu Gly Cys
        355                 360                 365 ccc atc gat ggt tac ttc ttc gag gcc aat cgg gag acg ctc atc acg      1152
Pro Ile Asp Gly Tyr Phe Phe Glu Ala Asn Arg Glu Thr Leu Ile Thr
    370                 375                 380 atc cct ggc cta gct ttc cgg gct ttc att att cag tgg ttc agt cgt      1200
Ile Pro Gly Leu Ala Phe Arg Ala Phe Ile Ile Gln Trp Phe Ser Arg
385                 390                 395                 400 tcg ggt ttg ttt aac tcc gga aat att tac aat tat gct tta agc cgg      1248
Ser Gly Leu Phe Asn Ser Gly Asn Ile Tyr Asn Tyr Ala Leu Ser Arg
```

```
                        405                 410                 415
tgt tgt tac agc cag ttg gct aat                                              1272
Cys Cys Tyr Ser Gln Leu Ala Asn
            420

<210> SEQ ID NO 88
<211> LENGTH: 424
<212> TYPE: PRT
<213> ORGANISM: Drosophila melanogaster

<400> SEQUENCE: 88

Met Leu Thr Asp Lys Phe Leu Arg Leu Gln Ser Ala Leu Phe Arg Leu
 1               5                  10                  15

Leu Gly Leu Glu Leu Leu His Glu Gln Asp Val Gly His Arg Tyr Pro
            20                  25                  30

Trp Arg Ser Ile Cys Cys Ile Leu Ser Val Ala Ser Phe Met Pro Leu
        35                  40                  45

Thr Ile Ala Phe Gly Leu Gln Asn Val Gln Asn Val Glu Gln Leu Thr
    50                  55                  60

Asp Ser Leu Cys Ser Val Leu Val Asp Leu Leu Ala Leu Cys Lys Ile
65                  70                  75                  80

Gly Leu Phe Leu Trp Leu Tyr Lys Asp Phe Lys Phe Leu Ile Gly Gln
                85                  90                  95

Phe Tyr Cys Val Leu Gln Thr Glu Thr His Thr Ala Val Ala Glu Met
            100                 105                 110

Ile Val Thr Arg Glu Ser Arg Arg Asp Gln Phe Ile Ser Ala Met Tyr
        115                 120                 125

Ala Tyr Cys Phe Ile Thr Ala Gly Leu Ser Ala Cys Leu Met Ser Pro
    130                 135                 140

Leu Ser Met Leu Ile Ser Tyr His Glu Gln Val Asn Cys Ser Arg Asn
145                 150                 155                 160

Phe His Phe Pro Val Cys Lys Lys Tyr Cys Leu Ile Ser Arg Ile
                165                 170                 175

Leu Arg Tyr Ser Phe Cys Arg Tyr Pro Trp Asp Asn Met Lys Leu Ser
            180                 185                 190

Asn Tyr Ile Ile Ser Tyr Phe Trp Asn Val Cys Ala Ala Leu Gly Val
        195                 200                 205

Ala Leu Pro Thr Val Cys Val Asp Thr Leu Phe Cys Ser Leu Ser His
    210                 215                 220

Asn Leu Cys Ala Leu Phe Gln Ile Ala Arg His Lys Met Met His Phe
225                 230                 235                 240

Glu Gly Arg Asn Thr Lys Glu Thr His Glu Asn Leu Lys His Val Phe
                245                 250                 255

Gln Leu Tyr Ala Leu Cys Leu Asn Leu Gly His Phe Leu Asn Glu Tyr
            260                 265                 270

Phe Arg Pro Leu Ile Cys Gln Phe Val Ala Ala Ser Leu His Leu Cys
        275                 280                 285

Val Leu Cys Tyr Gln Leu Ser Ala Asn Ile Leu Gln Pro Ala Leu Leu
    290                 295                 300

Phe Tyr Ala Ala Phe Thr Ala Val Val Gly Gln Val Ser Ile Tyr
305                 310                 315                 320

Cys Phe Cys Gly Ser Ser Ile His Ser Glu Cys Gln Leu Phe Gly Gln
                325                 330                 335

Ala Ile Tyr Glu Ser Ser Trp Pro His Leu Leu Gln Glu Asn Leu Gln
            340                 345                 350
```

```
Leu Val Ser Ser Leu Lys Ile Ala Met Met Arg Ser Ser Leu Gly Cys
        355                 360                 365

Pro Ile Asp Gly Tyr Phe Phe Glu Ala Asn Arg Glu Thr Leu Ile Thr
    370                 375                 380

Ile Pro Gly Leu Ala Phe Arg Ala Phe Ile Ile Gln Trp Phe Ser Arg
385                 390                 395                 400

Ser Gly Leu Phe Asn Ser Gly Asn Ile Tyr Asn Tyr Ala Leu Ser Arg
                405                 410                 415

Cys Cys Tyr Ser Gln Leu Ala Asn
            420

<210> SEQ ID NO 89
<211> LENGTH: 1176
<212> TYPE: DNA
<213> ORGANISM: Drosophila melanogaster
<220> FEATURE:
<221> NAME/KEY: CDS
<222> LOCATION: (1)..(1176)
<223> OTHER INFORMATION: DORLU 24.1

<400> SEQUENCE: 89
```

| | | | | | | | | | | | | | | | | |
|---|---|---|---|---|---|---|---|---|---|---|---|---|---|---|---|---|
| atg tca aag cta atc gag gtg ttt ctg ggt aat ctg tgg acg cag cgt | | | | | | | | | | | | | | | | 48 |
| Met Ser Lys Leu Ile Glu Val Phe Leu Gly Asn Leu Trp Thr Gln Arg | | | | | | | | | | | | | | | | |
| 1 | | | | 5 | | | | | 10 | | | | | 15 | | |

```
atg tca aag cta atc gag gtg ttt ctg ggt aat ctg tgg acg cag cgt      48
Met Ser Lys Leu Ile Glu Val Phe Leu Gly Asn Leu Trp Thr Gln Arg
  1               5                  10                  15 ttt acc ttc gcc cga atg ggt ttg gat ttg cag ccc gat aaa aag ggc      96
Phe Thr Phe Ala Arg Met Gly Leu Asp Leu Gln Pro Asp Lys Lys Gly
             20                  25                  30 aat gtt ttg cga tct ccg ctt ctt tat tgt att atg tgt ctg aca aca     144
Asn Val Leu Arg Ser Pro Leu Leu Tyr Cys Ile Met Cys Leu Thr Thr
         35                  40                  45 agc ttt gag ctc tgc acc gtg tgc gcc ttt atg gtc caa aat cgc aac     192
Ser Phe Glu Leu Cys Thr Val Cys Ala Phe Met Val Gln Asn Arg Asn
 50                  55                  60 caa atc gtg ctt tgt tcc gag gcc ctg atg cac gga cta cag atg gtc     240
Gln Ile Val Leu Cys Ser Glu Ala Leu Met His Gly Leu Gln Met Val
 65                  70                  75                  80 tcc tcg cta ctg aag atg gct ata ttc ttg gcc aaa tct cac gac ctg     288
Ser Ser Leu Leu Lys Met Ala Ile Phe Leu Ala Lys Ser His Asp Leu
                 85                  90                  95 gtg gac cta att caa cag att cag tcg cct ttt aca gag gag gat ctt     336
Val Asp Leu Ile Gln Gln Ile Gln Ser Pro Phe Thr Glu Glu Asp Leu
            100                 105                 110 gta ggt aca gag tgg aga tcc caa aat caa agg gga caa cta atg gct     384
Val Gly Thr Glu Trp Arg Ser Gln Asn Gln Arg Gly Gln Leu Met Ala
        115                 120                 125 gcc att tac ttt atg atg tgt gcc ggt acg agt gtg tca ttt ctg ttg     432
Ala Ile Tyr Phe Met Met Cys Ala Gly Thr Ser Val Ser Phe Leu Leu
    130                 135                 140 atg cca gtg gct ttg acc atg ctt aag tac cat tcc act ggg gaa ttc     480
Met Pro Val Ala Leu Thr Met Leu Lys Tyr His Ser Thr Gly Glu Phe
145                 150                 155                 160 gcg cct gtc agc tcg ttc cgg gtt ctg ctt cca tac gat gtg aca caa     528
Ala Pro Val Ser Ser Phe Arg Val Leu Leu Pro Tyr Asp Val Thr Gln
                165                 170                 175 ccg cat gtt tat gcc atg gac tgc tgc ttg atg gta ttt gtg tta agt     576
Pro His Val Tyr Ala Met Asp Cys Cys Leu Met Val Phe Val Leu Ser
            180                 185                 190 ttt ttt tgc tgc tcc acc acc gga gtg gat acc tta tat gga tgg tgt     624
Phe Phe Cys Cys Ser Thr Thr Gly Val Asp Thr Leu Tyr Gly Trp Cys
        195                 200                 205
```

```
gct tta ggc gtg agt tta caa tac cgt cgc ctc ggt caa caa ctt aaa      672
Ala Leu Gly Val Ser Leu Gln Tyr Arg Arg Leu Gly Gln Gln Leu Lys
    210                 215                 220 agg ata ccc tcc tgt ttc aat cca tct cgg tct gac ttt gga tta agt      720
Arg Ile Pro Ser Cys Phe Asn Pro Ser Arg Ser Asp Phe Gly Leu Ser
225                 230                 235                 240 ggg att ttt gtg gag cat gct cgt ctg ctt aaa ata gtc caa cat ttt      768
Gly Ile Phe Val Glu His Ala Arg Leu Leu Lys Ile Val Gln His Phe
        245                 250                 255 aat tat agt ttt atg gag atc gca ttt gtg gag gtt gtt ata atc tgt      816
Asn Tyr Ser Phe Met Glu Ile Ala Phe Val Glu Val Val Ile Ile Cys
            260                 265                 270 gga ctc tat tgc tca gta att tgt cag tat ata atg cca cac acc aac      864
Gly Leu Tyr Cys Ser Val Ile Cys Gln Tyr Ile Met Pro His Thr Asn
                275                 280                 285 caa aac ttc gcc ttt ctg ggt ttc ttt tca ttg gta gtt acc aca cag      912
Gln Asn Phe Ala Phe Leu Gly Phe Phe Ser Leu Val Val Thr Thr Gln
        290                 295                 300 ctg tgc atc tat ctt ttc ggt gcc gaa cag gtc cgt ttg gag gct gag      960
Leu Cys Ile Tyr Leu Phe Gly Ala Glu Gln Val Arg Leu Glu Ala Glu
305                 310                 315                 320 cga ttt tcc cgg ctg cta tac gaa gta att cct tgg caa aac ctt cct     1008
Arg Phe Ser Arg Leu Leu Tyr Glu Val Ile Pro Trp Gln Asn Leu Pro
                325                 330                 335 cct aaa cac cgg aaa ctt ttc ctt ttt cca att gag cgc gcc caa cga     1056
Pro Lys His Arg Lys Leu Phe Leu Phe Pro Ile Glu Arg Ala Gln Arg
            340                 345                 350 gaa act gtt ctc ggt gct tat ttc ttc gaa cta ggc aga cct ctt ctt     1104
Glu Thr Val Leu Gly Ala Tyr Phe Phe Glu Leu Gly Arg Pro Leu Leu
        355                 360                 365 gtt tgg ata ttt cgc aca gca ggc tct ttt aca act ttg atg aac gct     1152
Val Trp Ile Phe Arg Thr Ala Gly Ser Phe Thr Thr Leu Met Asn Ala
370                 375                 380 ctc tac gca aaa tac gaa acg cat                                     1176
Leu Tyr Ala Lys Tyr Glu Thr His
385                 390

<210> SEQ ID NO 90
<211> LENGTH: 392
<212> TYPE: PRT
<213> ORGANISM: Drosophila melanogaster

<400> SEQUENCE: 90

Met Ser Lys Leu Ile Glu Val Phe Leu Gly Asn Leu Trp Thr Gln Arg
 1               5                  10                  15

Phe Thr Phe Ala Arg Met Gly Leu Asp Leu Gln Pro Asp Lys Lys Gly
                20                  25                  30

Asn Val Leu Arg Ser Pro Leu Leu Tyr Cys Ile Met Cys Leu Thr Thr
            35                  40                  45

Ser Phe Glu Leu Cys Thr Val Cys Ala Phe Met Val Gln Asn Arg Asn
        50                  55                  60

Gln Ile Val Leu Cys Ser Glu Ala Leu Met His Gly Leu Gln Met Val
 65                 70                  75                  80

Ser Ser Leu Leu Lys Met Ala Ile Phe Leu Ala Lys Ser His Asp Leu
                85                  90                  95

Val Asp Leu Ile Gln Gln Ile Gln Ser Pro Phe Thr Glu Glu Asp Leu
            100                 105                 110

Val Gly Thr Glu Trp Arg Ser Gln Asn Gln Arg Gly Gln Leu Met Ala
```

```
            115                 120                 125
Ala Ile Tyr Phe Met Met Cys Ala Gly Thr Ser Val Ser Phe Leu Leu
    130                 135                 140

Met Pro Val Ala Leu Thr Met Leu Lys Tyr His Ser Thr Gly Glu Phe
145                 150                 155                 160

Ala Pro Val Ser Ser Phe Arg Val Leu Pro Tyr Asp Val Thr Gln
                165                 170                 175

Pro His Val Tyr Ala Met Asp Cys Cys Leu Met Val Phe Val Leu Ser
            180                 185                 190

Phe Phe Cys Cys Ser Thr Thr Gly Val Asp Thr Leu Tyr Gly Trp Cys
        195                 200                 205

Ala Leu Gly Val Ser Leu Gln Tyr Arg Arg Leu Gly Gln Gln Leu Lys
    210                 215                 220

Arg Ile Pro Ser Cys Phe Asn Pro Ser Arg Ser Asp Phe Gly Leu Ser
225                 230                 235                 240

Gly Ile Phe Val Glu His Ala Arg Leu Leu Lys Ile Val Gln His Phe
                245                 250                 255

Asn Tyr Ser Phe Met Glu Ile Ala Phe Val Glu Val Ile Ile Cys
            260                 265                 270

Gly Leu Tyr Cys Ser Val Ile Cys Gln Tyr Ile Met Pro His Thr Asn
        275                 280                 285

Gln Asn Phe Ala Phe Leu Gly Phe Ser Leu Val Val Thr Thr Gln
    290                 295                 300

Leu Cys Ile Tyr Leu Phe Gly Ala Glu Gln Val Arg Leu Glu Ala Glu
305                 310                 315                 320

Arg Phe Ser Arg Leu Leu Tyr Glu Val Ile Pro Trp Gln Asn Leu Pro
                325                 330                 335

Pro Lys His Arg Lys Leu Phe Leu Phe Pro Ile Glu Arg Ala Gln Arg
            340                 345                 350

Glu Thr Val Leu Gly Ala Tyr Phe Phe Glu Leu Gly Arg Pro Leu Leu
        355                 360                 365

Val Trp Ile Phe Arg Thr Ala Gly Ser Phe Thr Thr Leu Met Asn Ala
    370                 375                 380

Leu Tyr Ala Lys Tyr Glu Thr His
385                 390

<210> SEQ ID NO 91
<211> LENGTH: 1359
<212> TYPE: DNA
<213> ORGANISM: Drosophila melanogaster
<220> FEATURE:
<221> NAME/KEY: CDS
<222> LOCATION: (1)..(1359)
<223> OTHER INFORMATION: DORLU 25.1

<400> SEQUENCE: 91 atg aag agc aca ttc aag gaa gaa agg att aag gac gac tcc aag cgt      48
Met Lys Ser Thr Phe Lys Glu Glu Arg Ile Lys Asp Asp Ser Lys Arg
  1               5                  10                  15 cgc gac ctg ttt gta ttc gtg agg caa acc atg tgt ata gcg gcc atg      96
Arg Asp Leu Phe Val Phe Val Arg Gln Thr Met Cys Ile Ala Ala Met
                 20                  25                  30 tat ccc ttc ggt tac tac gtg aat gga tct gga gtc ctg gcc gtt ctg     144
Tyr Pro Phe Gly Tyr Tyr Val Asn Gly Ser Gly Val Leu Ala Val Leu
             35                  40                  45 gtg cga ttc tgt gac ttg acc tac gag ctc ttt aac tac ttc gtt tcg     192
Val Arg Phe Cys Asp Leu Thr Tyr Glu Leu Phe Asn Tyr Phe Val Ser
```

```
                50                      55                      60
gta cac ata gct ggc ctg tac atc tgc acc atc tac atc aac tat ggg      240
Val His Ile Ala Gly Leu Tyr Ile Cys Thr Ile Tyr Ile Asn Tyr Gly
 65                  70                  75                  80 caa ggc gat ttg gac ttc ttc gtg aac tgt ttg ata caa acc att att      288
Gln Gly Asp Leu Asp Phe Phe Val Asn Cys Leu Ile Gln Thr Ile Ile
                 85                  90                  95 tat ctg tgg aca ata gcg atg aaa ctc tac ttt cgg agg ttc aga cct      336
Tyr Leu Trp Thr Ile Ala Met Lys Leu Tyr Phe Arg Arg Phe Arg Pro
            100                 105                 110 ggt ttg ttg aat acc att ctg tcc aac atc aat gat gag tac gag aca      384
Gly Leu Leu Asn Thr Ile Leu Ser Asn Ile Asn Asp Glu Tyr Glu Thr
        115                 120                 125 cgt tcg gct gtg gga ttc agt ttc gtc aca atg gcg gga tcc tat cgg      432
Arg Ser Ala Val Gly Phe Ser Phe Val Thr Met Ala Gly Ser Tyr Arg
    130                 135                 140 atg tcc aag cta tgg atc aaa acc tat gtg tat tgc tgc tac ata ggc      480
Met Ser Lys Leu Trp Ile Lys Thr Tyr Val Tyr Cys Cys Tyr Ile Gly
145                 150                 155                 160 acc att ttc tgg ctg gct ctt ccc att gcc tac cgg gat agg agt ctt      528
Thr Ile Phe Trp Leu Ala Leu Pro Ile Ala Tyr Arg Asp Arg Ser Leu
                165                 170                 175 cct ctt gcc tgc tgg tat ccc ttt gac tat aca caa ccc ggt gtc tat      576
Pro Leu Ala Cys Trp Tyr Pro Phe Asp Tyr Thr Gln Pro Gly Val Tyr
            180                 185                 190 gag gta gtg ttc ctt ctc cag gcg atg gga cag atc caa gtg gcc gca      624
Glu Val Val Phe Leu Leu Gln Ala Met Gly Gln Ile Gln Val Ala Ala
        195                 200                 205 tcc ttt gcc tcc tcc agt ggc ctg cat atg gtg ctt tgt gtg ctg ata      672
Ser Phe Ala Ser Ser Ser Gly Leu His Met Val Leu Cys Val Leu Ile
    210                 215                 220 tca ggg cag tac gat gtc ctc ttt tgc agt ctc aag aat gta tta gcc      720
Ser Gly Gln Tyr Asp Val Leu Phe Cys Ser Leu Lys Asn Val Leu Ala
225                 230                 235                 240 agc agc tat gtc ctt atg gga gcc aat atg acg gaa ctg aat caa ttg      768
Ser Ser Tyr Val Leu Met Gly Ala Asn Met Thr Glu Leu Asn Gln Leu
                245                 250                 255 cag gct gag caa tct gcg gcc gat gtc gag cca ggt cag tat gct tac      816
Gln Ala Glu Gln Ser Ala Ala Asp Val Glu Pro Gly Gln Tyr Ala Tyr
            260                 265                 270 tcc gtg gag gag gag aca cct ttg caa gaa ctt cta aaa gtt ggg agc      864
Ser Val Glu Glu Glu Thr Pro Leu Gln Glu Leu Leu Lys Val Gly Ser
        275                 280                 285 tca atg gac ttc tcc tcc gca ttc agg ctg tct ttt gtg cgg tgc att      912
Ser Met Asp Phe Ser Ser Ala Phe Arg Leu Ser Phe Val Arg Cys Ile
    290                 295                 300 cag cac cat cga tac ata gtg gcg gca ctg aag aaa att gag agt ttc      960
Gln His His Arg Tyr Ile Val Ala Ala Leu Lys Lys Ile Glu Ser Phe
305                 310                 315                 320 tac agt ccc ata tgg ttc gtg aag att ggc gaa gtc acc ttt ctt atg     1008
Tyr Ser Pro Ile Trp Phe Val Lys Ile Gly Glu Val Thr Phe Leu Met
                325                 330                 335 tgc ctg gta gcc ttc gtc tcc acg aag agc acc gcg gcc aac tca ttc     1056
Cys Leu Val Ala Phe Val Ser Thr Lys Ser Thr Ala Ala Asn Ser Phe
            340                 345                 350 atg cga atg gtc tcc ttg ggc cag tac ctg ctc tta gtt ctc tac gag     1104
Met Arg Met Val Ser Leu Gly Gln Tyr Leu Leu Leu Val Leu Tyr Glu
        355                 360                 365 ctg ttc atc atc tgc tac ttc gcg gac atc gtt ttt cag aac agc cag     1152
```

```
Leu Phe Ile Ile Cys Tyr Phe Ala Asp Ile Val Phe Gln Asn Ser Gln
        370                 375                 380 cgg tgc ggt gaa gcc ctc tgg cga agt cct tgg cag cga cat ttg aag    1200
Arg Cys Gly Glu Ala Leu Trp Arg Ser Pro Trp Gln Arg His Leu Lys
385                 390                 395                 400 gat gtt cgc agt gat tac atg ttc ttt atg ctg aat tcc cgc agg cag    1248
Asp Val Arg Ser Asp Tyr Met Phe Phe Met Leu Asn Ser Arg Arg Gln
                405                 410                 415 ttc caa ctt acg gcc gga aaa ata agc aat cta aac gtg gat cgt ttc    1296
Phe Gln Leu Thr Ala Gly Lys Ile Ser Asn Leu Asn Val Asp Arg Phe
            420                 425                 430 aga ggg act att act act gcc ttc tcg ttt ctc acc ttg ctg caa aag    1344
Arg Gly Thr Ile Thr Thr Ala Phe Ser Phe Leu Thr Leu Leu Gln Lys
        435                 440                 445 atg gat gca cga gaa                                                1359
Met Asp Ala Arg Glu
    450
```

<210> SEQ ID NO 92
<211> LENGTH: 453
<212> TYPE: PRT
<213> ORGANISM: Drosophila melanogaster

<400> SEQUENCE: 92

```
Met Lys Ser Thr Phe Lys Glu Glu Arg Ile Lys Asp Asp Ser Lys Arg
  1               5                  10                  15

Arg Asp Leu Phe Val Phe Val Arg Gln Thr Met Cys Ile Ala Ala Met
             20                  25                  30

Tyr Pro Phe Gly Tyr Tyr Val Asn Gly Ser Gly Val Leu Ala Val Leu
         35                  40                  45

Val Arg Phe Cys Asp Leu Thr Tyr Glu Leu Phe Asn Tyr Phe Val Ser
 50                  55                  60

Val His Ile Ala Gly Leu Tyr Ile Cys Thr Ile Tyr Ile Asn Tyr Gly
 65                  70                  75                  80

Gln Gly Asp Leu Asp Phe Phe Val Asn Cys Leu Ile Gln Thr Ile Ile
                 85                  90                  95

Tyr Leu Trp Thr Ile Ala Met Lys Leu Tyr Phe Arg Arg Phe Arg Pro
            100                 105                 110

Gly Leu Leu Asn Thr Ile Leu Ser Asn Ile Asn Asp Glu Tyr Glu Thr
        115                 120                 125

Arg Ser Ala Val Gly Phe Ser Phe Val Thr Met Ala Gly Ser Tyr Arg
    130                 135                 140

Met Ser Lys Leu Trp Ile Lys Thr Tyr Val Tyr Cys Cys Tyr Ile Gly
145                 150                 155                 160

Thr Ile Phe Trp Leu Ala Leu Pro Ile Ala Tyr Arg Asp Arg Ser Leu
                165                 170                 175

Pro Leu Ala Cys Trp Tyr Pro Phe Asp Tyr Thr Gln Pro Gly Val Tyr
            180                 185                 190

Glu Val Val Phe Leu Leu Gln Ala Met Gly Gln Ile Gln Val Ala Ala
        195                 200                 205

Ser Phe Ala Ser Ser Ser Gly Leu His Met Val Leu Cys Val Leu Ile
    210                 215                 220

Ser Gly Gln Tyr Asp Val Leu Phe Cys Ser Leu Lys Asn Val Leu Ala
225                 230                 235                 240

Ser Ser Tyr Val Leu Met Gly Ala Asn Met Thr Glu Leu Asn Gln Leu
                245                 250                 255
```

```
Gln Ala Glu Gln Ser Ala Ala Asp Val Glu Pro Gly Gln Tyr Ala Tyr
            260                 265                 270

Ser Val Glu Glu Glu Thr Pro Leu Gln Glu Leu Leu Lys Val Gly Ser
            275                 280                 285

Ser Met Asp Phe Ser Ser Ala Phe Arg Leu Ser Phe Val Arg Cys Ile
            290                 295                 300

Gln His His Arg Tyr Ile Val Ala Ala Leu Lys Lys Ile Glu Ser Phe
305                 310                 315                 320

Tyr Ser Pro Ile Trp Phe Val Lys Ile Gly Glu Val Thr Phe Leu Met
                325                 330                 335

Cys Leu Val Ala Phe Val Ser Thr Lys Ser Thr Ala Ala Asn Ser Phe
                340                 345                 350

Met Arg Met Val Ser Leu Gly Gln Tyr Leu Leu Leu Val Leu Tyr Glu
            355                 360                 365

Leu Phe Ile Ile Cys Tyr Phe Ala Asp Ile Val Phe Gln Asn Ser Gln
    370                 375                 380

Arg Cys Gly Glu Ala Leu Trp Arg Ser Pro Trp Gln Arg His Leu Lys
385                 390                 395                 400

Asp Val Arg Ser Asp Tyr Met Phe Phe Met Leu Asn Ser Arg Arg Gln
                405                 410                 415

Phe Gln Leu Thr Ala Gly Lys Ile Ser Asn Leu Asn Val Asp Arg Phe
            420                 425                 430

Arg Gly Thr Ile Thr Thr Ala Phe Ser Phe Leu Thr Leu Leu Gln Lys
            435                 440                 445

Met Asp Ala Arg Glu
    450

<210> SEQ ID NO 93
<211> LENGTH: 1296
<212> TYPE: DNA
<213> ORGANISM: Drosophila melanogaster
<220> FEATURE:
<221> NAME/KEY: CDS
<222> LOCATION: (1)..(1296)
<223> OTHER INFORMATION: DORLU 26.1

<400> SEQUENCE: 93 atg aaa gtg ggt ttt gca act att ggc tat ata aag agt att cct tgc      48
Met Lys Val Gly Phe Ala Thr Ile Gly Tyr Ile Lys Ser Ile Pro Cys
  1               5                  10                  15 cag gat gtc gtt cac ata gtt ata tcc atc atg tcc gag tgg tta cgc      96
Gln Asp Val Val His Ile Val Ile Ser Ile Met Ser Glu Trp Leu Arg
             20                  25                  30 ttt ctg aaa cgc gat caa cag ctg gat gtg tac ttt ttt gca gtg ccc     144
Phe Leu Lys Arg Asp Gln Gln Leu Asp Val Tyr Phe Phe Ala Val Pro
         35                  40                  45 cgc ttg agt tta gac ata atg ggc tat tgg ccg ggc aaa act ggt gat     192
Arg Leu Ser Leu Asp Ile Met Gly Tyr Trp Pro Gly Lys Thr Gly Asp
     50                  55                  60 aca tgg ccc tgg aga tcc ctg att cac ttc gca atc ctg gcc att ggc     240
Thr Trp Pro Trp Arg Ser Leu Ile His Phe Ala Ile Leu Ala Ile Gly
 65                  70                  75                  80 gtg gcc acc gaa ctg cat gct ggc atg tgt ttt cta gac cga cag cag     288
Val Ala Thr Glu Leu His Ala Gly Met Cys Phe Leu Asp Arg Gln Gln
                 85                  90                  95 att acc ttg gca ctg gag acc ctc tgt cca gct ggc aca tcg gcg gtc     336
Ile Thr Leu Ala Leu Glu Thr Leu Cys Pro Ala Gly Thr Ser Ala Val
            100                 105                 110
```

```
acg ctg ctc aag atg ttc cta atg ctg cgc ttt cgt cag gat ctc tcc    384
Thr Leu Leu Lys Met Phe Leu Met Leu Arg Phe Arg Gln Asp Leu Ser
        115                 120                 125 att atg tgg aac cgc ctg agg ggc ctc ctc ttc gat ccc aac tgg gag    432
Ile Met Trp Asn Arg Leu Arg Gly Leu Leu Phe Asp Pro Asn Trp Glu
    130                 135                 140 cga ccc gag cag cgg gac atc cgg cta aag cac tcg gcc atg gcg gct    480
Arg Pro Glu Gln Arg Asp Ile Arg Leu Lys His Ser Ala Met Ala Ala
145                 150                 155                 160 cgc atc aat ttc tgg ccc ctg tca gcc gga ttc ttc aca tgc acc acc    528
Arg Ile Asn Phe Trp Pro Leu Ser Ala Gly Phe Phe Thr Cys Thr Thr
        165                 170                 175 tac aac cta aag ccg ata ctg atc gca atg ata ttg tat ctc cag aat    576
Tyr Asn Leu Lys Pro Ile Leu Ile Ala Met Ile Leu Tyr Leu Gln Asn
    180                 185                 190 cgt tac gag gac ttc gtt tgg ttt aca ccc ttc aat atg act atg ccc    624
Arg Tyr Glu Asp Phe Val Trp Phe Thr Pro Phe Asn Met Thr Met Pro
    195                 200                 205 aaa gtt ctg cta aac tat cca ttt ttt ccc ctg acc tac ata ttt att    672
Lys Val Leu Leu Asn Tyr Pro Phe Phe Pro Leu Thr Tyr Ile Phe Ile
210                 215                 220 gcc tat acg ggc tat gtg acc atc ttt atg ttc ggc ggc tgt gat ggt    720
Ala Tyr Thr Gly Tyr Val Thr Ile Phe Met Phe Gly Gly Cys Asp Gly
225                 230                 235                 240 ttt tat ttc gag ttc tgt gcc cac cta tca gct ctt ttc gaa gtg ctc    768
Phe Tyr Phe Glu Phe Cys Ala His Leu Ser Ala Leu Phe Glu Val Leu
        245                 250                 255 cag gcg gag ata gaa tca atg ttt aga ccc tac act gat cac ttg gaa    816
Gln Ala Glu Ile Glu Ser Met Phe Arg Pro Tyr Thr Asp His Leu Glu
    260                 265                 270 ctg tcg cca gtg cag ctt tac att tta gag caa aag atg cga tca gta    864
Leu Ser Pro Val Gln Leu Tyr Ile Leu Glu Gln Lys Met Arg Ser Val
    275                 280                 285 atc att agg cac aat gcc atc atc gat ttg acc aga ttt ttt cgt gat    912
Ile Ile Arg His Asn Ala Ile Ile Asp Leu Thr Arg Phe Phe Arg Asp
290                 295                 300 cgc tat acc att att acc ctg gcc cat ttt gtg tcc gcc gcc atg gtg    960
Arg Tyr Thr Ile Ile Thr Leu Ala His Phe Val Ser Ala Ala Met Val
305                 310                 315                 320 att gga ttc agc atg gtt aat ctc ctg aca ttg ggc aat aat ggt ctg   1008
Ile Gly Phe Ser Met Val Asn Leu Leu Thr Leu Gly Asn Asn Gly Leu
        325                 330                 335 ggc gca atg ctc tat gtg gcc tac acg gtt gcc gct ttg agc caa ctg   1056
Gly Ala Met Leu Tyr Val Ala Tyr Thr Val Ala Ala Leu Ser Gln Leu
    340                 345                 350 ctg gtt tat tgc tat ggc gga act ctg gtg gcc gaa agt agc act ggt   1104
Leu Val Tyr Cys Tyr Gly Gly Thr Leu Val Ala Glu Ser Ser Thr Gly
    355                 360                 365 ctg tgc cga gcc atg ttc tcc tgt ccg tgg cag ctt ttt aag cct aaa   1152
Leu Cys Arg Ala Met Phe Ser Cys Pro Trp Gln Leu Phe Lys Pro Lys
370                 375                 380 caa cgt cga ctc gtt cag ctt ttg att ctc aga tcg cag cgt cct gtt   1200
Gln Arg Arg Leu Val Gln Leu Leu Ile Leu Arg Ser Gln Arg Pro Val
385                 390                 395                 400 tcc atg gca gtg cca ttc ttt tcg cca tcg ttg gct acc ttt gct gcg   1248
Ser Met Ala Val Pro Phe Phe Ser Pro Ser Leu Ala Thr Phe Ala Ala
        405                 410                 415 att ctt caa act tcg ggt tcc ata att gcg ctg gtt aag tcc ttt cag   1296
Ile Leu Gln Thr Ser Gly Ser Ile Ile Ala Leu Val Lys Ser Phe Gln
    420                 425                 430
```

-continued

<210> SEQ ID NO 94
<211> LENGTH: 432
<212> TYPE: PRT
<213> ORGANISM: Drosophila melanogaster

<400> SEQUENCE: 94

Met Lys Val Gly Phe Ala Thr Ile Gly Tyr Ile Lys Ser Ile Pro Cys
1               5                   10                  15

Gln Asp Val Val His Ile Val Ile Ser Ile Met Ser Glu Trp Leu Arg
            20                  25                  30

Phe Leu Lys Arg Asp Gln Gln Leu Asp Val Tyr Phe Phe Ala Val Pro
        35                  40                  45

Arg Leu Ser Leu Asp Ile Met Gly Tyr Trp Pro Gly Lys Thr Gly Asp
    50                  55                  60

Thr Trp Pro Trp Arg Ser Leu Ile His Phe Ala Ile Leu Ala Ile Gly
65                  70                  75                  80

Val Ala Thr Glu Leu His Ala Gly Met Cys Phe Leu Asp Arg Gln Gln
                85                  90                  95

Ile Thr Leu Ala Leu Glu Thr Leu Cys Pro Ala Gly Thr Ser Ala Val
            100                 105                 110

Thr Leu Leu Lys Met Phe Leu Met Leu Arg Phe Arg Gln Asp Leu Ser
        115                 120                 125

Ile Met Trp Asn Arg Leu Arg Gly Leu Leu Phe Asp Pro Asn Trp Glu
    130                 135                 140

Arg Pro Glu Gln Arg Asp Ile Arg Leu Lys His Ser Ala Met Ala Ala
145                 150                 155                 160

Arg Ile Asn Phe Trp Pro Leu Ser Ala Gly Phe Phe Thr Cys Thr Thr
                165                 170                 175

Tyr Asn Leu Lys Pro Ile Leu Ile Ala Met Ile Leu Tyr Leu Gln Asn
            180                 185                 190

Arg Tyr Glu Asp Phe Val Trp Phe Thr Pro Phe Asn Met Thr Met Pro
        195                 200                 205

Lys Val Leu Leu Asn Tyr Pro Phe Pro Leu Thr Tyr Ile Phe Ile
    210                 215                 220

Ala Tyr Thr Gly Tyr Val Thr Ile Phe Met Phe Gly Gly Cys Asp Gly
225                 230                 235                 240

Phe Tyr Phe Glu Phe Cys Ala His Leu Ser Ala Leu Phe Glu Val Leu
                245                 250                 255

Gln Ala Glu Ile Glu Ser Met Phe Arg Pro Tyr Thr Asp His Leu Glu
            260                 265                 270

Leu Ser Pro Val Gln Leu Tyr Ile Leu Glu Gln Lys Met Arg Ser Val
        275                 280                 285

Ile Ile Arg His Asn Ala Ile Ile Asp Leu Thr Arg Phe Phe Arg Asp
    290                 295                 300

Arg Tyr Thr Ile Ile Thr Leu Ala His Phe Val Ser Ala Ala Met Val
305                 310                 315                 320

Ile Gly Phe Ser Met Val Asn Leu Leu Thr Leu Gly Asn Asn Gly Leu
                325                 330                 335

Gly Ala Met Leu Tyr Val Ala Tyr Thr Val Ala Ala Leu Ser Gln Leu
            340                 345                 350

Leu Val Tyr Cys Tyr Gly Gly Thr Leu Val Ala Glu Ser Ser Thr Gly
        355                 360                 365

Leu Cys Arg Ala Met Phe Ser Cys Pro Trp Gln Leu Phe Lys Pro Lys

| | | | | | | | | | | | |
|---|---|---|---|---|---|---|---|---|---|---|---|
| | | | 370 | | | 375 | | | 380 | | |
| Gln | Arg | Arg | Leu | Val | Gln | Leu | Leu | Ile | Leu | Arg | Ser | Gln | Arg | Pro | Val |
| 385 | | | | | 390 | | | | 395 | | | | | | 400 |

| Ser | Met | Ala | Val | Pro | Phe | Phe | Ser | Pro | Ser | Leu | Ala | Thr | Phe | Ala | Ala |
|---|---|---|---|---|---|---|---|---|---|---|---|---|---|---|---|
| | | | | 405 | | | | | 410 | | | | | 415 | |

| Ile | Leu | Gln | Thr | Ser | Gly | Ser | Ile | Ile | Ala | Leu | Val | Lys | Ser | Phe | Gln |
|---|---|---|---|---|---|---|---|---|---|---|---|---|---|---|---|
| | | | 420 | | | | | 425 | | | | | 430 | | |

<210> SEQ ID NO 95
<211> LENGTH: 1047
<212> TYPE: DNA
<213> ORGANISM: Drosophila melanogaster
<220> FEATURE:
<221> NAME/KEY: CDS
<222> LOCATION: (1)..(1047)
<223> OTHER INFORMATION: DORLU 27.1

<400> SEQUENCE: 95

| atg | tct | ggt | tgc | aga | gca | atg | gcc | tta | ttt | aca | acc | aca | gaa | gaa | cgt | 48 |
|---|---|---|---|---|---|---|---|---|---|---|---|---|---|---|---|---|
| Met | Ser | Gly | Cys | Arg | Ala | Met | Ala | Leu | Phe | Thr | Thr | Thr | Glu | Glu | Arg | |
| 1 | | | | 5 | | | | | 10 | | | | | 15 | | |

| ctg | ctg | ccc | tac | cga | tct | aaa | tgg | cac | acc | ttg | gta | tat | att | caa | atg | 96 |
|---|---|---|---|---|---|---|---|---|---|---|---|---|---|---|---|---|
| Leu | Leu | Pro | Tyr | Arg | Ser | Lys | Trp | His | Thr | Leu | Val | Tyr | Ile | Gln | Met | |
| | | | 20 | | | | | 25 | | | | | 30 | | | |

| gtt | ata | ttt | ttt | gct | tca | atg | agc | ttt | ggc | tta | acg | gaa | tcg | atg | gga | 144 |
|---|---|---|---|---|---|---|---|---|---|---|---|---|---|---|---|---|
| Val | Ile | Phe | Phe | Ala | Ser | Met | Ser | Phe | Gly | Leu | Thr | Glu | Ser | Met | Gly | |
| | | 35 | | | | | 40 | | | | | 45 | | | | |

| gac | cat | gtt | caa | atg | gga | cgg | gac | tta | gcc | ttc | atc | ctt | ggg | aca | tat | 192 |
|---|---|---|---|---|---|---|---|---|---|---|---|---|---|---|---|---|
| Asp | His | Val | Gln | Met | Gly | Arg | Asp | Leu | Ala | Phe | Ile | Leu | Gly | Thr | Tyr | |
| 50 | | | | | 55 | | | | | 60 | | | | | | |

| tat | ttc | tgc | tgg | tat | ggc | gat | gaa | ctt | gac | caa | gtg | atc | agc | gat | ctg | 240 |
|---|---|---|---|---|---|---|---|---|---|---|---|---|---|---|---|---|
| Tyr | Phe | Cys | Trp | Tyr | Gly | Asp | Glu | Leu | Asp | Gln | Val | Ile | Ser | Asp | Leu | |
| 65 | | | | 70 | | | | | 75 | | | | | 80 | | |

| gac | gct | cta | cat | cct | tgg | gca | cag | aaa | ggt | cct | aat | cca | gtt | gaa | tat | 288 |
|---|---|---|---|---|---|---|---|---|---|---|---|---|---|---|---|---|
| Asp | Ala | Leu | His | Pro | Trp | Ala | Gln | Lys | Gly | Pro | Asn | Pro | Val | Glu | Tyr | |
| | | | | 85 | | | | | 90 | | | | | 95 | | |

| cag | act | ggt | aaa | cgt | tgg | tac | ttc | gta | atg | gct | ttt | ttc | ttg | gca | acg | 336 |
|---|---|---|---|---|---|---|---|---|---|---|---|---|---|---|---|---|
| Gln | Thr | Gly | Lys | Arg | Trp | Tyr | Phe | Val | Met | Ala | Phe | Phe | Leu | Ala | Thr | |
| | | | 100 | | | | | 105 | | | | | 110 | | | |

| tca | tgg | tcg | ttc | ttc | ttg | tgc | att | ttg | cta | ttg | tta | ctt | ata | acc | tca | 384 |
|---|---|---|---|---|---|---|---|---|---|---|---|---|---|---|---|---|
| Ser | Trp | Ser | Phe | Phe | Leu | Cys | Ile | Leu | Leu | Leu | Leu | Leu | Ile | Thr | Ser | |
| | | 115 | | | | | 120 | | | | | 125 | | | | |

| ccc | atg | tgg | gtc | cat | cag | caa | aac | ctt | ccc | ttt | cat | gcg | gcg | ttt | cct | 432 |
|---|---|---|---|---|---|---|---|---|---|---|---|---|---|---|---|---|
| Pro | Met | Trp | Val | His | Gln | Gln | Asn | Leu | Pro | Phe | His | Ala | Ala | Phe | Pro | |
| | 130 | | | | | 135 | | | | | 140 | | | | | |

| ttt | caa | tgg | cac | gaa | aaa | tcg | ctt | cat | ccc | atc | agc | cac | gct | ata | atc | 480 |
|---|---|---|---|---|---|---|---|---|---|---|---|---|---|---|---|---|
| Phe | Gln | Trp | His | Glu | Lys | Ser | Leu | His | Pro | Ile | Ser | His | Ala | Ile | Ile | |
| 145 | | | | | 150 | | | | | 155 | | | | | 160 | |

| tat | ctg | ttt | cag | agc | tat | ttt | gca | gtg | tat | tgt | ctg | act | tgg | ctt | ttg | 528 |
|---|---|---|---|---|---|---|---|---|---|---|---|---|---|---|---|---|
| Tyr | Leu | Phe | Gln | Ser | Tyr | Phe | Ala | Val | Tyr | Cys | Leu | Thr | Trp | Leu | Leu | |
| | | | | 165 | | | | | 170 | | | | | 175 | | |

| tgc | ata | gag | gga | cta | tca | att | tgt | att | tat | gcg | gaa | att | act | ttc | ggc | 576 |
|---|---|---|---|---|---|---|---|---|---|---|---|---|---|---|---|---|
| Cys | Ile | Glu | Gly | Leu | Ser | Ile | Cys | Ile | Tyr | Ala | Glu | Ile | Thr | Phe | Gly | |
| | | | 180 | | | | | 185 | | | | | 190 | | | |

| att | gaa | gtt | tta | tgc | cta | gaa | cta | cgc | caa | att | cac | cga | cac | aat | tat | 624 |
|---|---|---|---|---|---|---|---|---|---|---|---|---|---|---|---|---|
| Ile | Glu | Val | Leu | Cys | Leu | Glu | Leu | Arg | Gln | Ile | His | Arg | His | Asn | Tyr | |
| | | 195 | | | | | 200 | | | | | 205 | | | | |

| ggc | ctt | caa | gaa | ctg | aga | atg | gag | acg | aac | cgc | ttg | gtc | aag | cta | cat | 672 |
|---|---|---|---|---|---|---|---|---|---|---|---|---|---|---|---|---|
| Gly | Leu | Gln | Glu | Leu | Arg | Met | Glu | Thr | Asn | Arg | Leu | Val | Lys | Leu | His | |
| | 210 | | | | | 215 | | | | | 220 | | | | | |

-continued

```
cag aag att atg ggt gtt aac ttt tcc ttg gtg tcc ttg tcg gtt ttg      720
Gln Lys Ile Met Gly Val Asn Phe Ser Leu Val Ser Leu Ser Val Leu
225                 230                 235                 240 gag gcc gtg gag gct cgg aag gac ccc aaa gtt gtg gcc cag ttt gca      768
Glu Ala Val Glu Ala Arg Lys Asp Pro Lys Val Val Ala Gln Phe Ala
            245                 250                 255 gtc ctt atg ttg ctc gcc tta gga cat cta tct atg tgg tcg tat tgt      816
Val Leu Met Leu Leu Ala Leu Gly His Leu Ser Met Trp Ser Tyr Cys
        260                 265                 270 gga gac cag tta tcc cag aag tca ttg caa att tcg gag gct gcc tat      864
Gly Asp Gln Leu Ser Gln Lys Ser Leu Gln Ile Ser Glu Ala Ala Tyr
    275                 280                 285 gag gct tac gac cca acc aaa gga tca aag gat gtg tat aga gac ctc      912
Glu Ala Tyr Asp Pro Thr Lys Gly Ser Lys Asp Val Tyr Arg Asp Leu
290                 295                 300 tgc gta ata atc agg cgt ggc cag gac cct ttg atc atg aga gcc agc      960
Cys Val Ile Ile Arg Arg Gly Gln Asp Pro Leu Ile Met Arg Ala Ser
305                 310                 315                 320 cca ttt ccg tcc ttt aat tta ata aac tac agc gct ata ctt aac caa     1008
Pro Phe Pro Ser Phe Asn Leu Ile Asn Tyr Ser Ala Ile Leu Asn Gln
            325                 330                 335 tgt tat gga atc ctg aca ttt ttg cta aag aca tta gac                  1047
Cys Tyr Gly Ile Leu Thr Phe Leu Leu Lys Thr Leu Asp
        340                 345
```

<210> SEQ ID NO 96
<211> LENGTH: 349
<212> TYPE: PRT
<213> ORGANISM: Drosophila melanogaster

<400> SEQUENCE: 96

Met Ser Gly Cys Arg Ala Met Ala Leu Phe Thr Thr Glu Glu Arg
 1               5                  10                  15

Leu Leu Pro Tyr Arg Ser Lys Trp His Thr Leu Val Tyr Ile Gln Met
                20                  25                  30

Val Ile Phe Phe Ala Ser Met Ser Phe Gly Leu Thr Glu Ser Met Gly
            35                  40                  45

Asp His Val Gln Met Gly Arg Asp Leu Ala Phe Ile Leu Gly Thr Tyr
        50                  55                  60

Tyr Phe Cys Trp Tyr Gly Asp Glu Leu Asp Gln Val Ile Ser Asp Leu
65                  70                  75                  80

Asp Ala Leu His Pro Trp Ala Gln Lys Gly Pro Asn Pro Val Glu Tyr
                85                  90                  95

Gln Thr Gly Lys Arg Trp Tyr Phe Val Met Ala Phe Phe Leu Ala Thr
            100                 105                 110

Ser Trp Ser Phe Phe Leu Cys Ile Leu Leu Leu Leu Ile Thr Ser
        115                 120                 125

Pro Met Trp Val His Gln Gln Asn Leu Pro Phe His Ala Ala Phe Pro
    130                 135                 140

Phe Gln Trp His Glu Lys Ser Leu His Pro Ile Ser His Ala Ile Ile
145                 150                 155                 160

Tyr Leu Phe Gln Ser Tyr Phe Ala Val Tyr Cys Leu Thr Trp Leu Leu
                165                 170                 175

Cys Ile Glu Gly Leu Ser Ile Cys Ile Tyr Ala Glu Ile Thr Phe Gly
            180                 185                 190

Ile Glu Val Leu Cys Leu Glu Leu Arg Gln Ile His Arg His Asn Tyr
        195                 200                 205

|                                                           |     |
|-----------------------------------------------------------|-----|
| Gly Leu Gln Glu Leu Arg Met Glu Thr Asn Arg Leu Val Lys Leu His<br>    210                 215                 220                         |     |
| Gln Lys Ile Met Gly Val Asn Phe Ser Leu Val Ser Leu Ser Val Leu<br>225                 230                 235                 240     |     |
| Glu Ala Val Glu Ala Arg Lys Asp Pro Lys Val Val Ala Gln Phe Ala<br>                245                 250                 255         |     |
| Val Leu Met Leu Leu Ala Leu Gly His Leu Ser Met Trp Ser Tyr Cys<br>            260                 265                 270             |     |
| Gly Asp Gln Leu Ser Gln Lys Ser Leu Gln Ile Ser Glu Ala Ala Tyr<br>        275                 280                 285                 |     |
| Glu Ala Tyr Asp Pro Thr Lys Gly Ser Lys Asp Val Tyr Arg Asp Leu<br>    290                 295                 300                     |     |
| Cys Val Ile Ile Arg Arg Gly Gln Asp Pro Leu Ile Met Arg Ala Ser<br>305                 310                 315                 320     |     |
| Pro Phe Pro Ser Phe Asn Leu Ile Asn Tyr Ser Ala Ile Leu Asn Gln<br>                325                 330                 335         |     |
| Cys Tyr Gly Ile Leu Thr Phe Leu Leu Lys Thr Leu Asp<br>            340                 345                                             |     |

<210> SEQ ID NO 97
<211> LENGTH: 1185
<212> TYPE: DNA
<213> ORGANISM: Drosophila melanogaster
<220> FEATURE:
<221> NAME/KEY: CDS
<222> LOCATION: (1)..(1185)
<223> OTHER INFORMATION: DORLU 28.1

<400> SEQUENCE: 97

|                                                                                              |     |
|----------------------------------------------------------------------------------------------|-----|
| atg gaa ttg aaa tcg atg gat ccg gtg gag atg ccc att ttt ggt agc<br>Met Glu Leu Lys Ser Met Asp Pro Val Glu Met Pro Ile Phe Gly Ser<br>1               5                  10                  15                         | 48  |
| act ctg aag cta atg aag ttc tgg tca tat ctg ttt gtt cac aac tgg<br>Thr Leu Lys Leu Met Lys Phe Trp Ser Tyr Leu Phe Val His Asn Trp<br>            20                  25                  30                             | 96  |
| cgc cgc tat gtc gca atg act ccg tac atc att atc aac tgt act cag<br>Arg Arg Tyr Val Ala Met Thr Pro Tyr Ile Ile Ile Asn Cys Thr Gln<br>        35                  40                  45                                 | 144 |
| tat gtg gat ata tat ctg agc acc gaa tcc ttg gac ttt atc atc aga<br>Tyr Val Asp Ile Tyr Leu Ser Thr Glu Ser Leu Asp Phe Ile Ile Arg<br>    50                  55                  60                                     | 192 |
| aat gta tac ctg gct gta ttg ttt acc aac acg gtg gtc aga ggt gta<br>Asn Val Tyr Leu Ala Val Leu Phe Thr Asn Thr Val Val Arg Gly Val<br>65                  70                  75                  80                     | 240 |
| ttg tta tgc gta cag cgg ttt agc tac gag cgt ttc att aat att ttg<br>Leu Leu Cys Val Gln Arg Phe Ser Tyr Glu Arg Phe Ile Asn Ile Leu<br>                85                  90                  95                         | 288 |
| aaa agc ttt tac att gag ttg ttg caa tca gat gac ccc atc ata aac<br>Lys Ser Phe Tyr Ile Glu Leu Leu Gln Ser Asp Asp Pro Ile Ile Asn<br>            100                 105                 110                            | 336 |
| att ttg gtc aag gaa acc aca cgc cta tca gtt tta att agt agg att<br>Ile Leu Val Lys Glu Thr Thr Arg Leu Ser Val Leu Ile Ser Arg Ile<br>        115                 120                 125                                | 384 |
| aat tta tta atg ggc tgc tgc act tgc att ggc ttt gtt aca tat ccc<br>Asn Leu Leu Met Gly Cys Cys Thr Cys Ile Gly Phe Val Thr Tyr Pro<br>    130                 135                 140                                     | 432 |
| att ttt ggt tcg gaa aga gtt ctg cca tat ggc atg tat ttg ccc act<br>Ile Phe Gly Ser Glu Arg Val Leu Pro Tyr Gly Met Tyr Leu Pro Thr<br>145                 150                 155                 160                     | 480 |

```
att gat gaa tac aaa tac gca tca cct tac tac gag att ttc ttt gtg      528
Ile Asp Glu Tyr Lys Tyr Ala Ser Pro Tyr Tyr Glu Ile Phe Phe Val
            165                 170                 175 att caa gcc att atg gct cca atg ggg tgt tgc atg tac ata cca tac      576
Ile Gln Ala Ile Met Ala Pro Met Gly Cys Cys Met Tyr Ile Pro Tyr
        180                 185                 190 aca aac atg gta gtg aca ttt acc ctt ttc gcc att ctc atg tgt cga      624
Thr Asn Met Val Val Thr Phe Thr Leu Phe Ala Ile Leu Met Cys Arg
        195                 200                 205 gtg ttg caa cat aag ttg aga agc cta gaa aag ctg aaa aat gaa caa      672
Val Leu Gln His Lys Leu Arg Ser Leu Glu Lys Leu Lys Asn Glu Gln
    210                 215                 220 gta cgt ggt gaa atc ata tgg tgc ata aaa tat caa tta aaa tta tca      720
Val Arg Gly Glu Ile Ile Trp Cys Ile Lys Tyr Gln Leu Lys Leu Ser
225                 230                 235                 240 gga ttt gtt gat tca atg aat gcc ttg aac acc cat ctt cat ttg gtg      768
Gly Phe Val Asp Ser Met Asn Ala Leu Asn Thr His Leu His Leu Val
                245                 250                 255 gag ttc ctt tgc ttt ggt gcc atg cta tgt gtt ctt ctt ttc tcc tta      816
Glu Phe Leu Cys Phe Gly Ala Met Leu Cys Val Leu Leu Phe Ser Leu
            260                 265                 270 ata att gct caa aca att gct cag acc gtc ata gtc atc gca tac atg      864
Ile Ile Ala Gln Thr Ile Ala Gln Thr Val Ile Val Ile Ala Tyr Met
        275                 280                 285 gta atg ata ttt gcc aac agt gta gtc ctt tac tac gtg gcc aat gag      912
Val Met Ile Phe Ala Asn Ser Val Val Leu Tyr Tyr Val Ala Asn Glu
        290                 295                 300 cta tac ttt caa gta aga gtt gtc caa ttt tct ttt aaa ttt ttg tat      960
Leu Tyr Phe Gln Val Arg Val Val Gln Phe Ser Phe Lys Phe Leu Tyr
305                 310                 315                 320 aag tat ggg att ttg cag agc ttt gat att gcc att gct gcc tat gag     1008
Lys Tyr Gly Ile Leu Gln Ser Phe Asp Ile Ala Ile Ala Ala Tyr Glu
                325                 330                 335 agc aat tgg atg gac ttt gat gtg gac aca caa aag act ttg aag ttc     1056
Ser Asn Trp Met Asp Phe Asp Val Asp Thr Gln Lys Thr Leu Lys Phe
            340                 345                 350 ctc atc atg cgc tcg caa aag ccc ttg gcg act ctg gtg ggt ggc aca     1104
Leu Ile Met Arg Ser Gln Lys Pro Leu Ala Thr Leu Val Gly Gly Thr
        355                 360                 365 tat ccc atg aac ttg aaa atg ctt cag tca cta cta aat gcc att tac     1152
Tyr Pro Met Asn Leu Lys Met Leu Gln Ser Leu Leu Asn Ala Ile Tyr
        370                 375                 380 tcc ttc ttc acc ctt ctg cgt cgc gtt tac ggc                         1185
Ser Phe Phe Thr Leu Leu Arg Arg Val Tyr Gly
385                 390                 395

<210> SEQ ID NO 98
<211> LENGTH: 395
<212> TYPE: PRT
<213> ORGANISM: Drosophila melanogaster

<400> SEQUENCE: 98

Met Glu Leu Lys Ser Met Asp Pro Val Glu Met Pro Ile Phe Gly Ser
 1               5                  10                  15

Thr Leu Lys Leu Met Lys Phe Trp Ser Tyr Leu Phe Val His Asn Trp
            20                  25                  30

Arg Arg Tyr Val Ala Met Thr Pro Tyr Ile Ile Asn Cys Thr Gln
        35                  40                  45

Tyr Val Asp Ile Tyr Leu Ser Thr Glu Ser Leu Asp Phe Ile Ile Arg
    50                  55                  60
```

```
Asn Val Tyr Leu Ala Val Leu Phe Thr Asn Thr Val Val Arg Gly Val
 65                  70                  75                  80

Leu Leu Cys Val Gln Arg Phe Ser Tyr Glu Arg Phe Ile Asn Ile Leu
                 85                  90                  95

Lys Ser Phe Tyr Ile Glu Leu Gln Ser Asp Asp Pro Ile Ile Asn
            100                 105                 110

Ile Leu Val Lys Glu Thr Thr Arg Leu Ser Val Leu Ile Ser Arg Ile
            115                 120                 125

Asn Leu Leu Met Gly Cys Cys Thr Cys Ile Gly Phe Val Thr Tyr Pro
130                 135                 140

Ile Phe Gly Ser Glu Arg Val Leu Pro Tyr Gly Met Tyr Leu Pro Thr
145                 150                 155                 160

Ile Asp Glu Tyr Lys Tyr Ala Ser Pro Tyr Tyr Glu Ile Phe Phe Val
                165                 170                 175

Ile Gln Ala Ile Met Ala Pro Met Gly Cys Cys Met Tyr Ile Pro Tyr
            180                 185                 190

Thr Asn Met Val Val Thr Phe Thr Leu Phe Ala Ile Leu Met Cys Arg
            195                 200                 205

Val Leu Gln His Lys Leu Arg Ser Leu Glu Lys Leu Lys Asn Glu Gln
210                 215                 220

Val Arg Gly Glu Ile Ile Trp Cys Ile Lys Tyr Gln Leu Lys Leu Ser
225                 230                 235                 240

Gly Phe Val Asp Ser Met Asn Ala Leu Asn Thr His Leu His Leu Val
                245                 250                 255

Glu Phe Leu Cys Phe Gly Ala Met Leu Cys Val Leu Leu Phe Ser Leu
                260                 265                 270

Ile Ile Ala Gln Thr Ile Ala Gln Thr Val Ile Val Ile Ala Tyr Met
            275                 280                 285

Val Met Ile Phe Ala Asn Ser Val Val Leu Tyr Tyr Val Ala Asn Glu
            290                 295                 300

Leu Tyr Phe Gln Val Arg Val Val Gln Phe Ser Phe Lys Phe Leu Tyr
305                 310                 315                 320

Lys Tyr Gly Ile Leu Gln Ser Phe Asp Ile Ala Ile Ala Ala Tyr Glu
                325                 330                 335

Ser Asn Trp Met Asp Phe Asp Val Asp Thr Gln Lys Thr Leu Lys Phe
                340                 345                 350

Leu Ile Met Arg Ser Gln Lys Pro Leu Ala Thr Leu Val Gly Gly Thr
            355                 360                 365

Tyr Pro Met Asn Leu Lys Met Leu Gln Ser Leu Leu Asn Ala Ile Tyr
370                 375                 380

Ser Phe Phe Thr Leu Leu Arg Arg Val Tyr Gly
385                 390                 395

<210> SEQ ID NO 99
<211> LENGTH: 1579
<212> TYPE: DNA
<213> ORGANISM: Drosophila melanogaster
<220> FEATURE:
<223> OTHER INFORMATION: DOR 22A.2, NCBI Accession No. AF127924
<220> FEATURE:
<221> NAME/KEY: intron
<222> LOCATION: (1)..(122)
<220> FEATURE:
<221> NAME/KEY: intron
<222> LOCATION: (251)..(310)
<220> FEATURE:
<221> NAME/KEY: intron
```

<222> LOCATION: (950)..(1579)

<400> SEQUENCE: 99

```
cgaaacaaag cttaagttct tgaaatcgcc aagtcatgtg agaccatttg caacagtgag      60
gcggcctata aaaagcactg ttttccagct caagcaaata atcaaaaaga gccacggacg     120
aaatgttaag ccagttcttt ccccacatta agaaaagcc attgagcgag cgggttaagt      180
cccgagatgc cttcgtttac ttagatcggg tgatgtggtc ctttggctgg acagtgcctg    240
aaaacaaaag gtaatgaaat cgatctaagc acatatataa gtattaaagc aaccataatt    300
tcacgataag gtgggatcta cattacaaac tgtggtcaac tttcgtgaca ttgttgatat    360
ttatccttct gccgatatcg gtaagcgttg agtatattca gcggttcaag accttctcgg   420
cgggtgagtt tcttagctca atccagattg gcgttaacat gtacggaagc agctttaaaa   480
gttatttgac catgatggga tataagaaga gacaggaggc taagatgtca ctggatgagc   540
tggacaagag atgcgtttgt gatgaggaga ggaccattgt acatcgacat gtcgccctgg   600
gaaacttttg ctatatttc tatcacattg cgtacactag cttttttgatt tcaaactttt    660
tgtcatttat aatgaagaga atccatgcct ggcgcatgta ctttccctac gtcgaccccg   720
aaaagcaatt ttacatctct agcatcgccg aagtcattct tagggatgg gccgtcttca    780
tggatctctg cacggatgtg tgtcctttga tctccatggt aatagcacga tgccacatca   840
cccttctgaa acagcgcctg cgaaatctac gatcggaacc aggaaggacg gaagatgagt   900
acttgaagga gctcgccgac tgcgttcgag atcaccgctt gatattggag taagctgttt  960
aaaaggactt accgtcatca atcttaaata taaatactac cgggttgttt tctatcaatg   1020
aaatttgttg cacttactgt aatttacaat ttgttttgac aaattttttt atttacctta  1080
cttttttcagc tatgtcgacg cattgcgatc cgtcttttcg gggacaattt ttgtgcagtt   1140
cctcttgatc ggtattgtac tgggtctgtc aatgataaat ataatgtttt tctcaacact   1200
ttcgactggt gtcgccgttg tccttttat gtcctgcgta tctatgcaga cgttcccctt    1260
ttgctatttg tgtaacatga ttatggatga ctgccaagag atggccgact cccttttttca  1320
atcggactgg acatctgccg atcgtcgcta caaatccact ttggtatact ttcttcacaa   1380
tcttcagcag cccattattc ttacggctgg tggagtcttt cctatttcca tgcaaacaaa   1440
tttaaatgtg agtatcaatc aatatgagct ataatgtatg tatgagatta aaattactat   1500
tcttttatag atggtgaagc tggcctttac tgtggttaca atagtgaaac aatttaactt   1560
ggcagaaaag tttcaataa                                                  1579
```

<210> SEQ ID NO 100
<211> LENGTH: 3500
<212> TYPE: DNA
<213> ORGANISM: Drosophila melanogaster
<220> FEATURE:
<223> OTHER INFORMATION: DOR 22C.1, segment of BDGP Clone No. AC004716
<220> FEATURE:
<221> NAME/KEY: intron
<222> LOCATION: (1)..(121)
<220> FEATURE:
<221> NAME/KEY: intron
<222> LOCATION: (454)..(516)
<220> FEATURE:
<221> NAME/KEY: intron
<222> LOCATION: (646)..(859)
<220> FEATURE:
<221> NAME/KEY: intron
<222> LOCATION: (1051)..(1137)
<220> FEATURE:
<221> NAME/KEY: intron

```
<222> LOCATION: (1320)..(2566)
<220> FEATURE:
<221> NAME/KEY: intron
<222> LOCATION: (2669)..(3205)
<220> FEATURE:
<221> NAME/KEY: intron
<222> LOCATION: (3359)..(3449)

<400> SEQUENCE: 100
tagttccatc gagtgcctat aaaagcggtg gccaacattg cgtctgacac ttgcccggag      60
cagctgacca ctggagttgc ggtaggagca tcgatagtat ccacttgagt tcatcccaga     120
aatgactgac agcgggcagc ctgccattgc cgaccacttt tatcggattc cccgcatctc     180
cggcctcatt gtcggcctct ggccgcaaag gataaggggc gggggcggtc gtccttggca     240
cgcccatctg ctcttcgtgt cgccttcgc catggtggtg gtgggtgcgg tgggcgaggt      300
gtcgtacggc tgtgtccacc tggacaacct ggtggtggcg ctggaggcct tctgccccgg     360
aaccaccaag gcggtctgcg ttttgaagct gtgggtcttc ttccgctcca atcgccggtg     420
ggcggagttg gtccagcgcc tgcgggctat tttgtgggaa tcgcggcggc aggaggccca     480
gaggatgctg gtcggactgg ccaccacggc caacaggctc agcctgttgt tgctcagctc     540
tggcacggcg acaaatgccg ccttcacctt gcaaccgctg attatgggtc tctaccgctg     600
gattgtgcag ctgccaggtc aaaccgagct gcccttttaat atcatgtgag taagctagtt    660
tgtggtttct aacgctattt cgtgcaactt tattacttac gtaagcatcg cgtatccgtt     720
aagatgaaaa gttcctcaac caatttggtt gatggcaggt gatacataag taatgattcc     780
aattgccccc gccagaagca cttaagatac gccatccgcc atccgccatt cgccattaat     840
cgcagttcct tttaaacaga ctgccctcgt ttgccgtgca gccaggagtc tttccgctca     900
cctacgtgct gctgaccgct tccggtgcct gcaccgtttt cgccttcagc ttcgtggacg     960
gattcttcat ttgctcgtgc ctctacatct gcggcgcttt ccggctggtg cagcaggaca    1020
ttcgcaggat atttgccgat ttgcatggcg gtgggtctgg ctctgctgcg gcacgatgac    1080
aatggttttc cctcgctcga tgactttcct tggctttcct ttcccttgca gactcagtgg    1140
atgtgttcac cgaggagatg aacgcggagg tgcggcacag actggcccaa gttgtcgagc    1200
ggcacaatgc gattatcgat ttctgcacgg acctaacacg ccagttcacc gttatcgttt    1260
taatgcattt cctgtccgcc gccttcgtcc tctgctcgac catcctggac atcatgttgg    1320
tgagccccct tcagaggcc ttcctttggg gcgggtatcc ttggggttaa tcaaaaaact     1380
gttgcaacca ggagtggtac caatatcaaa gcccccttta atattttgcc agtttgtcgc    1440
gccactggct tttcgcatcg cctgcattcg gcggctgttt taaaagtttt tcctgtcttt    1500
cactgtttgc tgttttccc tggcttttcc agccgctccg ttctgattcg ttttcccga      1560
tttgtttgtt tgctttgtgg ctgcggctgc ggctctctcc ggtggcaatt tataagcgca    1620
tgaattgtta ctgctcccca aaaagttttt aatgcgactt tcgcacgttt tccggtgtcc    1680
cggacaccgg agacccataa gctgtttgct gcaactggcg aacggagtgg aaatgttcgg    1740
gaaaggctca tggctcctgg cttctggccc caatgggata aatgctgcca gcaatttctt    1800
agcccttctg ccgcttcttt ttcggcccaa agtggtgttg agtaatccat tcgaaacttg    1860
tttatcgctc ggggatcctg cgaccagcga tctattatca cttttttaagt ctgttcgtga   1920
atggagggct gggaagacct aaaggcacac tgagttttga cacgtgctcg ataagagaaa    1980
tatgaataca aagtttgtac ttttccgaag ctatttttat ttgagcaaac ttgtatatcg    2040
aaaactcatg gttaatagaa atcagtaata tacagtagca gtcccttata aaccttcctt    2100
```

-continued

```
acttgaagtt agcaaccttc aagctaatgc caaaacacaa ttaaaataag ctcagaagaa     2160
gcggaagagc ggaaatgcaa tttattgtaa gccaatcctg ttggggactt ataaaatgga     2220
gcattgtcac agttttaggc actcgacgac atgcataaga tgcataattc tttttcaatg     2280
ccacaatggg aggaatgtca ggcgagtgga aaatgggaaa acgagaggaa aagcaatcag     2340
actgcagacc atttgccaaa gtgcatttct ctgatgtttt ccattttcgc gactacttca     2400
agcccgagca cgccacataa aacgacggta tatatacact tatattatat attagataat     2460
cccctgcact ttttcaccac cagcaatttc gctccaatta atgacgtccc cccccacac     2520 ttctcacttt ccgcaccctc caattcttcg tcttccgtct ccgcagaaca cgtcgtcgtt     2580
gagcggctta acctacatct gctatatcat cgcggcccta acgcagctat tcctctactg     2640
cttcggaggc aatcacgtca gcgagagtgt gagtacgact cctgaccaca ccccgaaatc     2700
tcccccactt tccactttc cgggctcagc ccatttcat ttccatcact cattcggcct     2760
tagatactct ggcgaaggag ttgtcactga actcgatgcg attggagtgt tgagtaaact     2820
aacttaacta ataataacc aagcatagct tactttaga agcttttatg aatatttatt     2880
aaattctctt gtttcccatt taaatcctgc catggatttc tccattatca tcttgtgctt     2940
tcctgctatt aagaatatgc tgtgtgtgta tttttcacc attcgtgtaa tttccatttg     3000
acgctaaaca tttagcagcc aggcggccac ataaaaaatg atgtgccatt cacaaattgc     3060
acttgcgata aaattttaat tacacaacaa agtgtgtaac cgcaccgccc accccagatc     3120
cacatccaca tccacatcca gctccagatt ccgtgccaca acccattcca ctgactaccg     3180
actccttctc cttctcttta cacagagtgc ggctgtggcg gacgtgctgt acgacatgga     3240
gtggtacaaa tgcgatgcga ggactaggaa agtgatttta atgatattgc gccgttcgca     3300
gcgggcaaaa acaattgcgg tgccgttttt tacgccctca ctgccagcac tccgatctgt     3360
atgggatgcc atgcgatgcg ttgattatga taataaatgt ttatgtttct gtttccgttt     3420
ccacttcgat catctgcccg gcactccaga tactcagcac agccggctca tatatcacgc     3480
tgctaaagac gttcctgtaa                                                 3500
```

<210> SEQ ID NO 101
<211> LENGTH: 1312
<212> TYPE: DNA
<213> ORGANISM: Drosophila melanogaster
<220> FEATURE:
<223> OTHER INFORMATION: DOR 23A.1, NCBI Accession No. AF127925
<220> FEATURE:
<221> NAME/KEY: intron
<222> LOCATION: (1)..(121)
<220> FEATURE:
<221> NAME/KEY: intron
<222> LOCATION: (838)..(888)

<400> SEQUENCE: 101

```
gatttaattt gcgatttaat aaccoctgac taatggcgca actgacacag aaaggtgata      60 taatggtcg aggtcctttt gaaagtatgc cagtgaaaaa gaaagacacc aagaattcaa     120
aatgaagctc agcgaaaccc taaaaatcga ctattttcga gtccagttga atgcctggcg     180
aatttgtggt gccttggatc tcagcgaggg taggtactgg agttggtcga tgctattgtg     240
catcttggtg tacctgccga cacccatgct actgagagga gtatacagtt cgaagatcc      300 ggtggaaaat aatttcagct tgagcctgac ggtcacttcg ctgtccaatc tcatgaagtt     360
ctgcatgtac gtggcccaac taacaaagat ggtcgaggtc cagagtctta ttggtcagct     420
```

```
ggatgcccgg gtttctggcg agagccagtc tgagcgtcat agaaatatga ccgagcacct    480
gctaaggatg tccaagctgt tccagatcac ctacgctgta gtcttcatca ttgctgcagt    540
tcccttcgtt ttcgaaactg agctaagctt acccatgccc atgtggtttc ccttcgactg    600
gaagaactcg atggtggcct acatcggagc tctggttttc caggagattg ctatgtctt     660 tcaaattatg caatgctttg cagctgactc gtttccccg ctcgtactgt acctgatctc     720
```
ggatgcccgg gtttctggcg agagccagtc tgagcgtcat agaaatatga ccgagcacct    480
gctaaggatg tccaagctgt tccagatcac ctacgctgta gtcttcatca ttgctgcagt    540
tcccttcgtt ttcgaaactg agctaagctt acccatgccc atgtggtttc ccttcgactg    600
gaagaactcg atggtggcct acatcggagc tctggttttc caggagattg ctatgtctt    660 tcaaattatg caatgctttg cagctgactc gtttccccg ctcgtactgt acctgatctc    720
cgagcaatgt caattgctga tcctgagaat ctctgaaatc ggatatggtt acaagactct    780
ggaggagaac gaacaggatc tggtcaactg catcagggga caaaacgcgc tgtataggta    840
atcctactat ctctatgttt ccagttctaa tactcaatct tcctttagat tactcgatgt    900
gaccaagagt ctcgtttcgt atcccatgat ggtgcagttt atggttattg gcatcaacat    960
cgccatcacc ctatttgtcc tgatatttta cgtggagacc ttgtacgatc gcatctatta   1020
tctttgcttt ctcttgggca tcaccgtgca gacatatcca ttgtgctact atggaaccat   1080
ggtgcaggag agttttgctg agcttcacta tgcggtattc tgcagcaact gggtggatca   1140
aagtgccagc tatcgtgggc acatgctcat cctggcggag cgcactaagc ggatgcagct   1200
tctcctcgcc ggcaacctgg tgcccatcca cctgagcacc tacgtggcct gttggaaggg   1260
agcctactcc ttcttcaccc tgatggccga tcgagatggc ctgggttctt ag           1312

<210> SEQ ID NO 102
<211> LENGTH: 1532
<212> TYPE: DNA
<213> ORGANISM: Drosophila melanogaster
<220> FEATURE:
<223> OTHER INFORMATION: DOR 24D1., segment of DBGP Clone No. AC004371
<220> FEATURE:
<221> NAME/KEY: intron
<222> LOCATION: (1)..(87)
<220> FEATURE:
<221> NAME/KEY: intron
<222> LOCATION: (403)..(456)
<220> FEATURE:
<221> NAME/KEY: intron
<222> LOCATION: (609)..(689)
<220> FEATURE:
<221> NAME/KEY: intron
<222> LOCATION: (1063)..(1114)
<220> FEATURE:
<221> NAME/KEY: intron
<222> LOCATION: (1214)..(1268)
<220> FEATURE:
<221> NAME/KEY: intron
<222> LOCATION: (1422)..(1481)

<400> SEQUENCE: 102
aatatataca tgcagttcca aaggctataa aggacgaggg tcaaaggatt atgggctgaa     60
aagtgtttgg tgtcctcgga gagaaagatg ttacctcgat tcctgaccgc ctcctatcca    120
atggagcgcc attatttcat ggtgccaaag tttgcattat cgctgattgg tttttatccc    180
gaacagaagc gaacggtttt ggtgaaactt tggagtttct tcaacttttt catcctcacc    240
tacggctgtt atgcagaggc ttactatggc atacactata taccgattaa catagccact    300
gcattggatg ccctttgtcc tgtggcctcc agcatttgt cgctggtgaa atggtcgcc     360 atttggtggt atcaagatga attaaggagt ttgatagagc gggtaagatt tttaacagag    420
caacagaagt ccaagaggaa actgggctat aagaagaggt tctatacact ggcaacgcaa    480
ctaacattcc tgctactatg ctgtggattt tgcaccagta cttcctattc cgtcagacat    540
ttgattgata atatcctgag acgcacccat ggcaaggact ggatctacga gactccgttc    600
aagatgatgt aaggaaaggg aagaatggtt tatatatact tttggaacga ataatgatg     660

```
tgatctaaac aagatgcact ttttttagg ttccccgatc ttctcctgcg tttgccactc      720
tatcccatca cctatatact cgtgcattgg catggctaca ttactgtggt ttgttttgtc      780
ggcgcggatg gtttcttcct ggggttctgt ttgtacttca ctgttttgct gctctgtctg      840
caggacgatg tttgtgattt actagaggtt gaaaacatcg agaagagtcc ctccgaagcg      900
gaggaagctc gcatagttcg ggaaatggaa aaactggtgg accggcataa cgaggtggcc      960
gagctgacag aaagattgtc gggtgttatg gtggaaataa cactggccca ctttgttact     1020
tcgagtttga taatcggaac cagcgtggtg gatattttat tagtgggtat ttacatttga     1080
ttagatcctt tcgatatatg ttcttaaatt ctagttttcc ggcctgggaa tcattgtgta     1140
tgtggtctac acttgtgccg taggtgtgga aatatttcta tactgtttag gaggatctca     1200
tattatggaa gcggtatatt cataagaaac tactataaag ttacttttaa attcattgca     1260
tttcttagtg ttccaatcta cgcgctcca cattttccag ccactggtat ggccacagtg      1320
ttcgggtcca aaagatgacc cttttgatgg tagctcgtgc tcaacgagtt ctcacaatta     1380
aaattccttt ctttttcccca tcattagaga ctctaacttc ggtaagctta tgcgaaaatg     1440
ttatggtaca cacaagtcta cattcctatg aggtcttgta gattttgcgc ttcactggat     1500
ctctgattgc cctggcaaag tcggttatat aa                                    1532
```

<210> SEQ ID NO 103
<211> LENGTH: 1691
<212> TYPE: DNA
<213> ORGANISM: Drosophila melanogaster
<220> FEATURE:
<223> OTHER INFORMATION: DOR 25A.1, segment of BDGP Clone No. AC005463
<220> FEATURE:
<221> NAME/KEY: intron
<222> LOCATION: (1)..(121)
<220> FEATURE:
<221> NAME/KEY: intron
<222> LOCATION: (898)..(1192)
<220> FEATURE:
<221> NAME/KEY: intron
<222> LOCATION: (1551)..(1613)

<400> SEQUENCE: 103

```
aagaggaacg cctactaaat tgcaaacat taattaagaa ctacaaatcg cggactataa       60
aagcattccg agctcctcct atcgccagtt atattatagc cttaaacatt cgaaacttta      120
gatgttcgga cactttaagc tcgtctatcc ggctcctata tcggagccca tacagtctag     180
ggattcgaat gcatacatga tggagacgct gcgaaattcg ggcttgaatt tgaagaacga     240
tttcggtata ggccgcaaga tttggagggt gttttcgttc acctacaata tggtgatact     300
tcccgtaagt ttcccaatca actatgtgat acatctggcg gagttcccgc cggagctgct     360
gctgcaatcc ctgcaactgt gcctcaacac ttggtgcttc gctctgaagt tcttcactct     420
gatcgtctat acgcaccgct tggagctggc caacaagcac tttgacgaat tggataagta     480
ctgcgtgaag ccggcggaga agcgcaaggt tcgcgacatg gtgccacta ttacaagact      540 gtacctgacc ttcgtcgtgg tctacgtcct ctacgccacc tccacgctac tggacggact     600
actgcaccac cgtgttccct acaatacgta ctatccgttc ataaactggc gagtcgatcg     660
gacccagatg tacatccaga gttttctgga gtacttcacc gtgggttatg ccatatatgt     720
ggccaccgcc accgattcct accctgtgat ttacgtggca gccctgcgaa ctcatattct     780
cttgctcaag gaccgtatca tttacttggg cgatcccagc aacgagggta gcagcgaccc     840
gagctacatg tttaaatcgt tggtggattg tatcaaggca cacagaacca tgctaaagta     900
```

-continued

```
agtcagtttc attatcctac cggaaatatc aacaaccgtg aattatgttt tcactcaacg      960
gatctgaatt tattcggaaa actgaataaa agtacaactt ttataagaac tcgctattga     1020
tatttctgaa tatataagag tatattttta cattcaggat aaaataaatg gtatatcaaa     1080
cgattcgaca taaaactatt ttatttcaaa taaattagct tacattttt aaaatatatg      1140 cattaattta aattttcaat gttaaaaacc catcccactg tttcccatgc agttttttgtg    1200 atgccattca accaatcatc tctggcacga tatttgccca attcatcata tgcggatcga    1260
tcctgggcat aattatgatc aacatggtat tgttcgctga tcaatcgacc cgattcggca   1320
tagtcatcta cgttatggcc gtccttctgc agacttttcc gctttgcttc tactgcaacg   1380
ccatcgtgga cgactgcaaa gaactggccc acgcactttt ccattccgcc tggtgggtgc   1440
aggacaagcg ataccagcgg actgtcatcc agttcctgca gaaactgcag cagcccatga   1500
ccttcaccgc catgaacata tttaacatta atttggccac taacatcaat gtaagtccac    1560
tgctctcggt tagaacgggg aaggaagcaa agtccgaact tcaatccttg caggtagcca   1620
agttcgcctt caccgtgtac gccatcgcga gcggtatgaa cctggaccaa aagttaagca   1680
ttaaggaata g                                                         1691
```

<210> SEQ ID NO 104
<211> LENGTH: 1333
<212> TYPE: DNA
<213> ORGANISM: Drosophila melanogaster
<220> FEATURE:
<223> OTHER INFORMATION: DOR 33B.1, region of BDGP Clone No. AC006240
<220> FEATURE:
<221> NAME/KEY: intron
<222> LOCATION: (1)..(121)
<220> FEATURE:
<221> NAME/KEY: intron
<222> LOCATION: (844)..(918)

<400> SEQUENCE: 104

```
ctggaatcaa ttaaatataa ttgcggggac aacaattacg tctacccgac ttaaatttaa      60
ttattaaaag ggaccagtat aaaaggaaag gcggtacata acttgtccaa ttgtttcaaa     120
tatggattca agaaggaaag tccgaagtga aaatctttac aaaacctatt ggctttactg     180
gcgacttctg ggagtcgagg gcgattatcc ttttcgacgg ctagtggatt ttacaatcac     240
gtctttcatt acgattttat ttcccgtgca tcttatactg ggaatgtata aaaagcccca    300
gattcaagtc ttcaggagtc tgcatttcac atcggaatgc cttttctgca gctataagtt    360
tttctgtttt cgttggaaac ttaaagaaat aaagaccatc gaaggattgc tccaggatct    420
cgatagtcga gttgaaagtg aagaagaacg caactacttt aatcaaaatc caagtcgtgt    480
ggctcgaatg ctttcgaaaa gttacttggt agctgctata tcggccataa tcactgcaac    540
tgtagctggt ttatttagta ctggtcgaaa tttaatgtat ctgggttggt ttccctacga    600
ttttcaagca accgccgcaa tctattggat tagttttttcc tatcaggcga ttggctctag   660
tctgttgatt ctgaaaaatc tggccaacga ttcatatccg ccgattacat tttgtgtggt   720
ctctggacat gtgagactat tgataatgcg tttaagtcga attggtcacg atgtaaaatt    780
atcaagttcg gaaaatacca gaaaactcat cgaaggtatc caggatcaca ggaaactaat    840
gaagtaagaa taaagattta agaaccgcat gtttgatagc tcagagaact gataattaat    900
caaatgtaac ttttccagga taatacgcct acttcgcagc actttacatc ttagccaact    960
gggccagttc ctttctagtg gaatcaacat ttccataaca ctcatcaaca tcctgttctt   1020
```

```
tgcggaaaac aactttgcaa tgctttatta tgcggtgttc tttgctgcaa tgttaataga    1080
actatttcca agttgttact atggaattct gatgacaatg gagtttgata agctaccata    1140
tgccatcttc tccagcaact ggcttaaaat ggataaaaga tacaatcgat ccttgataat    1200
tctgatgcaa ctaacactgg ttccagtgaa tataaaagca ggtggtattg ttggcatcga    1260
tatgagtgca tttttttgcca cagttcggat ggcatattcc ttttacactt tagccttgtc    1320
atttcgagta tag                                                      1333
```

```
<210> SEQ ID NO 105
<211> LENGTH: 1442
<212> TYPE: DNA
<213> ORGANISM: Drosophila melanogaster
<220> FEATURE:
<223> OTHER INFORMATION: DOR 33B.2, region of BDGP Clone No. AC006240
<220> FEATURE:
<221> NAME/KEY: intron
<222> LOCATION: (1)..(121)
<220> FEATURE:
<221> NAME/KEY: intron
<222> LOCATION: (849)..(1030)

<400> SEQUENCE: 105
```

```
tatagggtta tcaaactcgc agtaaattga tgggcgtaac gatgtgggac tataatttag     60
ccatttagaa cgactagtat aaaagaggaa atgccgcagg accttttcaa ttgtttcaaa    120
catggactta aaaccgcgag tcattcgaag tgaagatatc tacagaacct attggttata    180
ttggcatctt ttgggcctgg aaagcaattt ctttctgaat cgcttgttgg atttggtgat    240
tacaattttc gtaaccattt ggtatccaat tcacctgatt ctgggactgt ttatggaaag    300
atctttgggg gatgtctgca agggtctacc aattacggca gcatgctttt tcgccagctt    360
taaatttatt tgttttcgct tcaagctatc tgaaattaaa gaaatcgaaa tattatttaa    420
agagctggat cagcgagctt taagtcgaga ggaatgcgag ttttttcaatc aaaatacgag    480 acgtgaggcg aatttcattt ggaaaagttt cattgtggcc tatggactgt cgaatatctc    540
ggctattgca tcagttcttt tcggcggtgg acataagcta ttatatcccg cctggttttcc    600 atacgatgtg caggccacgg aactaatatt ttggctaagt gtaacatacc aaattgccgg    660
agtaagtttg gccatacttc agaatttggc caatgattcc tatccaccga tgacattttg    720
cgtggttgcc ggtcatgtaa gacttttggc gatgcgcttg agtagaattg gccaaggtcc    780
agaggaaaca atatacttaa ccggaaagca attaatcgaa agcatcgagg atcaccgaaa    840
actaatgaag taatgtacat atatagaatg gttttttagtt attatcatta aatgaacgtg    900
ttgtaggaaa accattctgt ttgtcgggtg tcacggaaat cgattttcct taatttacat    960
atgatattaa atacttcctt gcaaacaatt atcatattag taatttagaa tctttattat   1020
ttatttccag aatagtggaa ttactgcgca gcaccatgaa tatttcgcag ctcggccagt   1080
ttatttcaag tggtgttaat atttccataa cactagtcaa cattctcttc tttgcggata   1140
ataatttcgc tataacctac tacggagtgt acttcctatc gatggtgttg gaattattcc   1200
cgtgctgcta ttacggcacc ctgatatccg tggagatgaa ccagctgacc tatgcgattt   1260
actcaagtaa ctggatgagt atgaatcgga gctacagccg catcctactg atcttcatgc   1320
aactcaccct ggcggaagtg cagatcaagg ccggtgggat gattggcatc ggaatgaacg   1380
ccttctttgc caccgtgcga ttggcctact ccttcttcac tttggccatg tcgctgcgtt   1440
aa                                                                 1442
```

```
<210> SEQ ID NO 106
<211> LENGTH: 1354
<212> TYPE: DNA
<213> ORGANISM: Drosophila melanogaster
<220> FEATURE:
<223> OTHER INFORMATION: DOR 33B.3, region of BDGP Clone No. AC006240
<220> FEATURE:
<221> NAME/KEY: intron
<222> LOCATION: (1)..(120)
<220> FEATURE:
<221> NAME/KEY: intron
<222> LOCATION: (852)..(930)

<400> SEQUENCE: 106
tatatatatg aatatatgag catcttcttg ttcatagtgg tataatttct cgcagtgttt    60
cctctcatga catctgcata aaagctccag ccttgctggg aaatgtgcat taggtgaaca   120
atggtcatta tcgacagtct tagtttttat cgtccattct ggatctgcat gcgattgctg   180
gtaccgactt tcttcaagga ttcctcacgt cctgtccagc tgtacgtggt gttgctgcac   240
atcctggtca ccttgtggtt tccactgcat ctgctgctgc atcttctgct acttccatct   300
accgctgagt tctttaagaa cctgaccatg tctctgactt gtgtggcctg cagtctgaag   360
catgtggccc acttgtatca cttgccgcag attgtggaaa tcgaatcact gatcgagcaa   420
ttagacacat ttattgccag cgaacaggag catcgttact atcgggatca cgtacattgc   480
catgctaggc gctttacaag atgtctctat attagctttg gcatgatcta tgcgcttttc   540
ctgttcggcg tcttcgttca ggttattagc ggaaattggg aacttctcta tccagcctat   600
ttcccattcg acttggagag caatcgcttt tcggcgcag tagccttggg ctatcaggta   660
ttcagcatgt tagttgaagg cttccagggg ctgggcaacg atacctatac cccactgacc   720
ctatgccttc tggccggaca tgtccatttg tggtccatac gaatgggtca actgggatac   780
ttcgatgacg agacggtggt gaatcatcag cgtttgctgg attacattga gcagcataaa   840
ctcttggtgc ggtaagcttt gattaactaa cttttgacaa gaagtttatt cactttaact   900
ggttccaaaa acgatgcact caatgtgcag attccacaac ctggtgagcc ggaccatcag   960
cgaagtgcaa ctggtgcagc tgggcggatg tggagccact ctgtgcatca ttgtctccta   1020
catgctcttc tttgtgggcg acacaatctc gctggtctac tacttggtgt tctttggagt   1080
ggtctgcgtg cagctctttc ccagctgcta ttttgccagc gaagtagccg aggagttgga   1140
acggctgcca tatgcgatct tctccagcag atggtacgat caatcgcggg atcatcgatt   1200
cgatttgctc atctttacac aattaacact gggaaaccgg gggtggatca tcaaggcagg   1260
aggtcttatc gagctgaatt tgaatgcctt tttcgccacc ctgaagatgg cctattccct   1320
ttttgcagtt gtggtgcggg caaagggtat atag                               1354

<210> SEQ ID NO 107
<211> LENGTH: 1795
<212> TYPE: DNA
<213> ORGANISM: Drosophila melanogaster
<220> FEATURE:
<223> OTHER INFORMATION: DOR 43B.1, NCBI Accession No. AF127926
<220> FEATURE:
<221> NAME/KEY: intron
<222> LOCATION: (1)..(121)
<220> FEATURE:
<221> NAME/KEY: intron
<222> LOCATION: (539)..(692)
<220> FEATURE:
<221> NAME/KEY: intron
<222> LOCATION: (1013)..(1075)
<220> FEATURE:
<221> NAME/KEY: intron
```

```
<222> LOCATION: (1176)..(1319)
<220> FEATURE:
<221> NAME/KEY: intron
<222> LOCATION: (1422)..(1487)
<220> FEATURE:
<221> NAME/KEY: intron
<222> LOCATION: (1596)..(1690)

<400> SEQUENCE: 107
gcccgcagat tgccctcctc gatggcgaca attggtgcag aataaaagac atttgcccag      60
cactttgcag cacagtctgg agtggatctg ccggtaagga gcttatagaa agtgccgagc     120
aatgacaatc gaggatatcg gcctggtggg catcaacgtg cggatgtggc gacacttggc     180
cgtgctgtac cccactccgg gctccagctg gcgcaagttc gccttcgtgc tgccggtgac     240
tgcgatgaat ctgatgcagt tcgtctacct gctgcggatg tggggcgacc tgcccgcctt     300
cattctgaac atgttcttct tctcggccat tttcaacgcc ctgatgcgca cgtggctggt     360
cataatcaag cggcgccagt tcgaggagtt tctcggccaa ctggccactc tgttccattc     420
gattctcgac tccaccgacg agtggggcg tggcatcctg cggagggcgg aacgggaggc     480
tcggaacctg gccatcctta atttgagtgc ctccttcctg gacattgtcg gtgctctggt     540
atcgccgctt ttcagggagg agagaggtta gtacactcac agaatgggat taaaataacc     600
gtcattcaaa tcgaaaggat atttgtagag taaaagagtg gaaaattgct aaatagtggt     660
taaaactgca aagtagtttg tgcattgctt agttttcga atataaattc ccaattggtg     720
ttgtcacttt tttccttcca gctcatccct tcggcttagc tctaccagga gtgagcatga     780
ccagttcacc cgtctacgag gttatctact tggcccaact gcctacgccc tgctgctgt      840
ccatgatgta catgccttc gtcagccttt tgccggcct ggccatcttt gggaaggcca      900
tgctgcagat cctggtacac aggctgggcc agattggcgg agaagagcag tcggaggagg     960
agcgcttcca aaggctggcc tcctgcattg cgtaccacac gcaggtgatg cggtgagccg    1020
cagggggaaga aatcgggggt tggggaaatc tctaagctgc tcatttccat ttcagctatg    1080
tgtggcagct caacaaactg gtggccaaca ttgtggcggt ggaagcaatt atttttggct    1140
cgataatctg ctcactgctc ttctgtctga atattgtagg ccactgattt tgagttcggg    1200
tgccacagag cctccataaa ttggaagaac caaaactttg gatggcggt cttctatggc     1260
actgtggcac tccgagatct aagactgtgg tccttttaaa aataccatta ccattccaga    1320
taacctcacc cacccaggtg atctcgatag tgatgtacat tctgaccatg ctgtacgttc    1380
tcttcaccta ctacaatcgg gccaatgaaa tatgcctcga ggtgatacta ccaactccat    1440
tcaatttgat agctatccat gactccttat aacttgtatc catgcagaac aaccgggtgg    1500
cggaggctgt ttacaatgtg ccctggtacg aggcaggaac tcggtttcgc aaaaccctcc    1560
tgatcttctt gatgcaaaca caacaccga tggaggtggg tgggcattgg gtgcatttca    1620
tttgcgagtc attgcgagga ctgtaatcca tttccattcc gggtgctgtg cgctccattt    1680
catcttgcag ataagagtcg gcaacgttta ccccatgaca ttggccatgt tccagagtct    1740
gttgaatgcg tcctactcct actttaccat gctgcgtggc gtcaccggca aatga           1795

<210> SEQ ID NO 108
<211> LENGTH: 1426
<212> TYPE: DNA
<213> ORGANISM: Drosophila melanogaster
<220> FEATURE:
<223> OTHER INFORMATION: DOR 46F.1, region of BDGP Clone No. AC005974
<220> FEATURE:
<221> NAME/KEY: intron
```

```
<222> LOCATION: (1)..(120)
<220> FEATURE:
<221> NAME/KEY: intron
<222> LOCATION: (949)..(1040)
<220> FEATURE:
<221> NAME/KEY: intron
<222> LOCATION: (1130)..(1185)

<400> SEQUENCE: 108
ataatttaat gattaaccaa cgattaggtc gtctaatgac attttaaatg ccgttcagaa      60
gccttataaa cacttgaacg aatcaattaa tcttaagttc tggaaaaatc tggacgtgaa    120
atgagcaaag gagtagaaat cttttacaag ggccagaagg cattcttgaa catcctctcg    180
ttgtggcctc agatagaacg ccggtggaga atcatccacc aggtgaacta tgtccacgta    240
attgtgtttt gggtgctgct ctttgatctc ctcttggtgc tccatgtgat ggctaatttg    300
agctacatgt ccgaggttgt gaaagccatc tttatcctgg ccaccagtgc agggcacacc    360
accaagctgc tgtccataaa ggcgaacaat gtgcagatgg aggagctctt taggagattg    420
gataacgaag agttccgtcc tagaggcgcc aacgaagagt tgatctttgc agcagcctgt    480
gaaagaagta ggaagcttcg ggacttctat ggagcgcttt cgtttgccgc cttgagcatg    540
attctcatac cccagttcgc cttggactgg tcccaccttc cgctcaaaac atacaatccg    600
cttggcgaga ataccggctc acctgcttat tggctcctct actgctatca gtgtctggcc    660
ttgtccgtat cctgcatcac caacatagga ttcgactcac tctgctcctc actgttcatc    720
ttcctcaagt gccagctgga cattctggcc gtgcgactgg acaagatcgg tcggttaatc    780
actacttctg gtggcactgt ggaacagcaa cttaaggaaa atatccgcta tcacatgacc    840
atcgttgaac tgtcgaaaac cgtggagcgt ctactttgca agccgatttc ggtgcagatc    900
ttctgctcgg ttttggtgct gactgccaat ttctatgcca ttgctgtggt gagctgtgaa    960
ttcgcaacaa gaagactatc ataaatgctt tctagaaaaa caatggtctt aatttgtttt   1020
ccctatatac ataattgtag ttatctgacg agaggctgga gctctttaag tatgtgacct   1080
atcaggcgtg catgttgatt cagattttta tattgtgcta ctatgccggg tgggtattcc   1140
atatccgaaa tgcctcccca ggccagtaat gaatttcatc gtcagtgagg taacccagcg   1200
cagcctggac cttccgcacg agctgtacaa gacctcctgg gtggactggg actacaggag   1260
ccgaaggatt gcgctcctct ttatgcaacg ccttcactcg accttgagga ttaggacact   1320
taatccaagt cttggttttg acttaatgct cttcagctcg gtgagttctt tccgtgtttt   1380
gacttttttg tgcactgtag ccaatttcca taatgaggct cattag                  1426

<210> SEQ ID NO 109
<211> LENGTH: 1337
<212> TYPE: DNA
<213> ORGANISM: Drosophila melanogaster
<220> FEATURE:
<223> OTHER INFORMATION: DOR 46F.2, region of BDGP Clone No. AC005974
<220> FEATURE:
<221> NAME/KEY: intron
<222> LOCATION: (1)..(121)
<220> FEATURE:
<221> NAME/KEY: intron
<222> LOCATION: (1223)..(1283)

<400> SEQUENCE: 109
gcactgtagc caatttccat aatgaggctc attagcgaat ttaagttcgt ggcctataaa      60
aggctttcct cgtgcggttc atgatggaaa agtgaaaatt gtcagcatgt ctcagcatca    120
gatggttacg gaggactttt ataagtacca ggtgtggtac ttccaaatcc ttggtgtttg    180
```

```
gcagctcccc acttgggccg cagaccacca gcgtcgtttt cagtccatga ggtttggctt      240
catcctggtc atcctgttca tcatgctgct gcttttctcc ttcgaaatgt tgaacaacat      300
ttcccaagtt agggagatcc taaaggtatt cttcatgttc gccacggaaa tatcctgcat      360
ggccaaatta ttgcatttga agttgaagag ccgcaaactc gctggcttgg ttgatgcgat      420
gttgtcccca gagttcggcg ttaaaagtga acaggaaatg cagatgctgg aattggatag      480
agtggcggtt gtccgcatga ggaactccta cggcatcatg tccctgggcg cggcttccct      540
gatccttata gttccctgtt tcgacaactt tggcgagcta ccactggcca tgttggaggt      600
atgcagcatc gagggatgga tctgctattg gtcgcagtac cttttccact cgatttgcct      660
gctgcccact tgtgtgctga atataaccta cgactcggtg gcctactcgt tgctctgttt      720
cttgaaggtt cagctacaaa tgctggtcct gcgattagaa aagttgggtc ctgtgatcga      780
accccaggat aatgagaaaa tcgcaatgga actgcgtgag tgtgccgcct actacaacag      840
gattgttcgt ttcaaggacc tggtggagct gttcataaag gggccaggat ctgtgcagct      900
catgtgttct gttctggtgc tggtgtccaa cctgtacgac atgtccacca gtccattgc       960 aaacggcgat gccatcttta tgctcaagac ctgtatctat cagctggtga tgctctggca     1020
gatcttcatc atttgctacg cctccaacga ggtaactgtc cagagctcta ggttgtgtca     1080
cagcatctac agctcccaat ggacgggatg gaacagggca aaccgccgga ttgtccttct     1140
catgatgcag cgctttaatt ccccgatgct cctgagcacc tttaacccca cctttgcttt     1200
cagcttggag gcctttggtt ctgtagggca gcagaaattc ctttatatat catttattac     1260
tggttatgct cttctccttt cagatcgtca actgctccta cagctacttc gcactgctga     1320
agcgcgtcaa cagttaa                                                     1337

<210> SEQ ID NO 110
<211> LENGTH: 1466
<212> TYPE: DNA
<213> ORGANISM: Drosophila melanogaster
<220> FEATURE:
<223> OTHER INFORMATION: DOR 47E.1, NCBI Accession No. AF156880
<220> FEATURE:
<221> NAME/KEY: intron
<222> LOCATION: (1)..(121)
<220> FEATURE:
<221> NAME/KEY: intron
<222> LOCATION: (423)..(478)
<220> FEATURE:
<221> NAME/KEY: intron
<222> LOCATION: (669)..(728)
<220> FEATURE:
<221> NAME/KEY: intron
<222> LOCATION: (1345)..(1415)

<400> SEQUENCE: 110
gggtattaaa gagctgtact ttcgcatctg tatttcattt attcctactc aattgaaagg       60
tttaaaaccc ctgaactgaa cacacttgac ttagtgtgag gccgaattaa cccttgtcga      120
catggacagt tttctgcaag tacagaagag caccattgcc cttctgggct tgatctctt       180 tagtgaaaat cgagaaatgt ggaaacgccc ctatagagca atgaatgtgt ttagcatagc      240
tgccattttt cccttttatcc tggcagctgt gctccataat tggaagaatg tattgctgct      300
ggccgatgcc atggtggccc tactaataac cattctgggc ctattcaagt ttagcatgat      360
actttactta cgtcgcgatt tcaagcgact gattgacaaa tttcgtttgc tcatgtcgaa      420
tggtgagttg taatccattt cggccagaat gtgtatcatt tcatttatta ttttatagag      480
```

-continued

```
gcggaacagg gcgaggaata cgccgagatt ctcaacgcag caaacaagca ggatcaacga      540
atgtgcactc tgtttaggac ttgtttcctc ctcgcctggg ccttgaatag tgttctgccc      600
ctcgtgagaa tgggtctcag ctattggtta gcaggtcatg cagagcccga gttgccttt      660 ccctgtctgt atgtacaaat gatatatatg atatatggtg atcaagttat caggctttgt      720
tcctaaagtt ttccctggaa tatccacatc attcgcaatt atgttttgag cttcatctgg      780
agcgctttcg cctcgacagg tgtggtttta cctgctgtca gcttggatac catattctgt      840
tccttcacca gcaacctgtg cgccttcttc aaaattgcgc agtacaaggt ggttagattt      900
aagggcggat cccttaaaga atcacaggcc acattgaaca aagtctttgc cctgtaccag      960
accagcttgg atatgtgcaa cgatctgaat cagtgctacc aaccgattat ctgcgcccag     1020
ttcttcattt catctctgca actctgcatg ctgggatatc tgttctccat tacttttgcc     1080
cagacagagg gcgtctacta tgcctcattc atagccacaa tcattataca agcctatatc     1140
tactgctact gcggggagaa cctgaagacg gagagtgcca gcttcgagtg ggccatctac     1200
gacagtccgt ggcacgagag tttgggtgct ggtggagcct ctacctcgat ctgccgatcc     1260
ttgctgatca gcatgatgcg ggctcatcgg ggattccgca ttacgggata cttttttcgag    1320 gcaaacatgg aggccttctc atcggtgggt gaatcatttc cattgtacaa tacatggatt     1380
tacatgaata ctcttttcta actttccgtt tttagattgt tcgcacggcg atgtcctaca     1440
tcacaatgct gagatcattc tcctaa                                           1466
```

<210> SEQ ID NO 111
<211> LENGTH: 1724
<212> TYPE: DNA
<213> ORGANISM: Drosophila melanogaster
<220> FEATURE:
<223> OTHER INFORMATION: DOR 47E.2, region of BDGP Clone No. AC005638
<220> FEATURE:
<221> NAME/KEY: intron
<222> LOCATION: (1)..(121)
<220> FEATURE:
<221> NAME/KEY: intron
<222> LOCATION: (256)..(357)
<220> FEATURE:
<221> NAME/KEY: intron
<222> LOCATION: (491)..(552)
<220> FEATURE:
<221> NAME/KEY: intron
<222> LOCATION: (1071)..(1119)
<220> FEATURE:
<221> NAME/KEY: intron
<222> LOCATION: (1328)..(1456)
<220> FEATURE:
<221> NAME/KEY: intron
<222> LOCATION: (1616)..(1673)

<400> SEQUENCE: 111

```
ctcggtgggc gttttttgc aaaacaattg cttataaaca tggtaattag accctggagg       60
cctccttgta catataaaag gaactgaccg cccgcctgga gctcagttca ctttgcga       120 aatgaacgac tcgggttatc aatcaaatct cagccttctg cgggttttc tcgacgagtt      180 ccgatcggtt ctgcggcagg aaagtcccgg tctcatccca cgcctggctt tttactatgt      240
tcgcgccttt ctgaggtgaa tctggcatcg tccatcactc gatccaatct tttataatcc      300
acatttttgc catacccaca gtttgctgtg ccagtatccc aacaagaagt tggccagctt      360 gccctgtac cgatggatca acttgttcat catgtgcaat gtgatgacca ttttctggac       420
catgttcgtg gccctgcccg agtcgaagaa cgtgatcgaa atgggcgacg acttggtttg      480
gatttcgggg gtgagattta ctgattcacc cactcgcaaa tgaacaaact aatggttatt      540
```

```
tctgggtgat agatggcact ggtgttcacc aagatctttt acatgcattt gcgttgcgac      600
gagatcgatg aacttatttc ggattttgaa tactacaacc gggagctgag accccataat      660
atcgatgagg aggtgttggg ttggcagaga ctgtgctacg tgatagaatc gggtctatat      720
atcaactgct tttgcctggt caacttcttc agtgccgcta ttttcctgca acctctgttg      780
ggcgagggaa agctgcccct ccacagcgtc tatccgtttc aatggcatcg cttggatctg      840
catccctaca cgttctggtt cctctacatc tggcagagtc tgacctcgca gcacaaccta      900
atgagcattc taatggtgga tatggtaggc atttccacgt tcctccagac ggcgctcaat      960
ctcaagttgc tttgcatcga gataaggaaa ctgggggaca tggaggtcag tgataagagg     1020
ttccacgagg agttttgtcg tgtggttcgc ttccaccagc acattatcaa gtgagttttg     1080
tgtgccgagt tacaagtact acacgcgttt ttttggcaga ttggtgggga agccaatag      1140 agctttcaat ggcgccttca atgcacaatt aatggccagt ttctccctga tttccatatc     1200
cactttcgag accatggctg cagcggctgt ggatcccaaa atggccgcca agttcgtgct     1260
tctcatgctg gtggcattca ttcaactgtc gctttggtgc gtctctggaa ctttggttta     1320
tactcaggta tgtcgtttaa aatctttgaa aacttttaa caatcactcc ttttcctaat      1380
tagctgcacc tagatattga aaccttattg aaatttactt attttgagat ttttcctgtt     1440
caactttcat caatagtcag tggaggtggc tcaggctgct tttgatatca acgattggca     1500
caccaaatcg ccaggcatcc agagggatat atcctttgtg atactacgag cccagaaacc     1560
cctgatgtat gtggccgaac catttctgcc cttcaccctg ggaacctata tgcttgtaag     1620
gatataaaaa tgtatataat aaagatatca cgatatcaac cgtccatttt caggttctga     1680
agaactgcta tcgtttgctg gccctgatgc aagaatcgat gtag                       1724

<210> SEQ ID NO 112
<211> LENGTH: 1318
<212> TYPE: DNA
<213> ORGANISM: Drosophila melanogaster
<220> FEATURE:
<223> OTHER INFORMATION: DOR 59D.1, region of BDGP Clone No. AC005672
<220> FEATURE:
<221> NAME/KEY: intron
<222> LOCATION: (1)..(120)
<220> FEATURE:
<221> NAME/KEY: intron
<222> LOCATION: (846)..(903)

<400> SEQUENCE: 112
taattgaggt ggccacgcaa ggctaattac ataattgggc aatcgcaccg attgagccat       60
cacccaaaac ggtatttaag tgtggagaac cttacattaa agccgagaat tcaaggaacc      120
atggcagagg tcagagtgga cagtctggag tttttcaaga gccattggac cgcctggcgg      180
tacttgggag tggctcattt tcgggtcgag aactggaaga acctttacgt gttttacagc      240
attgtgtcga atcttctcgt gaccctgtgc taccccgttc acctgggaat atccctcttt      300
cgcaaccgca ccatcaccga ggacatcctc aacctgacca cctttgcgac ctgcacagcc      360
tgttcggtga agtgcctgct ctacgcctac aacatcaagg atgtgctgga gatggagcgg      420
ctgttgaggc ttttggatga acgcgtcgtg ggtccgagc aacgcagcat ctacggacaa       480
gtgagggtcc agctgcgaaa tgtgctatac gtgttcatcg gcatctacat gccgtgtgcc      540
ctgttcgccg agctatcctt tctgttcaag gaggagcgcg gtctgatgta tcccgcctgg      600
tttcccttcg actggctgca ctccaccagg aactattaca tagcgaacgc ctatcagata      660
```

-continued

| | | | | |
|---|---|---|---|---|
| gtgggcatct | cgtttcagct | gctgcaaaac | tatgttagcg | actgctttcc ggcggtggtg 720 |
| ctgtgcctga | tctcatccca | catcaaaatg | ttgtacaaca | gattcgagga ggtgggcctg 780 |
| gatccagcca | gagatgcgga | gaaggacctg | gaggcctgca | tcaccgatca caagcatatt 840 |
| ctagagtggg | caggcggctc | attgtaacgt | tcgtgttcta | ttcactttcc aacttttttc 900 |
| cagactattc | cgacgcatcg | aggccttcat | ttccctgccc | atgctaattc agttcacagt 960 |
| gaccgccttg | aatgtgtgca | tcggtttagc | agccctggtg | tttttcgtca gcgagcccat 1020 |
| ggcacggatg | tacttcatct | tctactccct | ggccatgccg | ctgcagatct ttccgtcctg 1080 |
| cttttccggc | accgacaacg | agtactggtt | cggacgcctc | cactacgcgg ccttcagttg 1140 |
| caattggcac | acacagaaca | ggagctttaa | gcggaaaatg | atgctgttcg ttgagcaatc 1200 |
| gttgaagaag | agcaccgctg | tggctggcgg | aatgatgcgt | atccacctgg acacgttctt 1260 |
| ttccaccta | aaggggcct | actccctctt | taccatcatt | attcggatga gaaagtag 1318 |

DROSOPHILA ODORANT RECEPTORS

RELATED APPLICATIONS

This application claims priority to U.S. provisional patent application Ser. No. 60/117,132 filed Jan. 25, 1999 which is herein incorporated by reference in its entirety.

U.S. GOVERNMENT SUPPORT

This work was supported by a grant from the National Institutes of Health (DC-02174).

FIELD OF THE INVENTION

This invention pertains to novel olfactory receptors and to methods of using such receptors. More particularly, this invention pertains to the nucleic acids and amino acids of novel olfactory receptors in Drosophila and to methods of using such nucleic acids and amino acids.

BACKGROUND OF THE INVENTION

Animals can detect a vast array of odors with remarkable sensitivity and discrimination. Olfactory information is first received by olfactory receptor neurons (olfactory receptors), which transmit signals into the central nervous system (CNS) where they are processed, ultimately leading to behavioral responses. An enormous amount of investigation into olfactory function, organization, and development has been carried out in insect model systems for many years (Kaissling et al., (1987) Ann. NY Acad. Sci. 510, 104–112; Hildebrand (1995) Proc. Natl. Acad. Sci. USA 92, 67–74). However, a number of central questions have been refractory to incisive analysis because the receptor molecules to which odor molecules bind have not been identified, in any insect.

To investigate the molecular mechanisms of olfactory function and development, applicants studied the olfactory system of *Drosophila melanogaster*, which is highly sensitive and capable of odor discrimination (Siddiqi, (1991) Olfaction in Drosophila, in: Wysocki & Kare (ed.), Chemical Senses, Marcel Dekker; Carlson (1996) Trends Genet. 12, 175–180). There are two olfactory organs on the adult fly, the third segment of the antenna and the maxillary palp (FIG. 1A). In both organs, olfactory receptors are housed in sensory hairs called sensilla. The organization of the approximately 1200 olfactory receptors of the antenna is complex but ordered. On the antenna there are different morphological categories of sensilla: s. trichodea, s. coeloconica, large s. basiconica, and small s. basiconica (FIG. 1B). The different morphological categories of sensilla are distributed in overlapping patterns across the surface of the antenna (FIGS. 1C–F) (Venkatesh & Singh, (1984) Int. J. Insect Morphol. Embryol. 13, 51–63; Stocker, (1994) Roux's Arch. Dev. Biol. 205, 62–72).

Electrophysiological studies show that each morphological category of sensilla can be divided into different functional types (denoted by different colors in FIGS. 1C–F), defined by the characteristic response profiles of their olfactory receptors (Rodrigues et al., (1991) Mol. Gen. Genet. 226, 265–276; Clyne et al., (1997) Invert. Neurosci. 3, 127–135; de Bruyne et al., unpublished results). For s. trichodea, the different functional types are segregated into zones on the surface of the antenna (FIG. 1C); segregation is also observed for the different functional types of s. coeloconica (FIG. 1D). This zonal organization is less conspicuous for the large and small s. basiconica, of which different functional types are intermingled (FIGS. 1E–F). Electrophysiological data suggest that there are on the order of thirty different classes of olfactory receptors in the antenna, a rough estimate based upon the odor response profiles of individual olfactory receptors (and in a few cases, the assumption that the neurons of particular functional types of sensilla have unique response profiles).

In contrast to the antenna, the organization of the approximately 120 olfactory receptors of the maxillary palp is less complex. There are approximately 60 s. basiconica on the maxillary palp, each housing two olfactory receptors (Singh & Nayak, (1985) Int. J. Insect Morphol. Embryol. 14, 291–306). The 120 olfactory receptors fall into six different classes based upon their odorant response profiles (Clyne et al., (1999) Neuron 22, 339–347; de Bruyne et al., (1999) J. Neurosci. 19, 4520–4532). Neurons of the six ORN classes are always found in characteristic pairs in three functional types of s. basiconica, with the total number of neurons in each class being equal. Each class is distributed broadly over all, or almost all, of the olfactory surface of the maxillary palp.

Thus electrophysiological and anatomical studies suggest that there are on the order of thirty-five classes of olfactory receptors in the adult fly (approximately thirty on the antenna and six on the palp), each class with a distinct odor sensitivity. Classes of olfactory receptors found in the antenna are arrayed in zones, while the classes of olfactory receptors found in the maxillary palp are distributed in a less ordered fashion. olfactory receptors in both the maxillary palp and the antenna extend their axons to the antennal lobe of the brain, where first-order processing of olfactory information occurs. The lobe contains approximately forty olfactory glomeruli, spheroidal modules where ORN axons converge and where their terminal branches form synapses with the dendrites of their target interneurons (Stocker, (1994) Cell Tissue Res. 275, 3–26; Hildebrand & Shepherd, (1997) Annu. Rev. Neurosci. 20, 595–631).

One possibility underlying the molecular basis for distinct odor sensitivities for different classes of olfactory receptors is that each class of ORN expresses a unique odorant receptor, as has been proposed for vertebrate olfactory systems (Ngai et al., (1993) Cell 72, 667–680; Ressler et al., (1993) Cell 73, 597–609; Vassar et al., (1993) Cell 74, 309–318; Buck, (1996) Annu. Rev. Neurosci. 19, 517–544; Hildebrand & Shepherd, (1997) Annu. Rev. Neurosci. 20, 595–631). Alternatively, each class of ORN might express a unique combination of a large set of receptors, as found in chemosensory cells of the nematode, *C. elegans* (Troemel et al., (1995) Cell 83, 207–218). Both models call for a family of receptor genes, and several lines of evidence suggest that for insects such a family would belong to the superfamily of seven-transmembrane G protein-coupled receptors (GPCRs). First, there is evidence that insects generate responses to odorants via GPCR-activated second-messenger systems. For example, a rapid and transient increase in inositol 1,4,5-trisphosphate (IP3) has been observed in response to stimulation with pheromone and other odors using antennal preparations from various insect species (Breer et al., (1990) Nature 345, 65–68; Boekhoff et al., (1993) Insect Biochem. Mol. Biol. 23, 757–762; Wegener et al., (1993) J. Insect Physiol. 39, 153–163). This increase in IP3 can be blocked by pertussis toxin, implicating a G protein signaling cascade (Boekhoff et al., (1990) Cell. Signal. 2, 49–56). In Drosophila, norpA mutants, which lack the phospholipase C that is an essential component of phototransduction, also exhibit reduced olfactory responses of the maxillary palp (Riesgo-Escovar et al., (1995) J. Comp. Physiol. A180, 151–160). A second reason to suspect that odorant receptors in Drosophila are GPCRs is that GPCRs have been shown to be odorant receptors in both vertebrates and *C. elegans*; moreover, abundant evidence indicates that olfactory information in these other organisms is transduced by GPCR-activated second messenger systems (Buck, (1996) Annu. Rev. Neurosci. 19, 517–544; Bargmann & Kaplan, (1998) Annu. Rev. Neurosci. 21, 279–308). It would thus seem unlikely that a family of receptors that have a completely novel structure and that use a completely different transduction mechanism would have arisen in insects.

There have been extensive efforts to identify odorant and pheromone receptors in a variety of insects using a wide range of strategies. These efforts have been driven in part by interest in analyzing receptor genes in the context of highly tractable experimental systems in which there is a wealth of knowledge about olfactory function and organization. For example, Drosophila offers the advantages of a model genetic organism together with the ability to measure olfactory function conveniently in vivo, through either physiological or behavioral means. Interest in insect odorant receptors has also arisen because of the critical role of olfaction in the attraction of many insect pests to their plant hosts, of insect vectors of disease to their human hosts, and of insects to their mates. Nevertheless, efforts to identify odorant receptors in insects, based upon searches for genes bearing sequence similarities to odorant receptor genes from other organisms, or on other strategies, have been unsuccessful.

Applicants have discovered a novel multigene family encoding candidate odorant receptors that were identified from the Drosophila genomic sequence database. The forty-nine genes described here were discovered using novel computer programs that identify diagnostic features of the protein structure of the seven-transmembrane GPCR superfamily. Members of this new family are highly divergent from previously defined genes. Nearly all of the genes are found to be expressed in one or both of the olfactory organs, and for a number of genes expression is restricted to a subset of olfactory receptors. Applicant's further demonstrate that expression of different genes is initiated at different times during the development of the adult antenna, and that expression of a subset of these candidate receptor genes depends on the POU domain transcription factor, Acj6 (abnormal chemosensory jump 6).

SUMMARY OF THE INVENTION

This invention provides isolated nucleic acid molecules including the following:
 a) isolated nucleic acid molecules that encode the amino acid sequences of Drosophila Odorant Receptor proteins;
 b) isolated nucleic acid molecules that encode protein fragments of at least 6 amino acids of a Drosophila Odorant Receptor proteins; and
 c) isolated nucleic acid molecules which hybridize to nucleic acid molecules which include nucleotide sequences encoding Drosophila Odorant Receptor proteins under conditions of sufficient stringency to produce a clear signal.

This invention also provides such isolated nucleic acid molecules wherein the nucleic acids include at least one exon-intron boundary located in one of the following positions:
 a) the nucleotides encoding the amino acids which include the third extracellular domain of a Drosophila Odorant Receptor protein;
 b) the nucleotides encoding the amino acids which include the fourth extracellular domain of a Drosophila Odorant Receptor protein; and
 c) the nucleotides encoding the amino acids which include the fourth intracellular domain of a Drosophila Odorant Receptor protein.

This invention further provides such isolated nucleic acid molecules which have the nucleic acid sequence of one of the following sequences: SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95 and 97.

This invention also provides such isolated nucleic acid molecules operably linked to one or more expression control elements.

This invention further provides vectors which include any of the aforementioned nucleic acid molecules and host cells which include such vectors.

This invention also provides host cells transformed so as to contain any of the aforementioned nucleic acid molecules, wherein such host cells can be either prokaryotic host cells or eukaryotic host cells.

This invention also provides methods for producing proteins or protein fragments wherein the methods include transforming host cells with any of the aforementioned nucleic acids under conditions in which the protein or protein fragment encoded by said nucleic acid molecule is expressed. This invention also provides such methods wherein the host cells are either prokaryotic host cells or eukaryotic host cells. This invention further provides isolated proteins or protein fragments produced by such methods.

This invention provides isolated proteins or protein fragments which include:
 a) isolated proteins encoded by one of the following amino acid sequences: SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96 and 98;
 b) isolated protein fragments which include at least 6 amino acids of any of the following sequences: SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96 and 98;
 c) isolated proteins which include conservative amino acid substitutions of any of the following sequences: SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96 and 98; and
 d) naturally occurring amino acid sequence variants of any of the following sequences: SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96 and 98.

The present invention further provides such isolated proteins or protein fragments which include at least one of the following conserved amino acids:
 a) Leucine in the third extracellular domain of a Drosophila Odorant Receptor protein;
 b) Histidine in the third extracellular domain of a Drosophila Odorant Receptor protein;
 c) Cysteine in the sixth transmembrane domain of a Drosophila Odorant Receptor protein;

d) Tryptophan in the fourth extracellular domain of a Drosophila Odorant Receptor protein;
e) Glutamine in the seventh transmembrane domain of a Drosophila Odorant Receptor protein;
f) Proline in the seventh transmembrane domain of a Drosophila Odorant Receptor protein;
g) Alanine in the fourth intracellular domain of a Drosophila Odorant Receptor protein; and
h) Tyrosine in the fourth intracellular domain of a Drosophila Odorant Receptor protein.

The present invention also provides isolated antibodies that bind to any of the aforementioned polypeptides.

The present invention also provides such antibodies which are either monoclonal antibodies or polyclonal antibodies.

This invention also provides methods of identifying agents which modulate the expression of any of the aforementioned proteins or protein fragments by:
a) exposing cells which express the proteins or protein fragments to the agents; and
b) determining whether the agent modulates expression of said proteins or protein fragments, thereby identifying agents which modulate the expression of the proteins or protein fragments.

The present invention also provides methods of identifying agents which modulate the activity of any of the aforementioned proteins or protein fragments by:
a) exposing cells which express the proteins or protein fragments to the agents; and
b) determining whether the agents modulate the activity of said proteins or protein fragments, thereby identifying agents which modulate the activity of the proteins or protein fragments.

The present invention also provides such methods where the agent modulates at least one activity of the proteins or protein fragments.

This invention provides methods of identifying agents which modulate the transcription of any of the aforementioned nucleic acid molecules by:
a) exposing cells which transcribe the nucleic acids to the agents; and
b) determining whether the agents modulate transcription of said nucleic acids, thereby identifying agents which modulate the transcription of the nucleic acid.

This invention further provides methods of identifying binding partners for the aforementioned proteins or protein fragments by:
a) exposing said proteins or protein fragments to potential binding partners; and
b) determining if the potential binding partners bind to said proteins or protein fragments, thereby identifying binding partners for the proteins or protein fragments.

The present invention also provides methods of modulating the expression of nucleic acids encoding the aforementioned proteins or protein fragments by administering an effective amount of agents which modulate the expression of the nucleic acids encoding the proteins or protein fragments.

This invention also provides methods of modulating at least one activity of the aforementioned proteins or protein fragments by administering an effective amount of the agents which modulate at least one activity of the proteins or protein fragments.

This invention provides methods of identifying novel olfactory receptor genes by:
a) selecting candidate olfactory receptor genes by screening nucleic acid databases using an algorithm trained to identify seven transmembrane receptors genes;
b) screening said selected candidate olfactory receptor genes by identifying nucleic acid sequences with conserved amino acid residues and intron-exon boundaries common to olfactory receptors, and having open reading frames of sufficient size so as to encode a seven transmembrane receptor; and
c) identifying the novel olfactory receptor genes and measuring the expression of olfactory receptor genes wherein the detection of expression confirms said candidate olfactory genes as olfactory genes.

This invention also provides methods of identifying novel olfactory receptor genes by:
a) selecting candidate olfactory receptor genes by screening nucleic acid databases for nucleic acid sequences with sufficient homology to at least one known olfactory receptor gene;
b) screening said selected candidate olfactory receptor genes by identifying nucleic acids with conserved amino acid residues and intron-exon boundaries common to olfactory receptors, and having open reading frames of sufficient size so as to encode a seven transmembrane receptor; and
c) identifying the novel olfactory receptor genes and measuring the expression of olfactory receptor genes wherein the detection of expression confirms said candidate olfactory genes as olfactory genes.

The present invention also provides transgenic insects modified to contain any of the aforementioned nucleic acid molecules.

This invention also provides such transgenic insects, wherein the nucleic acid molecules contain mutations that alter expression of the encoded proteins.

BRIEF DESCRIPTION OF THE DRAWINGS

FIG. 2 Genomic organization and hydropathy plots of DOR genes. (A) Genomic organization of DOR genes (not to scale). The genes shown are those identified from 16% of the total genomic sequence; most of the available sequence is from Chromosome 2. The approximate chromosomal location of each gene is indicated. Genes separated by less than one kilobase are jointly underlined. Within each cluster, all genes are oriented in the same direction. The transcriptional orientation of the DOR genes with respect to the chromosome is unknown for 2F.1, 25A.1, 47E.2, 59D.1, and the cluster at 33B. (B) The 2F.1 gene is flanked by two closely linked genes, fs(1)k10 and crn. The arrowheads indicate the 3' end of each gene; for 2F.1 the end of the arrow indicates the position of the polyA+ addition signal sequence. (C) Hydropathy plots of the genes whose expression patterns are shown in FIGS. 4–6. Hydrophobic peaks predicted by Kyte-Doolittle analysis appear above the center line. The approximate positions of the seven putative transmembrane domains are indicated above the first hydropathy plot.

FIG. 3 Amino acid sequence alignment of DOR genes. All DNA sequences were obtained from the BDGP database, and the determination of predicted amino acid sequences is described in the Examples. Residues conserved in >50% of the predicted proteins are shaded. The approximate locations of predicted transmembrane domains 1–7 are indicated. Exon-intron boundaries are shown with vertical lines.

DETAILED DESCRIPTION OF THE PREFERRED EMBODIMENT

I. Specific Embodiments

A. Drosophila Olfactory Receptor Proteins

Figure 1A:
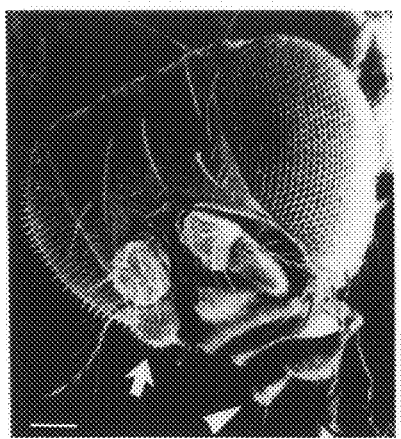
FIG. 1 An overview of the olfactory system of the adult Drosophila. (A) The two olfactory organs of the adult fly, the third antennal segment (arrow) and the maxillary palp (arrowhead), scale bar=100 $\mu$m. (B) Higher magnification of part of a third antennal segment showing the morphological categories of olfactory sensilla: s. basiconica [B], s. trichodea [T] and s. coeloconica [C], scale bar=5 $\mu$m. (C–F) Diagram of the olfactory sensilla on the anterior face of the third antennal segment. The different morphological categories of sensilla are indicated by different shapes, and the colors indicate different functional types of sensilla within each morphological category. Dorsal is at the top and medial is to the left. (C) Distribution of different functional types of s. trichodea. (D) Distribution of different functional types of s. coeloconica. (E) The large s. basiconica are densely clustered in a small dorso-medial region, where the different functional types are intermingled. For simplicity, only two types are shown. (F) The small s. basiconica are widely dispersed, and the different functional types are intermingled.
Figure 1B:
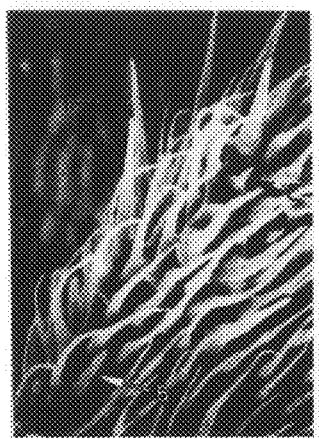
Figure 1C:
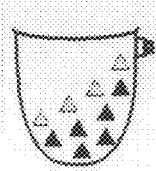
Figure 1D:
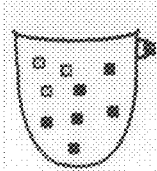

The present invention provides a family of isolated proteins, allelic variants of the proteins, and conservative amino acid substitutions of the proteins. As used herein, protein or polypeptide refers to any one of the proteins that has the amino acid sequence depicted in SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96 and 98. The invention also includes naturally occurring allelic variants and proteins that have a slightly different amino acid sequence than that specifically recited above. Allelic variants, though possessing a slightly different amino acid sequence than those recited above, will still have the same or similar biological functions associated with any of the amino acid proteins.

As used herein, the family of proteins related to any one of the amino acid sequences depicted in SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 5.6, 58, 60, 62, 64, 66, 68, 70, 72, 74, 76, 78, 80, 82, 84, 86, 88, 90, 92, 94, 96 and 98 refers to proteins that have been isolated from organisms in addition to Drosophila. The methods used to identify and isolate other members of the family of proteins related to these amino acid proteins are described below.

The proteins of the present invention are preferably in isolated form. As used herein, a protein is said to be isolated when physical, mechanical or chemical methods are employed to remove the protein from cellular constituents that are normally associated with the protein. A skilled artisan can readily employ standard purification methods to obtain an isolated protein.

The proteins of the present invention further include conservative amino acid substitution variants (i.e., conservative) of the proteins herein described. As used herein, a conservative variant refers to at least one alteration in the amino acid sequence that does not adversely affect the biological functions of the protein. A substitution, insertion or deletion is said to adversely affect the protein when the altered sequence prevents or disrupts a biological function associated with the protein. For example, the overall charge, structure or hydrophobic-hydrophilic properties of the protein can be altered without adversely affecting a biological activity. Accordingly, the amino acid sequence can often be altered, for example to render the peptide more hydrophobic or hydrophilic, without adversely affecting the biological activities of the protein.

Ordinarily, the allelic variants, the conservative substitution variants, and the members of the protein family, will have an amino acid sequence having at least 30% amino acid sequence identity with the sequences set forth in SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96 and 98 more preferably at least 35%, even more preferably at least 40%, and most preferably at least 45%. Identity or homology with respect to such sequences is defined herein as the percentage of amino acid residues in the candidate sequence that are identical with the known peptides, after aligning the sequences and introducing gaps, if necessary, to achieve the maximum percent homology, and not considering any conservative substitutions as part of the sequence identity. N-terminal, C-terminal or internal extensions, deletions, or insertions into the peptide sequence shall not be construed as affecting homology.

In addition to amino acid sequence identity, the proteins of the present invention have seven transmembrane domains as defined by hydropathy analysis (Kyte & Doolittle, (1982) J. Mol. Biol. 157, 105–132). Furthermore, the proteins of the present invention have conserved amino acid residues in defined domains of the protein. For example, the proteins of the present invention have at least one of the following conserved amino acids as depicted in FIG. 3, including but not limited to, Leucine in the third extracellular domain; Histidine in the third extracellular domain; Cysteine in the sixth transmembrane domain; Tryptophan in the fourth extracellular domain; Glutamine in the seventh transmembrane domain; Proline in the seventh transmembrane domain; Alanine in the fourth intracellular domain; or Tyrosine in the fourth intracellular domain. In addition, the conserved amino acids may be selected from any of the amino acid residues indicated as being conserved among DOR proteins as depicted in FIG. 3 (shaded).

Thus, the proteins of the present invention include molecules having the amino acid sequence disclosed in SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96 and 98; fragments thereof having a consecutive sequence of at least about 3, 4, 5, 6, 10, 15, 20, 25, 30, 35 or more amino acid residues of the proteins, for instance, antigenic fragments such as those found in the extracellular domains of the protein (see FIG. 3); amino acid sequence variants wherein an amino acid residue has been inserted N- or C-terminal to, or within, the disclosed sequence; and amino acid sequence variants of the disclosed sequences, or their fragments as defined above, that have been substituted by another residue. Contemplated variants further include those containing predetermined mutations by, e.g., homologous recombination, site-directed or PCR mutagenesis, and the corresponding proteins of other insect species, including but not limited to the order Diptera, Lepidoptera, Homopterera and Coleoptera, within these orders, preferably the genus Drosophila, Anopheles, Aedes, Ceratitis, Muscidae, Culicidae, Anagasta and Popilla and the alleles or other naturally occurring variants of the family of proteins; and derivatives wherein the protein has been covalently modified by substitution, chemical, enzymatic, or other appropriate means with a moiety other than a naturally occurring amino acid (for example a detectable moiety such as an enzyme or radioisotope).

As described below, members of the family of proteins can be used: 1) to identify agents which modulate at least one activity of the protein; 2) to identify binding partners for the protein, 3) as an antigen to raise polyclonal or monoclonal antibodies, and 4) in methods to modify insect behavior.

B. Nucleic Acid Molecules

The present invention further provides nucleic acid molecules which encode any of the proteins having SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96 and 98 and the related proteins herein described, preferably in isolated form. As used herein, "nucleic acid" is defined as RNA or DNA that encodes a protein or peptide as defined above, is complementary to a nucleic acid sequence encoding such peptides, hybridizes to such a nucleic acid and remains stably bound to it under appropriate stringency conditions, or encodes a polypeptide sharing at least 75% sequence identity, preferably at least 80%, and more preferably at least 85%, with the peptide sequences in conserved domains. Specifically contemplated are genomic DNA, cDNA, mRNA and antisense molecules, as well as nucleic acids based on alternative backbones or including alternative bases whether derived from natural sources or synthesized. Such hybridizing or complementary nucleic acids, however, are defined further as being novel and non-obvious over any prior art nucleic acid including that which encodes, hybridizes under appropriate stringency conditions, or is complementary to nucleic acid encoding a protein according to the present invention.

Homology or identity at the amino acid or nucleotide level is determined by BLAST (Basic Local Alignment Search Tool) analysis using the algorithm employed by the programs blastp, blastn, blastx, tblastn and tblastx (Karlin et al., (1990) Proc. Natl. Acad. Sci. USA 87, 2264–2268 and Altschul, (1993) J. Mol. Evol. 36, 290–300, fully incorporated by reference) which are tailored for sequence similarity searching. The approach used by the BLAST program is to first consider similar segments between a query sequence and a database sequence, then to evaluate the statistical significance of all matches that are identified and finally to summarize only those matches which satisfy a preselected threshold of significance. For a discussion of basic issues in similarity searching of sequence databases (see Altschul et al., (1994) Nature Genetics 6, 119–129 which is fully incorporated by reference). The search parameters for histogram, descriptions, alignments, expect (i.e., the statistical significance threshold for reporting matches against database sequences), cutoff, matrix and filter are at the default settings. The default scoring matrix used by blastp, blastx, tblastn, and tblastx is the BLOSUM62 matrix (Henikoff et al., (1992) Proc. Natl. Acad. Sci. USA 89, 10915–10919, fully incorporated by reference). For blastn, the scoring matrix is set by the ratios of M (i.e., the reward score for a pair of matching residues) to N (i.e., the penalty score for mismatching residues), wherein the default values for M and N are 5 and −4, respectively.

"Stringent conditions" are those that (1) employ low ionic strength and high temperature for washing, for example, 0.5 M sodium phosphate buffer at pH 7.2, 1 mM EDTA at pH 8.0 in 7% SDS at either 65° C. or 55° C., or (2) employ during hybridization a denaturing agent such as formamide, for example, 50% formamide with 0.1% bovine serum albumin, 0.1% Ficoll, 0.1% polyvinylpyrrolidone, 0.05 M sodium phosphate buffer at pH 6.5 with 0.75 M NaCl, 0.075 M sodium citrate at 42° C. Another example is use of 50% formamide, 5×SSC (0.75 M NaCl, 0.075 M sodium citrate), 50 mM sodium phosphate at pH 6.8, 0.1% sodium pyrophosphate, 5×Denhardt's solution, sonicated salmon sperm DNA (50 µg/ml), 0.1% SDS and 10% dextran sulfate at 55° C., with washes at 55° C. in 0.2×SSC and 0.1% SDS. A skilled artisan can readily determine and vary the stringency conditions appropriately to obtain a clear and detectable hybridization signal. Preferred molecules are those that hybridize under the above conditions to the complements of SEQ ID NO: 1, 3, 5, 7, 9, 11, 13, 15, 17, 19, 21, 23, 25,27,29,31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95 and 97, and which encode a functional protein.

As used herein, a nucleic acid molecule is said to be "isolated" when the nucleic acid molecule is substantially separated from contaminant nucleic acid encoding other polypeptides from the source of nucleic acid.

The present invention further provides fragments of any one of the encoding nucleic acids molecules. As used herein, a fragment of an encoding nucleic acid molecule refers to a small portion of the entire protein coding sequence. The size of the fragment will be determined by the intended use. For example, if the fragment is chosen so as to encode an active portion of the protein, the fragment will need to be large enough to encode the functional region(s) of the protein. For instance, fragments of the invention encode antigenic fragments such as the extracellular loops or N-terminal domain of the protein depicted in SEQ ID NO: 2 and as set forth in FIG. 3. If the fragment is to be used as a nucleic acid probe or PCR primer, then the fragment length is chosen so as to obtain a relatively small number of false positives during probing and priming.

Fragments of the encoding nucleic acid molecules of the present invention (i.e., synthetic oligonucleotides) that are used as probes or specific primers for the polymerase chain reaction (PCR), or to synthesize gene sequences encoding proteins of the invention can easily be synthesized by chemical techniques, for example, the phosphotriester method of Matteucci et al., (1981) J. Am. Chem. Soc. 103, 3185–3191) or using automated synthesis methods. In addition, larger DNA segments can readily be prepared by well known methods, such as synthesis of a group of oligonucleotides that define various modular segments of the gene, followed by ligation of oligonucleotides to build the complete modified gene.

The encoding nucleic acid molecules of the present invention may further be modified so as to contain a detectable label for diagnostic and probe purposes. A variety of such labels are known in the art and can readily be employed with the encoding molecules herein described. Suitable labels include, but are not limited to, fluorescent-labeled, biotin-labeled, radio-labeled nucleotides and the like. A skilled artisan can employ any of the art known labels to obtain a labeled encoding nucleic acid molecule.

Modifications to the primary structure itself by deletion, addition, or alteration of the amino acids incorporated into the protein sequence during translation can be made without destroying the activity of the protein. Such substitutions or other alterations result in proteins having an amino acid sequence encoded by a nucleic acid falling within the contemplated scope of the present invention.

C. Isolation of Other Related Nucleic Acid Molecules

As described above, the identification and characterization of the nucleic acid molecules having SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95 and 97 allows a skilled artisan to isolate nucleic acid molecules that encode other members of the protein family in addition to the sequences herein described. Further, the presently disclosed nucleic acid molecules allow a skilled artisan to isolate nucleic acid molecules that encode other members of the family of proteins in addition to the protein having SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96 and 98.

Essentially, a skilled artisan can readily use any one of the amino acid sequences selected from SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96 and 98, to generate antibody probes to screen expression libraries prepared from appropriate cells. Typically, polyclonal antiserum from mammals such as rabbits immunized with the purified protein (as described below) or monoclonal antibodies can be used to probe a cDNA or genomic expression library to obtain the appropriate coding sequence for other members of the protein family. The cloned cDNA sequence can be expressed as a fusion protein, expressed directly using its own control sequences, or expressed by constructions using control sequences appropriate to the particular host used for expression of the enzyme.

Alternatively, a portion of the coding sequence herein described can be synthesized and used as a probe to retrieve DNA encoding a member of the protein family from any organism. Oligomers containing approximately 18–20 nucleotides (encoding about a six to seven amino acid stretch) are prepared and used to screen genomic DNA or cDNA libraries to obtain hybridization under stringent conditions or conditions of sufficient stringency to eliminate an undue level of false positives.

Additionally, pairs of oligonucleotide primers can be prepared for use in a polymerase chain reaction (PCR) to selectively clone an encoding nucleic acid molecule. A PCR denature/anneal/extend cycle for using such PCR primers is well known in the art and can readily be adapted for use in isolating other encoding nucleic acid molecules. For example, degenerate primers can be used to clone any DOR gene across species. Specifically, based on the sequence information derived from the family of DORs, degenerate primers can be designed based on conserved sequences among olfactory receptors, which can then be used to clone nucleic acid molecules encoding olfactory receptor proteins from other species of insects.

Applicants have also identified a method for isolating nucleic acid molecules that encode other members of the protein family in addition to the sequences herein described. Essentially, a two-step strategy is employed to identify odorant receptor genes from the genomic database. First, a computer algorithm was designed to search genomic sequences for open reading frames (ORFs) from candidate odorant receptor genes. Second, RT-PCR is used to determine if transcripts from any of these ORFs are expressed in olfactory organs.

The algorithm is used to identify GPCR genes using statistical characterization of amino acid physico-chemical profiles in combination with a non-parametric discriminant function. The algorithm is trained on a set of putative sequences from a database. In the first step, three sets of descriptors are used to summarize the physico-chemical profiles of the sequences. These are GES scale of hydropathy (Engelman et al., (1986) Annu. Rev. Biophys. Biophys. Chem. 15, 321–353), polarity (Brown, (1991) Molecular Biology Labfax, Academic Press), and amino acid usage frequency. For the first two of these measurements, a computed sliding window profile is employed (White, (1994) Membrane Protein Structure, Oxford University Press) using a kernel of a certain number of amino acids as a constant function convoluted with a certain number of amino acids as a Gaussian function. These profiles are then summarized with three statistics; the periodicity, average derivative and the variance of the derivative.

Each sequence is then characterized by multiple variables using a non-parametric linear discriminant function that is optimized to separate the known family proteins from random proteins in the training set. The same linear discriminant function with the scores derived from the training set is used to screen any nucleic acid database for candidate genes. The candidate sequences are given significance values by an odds ratio of the proteins and non-family proteins, computed using the observed empirical distribution of the training set. Those sequences with a sufficiently high odds ratio are considered for further analysis. The algorithm can also be used to identify any protein family by altering the training set of sequences.

The method of identification further includes steps for identifying novel olfactory receptor genes comprising selecting candidate olfactory receptor genes by screening a nucleic acid database using an algorithm trained to identify seven transmembrane receptors genes; screening said selected candidate olfactory receptor genes by identifying nucleic acid sequences with conserved amino acid residues and intron-exon boundaries common to olfactory receptors, and open reading frames of sufficient size as to encode a seven transmembrane receptor. As an additional step, the expression of olfactory receptor genes is measured to confirm candidate olfactory gene as an olfactory gene. The exon-intron boundaries and conserved amino acid residues may be selected from any of the positions depicted in FIG. 3. Alternatively, selecting candidate olfactory receptor genes by screening a nucleic acid database for nucleic acid sequences with sufficient homology to at least one known olfactory receptor gene is also encompassed in the invention. In a preferred embodiment, the nucleic acid database is a genomic database, an EST database or even an olfactory receptor database as previously described (Skoufos et al., (1999) Nucleic Acids Research 27, 343–345).

In one example of the invention, the training set could consist of a subset of seven transmembrane proteins such as dopaminergic receptors and could be used to search genomic sequences for new subtypes of dopaminergic receptors. In another example, the training set could consist of ion channels and could be used to identify new subtypes of ion channels in a particular family. In yet another example, the training set could consist of known sequences coding for a receptors from a particular family and could be used to identify homologs across species. Specifically, olfactory receptors of one species could be used as a training set to identify olfactory receptors in another species.

D. rDNA Molecules Containing a DNA molecule

The present invention further provides recombinant DNA molecules (rDNAs) that contain a coding sequence. As used herein, a rDNA molecule is a DNA molecule that has been subjected to molecular manipulation in situ. Methods for generating rDNA molecules are well known in the art, for example, see Sambrook et al., (1985) Molecular Cloning—A Laboratory Manual, Cold Spring Harbor Laboratory Press. In the preferred rDNA molecules, a coding DNA sequence is operably linked to expression control sequences or vector sequences.

The choice of vector and expression control sequences to which one of the protein family encoding sequences of the present invention is operably linked depends directly, as is well known in the art, on the functional properties desired, e.g., protein expression, and the host cell to be transformed. A vector contemplated by the present invention is at least capable of directing the replication or insertion into the host chromosome, and preferably also expression, of the structural gene included in the rDNA molecule.

Expression control elements that are used for regulating the expression of an operably linked protein encoding sequence are known in the art and include, but are not limited to, inducible promoters, constitutive promoters, secretion signals, and other regulatory elements. Preferably, the inducible promoter is readily controlled, such as being responsive to a nutrient in the host cell's medium.

In one embodiment, the vector containing a coding nucleic acid molecule will include a prokaryotic replicon, i.e., a DNA sequence having the ability to direct autonomous replication and maintenance of the recombinant DNA molecule extra-chromosomally in a prokaryotic host cell, such as a bacterial host cell, transformed therewith. Such replicons are well known in the art. In addition, vectors that include a prokaryotic replicon may also include a gene whose expression confers a detectable marker such as a drug resistance. Typical bacterial drug resistance genes are those that confer resistance to ampicillin or tetracycline.

Vectors that include a prokaryotic replicon can further include a prokaryotic or bacteriophage promoter capable of directing the expression (transcription and translation) of the coding gene sequences in a bacterial host cell, such as E. coli. A promoter is an expression control element formed by a DNA sequence that permits binding of RNA polymerase and transcription to occur. Promoter sequences compatible with bacterial hosts are typically provided in plasmid vectors containing convenient restriction sites for insertion of a DNA segment of the present invention. Typical of such vector plasmids are pUC8, pUC9, pBR322 and pBR329 available from BioRad Laboratories, pPL and pKK223 available from Pharmacia.

Expression vectors compatible with eukaryotic cells, preferably those compatible with vertebrate cells such as insect cells, can also be used to form a rDNA molecules that contains a coding sequence. Eukaryotic cell expression vectors are well known in the art and are available from several commercial sources. Typically, such vectors are provided containing convenient restriction sites for insertion of the desired DNA segment. Typical of such vectors are pSVL and pKSV-10 (Pharmacia), pBPV-1/pML2d (International Biotechnologies, Inc.), pTDT1 (ATCC, #31255), the vector pCDM8 described herein, and the like eukaryotic expression vectors. Vectors may be modified to include insect cell specific promoters if needed.

Eukaryotic cell expression vectors used to construct the rDNA molecules of the present invention may further include a selectable marker that is effective in an eukaryotic cell, preferably a drug resistance selection marker. A preferred drug resistance marker is the gene whose expression results in neomycin resistance, i.e., the neomycin phosphotransferase (neo) gene (Southern et al., (1982) J. Mol. Appl. Genet. 1, 327–341). Alternatively, the selectable marker can be present on a separate plasmid, and the two vectors are introduced by co-transfection of the host cell, and selected by culturing in the appropriate drug for the selectable marker.

E. Host Cells Containing an Exogenously Supplied Coding Nucleic Acid

The present invention further provides host cells transformed with a nucleic acid molecule that encodes a protein of the present invention. The host cell can be either prokaryotic or eukaryotic. Eukaryotic cells useful for expression of a protein of the invention are not limited, so long as the cell line is compatible with cell culture methods and compatible with the propagation of the expression vector and expression of the gene product. Preferred eukaryotic host cells include, but are not limited to, yeast, insect and mammalian cells, preferably insect cells such as those from a Drosophila cell line. Preferred Drosophila host cells include Drosophila Schneider line 2, and the like insect tissue culture cell lines.

Any prokaryotic host can be used to express a rDNA molecule encoding a protein of the invention. The preferred prokaryotic host is E. coli.

Transformation of appropriate cell hosts with a rDNA molecule of the present invention is accomplished by well known methods that typically depend on the type of vector used and host system employed. With regard to transformation of prokaryotic host cells, electroporation and salt treatment methods are typically employed, see, for example, Cohen et al., (1972) Proc. Natl. Acad. Sci. USA 69, 2110–2114; and Maniatis et al., (1982) Molecular Cloning—A Laboratory Manual, Cold Spring Harbor Laboratory Press. With regard to transformation of vertebrate cells with vectors containing rDNAs, electroporation, cationic lipid or salt treatment methods are typically employed, see, for example, Graham et al., (1973) Virology 52, 456–467; and Wigler et al., (1979) Proc. Natl. Acad. Sci. USA 76, 1373–1376.

Successfully transformed cells, i.e., cells that contain a rDNA molecule of the present invention, can be identified by well known techniques including the selection for a selectable marker. For example, cells resulting from the introduction of an rDNA of the present invention can be cloned to produce single colonies. Cells from those colonies can be harvested, lysed and their DNA content examined for the presence of the rDNA using a method such as that described by Southern, (1975) J. Mol. Biol. 98, 503–517; or Berent et al., (1985) Biotech. Histochem. 3, 208; or the proteins produced from the cell assayed via an immunological method.

F. Production of Recombinant Proteins using a rDNA Molecule

The present invention further provides methods for producing a protein of the invention using nucleic acid molecules herein described. In general terms, the production of a recombinant form of a protein typically involves the following steps: First, a nucleic acid molecule is obtained that encodes a protein of the invention, such as any of the nucleic acid molecule depicted in SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95 and 97. The nucleic acid molecule is then preferably placed in operable linkage with suitable control sequences, as described above, to form an expression unit containing the protein open reading frame. The expression unit is used to transform a suitable host and the transformed host is cultured under conditions that allow the production of the recombinant protein. Optionally the recombinant protein is isolated from the medium or from the cells; recovery and purification of the protein may not be necessary in some instances where some impurities may be tolerated.

Each of the foregoing steps can be done in a variety of ways. For example, the desired coding sequences may be obtained from genomic fragments and used directly in appropriate hosts. The construction of expression vectors that are operable in a variety of hosts is accomplished using appropriate replicons and control sequences, as set forth above. The control sequences, expression vectors, and transformation methods are dependent on the type of host cell used to express the gene and were discussed in detail earlier. Suitable restriction sites can, if not normally available, be added to the ends of the coding sequence so as to provide an excisable gene to insert into these vectors. A skilled artisan can readily adapt any host-expression system known in the art for use with the nucleic acid molecules of the invention to produce recombinant protein.

G. Methods to Identify Binding Partners

Another embodiment of the present invention provides methods for use in isolating and identifying binding partners of any of the DOR proteins of the invention. In detail, a protein of the invention is mixed with a potential binding partner or an extract or fraction of a cell under conditions that allow the association of potential binding partners with the protein of the invention. After mixing, peptides, polypeptides, proteins or other molecules that have become associated with a protein of the invention are separated from the mixture. The binding partner that bound to the protein of the invention can then be removed and further analyzed. To identify and isolate a binding partner, the entire protein, for instance a protein comprising the entire amino acid sequence of any of the proteins depicted in SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96 and 98 can be used. Alternatively, a fragment of any of the proteins can be used.

As used herein, a cellular extract refers to a preparation or fraction which is made from a lysed or disrupted cell. The preferred source of cellular extracts will be cells derived from Drosophila, for instance, antennae and maxillary palp cellular extract.

A variety of methods can be used to obtain an extract of a cell. Cells can be disrupted using either physical or chemical disruption methods. Examples of physical disruption methods include, but are not limited to, sonication and mechanical shearing. Examples of chemical lysis methods include, but are not limited to, detergent lysis and enzyme lysis. A skilled artisan can readily adapt methods for preparing cellular extracts in order to obtain extracts for use in the present methods.

Once an extract of a cell is prepared, the extract is mixed with any of the proteins of the invention under conditions in which association of the protein with the binding partner can occur. A variety of conditions can be used, the most preferred being conditions that closely resemble conditions found in the cytoplasm of a Drosophila cell. Features such as osmolarity, pH, temperature, and the concentration of cellular extract used, can be varied to optimize the association of the protein with the binding partner.

After mixing under appropriate conditions, the bound complex is separated from the mixture. A variety of techniques can be utilized to separate the mixture. For example, antibodies specific to a protein of the invention can be used to immunoprecipitate the binding partner complex. Alternatively, standard chemical separation techniques such as chromatography and density-sediment centrifugation can be used.

After removal of non-associated cellular constituents found in the extract, the binding partner can be dissociated from the complex using conventional methods. For example, dissociation can be accomplished by altering the salt concentration or pH of the mixture.

To aid in separating associated binding partner pairs from the mixed extract, the protein of the invention can be immobilized on a solid support. For example, the protein can be attached to a nitrocellulose matrix or acrylic beads. Attachment of the protein to a solid support aids in separating peptide-binding partner pairs from other constituents found in the extract. The identified binding partners can be either a single protein or a complex made up of two or more proteins. Alternatively, binding partners may be identified using a Far-Western assay according to the procedures of Takayama et al., (1997) Methods Mol. Biol. 69, 171–184 or identified through the use of epitope tagged proteins or GST fusion proteins.

Alternatively, the nucleic acid molecules of the invention can be used in a yeast two-hybrid system. The yeast two-hybrid system has been used to identify other protein partner pairs (Alifragis et al., (1997) Proc. Natl. Acad. Sci. USA 94, 13099–13104; Dong et al., (1999) Gene 237, 421–428) and can readily be adapted to employ the nucleic acid molecules herein described.

In another embodiment, binding partners may be identified in insects using single unit recordings as previously described (Kaissling, (1995) Single unit and electroantennogram recordings in insect olfactory organs, in: Spielman & Brand (ed.) Experimental Cell Biology of Taste and Olfaction, CRC Press). Using single unit recordings in vivo, response profiles are established for potential ligands, these profiles are then categorized into distinct functional classes indicative of distinct receptor-ligand interactions (see, e.g., U.S. Pat. No. 5,993,778). Single unit recordings in transgenic insects which contain transgenes resulting in over- or under-expression of a gene are also useful for identifying and characterizing ligands which bind to multiple olfactory receptors as well as identifying characterizing new olfactory receptors.

The nucleic acids of the invention and their corresponding proteins can be used on an array or microarray for high-throughput screening for agents which interact with either the nucleic acids of the invention or their corresponding proteins. An "array" or "microarray" generally refers to a grid system which has each position or probe cell occupied by a defined nucleic acid fragments also known as oligonucleotides. The arrays themselves are sometimes referred to as "chips" or "biochips". High-density nucleic acid and protein microarrays often have thousands of probe cells in a variety of grid styles.

A typical molecular detection chip includes a substrate on which an array of recognition sites, binding sites or hybridization sites are arranged. Each site has a respective molecular receptor which binds or hybridizes with a molecule having a predetermined structure. The solid support substrates which can be used to form surface of the array or chip include organic and inorganic substrates, such as glass, polystyrenes, polyimides, silicon dioxide and silicon nitride. For direct attachment of probes to the electrodes, the electrode surface must be fabricated with materials capable of forming conjugates with the probes.

Once the array is fabricated, a sample solution is applied to the molecular detection chip and molecules in the sample bind or hybridize at one or more sites. The sites at which binding occurs are detected, and one or more molecular structures within the sample are subsequently deduced. Detection of labeled batches is a traditional detection strategy and includes radioisotope, fluorescent and biotin labels, but other options are available, including electronic signal transduction.

Polymer arrays of nucleic acid probes can be used to extract information from, for example, nucleic acid samples. These samples are exposed to the probes under conditions that permit binding. The arrays are then scanned to determine to which probes the sample molecules have interacted with the nucleic acids of the polymer array. One can obtain information by careful probe selection and using algorithms to compare patterns of interactions. For example, the method is useful in screening for novel olfactory receptors in multiple organisms. For example, Drosophila degenerate olfactory receptor oligonucleotide arrays can be used to examine a nucleic acid sample from another insect species in order to identify novel olfactory receptors in that species.

In typical applications, a complex solution containing one or more substances to be characterized contacts a polymer array comprising nucleic acids. For example, the array is comprised of nucleic acid probes. The probes of the array can be either DNA or RNA, which may be either single-stranded or double-stranded. In a preferred embodiment of the invention, the probes are arranged (either by immobilization, typically by covalent attachment, of a pre-synthesized probe or by synthesis of the probe on the substrate) on the substrate or chips in lanes stretching across the chip and separated, and these lanes are in turned arranged in blocks of preferably five lanes, although blocks of other sizes will have useful application. The present invention provides individual probes, sets of probes, and arrays of probe sets on chips, in specific patterns which are used to characterize the substances in a complex mixture by producing a distinct image which is representative of the binding interactions between the probes on the chip and the substances in the complex mixture. The pattern of hybridization to the chip allows inferences to be drawn about the substances present in the complex mixture.

The substances in the complex solution will bind to the nucleic acids on the array. The substances of the complex mixture which bind to the nucleic acids of the array may include, but are not limited to, complementary nucleic acids, non-complementary nucleic acids, proteins, antibodies, oligosaccharides, etc. The types of binding may include, but are not limited to, specific and non-specific, competitive and non-competitive, allosteric, cooperative, non-cooperative, complementary and non-complementary, etc. For example, the nucleic acids of the array can bind to complementary nucleic acids in the complex mixture but can also bind in a tertiary manner, independent of base pairing, to non-complementary nucleic acids.

The nucleic acids of the array or the substances of the complex mixture may be tagged with a detectable label. The detectable label can be, for example, a luminescent label, a light scattering label or a radioactive label. Accordingly, locations at which substances interact can be identified by either determining if the signal of the label has been quenched by binding or identifying locations where the signal of the label is present in cases where the substances of the complex mixture have been labeled. Based on the locations where binding is detected, information regarding the complex mixture can be obtained.

The methods of this invention will find particular use wherever high through-put of samples is required. In particular, this invention is useful in ligand screening settings and for determining the composition of complex mixtures.

Polypeptides are an exemplary system for exploring the relationship between structure and function in biology. When the twenty naturally occurring amino acids are condensed into a polymeric molecule they form a wide variety of three-dimensional configurations, each resulting from a particular amino acid sequence and solvent condition. For example, the number of possible polypeptide configurations using the twenty naturally occurring amino acids for a polymer five amino acids long is over three million. Typical proteins are more than one-hundred amino acids in length.

In typical applications, a complex solution containing one or more substances to be characterized contacts a polymer array comprising polypeptides. The polypeptides of the invention can be prepared by classical methods known in the art, for example, by using standard solid phase techniques. The standard methods include exclusive solid phase synthesis, partial solid phase synthesis methods, fragment condensation, classical solution synthesis and recombinant DNA technology (see Merrifield, (1963) Am. Chem. Soc. 85, 2149–2152). On solid phase, the synthesis is typically commenced from the C-terminal end of the peptide using an alpha-amino protected resin. A suitable starting material can be prepared, for instance, by attaching the required alpha-amino acid to a chloromethylated resin, a hydroxy-methyl resin or a benzhydrylamine resin.

The alpha-amino protecting groups are those known to be useful in the art of stepwise synthesis of peptides. Included are acyl type protecting groups, aromatic urethane type protecting groups, aliphatic urethane protecting groups and alkyl type protecting groups. The side chain protecting group remains intact during coupling and is not split off during the deprotection of the amino-terminus protecting group or during coupling. The side chain protecting group must be removable upon the completion of the synthesis of the final peptide and under reaction conditions that will not alter the target peptide.

After removal of the alpha-amino protecting group, the remaining protected amino acids are coupled stepwise in the desired order. An excess of each protected amino acid is generally used with an appropriate carboxyl group activator such as dicyclohexylcarbodiimide (DCC) in solution, for example, in methylene chloride, dimethyl formamide (DMF) mixtures.

These procedures can also be used to synthesize peptides in which amino acids other than the twenty naturally occurring, genetically encoded amino acids are substituted at one, two, or more positions of any of the compounds of the invention. For instance, naphthylalanine can be substituted for tryptophan, facilitating synthesis. Other synthetic amino acids that can be substituted into the peptides of the present invention include L-hydroxypropyl, L-3, 4-dihydroxyphenylalanyl, d-amino acids such as L-d-hydroxylysyl and D-d-methylalanyl, L-α-methylalanyl and β-amino acids non-naturally occurring synthetic amino acids can also be incorporated into the peptides of the present invention (see Roberts et al., (1983) Peptide Synthesis 5, 341–449).

One can replace the naturally occurring side chains of the twenty genetically encoded amino acids (or D amino acids) with other side chains, for instance with groups such as alkyl, lower alkyl, cyclic four, five, six, to seven-membered alkyl, amide, amide lower alkyl, amide di(lower alkyl), lower alkoxy, hydroxy, carboxy and the lower ester derivatives thereof, and with four, five, six, to seven-membered heterocyclic. In particular, proline analogs in which the ring size of the proline residue is changed from five members to four, six or seven members can be employed. Cyclic groups can be saturated or unsaturated, and if unsaturated, can be aromatic or non-aromatic. Heterocyclic groups preferably contain one or more nitrogen, oxygen, and/or sulphur heteroatoms. Examples of such groups include the furazanyl, furyl, imidazolidinyl, imidazolyl, imidazolinyl, isothiazolyl, isoxazolyl, morpholinyl, oxazolyl, piperazinyl, piperidyl, pyranyl, pyrazinyl, pyrazolidinyl, pyrazolinyl, pyrazolyl, pyridazinyl, pyridyl, pyrimidinyl, pyrrolidinyl, pyrrolinyl, pyrrolyl, thiadiazolyl, thiazolyl, thienyl, thiomorpholinyl and triazolyl. These heterocyclic groups can be substituted or unsubstituted. Where a group is substituted, the substituent can be alkyl, alkoxy, halogen, oxygen, or substituted or unsubstituted phenyl.

One can also readily modify the peptides of the instant invention by phosphorylation (see Bannwarth et al., (1996) Biorg. Med. Chem. Let. 6, 2141–2146) and other methods for making peptide derivatives of the compounds of the present invention are described in Hruby et al., (1990) Biochem. J. 268, 249–262). Thus, the peptide compounds of the invention also serve as a basis to prepare peptide mimetics with similar biological activity. The array can also comprise peptide mimetics with the same or similar desired biological activity as the corresponding peptide compound but with more favorable activity than the peptide with respect to solubility, stability, and susceptibility to hydrolysis and proteolysis (see Morgan et al., (1989) Ann. Rep. Med. Chem. 24, 243–252).

Peptides suitable for use in this embodiment generally include those peptides, for example, ligands, that bind to a receptor, such as seven transmembrane proteins. Such peptides typically comprise about 150 amino acid residues or less and, more preferably, about 100 amino acid residues or less.

The peptides of the present invention may exist in a cyclized form with an intramolecular disulfide bond between the thiol groups of the cysteines. Alternatively, an intermolecular disulfide bond between the thiol groups of the cysteines can be produced to yield a dimeric (or higher oligomeric) compound. One or more of the cysteine residues may also be substituted with a homocysteine. Other embodiments of this invention provide for analogs of these disulfide derivatives in which one of the sulfurs has been replaced by a $CH_2$ group or other isostere for sulfur. These analogs can be made via an intramolecular or intermolecular displacement, using methods known in the art.

H. Methods to Identify Agents that Modulate Expression of DORs

Another embodiment of the present invention provides methods for identifying agents that modulate the expression of a nucleic acid encoding any one of the DOR proteins of the invention such as any protein having the amino acid sequence depicted in SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96 and 98. Such assays may utilize any available means of monitoring for changes in the expression level of the nucleic acids of the invention. As used herein, an agent is said to modulate the expression of a nucleic acid of the invention, for instance a nucleic acid encoding any one of the proteins having the amino acid sequence depicted in SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96 and 98, if it is capable of up- or down-regulating expression of the nucleic acid in a cell.

In one assay format, cell lines that contain reporter gene fusions between the open reading frame of any one of the nucleotides depicted in SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95 and 97 and any assay fusion partner may be prepared. Numerous assay fusion partners are known and readily available including the firefly luciferase gene and the gene encoding chloramphenicol acetyltransferase (Alam et al., (1990) Anal. Biochem. 188, 245–254). Cell lines containing the reporter gene fusions are then exposed to the agent to be tested under appropriate conditions and time. Differential expression of the reporter gene between samples exposed to the agent and control samples identifies agents which modulate the expression of a nucleic acid encoding at least one of the proteins having the sequence depicted in SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96 and 98.

Additional assay formats may be used to monitor the ability of the agent to modulate the expression of a nucleic acid encoding at least one protein of the invention selected from the group of proteins having SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96 and 98. For instance, mRNA expression may be monitored directly by hybridization to the nucleic acids of the invention. Cell lines are exposed to the agent to be tested under appropriate conditions and time and total RNA or mRNA is isolated by standard procedures such those disclosed in Sambrook et al., (1985) Molecular Cloning—A Laboratory Manual, Cold Spring Harbor Laboratory Press.

Probes to detect differences in RNA expression levels between cells exposed to the agent and control cells may be prepared from the nucleic acids of the invention. It is preferable, but not necessary, to design probes which hybridize only with target nucleic acids under conditions of high stringency. Only highly complementary nucleic acid hybrids form under conditions of high stringency. Accordingly, the stringency of the assay conditions determines the amount of complementary nucleotides which should exist between two nucleic acid strands in order to form a hybrid. Stringency should be chosen to maximize the difference in stability between the probe:target hybrid and potential probe:non-target hybrids.

Probes may be designed from the nucleic acids of the invention through methods known in the art. For instance, the G+C content of the probe and the probe length can affect probe binding to its target sequence. Methods to optimize probe specificity are commonly available in Sambrook et al., (1985) Molecular Cloning—A Laboratory Manual, Cold Spring Harbor Laboratory Press; or Ausubel et al., (1995) Current Protocols in Molecular Biology, Greene Publishing Company.

Hybridization conditions are modified using known methods, such as those described by Sambrook et al., (1985) and Ausubel et al., (1995) as required for each probe. Hybridization of total cellular RNA or RNA enriched for polyA+ RNA can be accomplished in any available format. For instance, total cellular RNA or RNA enriched for polyA RNA can be affixed to a solid support and the solid support exposed to at least one probe comprising at least one, or part of one of the sequences of the invention under conditions in which the probe will specifically hybridize. Alternatively, nucleic acid fragments comprising at least one, or part of one of the sequences of the invention can be affixed to a solid support, such as a porous glass wafer. The glass wafer can then be exposed to total cellular RNA or polyA RNA from a sample under conditions in which the affixed sequences will specifically hybridize. Such glass wafers and hybridization methods are widely available, for example, those disclosed by Beattie (WO 95/11755). By examining for the ability of a given probe to specifically hybridize to an RNA sample from an untreated cell population and from a cell population exposed to the agent, agents which up- or down-regulate the expression of a nucleic acid encoding at least one protein having the amino acid sequence depicted in SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96 and 98 are identified.

Hybridization for qualitative and quantitative analysis of mRNA may also be carried out by using a RNase Protection Assay (i.e., RPA, see Ma et al., (1996) Methods 10, 273–238). Briefly, an expression vehicle comprising cDNA encoding the gene product and a phage specific DNA dependent RNA polymerase promoter (e.g., T7, T3 or SP6 RNA polymerase) is linearized at the 3' end of the cDNA molecule, downstream from the phage promoter, wherein such a linearized molecule is subsequently used as a template for synthesis of a labeled antisense transcript of the cDNA by in vitro transcription. The labeled transcript is then hybridized to a mixture of isolated RNA (i.e., total or fractionated mRNA) by incubation at 45° C. overnight in a buffer comprising 80% formamide, 40 mM Pipes, pH 6.4, 0.4 M NaCl and 1 mM EDTA. The resulting hybrids are then digested in a buffer comprising 40 µg/ml ribonuclease A and 2 µg/ml ribonuclease. After deactivation and extraction of extraneous proteins, the samples are loaded onto urea-polyacrylamide gels for analysis.

In another assay fonnat, agents which effect the expression of the instant gene products, cells or cell lines would first be identified which express said gene products physiologically. Cells and cell lines so identified would be expected to comprise the necessary cellular machinery such that the fidelity of modulation of the transcriptional apparatus is maintained with regard to exogenous contact of agent with appropriate surface transduction mechanisms and the cytosolic cascades. Further, such cells or cell lines would be transduced or transfected with an expression vehicle (e.g., a plasmid or viral vector) construct comprising an operable non-translated 5'-promoter containing end of the structural gene encoding the instant gene products fused to one or more antigenic fragments, which are peculiar to the instant gene products, wherein said fragments are under the transcriptional control of said promoter and are expressed as polypepfides whose molecular weight can be distinguished from the naturally occurring polypeptides or may further comprise an immunologically distinct tag. Such a process is well known in the art (see Maniatis et al., (1982) Molecular Cloning—A Laboratory Manual, Cold Spring Harbor Laboratory Press).

Cells or cell lines transduced or transfected as outlined above would then be contacted with agents under appropriate conditions; for example, the agent comprises an acceptable excipient and is contacted with cells comprised in an aqueous physiological buffer such as phosphate buffered saline (PBS) at physiological pH, Eagles balanced salt solution (BSS) at physiological pH, PBS or BSS comprising serum or conditioned media comprising PBS or BSS and/or serum incubated at 37° C. Said conditions may be modulated as deemed necessary by one of skill in the art. Subsequent to contacting the cells with the agent, said cells will be disrupted and the polypeptides from disrupted cells are fractionated such that a polypeptide fraction is pooled and contacted with an antibody to be further processed by immunological assay (e.g., ELISA, immunoprecipitation or Western blot). The pool of proteins isolated from the "agent contacted" sample will be compared with a control sample where only the excipient is contacted with the cells and an increase or decrease in the immunologically generated signal from the "agent contacted" sample compared to the control will be used to distinguish the effectiveness of the agent.

I. Methods to Identify Agents That Modulate Activity of DORs

Another embodiment of the present invention provides methods for identifying agents that modulate at least one activity of a protein of the invention such as any one of the proteins having the amino acid sequence of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96 and 98. Such methods or assays may utilize any means of monitoring or detecting the desired activity.

In one format, the relative amounts of a protein of the invention between a cell population that has been exposed to the agent to be tested compared to an un-exposed control cell population may be assayed. In this format, probes such as specific antibodies are used to monitor the differential expression of the protein in the different cell populations. Cell lines or populations are exposed to the agent to be tested under appropriate conditions and time. Cellular lysates may be prepared from the exposed cell line or population and a control, unexposed cell line or population. The cellular lysates are then analyzed with the probe.

Antibody probes are prepared by immunizing suitable mammalian hosts in appropriate immunization protocols using the peptides, polypeptides or proteins of the invention if they are of sufficient length, or if desired, required to enhance immunogenicity, conjugated to suitable carriers. Methods for preparing immunogenic conjugates with carriers such as BSA, KLH, or other carrier proteins are well known in the art. In some circumstances, direct conjugation using, for example, carbodiimide reagents may be effective; in other instances linking reagents such as those supplied by Pierce Chemical Co., may be desirable to provide accessibility to the hapten. The hapten peptides can be extended at either the amino or carboxy terminus with a cysteine residue or interspersed with cysteine residues, for example, to facilitate linking to a carrier. Administration of the immunogens is conducted generally by injection over a suitable time period and with use of suitable adjuvants, as is generally understood in the art. During the immunization schedule, titers of antibodies are taken to determine adequacy of antibody formation.

While the polyclonal antisera produced in this way may be satisfactory for some applications, for some applications, use of monoclonal preparations is preferred. Immortalized cell lines which secrete the desired monoclonal antibodies may be prepared using the standard method of Kohler & Milstein, (1975) Nature 256, 495–497 or modifications which effect immortalization of lymphocytes or spleen cells, as is generally known. The immortalized cell lines secreting the desired antibodies are screened by immunoassay in which the antigen is the peptide hapten, polypeptide or protein. When the appropriate immortalized cell culture secreting the desired antibody is identified, the cells can be cultured either in vitro or by production in ascites fluid.

The desired monoclonal antibodies are then recovered from the culture supernatant or from the ascites supernatant. Fragments of the monoclonal or polyclonal antisera which contain the immunologically significant portion can be used as antagonists, as well as the intact antibodies. Use of immunologically reactive fragments, such as the Fab, Fab' of F(ab')$_2$ fragments is often preferable, as these fragments are generally less immunogenic than the whole immunoglobulin.

The antibodies or fragments may also be produced, using current technology, by recombinant means. Antibody regions that bind specifically to the desired regions of the protein can also be produced in the context of chimeras with multiple species origin, particularly humanized antibodies.

Agents that are assayed in the above method can be randomly selected or rationally selected or designed. As used herein, an agent is said to be randomly selected when the agent is chosen randomly without considering the specific sequences involved in the association of the a protein of the invention alone or with its associated substrates, binding partners, etc. An example of randomly selected agents is the use a chemical library or a peptide combinatorial library, or a growth broth of an organism.

As used herein, an agent is said to be rationally selected or designed when the agent is chosen on a non-random basis which takes into account the sequence of the target site and its conformation in connection with the agent's action. Agents can be rationally selected or rationally designed by utilizing the peptide sequences to identify proposed binding motifs, glycosylation and phosphorylation sites on the protein.

The agents of the present invention can be, as examples, peptides, small molecules, vitamin derivatives, as well as carbohydrates. A skilled artisan can readily recognize that there is no limit as to the structural nature of the agents of the present invention. Dominant-negative proteins, DNA encoding these proteins, antibodies to these proteins, peptide fragments of these proteins or mimics of these proteins may be contacted with cells to affect function. "Mimic" as used herein refers to the modification of a region or several regions of a peptide molecule to provide a structure chemically different from the parent peptide but topographically and functionally similar to the parent peptide (see Meyers, (1995) Molecular Biology & Biotechnology, VCH Publishers).

The peptide agents of the invention can be prepared using standard solid phase (or solution phase) peptide synthesis methods, as is known in the art. In addition, the DNA encoding these peptides may be synthesized using commercially available oligonucleotide synthesis instrumentation and produced recombinantly using standard recombinant production systems. The production using solid phase peptide synthesis is necessitated if non-gene-encoded arnino acids are to be included.

Another class of agents of the present invention are antibodies immunoreactive with critical positions of proteins of the invention. Antibody agents are obtained by immunization of suitable mammalian subjects with peptides, containing as antigenic regions, those portions of the protein intended to be targeted by the antibodies.

J. Transgenic Organisms

Transgenic insects containing mutant, knock-out or modified genes corresponding to any one of the cDNA sequences depicted in SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95 and 97 are also included in the invention. Transgenic insects are genetically modified insects into which recombinant, exogenous or cloned genetic material has been experimentally transferred. Such genetic material is often referred to as a "tansgene". The nucleic acid sequence of the transgene, in this case a form of any one of the sequences depicted in SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95 and 97, may be integrated either at a locus of a genome where that particular nucleic acid sequence is not otherwise normally found or at the normal locus for the transgene. The transgene may consist of nucleic acid sequences derived from the genome of the same species or of a different species than the species of the target insect.

The term "germ cell line transgenic insect" refers to a transgenic insect in which the genetic alteration or genetic information was introduced into a germ line cell, thereby conferring the ability of the transgenic insect to transfer the genetic information to offspring. If such offspring in fact possess some or all of that alteration or genetic information, then they too are transgenic insects.

The alteration or genetic information may be foreign to the species of insect to which the recipient belongs, foreign only to the particular individual recipient, or may be genetic information already possessed by the recipient. In the last case, the altered or introduced gene may be expressed (i.e., over-expression and knock-out) differently than the native gene.

Transgenic insects can be produced by a variety of different methods including P element-mediated transformation by microinjection (see, e.g. Rubin & Spradling, (1982) Science 218, 348–353; Orr & Sohal, (1993) Arch. Biochem. Biophys. 301, 34–40), transformation by microinjection followed by transgene mobilization (Mockett et al., (1999) Arch. Biochem. Biophys. 371, 260–269), electroporation (Huynh & Zieler, (1999) J. Mol. Biol. 288, 13–20) and through the use of baculovirus (Yamao et al., (1999) Genes Dev. 13, 511–516. Furthermore, the use of adenoviral vectors to direct expression of a foreign gene to olfactory neuronal cells can also be used to generate transgenic insects (see, e.g., Holtmaat et al., (1996) Brain. Res. Mol. Brain Res. 41, 148–156).

A number of recombinant or transgenic insects have been produced, including those which over-express superoxide dismutase (Mockett et al., (1999) Arch. Biochem. Biophys. 371, 260–269); express Syrian hamster prion protein (Raeber et al., (1995) Mech. Dev. 51, 317–327); express cell-cycle inhibitory peptide aptamers (Kolonin & Finley (1998) Proc. Natl. Acad. Sci. USA 95, 14266–14271); and those which lack expression of the putative ribosomal protein S3A gene (Reynaud et al., (1997) Mol. Gen. Genet. 256, 462–467).

While insects remain the preferred choice for most transgenic experimentation, in some instances it is preferable or even necessary to use alternative animal species. Transgenic procedures have been successfully utilized in a variety of animals, including mice, rats, sheep, goats, pigs, dogs, cats, monkeys, chimpanzees, hamsters, rabbits, cows and guinea pigs (see, e.g., Kim et al., (1997) Mol. Reprod. Dev. 46, 515–526; Houdebine, (1995) Reprod. Nutr. Dev. 35, 609–617; Petters, (1994) Reprod. Fertil. Dev. 6, 643–645; Schnieke et al., (1997) Science 278, 2130–2133; and Amoah, (1997) J. Anim. Sci. 75, 578–585).

The method of introduction of nucleic acid fragments into insect cells can be by any method which favors co-transformation of multiple nucleic acid molecules. For instance, Drosophila embryonic Schneider line 2 (S2) cells can be stably transfected as previously described (Schneider, (1972) J. Embryol. Exp. Morphol. 27, 353–365). Detailed procedures for producing transgenic insects are readily available to one skilled in the art (see Rubin & Spradling, (1982) Science 218, 348–353; Orr & Sohal, (1993) Arch. Biochem. Biophys. 301, 34–40, herein incorporated by reference in their entirety).

K. Uses for Agents That Modulate at Least One Activity of DORs

1. Introduction.

Organisms, including insects, are continually exposed to a great number of volatiles released by other organisms as well as by other aspects of their environment. The olfactory receptor genes of the present invention play an important role in the detection and processing of these chemical stimuli, some of which have been implicated in initiating and modulating host-seeking and other behaviors, such as mating behaviors (see, for example, Roth, (1951) Ann. Entomol. Soc. Am. 44, 59–74; Jones et al., (1976) Ent. Exp. Appn. 19, 19–22; Gillies, (1980) Bull. Ent. Res. 70, 525–532; Kline et al., (1991) J. Med. Entomol. 28, 254–258). For a recent, thorough review of the many practical applications of the present invention (see Karg & Suckling, (1999) Applied aspects of insect olfaction, in: Hansson (ed.), Insect Olfaction, Springer, which is incorporated by reference in its entirety).

Most importantly, the DOR genes of the present invention may be used to track down odor receptor genes in insects that damage crops or transmit diseases. The present invention provides the tools and methodologies for finding specific compounds that interfere with the insects' ability to detect odors.

Of course, the present invention has important implications for improved methods of using pheromones and other semiochemicals for pest control. In addition, recent advancements in many other fields have greatly increased the variety of additional technologies for which the present invention also has significant applications. Examples of such advancements include, but are not limited to the following: i) the development and application of new techniques of chemical identification and synthesis; ii) new chemical release techniques; iii) more sophisticated application technologies; and iv) more detailed information about the behavior of specific organisms.

While not wishing to be bound by the specific embodiments discussed herein, the following sections provide an overview of the wide variety of applications for which the present invention may be employed.

2. Definitions.

As used herein, the term "allomones" refers to any chemical substance produced or acquired by an organism that, when it contacts an individual of another species, evokes in the receiver a behavioral or developmental reaction adaptively favorable to the transmitter.

As used herein, the term "host" refers to any organism on which another organism depends for some life finction. Examples of hosts include, but are not limited to, humans which may serve as a host for the feeding of certain species of mosquito and the leaves of soybeans (*Glycine max*(L.)) which may act as hosts for the oviposit of the green cloverworm (*Plathypena scabra* (F.)).

As used herein, the term "kairomones" refers to any of a heterogeneous group of chemical messengers that are emitted by organisms of one species but benefit members of another species. Examples include, but are not limited to, attractants, phagostimulants, and other substances that mediate the positive responses of, for example, predators to their prey, herbivores to their food plants, and parasites to their hosts. Kairomones suitable for the purposes of the invention and methods of obtaining them are described, for example, Science (1966) 154, 1392–93; Hedin, (1985) Bioregulators for Pest Control, American Chemical Society, Washington, 353–366.

As used herein, the term "pheromone" refers to a substance, or characteristic mixture of substances, that is secreted and released by an organism and detected by a second organism of the same or a closely related species, in which it causes a specific reaction, such as a definite behavioral reaction or a developmental process. Examples include, but are not limited to, the mating pheromones of fungi and insects. More than a thousand moth sex pheromones (Toth et al., (1992) J. Chem. Ecol. 18, 13–25; Am et al., (1998) Appl. Entomol. Zoo. 33, 507–511) and hundreds of other pheromones have now been identified, including aggregation pheromones from beetles and other groups of insects. Various compositions, including resins and composite polymer dispensers, have been developed for the controlled release of pheromones have been developed (see, e.g., U.S. Pat. No. 5,750,129 & 5,504,142).

As used herein, the term "semiochemical" refers to any chemical substance that delivers a message or signal from one organism to another. Examples of such chemicals include, but are not limited to, pheromones, kairomones, oviposition deterrents, or stimulants, and a wide range of other classes of chemicals (see, for example, Nordlund, (1981) Semiochemicals: A review of the terminology, in: Nordlund et al., (ed.) Semiochemicals: Their Role in Pest Control, John Wiley; Howse et al., (1998) Insect Pheromones and Their Use in Pest Management, Chapman & Hall, London).

As used herein, the term "synomones" refers to any chemical substance which benefits both the emitter and receiver. Examples include, but are not limited to, compounds involved in floral attraction of pollinators and species-isolating mechanisms, such as sex pheromones of related species, where an inhibitor often functions to prevent mating among sympatric species.

As used herein, the term "volatile" refers to a chemical which evaporates readily at those temperatures and pressures which are considered the relevant temperatures and pressures for the reference organism of interest.

3. As Tools for Further Scientific Research.

Identification of Olfactory Receptor Genes in Other Organisms. The algorithms of the present invention may be used directly to search for olfactory receptor genes in other organisms, as explained elsewhere herein.

Alternatively, nucleic acid probes or primers may be designed based on the DOR genes of the present invention. Such probes or primers may be used to identify and isolate olfactory receptor genes in other organisms. Methods of creating and using the necessary nucleic acid probes and primers are discussed elsewhere herein.

The highest probability of success in locating olfactory genes in other organisms using the DOR genes of the present invention will most likely occur by using a boot-strapping or leapfrogging method. Such methods involve first probing organisms most related to fruit flies and successively progressing to more unrelated organisms, using the most newly identified olfactory receptor genes to identify similar genes in the next, more unrelated, insect of interest. Thus, the first organisms to probe with the DOR genes of the present invention most preferably may be other flies from the order Diptera (i.e., the two-winged or true flies). Examples of suitable flies include, but are not limited to, the tsetse fly, horse fly, house fly, bluebottle fly, hover fly and mosquito. Dipterans which transmit diseases causing serious health problems are of particular interest (e.g., horse fly, tsetse fly, mosquito).

After the identification of olfactory receptor genes in various Diptera insects, the next organisms to probe most preferably may be from orders within the same subclass as Diptera. Finally, the next insects to use would be those from orders not within the same subclass as Diptera.

The insects which cause substantial health risks, crop damage, or other significant damage (e.g., to housing structure or cotton clothing) may be the most desirable targets for such studies. Examples of such insects include, but are not limited to, green cloverworm, Mexican bean beetle, potato leafhopper, corn earworm, green stink bug, northern corn rootworm, western corn rootworm, cutworms, wireworms, thrips, fleas, aphids (e.g., pea aphid, spotted alfalfa aphid), European corn borer, fall armyworm, southwestern corn borer, grasshoppers, Japanese beetle, termites, leafhoppers (e.g., potato leafhopper, three-cornered alfalfa hopper), stink bugs, crickets, Hessian fly, greenbugs and weevils (e.g., alfalfa weevil, bollweevil).

Olfactory receptor genes identified by this process may then be used to screen non-Insecta organisms for olfactory receptor genes. Organisms of interest may include, but be limited to, mites, ticks, spiders, nematodes, centipedes, mice, rats, salmon, pigeons, dogs, horses and humans.

Genetic Manipulations. The tools and methodologies of the present invention may be used by neurobiologists to probe more complex workings of an organism's response system, including those of a mammal's brain.

Knock-outs. By systematically knocking out the olfactory receptor genes of the present invention and observing the effects on odor sensitivity and behavior, researchers will be able to piece together a wiring diagram of the olfactory system of the fruit fly.

The term "knock-out" generally refers to mutant organisms which contain a null allele of a specific gene. Methods of making knock-out or disruption transgenic animals, especially mice, are generally known by those skilled in the art and are discussed herein and elsewhere (see, for example, the section herein entitled Transgenic Organisms and the following: Manipulating the Mouse Embryo, (1986) Cold Spring Harbor Laboratory Press; Capecchi, (1989) Science 244, 1288–1292; Li et al., (1995) Cell 80, 401–411; U.S. Pat. No. 5,981,830 & 5,789,654, each of which is incorporated herein by reference.

Parallel studies may be conducted in other organisms by using the olfactory receptor genes and the methods of the present invention to identify the olfactory receptor genes of other organisms and then creating knock-outs for the olfactory receptor genes of those organisms.

Disabling Genes. Using the olfactory receptor genes of the present invention, it is now possible to selectively disable specific DOR genes and look for changes in odor response and behavior. Parallel studies may be conducted in other organisms by using the olfactory receptor genes and the methods of the present invention to identify the olfactory receptor genes of other organisms and then disabling olfactory receptor genes of those organisms.

Methods of disabling genes are generally known by those skilled in the art. An example of an effective disabling modification would be a single nucleotide deletion occurring at the beginning of a olfactory receptor gene that would produce a translational reading frameshift. Such a frameshift would disable the gene, resulting in non-expressible gene product and thereby disrupting functional protein production by that gene. Protease production by the gene could be disrupted if the regulatory regions or the coding regions of the protease genes are disrupted.

In addition to disabling genes by deleting nucleotides, causing a transitional reading frameshift, disabling modifications would also be possible by other techniques including insertions, substitutions, inversions or transversions of nucleotides within the gene's DNA that would effectively prevent the formation of the protein coded for by the DNA.

It is also within the capabilities of one skilled in the art to disable genes by the use of less specific methods. Examples of less specific methods would be the use of chemical mutagens such as hydroxylamine or nitrosoguanidine or the use of radiation mutagens such as gamma radiation or ultraviolet radiation to randomly mutate genes, such as the DOR genes of the present invention. Such mutated strains could, by chance, contain disabled olfactory receptor genes such that the genes are no longer capable of producing functional proteins for any one or more of the domains. The presence of the desired disabled genes could be detected by routine screening techniques. For further guidance, see U.S. Pat. No. 5,759,538.

Over-expression. Using the olfactory receptor genes of the present invention, it is now possible to selectively over-express specific DOR genes and look for changes in odor response and behavior. Parallel studies may be conducted in other organisms by using the olfactory receptor genes and the methods of the present invention to identify the olfactory receptor genes of other organisms and then overexpress the olfactory receptor genes of those organisms.

Methods of overexpressing genes are generally known by those skilled in the art. For examples of producing cells which overexpress specific genes, see, for example, U.S. Pat. Nos. 5,905,146; 5,849,999; 5,859,311; 5,602,309; 5,952,169 and 5,772,997 (HER2 receptor).

Modulating or Inhibiting Expression. Using the olfactory receptor genes of the present invention, it is now possible to selectively modulate or inhibit specific DOR genes using antisense oligomers which specifically hybridize with the DNA or RNA encoding the DOR genes. One skilled in the art could so modulate or inhibit the expression of the DOR genes and detect for changes in odor response and behavior. Parallel studies may be conducted in other organisms by using the olfactory receptor genes and the methods of the present invention to identify the olfactory receptor genes in other organisms and then use antisense oligers to the olfactory receptor genes of those organisms. Methods for inhibiting expression of genes, especially genes coding for receptor genes, using antisense constructs, including generation of antisense sequences in situ are described, for example, in U.S. Pat. Nos. 5,856,099; 5,556,956; 5,716,846; 5,135,917 and 6,004,814.

Other methods that can be used to inhibit expression of an endogenous gene are applicable to the present invention. For example, formation of a triple helix at an essential region of a duplex gene serves this purpose. The triplex code, permitting design of the proper single stranded participant is also known in the art. (See H. E. Moser, et al., (1987) Science 238: 645–650 and M. Cooney, et al, (1988) Science 241: 456459). Regions in the control sequences containing stretches of purine bases are particularly attractive targets. Triple helix formation along with photocrosslinking is described, e.g., in Praseuth et al., (1988) Proc. Natl Acad. Sci. USA 85:1349–1353.

Studying Behavior. The present invention is useful for studying the developmental aspects of the olfactory receptor genes which appear to be active at different times during development. Such studies may help organize the olfactory systems in various organisms and may help explain the behavior of various organisms.

The tools and methodologies of the present invention may be used to study the influence of environmental conditions on pheromone communication. For example, newly identified olfactory receptor genes may be used to study the effects of different rearing temperatures and light regimes (selected to mimic those occurring in the spring and summer growing seasons) on the response of various Lepidoptera insects, such as the cabbage looper moth (Trichoplusia ni (Hubner)). For a description of the methods which might be used for such a study, see, for example, Grant et al., (1996) Physiol. Entomol. 21, 59–63.

4. For Organism Detection, Monitoring and Control.

General Pest Management. The olfactory receptor genes identified herein and identified using the methods of the present invention may be used to identify compounds which may be used for pest management. It is especially desirable to utilize various aspects of the present invention for pest management related to crop protection.

The application of pheromones is now firmly established as a key component of pest management and control, especially within the framework of integrated pest management (IPM). An object of organism control is to modulate an organism's behavior or activity so as to reduce the irritation, sickness, or death of the host (e.g., a plant host), or to decrease the general health and proliferation of the organism.

For example, the propagation of a mouse population in a given area of actual or potential mice infestation may be prevented or inhibited by treating such an area with an effective amount of male mouse pheromones, wherein such pheromones have male mouse aversion signaling properties (see, e.g., U.S. Pat. No. 5,252,326).

Insect Repellents and Insecticides. The present invention provides the tools and methodologies useful for identifying compounds which modulate insect behavior by exploiting the sensory capabilities of the target insect. For example, attempts have been made to describe and synthesize the complex interactions which underlie host-seeking behavior in mosquitoes. Using the methods and olfactory receptor genes of the present invention, it is possible to design specific compounds which target mosquito olfactory receptor genes. Thus, the present invention provides the ability to alter or to eliminate the orientation and feeding behaviors of mosquitoes and thereby have a positive impact on world health by controlling mosquito-borne diseases, such as malaria.

Mosquito olfactory receptor genes may be identified and/or targeted using various aspects of the present invention. For example, the olfactory receptor genes of the present invention may be used to design probes as discussed elsewhere herein for the identification and characterization of mosquito olfactory receptor genes. Alternatively, the algorithm of the present invention may be used to identify mosquito olfactory receptor genes in the genetic databases for mosquitoes. Once the mosquito olfactory receptor genes are identified, then various screening methods described elsewhere herein, such as the high throughput assays discussed elsewhere herein, may be used to identify synthetic and natural compounds which may modulate the behavior of the insect.

Mating Enhancement and Disruption. The olfactory receptor genes identified herein and identified using the methods of the present invention may be used to identify compounds which interfere with the orientation and mating of a wide range of organisms, including insects. Thus, the present invention enables the identification of compositions which disrupt insect mating by selective inhibition of specific receptor genes involved in mating attraction (see, e.g., U.S. Pat. No. 5,064,820).

Animal Repellants. The olfactory receptor genes identified herein and identified using the methods of the present invention may be used to identify compounds which may be used as animal repellants. Such compositions may be used to repel both predatory and non-predatory animals (see, e.g., U.S. Pat. No. 4,668,455).

6. Organism Attraction.

Insect Attractants. The olfactory receptor genes identified herein and identified using the methods of the present invention may be used to identify compounds which attract specific insects to a particular location (see, e.g., U.S. Pat. No. 4,880,624 & 4,851,218).

For example, aspects of the present invention may to used in various methods which reduce or eliminate the levels of particular insect pests, such as mosquitoes and tsetse flies. As a particular example, insect traps can be created wherein the pheromone attracts a particular insect, like the tsetse fly, and the insect so attracted dies in the trap. In this way, the population of tsetse flies may be reduced or eliminated in a particular area.

The insect attractant compositions so identified may also be combined with an insecticide, for example as an insect bait in microencapsulated form. Alternatively, or in addition, the insect attractant composition may be placed inside an insect trap, or in the vicinity of the entrance to an insect trap.

In addition to killing insects, the trapping of insects is often very important for estimating or calculating how many insects of a particular type are feeding within a specific area. Such estimates are used to determine where and when insecticide spraying should be commenced and terminated.

Insect traps which may be used are, for example, those as described in PCT/BG93/01442 and U.S. Pat. No. 5,713,153. Specific examples of insect traps include, but are not limited to, the Gypsy Moth Delta Trap®, Boll Weevil Scout Trap®, Jackson trap, Japanese beetle trap, McPhail trap, Pherocon IC trap, Pherocon II trap, Perocon AM trap and Trogo trap.

Kairomones may be used as an attractancy for the enhancement of the pollination of selected plant species.

Attractant compositions which demonstrate biological activity toward one sex which is greater than toward the opposite sex may be useful in trapping one sex of a specific organism over another. For example, a composition may be a highly effective attractant for male apple ermine moths (*Yponomeuta malinellus* (Zeller)) and not so effective an attractant for female apple ermine moths. By attracting adult males to field traps, the composition provides a means for detecting, monitoring, and controlling this agricultural pest (see, e.g., U.S. Pat. No. 5,380,524).

Attracting Predators and Parasitoids. The olfactory receptor genes of the present invention and the olfactory receptor genes identified using the methods of the present invention may also be used to identify chemicals which attract various predators and parasitoids. Attracting the predators and parasitoids which attack certain pests offers an alternative method of pest management.

Animal Attractants. The olfactory receptor genes identified herein and those identified by the methods of the present invention may be used to identify chemicals which attract household domesticated animals. For example, a pheromone-containing litter preparation may attract the animals and absorb liquids and liquid-containing waste released by the attracted animal (see, e.g., U.S. Pat. No. 5,415,131).

Synthetic Perfumes. A "perfume" or a "fragrance composition" is a specific pleasantly odorous cosmetic composition for topical application to an individual. The olfactory receptor genes identified herein and those identified by the methods of the present invention may be used to identify chemicals which may be produced and used as synthetic perfumes. Such perfumes may be used to disguise odors or enhance attraction between humans (see, e.g., U.S. Pat. No. 5,278,141).

7. Pharmaceuticals.

The olfactory receptor genes identified herein and those identified using the methods of the present invention may be used to identify pharmaceutical compounds useful for altering the behavior and physiology of animals. Examples of such compounds include, but are not limited to, certain Androstene steroids that effectuate a change in human hypothalamic function (see, e.g., U.S. Pat. No. 5,969,168).

8. Industrial Applications.

The olfactory receptor genes identified by the methods of the present invention may be used for a number of different industrial applications including, but not limited to the following:

a) Identification of appetite suppressant compounds and using same to suppress and/or control appetite.

b) Trapping odors of a specific type.

c) As Biosensors.

1) Explosive and drug detectors. The detectors may be synthetic, such as biologically-inspired robotic sensors, or biological sensors, such as sniffing dogs which are especially sensitive to certain odors.

2) Population of olfactory receptor genes expressed in cell culture. Olfactory receptor genes can be introduced into a cell line and the transformed cells maintained in culture through multiple generations. By creating specific cell lines which express multiple olfactory genes at once, it would be possible to use such cell cultures to investigate how odorants interact with odorant receptor genes. Thus, the present invention provides methods for identifying odorant fingerprints, wherein such methods include contacting a series of cells containing and expressing known odor receptor genes with a desired sample, and determining the type and quantity of the odorant ligands present in the sample (see, e.g., U.S. Pat. No. 5,993,778). As discussed elsewhere herein, the interaction of substances with the receptors can be identified using appropriate labels, such as those provided by luciferase, the jellyfish green fluorescent protein (GFP) or β-galactosidase.

3) Biochip Arrays. As discussed elsewhere herein, biochip arrays of odorant receptor genes can be generated. The arrays may be used to detect olfactory receptor ligands via an appropriate marker or via a chemical or electrical signal. Arrays may be designed for specific purposes, such as, but not limited to, detecting perfumes, explosives, drugs, pollutants, and toxins.

d) Training organisms to conduct certain tasks. Examples include, but are not limited to, the following:

1) Training mice to pull guide line for stringing fiber optic cable through existing conduit holding copper wire.

2) Training mice to find their way through a maze based on smell (see, e.g., Otto et al., (1991) Hippocampus 1, 181–192; Granger et al., (1991) Psych. Science 2, 116–118).

3) Improving the orientation and homing performance of pigeons (see, e.g., Wiltschko, (1996) J. Exp. Biol. 199, 113–119) and fish (see, e.g., Cao et al. (1998) Proc. Natl. Acad. Sci. USA 95(20):11987–11992).

4) Orient or reorient the behavior of worker bees of a rearing colony by incorporating a composition which includes one or more pheromones which elicits particular bee behavior towards the larvae. Thus, the beekeeper may orient or reorient the bees towards a particular activity such as, but not limited to, inducing improved acceptance of the larvae at the beginning of rearing, to increase the production of royal jelly, regulate the feeding of the larvae as to favor the development of queen bees, etc. (see, e.g., U.S. Pat. No. 5,695,383).

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

EXAMPLES

Example 1

Identification of Candidate Olfactory Receptor Genes

In vertebrates and nematodes it is estimated that there are hundreds of olfactory receptor genes, widely distributed in the genome (Buck & Axel, (1991) Cell 65, 175–187; Troemel et al., (1995) Cell 83, 207–218). With approximately 10% of the Drosophila genome sequenced, it was likely that some of the Drosophila odorant receptor genes have been sequenced. A two-step strategy was developed to identify odorant receptor genes from the genomic database. First, a computer algorithm was designed to search the Drosophila genomic sequence for open reading frames (ORFs) from candidate odorant receptor genes. Second, RT-PCR was used to determine if transcripts from any of these ORFs were expressed in olfactory organs. Finally, in situ hybridization was used to localize expression of DOR genes.

Step 1: Computer algorithm for identification of GPCR genes. The algorithm used to identify GPCR genes used statistical characterization of amino acid physico-chemical profiles in combination with a non-parametric discriminant function. The key approach is to use the information in the interplay between the local structure (transmembrane alpha helix) and the global structure (repeated multiple domains) and characterize this information with concise statistical variables. The algorithm was trained on a set of 100 putative GPCR sequences from the GPCR database (GPCRDB) at http://swift.embl-heidelberg.de/7tm and a set of 100 random proteins selected from the SWISSPROT database (this training set was later expanded, but that version was not used for the genes reported in this paper). In the first step, three sets of descriptors were used to summarize the physico-chemical profiles of the sequences. These were GES scale of hydropathy (Engelman et al., (1986) Annu. Rev. Biophys. Biophys. Chem. 15, 321–353), polarity (Brown, (1991) Molecular Biology Labfax, Academic Press), and amino acid usage frequency. For the first two of these measurements, a sliding window profile was employed (White, (1994) Membrane Protein Structure, Oxford University Press) using a kernel of 15 amino acid constant function convoluted with a 16 amino acid Gaussian function. These profiles were then summarized with three statistics; the periodicity (characterizing the quasi-periodic presence of the transmembrane domain), average derivative (characterizing the abrupt change between the transmembrane domain and non-transmembrane domain), and the variance of the derivative (also characterizing the abrupt change). GES periodicity, variance of polarity derivative, polarity periodicity and amino acid frequency were used as the four variables and each sequence was therefore characterized by four variables. These four variables were used in a non-parametric linear discriminant function that was then optimized to separate the known GPCRs from random proteins in the training set. The same linear discriminant function with the scores derived from the training set was then used to screen the genomic database for candidate genes. The candidate sequences were given significance values by an odds ratio of the GPCRs and non-GPCRs computed using the observed empirical distribution of the training set. More detailed infonnation about the algorithm is available at http://www.neuron.org/cgi/content/full/22/2/327/dc1.

The computational screens used the genomic sequence data obtained by FTP from the Berkeley Drosophila Genome Project (BDGP, http://www.fruitfly.org, version 6/98). First, the ORFs of 300 bases or longer in all six frames were identified. Next, a program written to identify GPCRs statistically by their physico-chemical profile was used to screen for candidate ORFs as described above. The number of possible candidates was reduced by comparing them to Drosophila codon usage tables (http://flybase.bio.indiana.edu, version 10). Candidate ORFs whose codon usage differed at a significance level of 0.0005 by the chi-square statistic were discarded from the candidate set. Using these screening steps, 34 candidate ORFs were obtained.

Further analysis revealed that eight of the thirty-four candidate ORFs corresponded to genes of known function, for example a cyclic nucleotide-gated channel (Baumann et al., (1994) EMBO J. 13, 5040–5050) and these ORFs were not further analyzed. Most of the remaining ORFs encoded fewer than seven predicted transmembrane domains. The genomic DNA surrounding each of the computer-identified ORFs was therefore examined for the presence of neighboring ORFs encoding additional transmembrane domains to which the original ORFs might be spliced. Drosophila 5' and 3' intron-exon consensus splice sequences were used in this analysis to help identify linked exons (Mount et al., (1992) Nucleic Acids Res. 20, 4255–4262). This analysis yielded several genes that encoded seven-transmembrane-domain proteins (22A.1 and 22A.2).

Step 2: Sequence analysis of DOR olfactory genes. To determine if these two candidates were part of a larger family of genes encoding seven-transmembrane-domain proteins, BLAST searches of the Drosophila genome database were conducted using the candidate gene sequences to identify related genes (Altschul et aL, (1990) J. Mol. Biol. 215, 403–410). The computer algorithms employed identified the ORFs for the second exons of 22A.1 and 22A.2, which encode transmembrane domains 1–4. These ORFs are on the BDGP P1 clone designated DS005342. The DS005342 sequence was examined around the initial ORFs for neighboring ORFs which encoded additional potential transmembrane domains. Key to the identification of these neighboring ORFs was the presence of intron-exon consensus splice sequences: GTRAGT for the 5' end and HAG for the 3' end (Mount et al., (1992) Nucleic Acids Res. 20, 4255–4262). 22A.1 and 22A.2 were found to have two other introns in corresponding locations, all of which had conserved splice sequences.

The amino acid sequences of 22A.1 and 22A.2 were used in searches of the Drosophila genome database using the tBLASTn program of the BDGP. These searches yielded partial sequences of other members of the DOR family. To complete the sequences of these genes, an analysis of the genomic DNA around each identified ORF was carried out as was done for 22A.1 and 22A.2, using the locations of conserved introns in the genes, the intron consensus splice sequences, and the tBLASTn alignments as guides. Use of the genes identified in the second round as query sequences in tBLASTn searches and subsequent similar analysis of genomic DNA yielded the remaining genes. Additional searches of GenBank and SwissProt databases were performed with the NCBI (National Center for Biotechnology Information) BLAST network.

The sequence alignment in FIG. 3 is based on the alignments predicted by the tBLASTn program of the BDGP but was edited extensively. The 5' splice sequences for the most 3' introns of both 2F.1 and 47E.1 were unfavorable. It was assumed that these introns were spliced nonetheless, as the resulting amino acid sequence displayed greater sequence identity to other DOR family members. If these introns were not spliced out, then the lengths of 2F.1 and 47E.1 would not be significantly altered from the lengths indicated in FIG. 3. 2F.1 was independently predicted to be a gene (GenBank accession number 2661571) by the EMBL genefinder program subsequent to the submission of the provisional application to which this application claims priority.

Homologs of the two candidates were found, and their sequences were used in turn for further database searches. In total, forty-nine genes have been identified from the approximately 16% genomic sequence currently available. Applicants have tentatively named this family of genes DOR (for Drosophila Olfactory Receptor), and each individual gene was named based upon its cytogenetic location in the genome. Thus the two genes identified initially are DOR22A.1 and DOR22A.2, which were abbreviated here as 22A.1 and 22A.2 (the final digit in this nomenclature is used to distinguish the genes at a site and does not refer to the cytogenetic band number). The genomic locations of all the DOR genes identified so far are indicated in FIG. 2A, and an alignment of their amino acid sequences is presented in FIG. 3. Of the forty-nine family members, the great majority have been found to be expressed in either the antenna or the maxillary palp, or in both, based upon RT-PCR analysis (Table 1) and in situ hybridizations to RNA in tissue sections.

The DOR genes have no significant similarities to any known genes, and do not appear in any of the Drosophila EST databases. However, Kyte-Doolittle hydropathy plots of the predicted proteins show that each has approximately seven peaks that could represent transmembrane domains (FIG. 2C) (Kyte & Doolittle, (1982) J. Mol. Biol. 157, 105–132). The lengths of the sixteen proteins are between 369 and 403 amino acids, similar to the lengths of most previously described families of GPCRs (Probst et al., (1992) DNA Cell Biol. 11, 1–20). In addition, the spacing of the putative transmembrane domains gives rise to predicted intracellular and extracellular loops similar in size to those in many families of GPCRs (Probst et al., (1992) DNA Cell Biol. 11, 1–20).

Amino acid sequence identity among the DOR genes ranges from approximately 10–75%, with many genes showing a relatively low level of identity to each other (approximately 20%). Two pairs of clustered genes, 22A.1/22A.2 and 33B.1/33B.2 show the highest identity, with 75% and 57% homology, respectively. However, not all clustered genes show high degrees of similarity. 33B.3, for example, is only 28% identical to both 33B.1 and 33B.2 and 46F.1 and 46F.2 are only 29% identical. In addition to exhibiting sequence identity, many of the genes contain introns in corresponding locations (FIG. 3), consistent with their constituting a family derived from a common ancestral gene. Examples of genomic DNA encoding the complete structural gene for DOR proteins containing the introns can be found in SEQ ID NO: 99–114, while the corresponding cDNA containing the intact ORF can befoundinSEQIDNO: 1, 3, 5, 7, 9, 11, 13, 15, 17, 19, 21, 23, 25, 27, 29and31.

There are sixty-seven residues that are conserved among at least 50% of the genes, and most of these (49) are in the C-terminal halves of the proteins (FIG. 3). Among the conserved residues are a serine and a threonine in the intracellular C-terminal tail, residues frequently conserved in this region of GPCRs (Probst et al., (1992) DNA Cell Biol. 11, 1–20). The most divergent region in the sequences is a stretch of thirty amino acids representing part of the first extracellular loop and nearly all of transmembrane domain three. The divergence in this region also occurs in the most conserved pairs of genes: 22A.1 and 22A.2 are 75% identical overall, but only 50% identical in this region, and 33B.1 and 33B.2 are 57% identical overall, but only 33% identical in this region. This divergence has also been observed in other species. In particular, transmembrane domains three, four and five were exceptionally divergent in rat odorant receptors and have been proposed to play a role in odorant binding (Buck & Axel, (1991) Cell 65, 175–187).

Some of the genes are clustered in the genome (FIG. 2A), while others are apparently isolated. Within a cluster the average intergenic distance is on the order of 500 bases. Clustered DOR genes do not necessarily have introns in corresponding locations (e.g. 46F.1 and 46F.2), but all clustered genes have their transcriptional orientations in the same direction (FIG. 2A). At least one of the DOR genes (2F.1) is flanked closely on both sides by two apparently unrelated genes (FIG. 2B) (Haenlin et al., (1987) EMBO J. 6, 801–807).

A novel strategy to search the Drosophila genomic sequence database for genes encoding potential GPCRs was employed, leading to the identification of a multigene family with properties expected of odorant receptors. In addition to these genes, a wide variety of other transmembrane proteins were identified by this strategy, a few previously identified by other means and many representing novel proteins with similarity to known transmembrane proteins. These results suggest that the algorithm may be of widespread use in identifying new receptors, channels, and other transmembrane proteins.

The family of candidate odorant receptor genes currently contains forty-nine members, identified from the 16% of the Drosophila genomic sequence that is available. By extrapolation the size of this family may be on the order of 100 genes, making it the largest gene family identified in Drosophila.

There are several lines of evidence indicating that these genes encode Drosophila odorant receptors. First, the predicted proteins encoded by the genes each contain approximately seven potential transmembrane domains, as expected of GPCRs. Second, genes are expressed in one or both of the two olfactory organs, and for a number of genes this expression is restricted to a subset of olfactory receptors, as expected for odorant receptors. Third, the large number of family members, and the clustered location of many of these genes in the Drosophila genome, is reminiscent of odorant receptors in other organisms.

Additional lines of evidence is available which indicates DOR proteins as odor receptors. First, antibodies raised against the product of the DOR22A.2 gene label a small number of sensilla on the fly's antenna whose location corresponds to the same region labeled by in situ hybridization. Most important, staining appears localized to the cavities of the labeled sensilla, where the dendritic cells are located. This is exactly the localization expected of an odorant receptor. Second, different DOR genes are expressed (as determined by in situ hybridization) in different subsets of olfactory receptor neurons, as expected of odor receptor genes. Third, as expected, the number of olfactory receptor neurons labeled by individual DOR genes corresponds with the number of olfactory receptor neurons exhibiting a particular odor-sensifivity because the number of neurons expressing a particular DOR gene is predicted to equal the number of neurons with a particular odor response spectrum. Finally, many of the DOR genes are not expressed in the Acj6 POU-domain transcription factor mutant, where a subset of olfactory receptor neurons displayed abnormal odorant specificities. A correlation between DOR gene expression and odorant-specificity therefore exists, as is expected with odorant receptor genes.

Comparison of the sequences of these candidate odorant receptors to those from other organisms shows that they are extremely divergent from known odorant receptors and other GPCR families. This is not surprising, as searches for these genes based on sequence similarity to odorant receptors from other organisms had not succeeded, and the odorant receptor families in vertebrates and C. elegans are essentially unrelated. There is a great deal of sequence divergence among the DOR genes, much more than among the rat sequences previously reported (Buck & Axel, (1991) Cell 65, 175–187), for example. Moreover, genomic Southern blots have shown that none of nine DOR genes tested defines a subfamily of more than two or so well-conserved genes. The DOR family therefore differs in this respect from the mouse family, for example, where most odorant receptor genes belong to subfamilies of approximately seven to ten genes (Ressler et al., (1993) Cell 73, 597–609).

Although at present the clusters of DOR genes identified thus far contain smaller numbers of genes (less than three) than in other organisms (Troemel et al., (1995) Cell 83, 207–218; Sullivan et al., (1996) Proc. Natl. Acad. Sci. USA 93, 884–888; Barth et al., (1997) Neuron 19, 359–369), a number of interesting features of the clustered genes are already apparent. As found in other organisms (Barth et al., (1997) Neuron 19, 359–369), Drosophila odorant receptor genes within a cluster are not necessarily coordinately regulated, such that genes within a cluster are expressed in different classes of cells, and even in different olfactory organs (e.g. 46F.1 is expressed in the maxillary palp whereas 46F.2 is expressed in the antenna). So far, all genes identified within a cluster, however, are transcribed in the same orientation. Genes within a cluster sometimes do, but sometimes do not, share intron positions, suggesting that introns may have become lost following gene duplication; a phylogenetic study revealed extensive gene duplication and intron loss among the chemoreceptor genes of C. elegans (Robertson, (1998) Genome Res. 8, 449–463).

Step 3: Identification of olfactory receptor genes using RT-PCR. RT-PCR with primers designed from two of these final candidates yielded amplification products from antennal cDNA. From RT-PCR experiments, the two genes did not appear to be expressed in the maxillary palp, abdomen, thorax, or head from which olfactory organs had been removed, suggesting that these genes were expressed specifically in the antenna. These two genes are located within 500 base pairs of each other at cytological position 22A (FIG. 2A), and their predicted proteins are 75% homologous at the amino acid level.

For preparation of RNA, individual flies were frozen in liquid nitrogen, and antennae and maxillary palps were dissected. On average 150 antennae or 200 maxillary palps were used for RNA preparation. Total RNA was prepared as described elsewhere (McKenna et al., (1994) J. Biol. Chem. 269,16340–16347). The RNA was treated with DNaseI (Gibco-BRL) for thirty minutes at 37° C., phenol/chloroform extracted, and precipitated. The entire RNA preparation was used for oligo dT-primed cDNA synthesis using Superscript II Reverse Transcriptase (Gibco-BRL) according to the manufacturer's directions. PCR was performed using Taq polymerase (Sigma) under standard cycling conditions, with an annealing temperature of 60° C., gene-specific primer concentration of 1 pM, and magnesium concentration of 2.5 mM. For all genes except 2F.1, primer pairs which span introns were used in order to distinguish PCR bands amplified from cDNA from those amplified from any remaining genomic DNA.

Example 2

Hybridization of DOR Gene Probes to Related Sequences

To determine whether any of the DOR genes have closely related homologs, coding regions from nine of the genes were used to probe Southern blots of Drosophila genomic DNA at high or low stringency. For the closely related genes such as 22A.1 and 22A.2, a combined probe was used. For genomic southern blots, hybridizations were at 65° C. (high stringency) or 55° C. (low stringency), in 7% SDS, 0.5 M sodium-phosphate buffer pH 7.2, 1 mM EDTA, pH 8.0.

Each probe detected only its own sequence at high stringency, while at low stringency most gene probes detected one or two novel bands (data not shown). As expected, because of the overall low level of similarity, none of these extra bands corresponded to any of the other known DOR genes. These data indicate that some of these genes have one or two closely related homologs, but that none belongs to a large subfamily of highly related genes.

Example 3

Localization of DOR Gene Expression

Olfactory receptor neurons of the adult fly are located in both the antenna and the maxillary palp. To ask whether any of the DOR genes are expressed in these neurons, in situ hybridization was carried out using adult tissue sections.

For in situ hybridization experiments, coding regions of the DOR genes were subcloned into the pGEM-T Easy vector (Promega). Digoxygenin-labeled RNA probes were generated and hydrolyzed according to the manufacturer's instructions (Boehringer Mannheim). In situ hybridizations to RNA in tissue sections were performed using a modified version of procedures described elsewhere (Roberts, (1998) Drosophila: A Practical Approach, Oxford University Press; Chadwick & McGinnis, (1987) EMBO J. 6, 779–789). Briefly, heads were dissected from animals and fixed in 4% paraformaldehyde/PBS for fifteen minutes. Tween-20 was then added to 0.1% and heads were fixed for an additional thirty minutes. Samples were washed twice for five minutes in 0.1% Tween 20/PBS (PBST), cut into 8 μm frozen sections, and mounted on poly-L-Lysine treated slides (Sigma). Sections were dried onto slides for thirty minutes at room temperature and then fixed for an additional thirty minutes in 4% paraformaldehyde/PBST. Samples were washed for a total of two hours in PBST with five changes of buffer, followed by an incubation for five minutes in 1:1 PBST:hybridization buffer (50% formamide, 5×SSC, 50 mg/ml heparin, 0.1% Tween 20), and then prehybridized for two hours at 55° C.

Figure 4A:
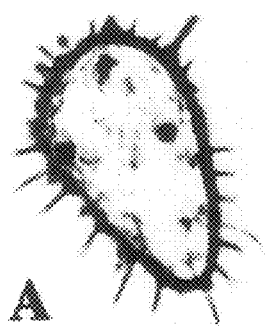
FIG. 4 DOR genes are expressed in subsets of olfactory receptor neurons in the maxillary palp. In situ hybridizations to tissue sections of maxillary palps. Panel A shows a frontal section; all other sections are sagittal. (A) A 46F.1 probe reveals expression in a subset of olfactory receptors which are broadly distributed. The background staining at the periphery of the organ represents non-specific labeling of the cuticle, observed equally for sense and antisense probes. (B) A 33B.3 probe also hybridizes to a subset of cells. Unlabeled olfactory receptors are visible under the cuticular surface (top center). (C) At higher magnification it can be seen that the cells expressing 46F.1 are neurons. Note the axons projecting from the cells into the nerve (n) which runs through the middle of the maxillary palp. The arrowhead indicates an ORN which is not expressing 46F.1, adjacent to an ORN which is strongly stained. The light staining of the nerve is background staining, observed equally for sense and antisense probes. (D) 33B.3 is not expressed in the acj6 null mutant, acj6$^6$.
Figure 4B:
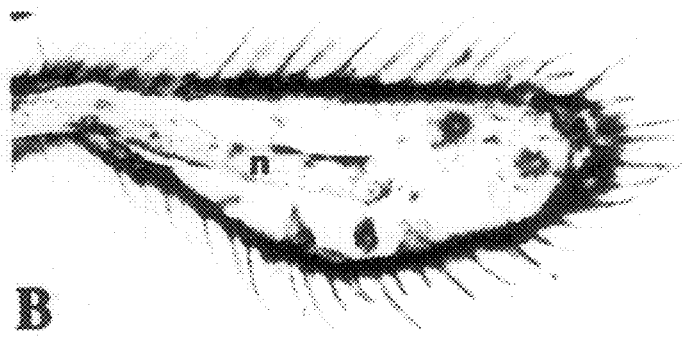
Figure 4C:

Of eleven genes examined, seven displayed detectable expression, which in every case was restricted to the olfactory organs (Table 2). The 46F.1 probe hybridized to a subset of olfactory receptors in the maxillary palp (FIG. 4A). Counting of labeled olfactory receptors in serial sections revealed that the total number of 46F.1-staining olfactory receptors per maxillary palp was 18±1 (Table 2), or 15% of the 120 olfactory neurons in the maxillary palp. A similar number of neurons, 17±1, was labeled by another probe, 33B.3 (FIG. 4B). The neuronal identity of the labeled cells was apparent from the presence in many cases of a well-defined axon projecting from the labeled cell body and joining the maxillary nerve (FIGS. 4B–C). For both probes, the labeled neurons were distributed broadly over the olfactory surface of the organ, and were interspersed among unlabeled neurons (FIGS. 4A–C). Staining in many cells appeared annular, which was interpreted to reflect a peri-nuclear distribution of MRNA, as expected of an mRNA present at highest concentrations in the cell bodies of these olfactory receptors (FIG. 4B). The 33B.3 and 46F.1 genes are evidently expressed in different subsets of olfactory receptors, because the number of neurons hybridizing with a mixed probe was greater than the number of neurons that hybridized when either probe was used individually (data not shown). No hybridization detected in the antenna, head, or thorax for either probe.

Figure 1E:
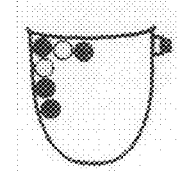
Figure 1F:
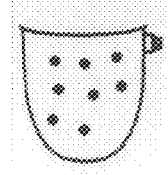
Figure 5A:
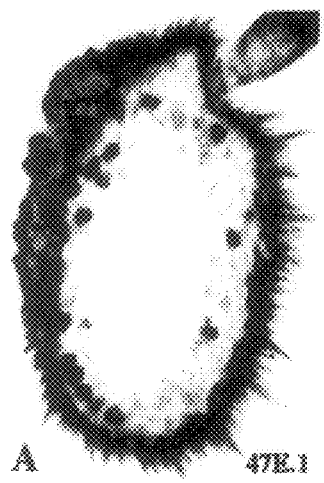
FIG. 5 DOR genes are expressed in subsets of antennal cells. Shown are in situ hybridizations to tissue sections of third antennal segments. In panels A, B, D, and F the plane of section passes through the fluid-filled interior of the antenna. (A,B) A 47E.1 probe hybridizes to a subset of cells which are broadly distributed. (C,D) A 25A.1 probe hybridizes to a smaller subset of cells. The angle of section in panel C differs somewhat from the other panels. (E) A 22A.2 probe hybridizes to a subset of cells in the dorso-medial region where the large s. basiconica are located. (F) 22A.2 is expressed in the acj6$^6$ mutant, in contrast to 33B.3 (FIG. 4D). (G) Summary of distributions of labeled cells for 47E.1 (open circles), 25A.1 (black dots), and 22A.2 (gray dots) on the anterior face of the antenna, based on analysis of expression in 30–50 antennae for each gene.
Figure 5C:
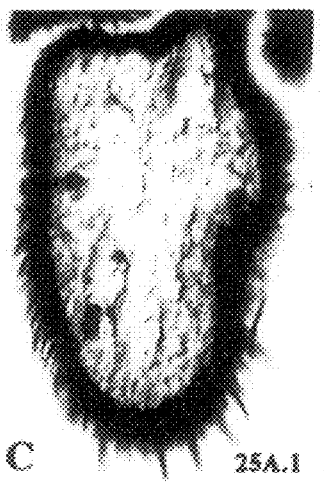
Figure 5E:
Figure 5B:
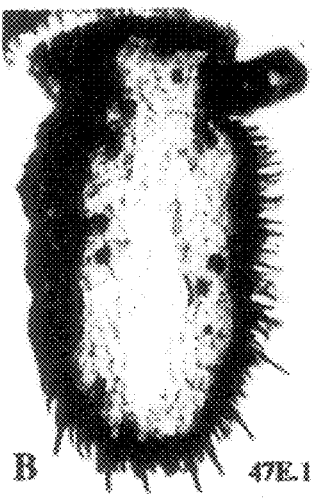
Figure 5D:
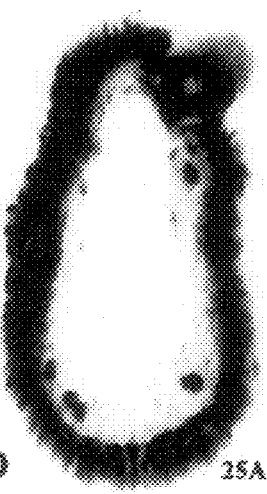

Many of the DOR genes are expressed in the antenna and not in the maxillary palp, as determined by RT-PCR (Table 1). For several genes this localization was confirmed by in situ hybridization. The 47E.1 probe hybridized to 40±1 cells in a broad area across the antenna (FIGS. 5A–B), including both anterior and posterior faces, similar to the distribution pattern of small s. basiconica (FIG. 1F). A probe from the 25A.1 gene hybridized to fewer cells, 16±1, but in a region of the antenna similar to that of 47E.1 staining, as judged by reconstruction of serial sections (FIGS. 5C–D). The 22A.2 probe hybridized to 22±1 cells in a different distribution, clustered in the dorso-medial region of the antenna (FIG. 5E). This pattern matches the distribution of the large s. basiconica (FIG. 1E). The expression patterns of the three genes in the antenna are illustrated schematically in FIG. 5G. None of these three probes revealed expression in the maxillary palp, head, or thorax. This data demonstrates that the DOR family is expressed in olfactory receptors, and that the expression of individual members is restricted to distinct subsets of cells in the olfactory organs.

The number and broad distribution of maxillary palp neurons expressing 46F.1 and 33B.3 are intriguing in light of electrophysiological studies. There are approximately 120 olfactory receptors on the palp, which fall into six different classes based upon their odorant response profiles. Each class contains roughly equal numbers of neurons, distributed broadly over the olfactory surface of the palp. Thus, if an individual receptor gene is expressed in all olfactory receptors of a functional class, one might expect a gene to be expressed in a broad distribution, in approximately twenty neurons, in good agreement with the distribution and numbers observed for both 46F.1 and 33B.3 (18±1 and 17±1, respectively).

The two DOR genes whose expression was detected by in situ hybridization in the maxillary palp are expressed in olfactory receptors housed within s. basiconica, the only morphological class of sensilla on the palp. In the antenna, the 22A.2 probe consistently hybridized to a subset of cells in a portion of the dorso-medial region of the antenna that contains almost exclusively large s. basiconica (FIG. 1E). The 47E.1 and 25A.1 probes hybridize to subsets of cells in a distinctly different region of the antenna which may correlate with the distribution of small s. basiconica, of which at least two functional types are intermingled (FIG. 1F). Of particular interest, the numbers of cells to which 47E.1 and 25A.1 hybridize are different: 40±1 and 16±1; one possible interpretation is that they are expressed in distinct finctional types of small s. basiconica. This region also contains s. trichodea and s. coeloconica, and although the labeling patterns do not correlate with the distribution of either of two functional classes of s. trichodea (Clyne et al., (1997) Invert. Neurosci. 3, 127–135), a definitive identification of the sensillar type may require further investigation. If in fact all the DOR genes are expressed in only one of the morphological categories of sensilla, the s. basiconica, it is possible that there are other, as yet unidentified, families of receptors that are expressed in the other morphological categories of sensilla. This would mean that the number of odorant receptors in Drosophila might be substantially larger than one-hundred.

Applicants have identified three DOR genes that are expressed in the maxillary palp (Table 1), from the 16% of the genome analyzed. As these three genes, like most DOR genes, are not clustered in the genome, linear extrapolation suggests that the entire genome contains on the order of eighteen DOR genes expressed in the maxillary palp, an organ which has six functional classes of neurons (Clyne et al., (1999) Neuron 22, 339–347; de Bruyne et al., (1999) J. Neurosci. 19, 4520–4532). If all neurons within a functional class, i.e. with the same odor-specificity, are identical in terms of their receptor expression, then the ratio of expressed genes to neuronal classes in this organ would be consistent with a model in which an individual ORN expresses a small number of odorant receptors; however, further data is needed to establish conclusively the number of receptor genes expressed per cell. Olfactory neurons in other organisms appear to lie at either of two extremes: in the vertebrates, it is believed only one receptor is expressed per ORN (Ngai et al., (1993) Cell 72, 667–680; Ressler et al., (1993) Cell 73, 597–609; Vassar et al., (1993) Cell 74, 309–318); in C. elegans, approximately 550 chemoreceptors are likely to be distributed amongst fourteen classes of chemosensory neurons (Troemel et al., (1995) Cell 83, 207–218).

Olfactory receptors in Drosophila and other insects project to an olfactory processing center, the antennal lobe, which is much like the olfactory bulb of vertebrates. Like its vertebrate counterpart, the antennal lobe contains olfactory glomeruli, of which the antennal lobe of Drosophila has approximately forty (Stocker et al., (1995) Roux's Arch Dev Biol 205, 62–72; Laissue et al., (1999) J. Comp. Neurol. 405, 543–552). In vertebrates there is an approximate equivalence between the estimated number of odorant receptor genes and the number of glomeruli (Barth et al., (1996) Neuron 16, 23–34; Buck, (1996) Annu. Rev. Neurosci. 19, 517–544); since C. elegans does not contain glomeruli, it has not been possible until now to consider whether the evolutionary conservation of this equivalence extends to invertebrates. If in fact the number of DOR genes is one-hundred, then the ratio of odorant receptor genes to glomeruli would exceed two, and would rise if additional families of odorant receptor genes were discovered. Of particular interest, the number of glomeruli receiving input from the maxillary palp has been variously estimated as three and five (Venkatesh & Singh, (1984) Int. J. Insect. Morphol. Embryol. 13, 51–63; Stocker et al., (1995) Roux's Arch Dev Biol 205, 62–72); if our estimate of eighteen genes expressed in the maxillary palp is correct, then the ratio of these receptor genes to their corresponding glomeruli would fall in the range of three to six.

Example 4

DOR Gene Expression During Development

Recent evidence supports a dual role for the vertebrate olfactory receptors. First, these receptors have an instructive role in guiding the axons of olfactory receptors to the correct glomeruli during development (Mombaerts et al., (1996) Cell 87, 675–686; Wang et al., (1998) Cell 93, 47–60), and second as odorant receptors in the adult (Zhao et al., (1998) Science 279, 237–242). To address the possibility that the DOR genes might also play a role in development, three DOR probes were hybridized to antennal sections from different stages of pupal development. In Drosophila, ORN axons first leave the developing antenna at approximately sixteen hours after puparium formation (APF) (Lienhard & Stocker, (1991) Development 112, 1063–1075; Ray & Rodrigues, (1995) Dev. Biol. 167, 426–438; Reddy et al., (1997) Development 124, 703–712), and the diameter of the antennal nerve continues to increase until 72 hours APF (Stocker et al., (1995) Roux's Arch. Dev. Biol. 205, 62–72). Glomeruli first become visible in the antennal lobe at approximately 48 hours APF. Developing antennae were therefore examined at 16, 24, 36, 48, 54, 60, 72 and 93 hours APF (adults eclosed from the pupal case at approximately 100 hours). For these developmental studies, Drosophila were collected as white prepupae and kept at 25° C. on moist filter paper for the indicated number of hours, at which time they were fixed. At 25° C. the approximate time from the white prepupal stage to eclosion is 100 hours (Lockett & Ashburner, (1989) Dev. Biol. 134, 430–437).

Figure 6A:
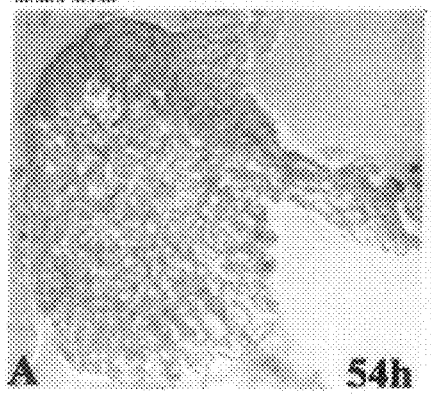
FIG. 6 Expression of DOR genes during antennal development. In situ hybridizations to tissue sections of third antennal segments at different times during pupal development. The times indicated refer to hours APF (after puparium formation). Arrows indicate labeled cells. (A) Expression of 22A.2 is not observed at 54 hours APF. Note that background staining is absent in sections taken at 54 hours (or at earlier times), presumably due to the immaturity of the cuticle. (B) Expression of 22A.2 is observed at 60 hours APF. (C) 47E.1 expression is not observed at 72 hours APF. Background staining is observed with both sense and antisense probes on the cuticular surface of the sacculus (s), a multi-chambered sensory pit and the dot at the bottom of the third antennal segment is non-specific staining of a section of tracheal tissue. (D) Expression of 47E.1 is detected at 93 hours APF. (E) The odor binding protein OS-E is not expressed at 72 hours APF. The small dots at the bottom of the antenna are non-specific staining of a section of tracheal tissue, observed with both sense and antisense probes. (F) Abundant expression of OS-E is seen at 93 hours APF.
Figure 6B:
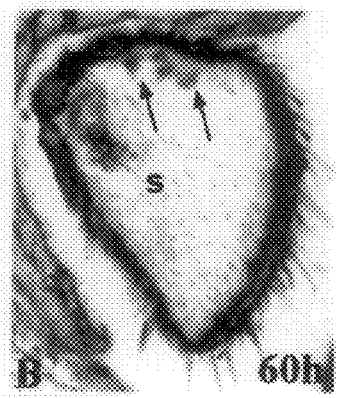
Figure 6C:
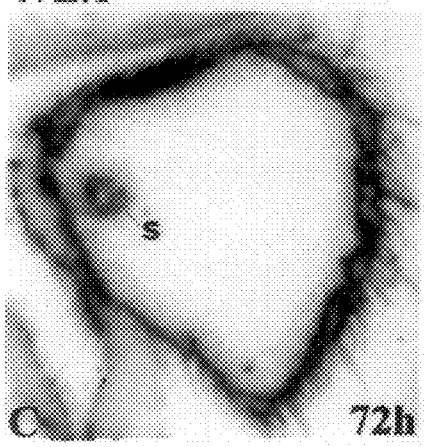
Figure 6D:
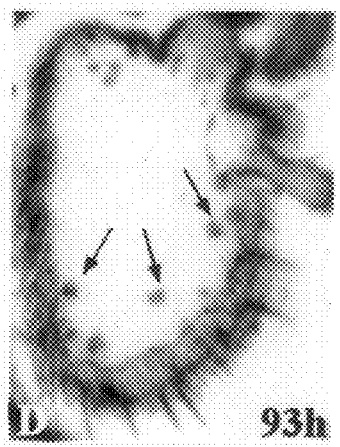
Figure 6E:
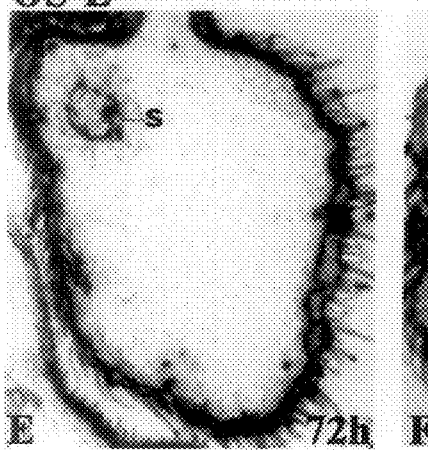
Figure 6F:
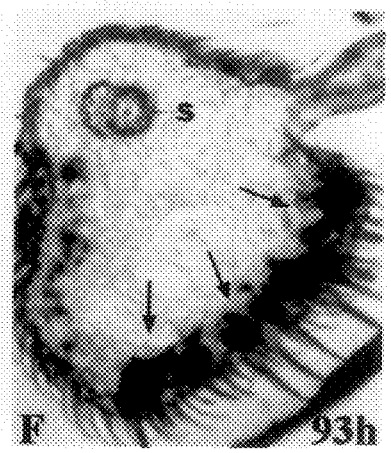

Cells positive for 22A.2 were first seen at 60 hours APF, indicating that detectable expression begins between 54 and 60 hours, well within the period in which the antennal nerve is still increasing in diameter (FIGS. 6A–B). A subset of cells was labeled at this time, and they were restricted to a subregion of the developing antenna; the pattern appears comparable to that of the mature antenna, although this pattern was not characterized in as much detail as that of the adult. Labeling with 22A.2 was also observed in antennae at all subsequent time points. Interestingly, cells positive for 47E.1 and 25A.1 were not observed until much later, at the 93 hour time point; they were not observed at any of the earlier times (FIGS. 6C–D and data not shown). For comparison, in situ hybridization was also performed with a probe representing the odorant-binding protein OS-E (McKenna et al., (1994) J. Biol. Chem. 269, 16340–16347), which is believed to play a role in olfactory function, but which has not been implicated in a developmental process. OS-E was also first observed at 93 hours, at which time it expression increased (FIGS. 6E–F).

Example 5

Regulation of DOR Expression by POU Domain Transcription Factor acj6

Figure 4D:
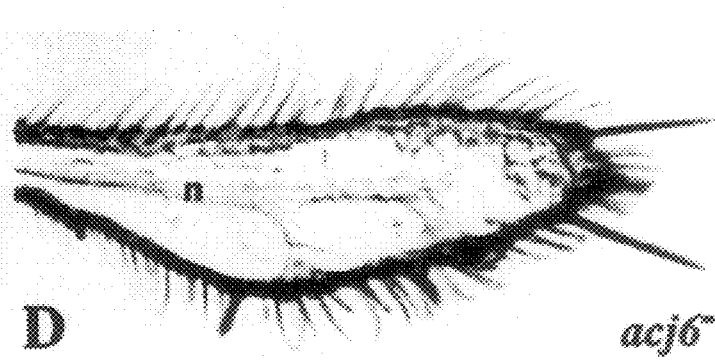
Figure 5F:
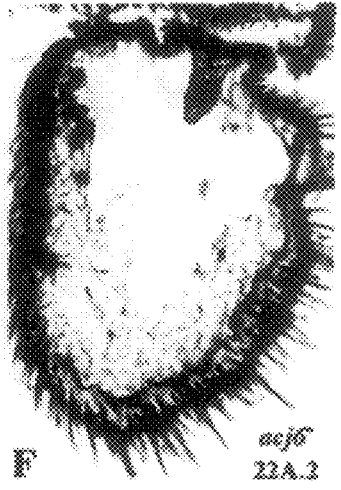
Figure 5G:
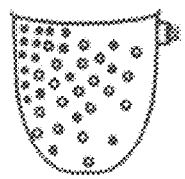

Little is known about the regulation of odor receptor genes, a process critical to the establishment of olfactory neuron identity and ultimately to the process of olfactory coding. In C. elegans the odr7 gene, a member of the nuclear receptor superfamily, has been shown to regulate the odorant receptor gene odr10 (Sengupta et al., (1994) Cell 79, 971–980; Sengupta et al., (1996) Cell 84, 899–909). In Drosophila, null mutations of the acj6 gene, which encodes a POU domain transcription factor, eliminate the odor response of three of the six classes of maxillary palp olfactory receptors (Clyne et al., (1999) Neuron 22, 339–347). A fourth ORN class on the maxillary palp is altered to a new class of ORN with a novel odor sensitivity. These data suggest that Acj6 plays a role in the differentiation of certain maxillary palp olfactory receptors, perhaps by determining which olfactory receptor gene(s) are expressed. To address the possibility that Acj6 regulates odorant receptor genes, probes from the 33B.3 and 46F.1 genes were hybridized to sections of maxillary palps from the null mutant, acj6$^6$. No hybridization was detected in either case (FIG. 4D and data not shown), nor was expression of either gene detected by RT-PCR from acj6$^6$ maxillary palps (Table 1).

acj6 mutations also affect the physiological response of the antennal neurons to odors (Ayer & Carlson, (1991) Proc. Nat. Acad. Sci. USA 88, 5467–5471; Ayer & Carlson, (1992) J. Neurobiol. 23, 965–982). 22A.2, 25A.1, and 47E.1 probes were therefore hybridized to sections of acj6$^6$ antennae. All three probes hybridized to groups of cells in the same locations as in the wild type antenna (FIG. 5F and data not shown). RT-PCR amplification showed that expression of certain other DOR genes, 33B.1, 33B.2, 33B.3, and 46F.2 was eliminated in the antenna of acj6$^6$ (Table 1). Thus, in the acj6$^6$ mutant, one subset of candidate odorant receptor genes was not expressed while a different subset remained unaffected. Interestingly, genes within a cluster all showed similar dependency on Acj6: 33B.1, 33B.2, and 33B.3, for example, all depended on Acj6, whereas 22A.1 and 22A.2 did not. In summary, these data support a role for acj6 in the regulation of a subset of olfactory receptor genes.

The DOR family is subject to complex regulation. First, the expression of individual DOR genes exhibits highly specific tissue and spatial localization. Some genes are expressed in the antenna but not the maxillary palp; others show expression in the maxillary palp but not the antenna. Within an organ, expression of a particular DOR gene is restricted to a subset of cells. In the antenna, the patterns of expression are spatially regulated, exhibiting regional specificity of expression as detailed above. In the maxillary palp, expression is limited to a population of neurons approximately equal in number to the neurons of a functional class.

DOR genes are also subject to interesting temporal regulation. One gene, 22A.2, is expressed in the developing antenna during a time when the antennal nerve is still increasing in diameter (Stocker et al., (1995) Roux's Arch. Dev. Biol. 205, 62–72). These data leave open a possible role for Drosophila olfactory receptors in axon guidance and glomerulus formation, a role for which evidence has been found in vertebrates (Mombaerts et al., (1996) Cell 87, 675–686; Wang et al., (1998) Cell 93, 47–60) but not C. elegans. In zebrafish, odorant receptors show asynchronous onset of expression during development of the olfactory placode (Barth et al., (1996) Neuron 16, 23–34). The DOR genes also show heterogeneity in their temporal regulation: expression of two other DOR genes begins much later than for the 22A.2 gene. If in fact individual olfactory receptors express more than one DOR gene, perhaps some have acquired a specialized role in development.

Evidence also exists indicating that different DOR genes are expressed at different levels of abundance within cells. Although RT-PCR experiments demonstrated expression of 25A.1 in both antenna and maxillary palp, in situ hybridization revealed expression of 25A.1 only in the antenna of each animal examined; conversely, although RT-PCR experiments showed expression of 33B.3 in both olfactory organs, in situ hybridization detected label only in the maxillary palp of each animal examined (Tables 1 and 2). These results suggest that a receptor gene may be expressed at different cellular levels in the two organs, and that different genes may be expressed at different cellular levels in the same organ. Such an explanation would suggest that there are mechanisms governing not only the spatial and temporal control of DOR genes, but also their levels of expression.

If DOR genes are in fact expressed at different cellular levels in particular olfactory receptors, then perhaps the four DOR genes that were undetectable in the antenna by in situ hybridization, despite clear evidence for their antennal expression from RT-PCR, a more sensitive technique, are among those expressed at low levels. It is important to note that in C. elegans, expression of a number of candidate odorant receptors was undetectable using GFP fusion genes (Troemel et al., (1995) Cell 83, 207–218).

As a first step in investigating the mechanisms through which the complex regulation of DOR genes is achieved, the role of the POU domain transcription factor Acj6 was tested, which was previously found to act in governing olfactory neuron identity. Applicants found that Acj6 is in fact required for expression of the DOR family. Two lines of evidence, RT-PCR and in situ hybridization analysis, both indicate that proper expression of a specific subset of DOR genes depends on Acj6. The results indicate that the odor-specificity of a subset of olfactory receptors is governed at least in part by the action of the Acj6 POU domain transcription factor on DOR genes, and are fully consistent with the notion that DOR genes encode odorant receptors.

The isolation of genes likely to encode odorant receptors in Drosophila opens a number of avenues for future investigation. Drosophila provides the ability to manipulate odor receptors genetically and test the functional consequences of such manipulations in vivo, either physiologically or behaviorally. Such analysis may be useftil in examining potential roles of DOR proteins in olfactory response and in development. It may also be possible to isolate homologous genes in other insects, including some which provide excellent opportunities for research and some of agricultural or medical importance which rely on olfactory cues to locate their hosts.

Example 6

Transgenic Drosophila

P element mediated germline transformation of Drosophila can be carried out as previously described (Rubin & Spradling, (1982) Science 218, 348–353). Drosophila embryos are isolated and microinjected with P element expression constructs as previously described (Karess & Rubin, (1984) Cell 38, 135–146) containing a particular DOR nucleotide sequence, at 0.5 mg/ml together with a helper plasmid at 0.1 mg/ml. $G_0$ injected adults are individually back crossed to the recipient strain and the $G_1$ progeny screened for the w+ transformation marker (Klemenz et al., (1987) Nucleic Acids Res. 10, 3947–3959). Transformed lines homozygous for the transgene are established from orange eyed Gi flies as previously described (Klemenz et al., (1987) Nucleic Acids Res. 10, 3947–3959).

A line of Drosophila in which the DOR33B.3 gene can be over-expressed was constructed as described above. The DOR33B.3 coding sequences were joined to an upstream activating sequence (UAS) and introduced by P element-mediated germline transformation into Drosophila. A yeast GAL4 transcription factor gene, coupled to a heat shock promoter, was then crossed into the transgenic line. As expected, heat shock of this line resulted in induction of DOR33B.3 expression. The heat shock-induced expression of GAL4, results in binding of GAL4 to the UAS, and subsequent induction of DOR33B.3 expression. This transgenic line of Drosophila, and three other transgenic lines containing other DOR genes, can be tested for elevated responses to any of fifty different odors. Elevated response to any particular odorant is indicative of an ligand which binds and activates the over- expressed receptor (see, e.g., Zhao & Firestein, (1998) Science 279, 237–242).

Although the present invention has been described in detail with reference to examples above, it is understood that various modifications can be made without departing from the spirit of the invention. Accordingly, the invention is limited only by the following claims. All cited patents and publications referred to in this application are herein incorporated by reference in their entirety. The results of the experiments disclosed herein have been published in the journal Neuron (22, 327–338) in February, 1999, this article herein incorporated by reference in its entirety.

We claim:

1. An isolated nucleic acid molecule that encodes the amino acid sequence of a Drosophila Odorant Receptor protein or fragment thereof, wherein the nucleic acid molecule comprises:

(i) nucleotides of SEQ ID NO: 31 which encode the amino acids which comprise the third extracellular domain;

(ii) nucleotides of SEQ ID NO: 31 which encode the amino acids which comprise the fourth extracellular domain; and (iii) nucleotides of SEQ ID NO: 31 which encode the amino acids which comprise the fourth intracellular domain;

wherein the nucleic acid molecule encodes a protein or fragment thereof which causes the firing of an olfactory neuron when stimulated.

2. The nucleic acid molecule of claim 1, wherein the nucleic acid molecule comprises the sequence of SEQ ID NO: 31.

3. The nucleic acid molecule of either claim 1 or 2, wherein said nucleic acid molecule is operably linked to one or more expression control elements.

4. An isolated host cell comprising the nucleic acid molecule of claim 1 or 2.

5. The isolated host cell of claim 4, wherein the host cell is a prokaryotic host cell or a eukaryotic host cell.

6. A vector comprising the nucleic acid molecule of claim 1 or 2.

7. An isolated host cell comprising the vector of claim 6.

8. The isolated host cell of claim 7, wherein the host cell is a prokaryotic host cell or a eukayotic host cell.

9. A method for producing a protein or polypeptide comprising the step of culturing a host cell transformed with the nucleic acid molecule of claims 1 or 2 under conditions in which the protein or polypeptide encoded by the nucleic acid molecule is expressed.

10. An isolated nucleic acid molecule encoding the amino acid sequence of SEQ ID NO: 32.

11. An isolated nucleic acid molecule that hybridizes to the nucleotide sequence of SEQ ID NO: 31 under the following conditions: 7% SDS, 0.5 M sodium phosphate buffer at pH 7.2, 1 nM EDTA, pH 8.0 and 55° C., wherein the nucleic acid molecule encodes an amino acid sequence which causes the firing of an olfactory neuron when stimulated.

12. An isolated nucleic acid molecule that hybridizes to the nucleotide sequence of SEQ ID NO: 31 under the following conditions: 7% SDS, 0.5 M sodium phosphate buffer at pH 7.2, 1 nM EDTA, pH 8.0 and 65° C., wherein the nucleic acid molecule encodes an amino acid sequence which causes the firing of an olfactory neuron when stimulated.

13. An isolated nucleic acid molecule encoding a fragment of at least 25 consecutive amino acids of SEQ ID NO: 32, wherein the fragment has odorant receptor activity, or is capable of generating an antibody which binds SEO ID NO: 32.

* * * * *